US007043476B2

United States Patent
Robson

(10) Patent No.: US 7,043,476 B2
(45) Date of Patent: May 9, 2006

(54) METHOD AND APPARATUS FOR DATA MINING TO DISCOVER ASSOCIATIONS AND COVARIANCES ASSOCIATED WITH DATA

(75) Inventor: Barry Robson, Bronxville, NY (US)

(73) Assignee: International Business Machines Corporation, Armonk, NY (US)

( * ) Notice: Subject to any disclaimer, the term of this patent is extended or adjusted under 35 U.S.C. 154(b) by 664 days.

(21) Appl. No.: 10/269,375

(22) Filed: Oct. 11, 2002

(65) Prior Publication Data

US 2004/0073534 A1 Apr. 15, 2004

(51) Int. Cl.
*G06F 17/30* (2006.01)

(52) U.S. Cl. .................. 707/7; 707/102; 707/100; 707/101; 707/103 R; 707/104.1

(58) Field of Classification Search ............... 707/7, 707/100, 101, 102, 103 R, 104.1
See application file for complete search history.

(56) References Cited

PUBLICATIONS

Muqattash et al., APplication of Data Mining and Mathematical Analysis to the Zeta Function and the Riemann Hypothesis, Ursinus College Department of Mathematics and Computer Science, Nov. 2004, pp. 1–65.*
Bohigas et al., What's Happenning in the Mathematical Sciences, Lecture Notes in Physics, vol. 209, 1994, pp. 2–17.*
Borwein et al., Searching Symbolically for Apery–Like Formulae for values of the Rieman Zeta Function, ACM Sigsam Bulletin, vol. 30, Issue 2, Jnes 1996, pp. 2–7.*
Mannila, Theoretical Frameworks for Data Mining, SIGKDD Explorations, vol. 1, Issue 2, Jan. 2000, pp. 30–32.*
Alstrup et al., Pattern Matching in Dynamic Texts, pp. 819–828.*
Skorobogatov et al., On the Decoding of Algebraic–Geometric Codes, IEEE, 1990, pp. 1051–1060.*
Demillo, Social Process and Proofs of Theorems and Programs, Mc Graw–Hill 1953, p. 206–214.*
While et al., An Implementation of Parallel Pattern–Maching via Concurrent Hakell, Australian Computer Society Inc., 2001, pp. 293–302.*

(Continued)

*Primary Examiner*—Frantz Coby
(74) *Attorney, Agent, or Firm*—Ryan, Mason & Lewis, LLP; Casey P. August, Esq.

(57) ABSTRACT

Data mining techniques are provided which are effective and efficient for discovering useful information from an amorphous collection or data set of records. For example, the present invention provides for the mining of data, e.g., of several or many records, to discover interesting associations between entries of qualitative text, and covariances between data of quantitative numerical types, in records. Although not limited thereto, the invention has particular application and advantage when the data is of a type such as clinical, pharmacogenomic, forensic, police and financial records, which are characterized by many varied entries, since the problem is then said to be one of "high dimensionality" which has posed mathematical and technical difficulties for researchers. This is especially true when considering strong negative associations and negative covariance, i.e., between items of data which may so rarely come together that their concurrence is never seen in any record, yet the fact that this is not expected is of potential great interest.

34 Claims, 23 Drawing Sheets

OTHER PUBLICATIONS

Karim K Hirji, Exploring Data Mining Implementation, Communication of the ACM, Jul. 2001, vol. 44, No. 7, pp. 87–93.*

J. Garnier et al., "Analysis of the Accuracy and Implications of Simple Methods for Predicting the Secondary Structure of Globular Proteins," J. Mol. Biol., 120, pp. 97–120, 1978.

B. Robson et al., "Refined Models for Computer Calculations in Protein Engineering—Calculation and Testing of Atomic Potential Functions Compatible with More Efficient Calculations," J. Mol. Biol., 188, pp. 259–281, 1986.

B. Robson, "Studies in the Assessment of Folding Quality for Protein Modeling and Structure Prediction," Journal of Proteome Research, vol. 1, No. 2, pp. 115–133, 2002.

T. Bayes, "An Essay Towards Solving a Problem in the Doctrine of Chances," Phil. Trans. Roy. Soc. Ser. B, 53, pp. 370–403, 1763.

H.H. Goode, "Recent Developments in Information and Decision Processes," Machol & Grey, Rds., pp. 71–91, 1962.

R. Pain et al., "Analysis of the Code Relating Sequence to Conformation in Globular Proteins," vol. 227, pp. 62–63, 1970.

S.S. Wilks, Mathematical Statistics, Section 7.7, pp. 177–182, 1962.

J. Garnier et al., "The GOR Method for Predicting Secondary Structures in Proteins," 'Prediction of Protein Structure and the Principles of Protein Conformation,' Ed. G.D. Fasman, pp. 417–465, 1989.

J. Garnier et al., "GOR Method for Predicting Protein Secondary Structure from Amino Acid Sequence," Methods in Enzymology, vol. 266, 'Computer Methods for Macromolecular Sequence Analysis,' Ed. R.F. Dolittle, pp. 540–553, 1996.

B. Robson, "Analysis of the Code Relating Sequence to Conformation in Globular Proteins: Theory and Application of Expected Information," Biochem. J. 151, pp. 853–867, 1974.

B. Robson, "Fastfinger: A Study into the Use of Compressed Residue Pair Separation Matrices for Protein Sequence Comparison," IBM Systems Journal, vol. 40, No. 2, pp. 442–463, 2001.

* cited by examiner

FIG. 3A

TABLE 1a: DEMONSTRATION FILE OF QUALITATIVE PATIENT RECORD EXTRACTS WITH ONE "RECORD" PER LINE, NON-RECTANGULAR, NO METADATA.

```
alcoholism, hepatic dysfunction, snp a, snp c, snp d, snp e, snp p, snp q
alcoholism, hepatic dysfunction, snp a, snp c, snp d, snp e, snp r
alcoholism, hepatic dysfunction, pancreatitis, snp a, snp d, snp e, snp p, snp q
alcoholism, hepatic dysfunction, pancreatitis, snp a, snp e, snp p, snp q
alcoholism, hepatic dysfunction, pancreatitis, snp a, snp c, snp d, snp e, snp p, snp q
alcoholism, hepatic dysfunction, snp a, snp c, snp e, snp p, snp q
alcoholism, hepatic dysfunction, pancreatitis, spider bite
snp a, snp b, hepatitis c, pancreatitis
hepatic dysfunction, alcoholism, snp a, pancreatitis
cancer, snp a, snp d, snp b, snp c, snp e, snp r, snp f, snp g, snp h, snp i, snp j
scorpion bite, pancreatitis, snp q, hepatitis A
cancer, snp d, snp b, snp r, snp c, snp h
hepatic dysfunction, spider bite, hepatitis c
hepatic dysfunction, snp c, snp d, snp f, snp g, snp p, snp q, hepatitis c
hepatic dysfunction, snp c, snp f, snp g, snp p, snp q, hepatitis B
hepatic dysfunction, snp c, snp d, snp f, snp g, snp p, snp q
cancer, snp a, snp b, snp c, snp r, spider bite, hepatitis B
cancer, snp a, snp d, snp b, snp r, hepatitis c
scorpion bite, snp e, snp p, pancreatitis
cancer, snp a, snp d, snp b, snp c, snp e, snp r, hepatitis B
schizophrenia, snp a, snp b, snp c, snp d, snp e
schizophrenia, snp a, snp b, snp c, snp e
schizophrenia, snp a, snp b, snp c
snp a, snp b, scorpion bite, scorpion bite, pancreatitis
snp b, pancreatitis, scorpion bite
hepatic dysfunction, alcoholism, pancreatitis
scorpion bite, snp d, hepatic dysfunction, cancer
hepatic dysfunction, snp p
hepatic dysfunction, snp a, snp c, snp d, snp p
hepatic dysfunction, snp a, snp c, snp d, snp x
alcoholism, snp a
hepatic dysfunction, alcoholism
```

FIG. 3B

TABLE 1a (cont'd):

```
alcoholism, snp c, hepatic dysfunction
alcoholism, schizophrenia
schizophrenia, scorpion bite
heart attack, snp a, snp b, snp p
heart attack, scorpion bite, snp b, snp p, pancreatitis
heart attack, hepatitis A, snp b
heart attack, snp p, snp a
snp b, snp c, spider bite
stress, snp a, snp b, snp c, snp d, snp e
stress, hepatitis A, snp b, snp c
stress, schizophrenia, snp a, snp e
stress, heart attack, spider bite
stress, heart attack, snp p, pancreatitis
stress, heart attack, snp a, snp p
stress, snp a, snp p
stress, scorpion bite, snp p, snp b, pancreatitis
stress, snp c, snp p
schizophrenia, snp b, snp e
schizophrenia, snp a, snp b, snp c
pancreatitis, schizophrenia, scorpion bite
schizophrenia, snp a, snp b, snp c
snp a, snp e
snp b, snp c, snp d
snp b, snp c, snp d, pancreatitis
snp p, snp q
snp p, snp q, scorpion bite, pancreatitis
snp p, snp q, scorpion bite, scorpion bite, pancreatitis
snp a, snp b, snp c
cancer, scorpion bite, snp d, pancreatitis, alcoholism, hepatic dysfunction, schizophrenia
hepatic dysfunction, alcoholism, snp a, snp c
snp a, snp c
hepatic dysfunction, alcoholism, snp b, snp a, snp c
hepatic dysfunction, hepatitis A
hepatic dysfunction, alcoholism, snp a
```

FIG. 3C

TABLE 1b: SMALL TEST FILE EXAMPLE, .CSV FORMAT, WITH FIRST LINE AS METADATA

```
CRS number,"Histamine with Ca peak, mean", Normalized intensity for
AI571206, Normalized intensity for U48959,
7662,1.291,0.434, 0,
7662,1.291,0,     7.237,
7695,1.399,0.474, 0,
7695,1.399,0,     7.451,
7751,1.169,1.373, 0,
7902,1.389,0.929, 0,
7902,1.389,0,     4.196,
7916,1.464,0.892, 0,
```

FIG. 3D

TABLE 1c: PORTION OF TABULATED FILE OF NUMERIC DATA, WITH FIRST LINE AS METADATA

| ID | AGE | CHOL | CPD | DRINK | EXAMDTH | GLUC | HBP | HDL | HGT |
|---|---|---|---|---|---|---|---|---|---|
| 4 | 49 | 202 | 20 | 0 | 21 | 103 | 0 | 30 | 65 |
| 5 | 34 | 217 | 16 | 0 | 11 | 98 | 0 | 60 | 63 |
| 11 | 77 | 257 | 0 | 2 | 10 | 75 | 0 | 57 | 60 |
| 12 | 46 | 184 | 15 | 3 | 16 | 84 | 0 | 82 | 60 |
| 15 | 52 | 248 | 0 | 1 | 17 | 84 | 0 | 28 | 64 |
| 16 | 35 | 229 | 0 | 13 | 11 | 76 | 0 | 43 | 62 |
| 20 | 69 | 243 | 0 | 0 | 6 | 115 | 1 | -9 | 63 |
| 21 | 58 | 188 | 0 | 0 | 21 | 146 | 1 | 50 | 63 |
| 24 | 60 | 183 | 0 | 42 | 19 | 128 | 0 | 45 | 73 |
| 25 | 45 | 166 | 0 | 1 | 11 | 148 | 1 | 41 | 72 |
| 27 | 65 | 236 | 0 | 5 | 17 | 119 | 1 | 45 | 68 |
| 28 | 53 | 230 | 25 | 48 | 11 | 107 | 0 | 65 | 62 |
| 31 | 67 | 203 | 0 | 7 | 10 | 65 | 0 | 45 | 67 |
| 32 | 60 | 224 | 0 | 13 | 9 | 78 | 0 | -9 | 62 |
| 33 | 42 | 172 | 2 | 5 | 11 | 80 | 0 | 46 | 59 |
| 34 | 50 | 236 | 0 | 2 | 11 | 102 | 0 | 52 | 64 |
| 35 | 55 | 193 | 20 | 38 | 21 | 85 | 0 | 38 | 66 |
| 36 | 48 | 185 | 0 | 13 | 11 | 188 | 0 | 54 | 66 |
| 37 | 38 | 208 | 0 | 8 | 11 | 106 | 0 | 68 | 59 |
| 38 | 57 | 228 | 0 | 2 | 11 | 109 | 1 | 44 | 63 |
| 39 | 54 | 166 | 0 | 0 | 21 | 101 | 0 | 59 | 61 |
| 40 | 33 | 198 | 0 | 6 | 11 | 115 | 0 | 55 | 68 |
| 41 | 54 | 198 | 0 | 11 | 11 | 76 | 1 | 56 | 60 |
| 42 | 35 | 194 | 20 | 47 | 11 | 93 | 0 | 51 | 67 |
| 43 | 42 | 263 | 0 | 0 | 11 | 94 | 0 | 57 | 59 |
| 46 | 56 | 249 | 0 | 0 | 19 | 87 | 0 | 49 | 70 |
| 47 | 48 | 260 | 0 | 11 | 11 | 105 | 0 | 53 | 66 |
| 48 | 41 | 161 | 0 | 0 | 11 | 95 | 0 | 50 | 62 |
| 49 | 38 | 210 | 0 | 0 | 11 | 103 | 0 | 35 | 60 |
| 50 | 59 | 216 | 0 | 0 | 11 | 95 | 1 | 44 | 60 |
| 51 | 68 | 287 | 0 | 4 | 9 | 99 | 0 | 42 | 61 |
| 53 | 43 | 190 | 0 | 0 | 11 | 97 | 0 | 30 | 69 |
| 54 | 59 | 219 | 0 | 0 | 21 | 89 | 0 | 45 | 59 |
| 55 | 45 | 222 | 9 | 1 | 6 | 90 | 0 | -9 | 63 |
| 56 | 44 | 186 | 0 | 0 | 11 | 97 | 0 | 57 | 64 |
| 57 | 41 | 189 | 20 | 0 | 11 | 92 | 0 | 60 | 61 |
| 58 | 34 | 176 | 4 | 14 | 11 | 118 | 0 | 37 | 70 |
| 59 | 57 | 195 | 15 | 0 | 21 | 130 | 0 | 58 | 61 |
| 62 | 57 | 172 | 20 | 2 | 9 | 84 | 0 | 54 | 67 |
| 63 | 55 | 195 | 0 | 2 | 11 | 107 | 0 | 57 | 59 |
| 64 | 31 | 189 | 0 | 0 | 11 | 85 | 0 | 40 | 62 |
| 65 | 47 | 203 | 0 | 0 | 11 | 80 | 0 | 55 | 63 |
| 66 | 49 | 192 | 0 | 23 | 21 | 96 | 0 | 46 | 62 |
| 67 | 31 | 188 | 25 | 29 | 11 | 99 | 0 | 47 | 64 |
| 68 | 45 | 171 | 40 | 16 | 11 | 90 | 0 | 59 | 66 |
| 70 | 44 | 189 | 40 | 4 | 11 | 143 | 0 | 49 | 63 |

FIG. 4

TABLE 2: EXAMPLE CONVERT FILE

```
$set = 0 if $set eq 'yes';
$set = 1 if $set eq 'no';
$set = 0 if $set eq 'y';
$set = 1 if $set eq 'n';
$set = 0 if $set eq 'm';
$set = 1 if Sset eq 'f';
$set = 0 if $set eq 'M';
$set = 1 if Sset eq 'F';
$set = 0 if $set eq 'male';
$set = 1 if $set eq 'female';
$set = 0 if $set eq 'normal';
$set = 1 if $set eq 'rheumatic';
$set = 0 if $set eq 'brown';
$set = 1 if $set eq 'blue';
$set = 2 if $set eq 'gray';
$set = 0 if $set eq 'non smoker';
$set = 1 if $set eq 'former smoker';
$set = 2 if $set eq 'smoker';
$set = 0 if $set eq 'true';
$set = 1 if $set eq 'false';
$set = 0 if $set eq 'TRUE';
$set = 1 if $set eq 'FALSE';
$set *= 1000 if $qualifier /U48959/; #test scaling
$set = $unknown if $qualifier=~/AI571206/; #test removing from associations
$uninteresting[1] = 'AI571206'; #test removal as uninteresting
```

FIG. 5

TABLE 3: SAMPLE CONTROL FILE comment - standard pharmacogenomic data test
comment lines can begin with comment or #
alternative common examples are given with # below
input file=test.dat
set Riemann zeta s=1
report scores above nats=0
report scores below nats=0
first line metadata=on
divide all data by n=off
ignore unknown=-9
delimit record=\n
delimit line=\n
delimit item=1 wsOR\t
alternative example delimit item=<tag>item</tag>
shift item=off
columns=off
maximum items per record sample=5
maximum number of item types=300
maximum number of items per event=5
shift record=off
minimum frequency=off
maximum sparse frequency=off
skip lines matching=^#
lines to skip after matches=off
run test=off
advanced mode=on
allow duplicates=off
associations=on
fuzzy=on
pairs=on
unseen=on
high dimensional covariance=0.01%=50
uninteresting OR=ID=HRX
interesting AND=TRIG=HGT result must match=off

FIG. 6

TABLE 4: EXAMPLE SCREEN OUTPUT

SUMMARY: Information for conjoint vs. random events.
297 counts distributed over 26 events, maximum record length 26 events, and maximum possible sample chunk size per record was set as 6.
Multiplets sampled from the highest & lowest of each 6 items/record, with skew seen in random number generator = 49.8965879029866% vs ideal 50%.

---

Potential complexity of problem:-
Number of potential conjoint events for maximum 26/record:-
Each event can appears in a record only once :67108863
One event can appears in a record x 2 :134217726
Two events can appear in a record x 3 :268435426
Number of potential conjoint events from 26 events to calculate expectations:-
Each event appears only once :67108863
If events can each appear x 2 :4.5035996273705e+015
If events can each appear x 3 :3.02231454903657e+023
If events can each appear x 4 :2.02824096036517e+031

---

These were pruned as follows:-
60 events were > 1 nat or <-1 nat and therefore listed
(including the null state for test purposes).
955 types of combinatorial events (plus 1 catchall) were generated.
955 types survived to information calculation.
3164 record content items were recognized.
3164 were recovered non-numerically
0 were recovered numerically from small codes <10000000000000
0 were recovered numerically from big codes >10000000000000
1786 of these were from nonzero events > 1 nat,
Start time Wed Jul 10 18:12:42 2002
Stop time Wed Jul 10 18:12:52 2002

FIG. 7A
TABLE 5: OUTPUT RANKING OF SIGNIFICANT CONJOINT EVENTS

```
3.25156===hepatic_dysfunction alcoholism [saw 15 expected 1] (coded +7+19+) INCIDENTS:
1.1 2.1 3.1 4.1 5.1 6.1 7 9 26 32 33 61.1 62 64 66
3.18013===snp_c snp_d [saw 14 expected 1] (coded +3+17+) INCIDENTS: 1.1 2.1 5.1 10.1
12 14.1 16.1 20.1 21 29 30 41 55 56
3.10321===snp_a snp_e [saw 13 expected 1] (coded +2+23+) INCIDENTS: 1.1 2.1 3.1 4.1
5.1 6.1 10.1 20.1 21 22 41 43 54
3.01987===pancreatitis scorpion_bite [saw 12 expected 0] (coded +13+29+) INCIDENTS:
11 19 24 24 25 37 48 52 58 59 59 61.1
2.92896===snp_a snp_d [saw 11 expected 1] (coded +2+17+) INCIDENTS: 1.1 2.1 3.1 5.1
10.1 18 20.1 21 29 30 41
2.92896===snp_a alcoholism [saw 11 expected 0] (coded +2+19+) INCIDENTS: 1.1 2.1 3.1
4.1 5.1 6.1 9 31 62 64 66
2.92896===snp_p snp_q [saw 11 expected 0] (coded +11+31+) INCIDENTS: 1.1 3.1 4.1 5.1
6.1 14.1 15.1 16.1 57 58 59
2.82896===hepatic_dysfunction snp_p [saw 10 expected 1] (coded +7+11+) INCIDENTS: 1.1
3.1 4.1 5.1 6.1 14.1 15.1 16.1 28 29
2.82896===hepatic dysfunction snp_d [saw 10 expected 1] (coded +7+17+) INCIDENTS: 1.1
2.1 3.1 5.1 14.1 16.1 27 29 30 61.1
2.82896===snp_a snp_c snp_b [saw 10 expected 0] (coded +2+3+5+) INCIDENTS: 17 20 21
22 23 41 51 53 60 64
2.71785===snp_c snp_e [saw 9 expected 1] (coded +3+23+) INCIDENTS: 1.1 2.1 5.1 6.1
10.1 20.1 21 22 41
2.71785===snp_p pancreatitis [saw 9 expected 1] (coded +11+13+) INCIDENTS: 3.1 4.1
5.1 19 37 45 48 58 59
2.59285===snp_d snp_e [saw 8 expected 0] (coded +17+23+) INCIDENTS: 1.1 2.1 3.1 5.1
10.1 20.1 21 41
2.59285===hepatic_dysfunction snp_q [saw 8 expected 0] (coded +7+31+) INCIDENTS: 1.1
3.1 4.1 5.1 6.1 14.1 15.1 16.1
2.59285===snp_a hepatic_dysfunction alcoholism [saw 8 expected 1] (coded +5+17+) INCIDENTS: 10.1 12 18 20.1 21
INCIDENTS: 1 2 4 5 9 62 64 66
2.59285===snp_b snp_d [saw 8 expected 1] (coded +2+7+19+)
41 55 56
```

FIG. 7B

TABLE 5 (cont'd): OUTPUT RANKING OF SIGNIFICANT CONJOINT EVENTS

2.45 ═══ snp_a snp_c snp_d [saw 7 expected 0] (coded +2+3+17+) INCIDENTS: 1 2 10 21 29 30 41

2.45 ═══ hepatic_dysfunction pancreatitis [saw 7 expected 1] (coded +7+13+) INCIDENTS: 3.1 4.1 5.1 7 9 26 61.1

2.45 ═══ snp_c alcoholism [saw 7 expected 1] (coded +3+19+) INCIDENTS: 1.1 2.1 5.1 6.1 33 62 64

2.45 ═══ pancreatitis alcoholism [saw 7 expected 1] (coded +13+19+) INCIDENTS: 3.1 4.1 5.1 7 9 26 61.1

2.28333 ═══ snp_p pancreatitis scorpion_bite [saw 6 expected 0] (coded +11+13+29+) INCIDENTS: 19 37 48 58 59 59

2.28333 ═══ snp_a schizophrenia [saw 6 expected 1] (coded +2+37+) INCIDENTS: 21 22 23 43 51 53

2.28333 ═══ snp_d cancer [saw 6 expected 0] (coded +17+47+) INCIDENTS: 10.1 12 18 20.1 27 61.1

2.28333 ═══ snp_a snp_c hepatic_dysfunction [saw 6 expected 0] (coded +2+3+7+) INCIDENTS: 1 2 29 30 62 64

2.28333 ═══ snp_c snp_q [saw 6 expected 1] (coded +3+31+) INCIDENTS: 1.1 5.1 6.1 14.1 15.1 16.1

2.28333 ═══ snp_p snp_d (saw 6 expected 1] (coded +11+17+) INCIDENTS: 1.1 3.1 5.1 14.1 16.1 29

2.28333 ═══ snp_p snp_e [saw 6 expected 1] (coded +11+23+) INCIDENTS: 1.1 3.1 4.1 5.1 6.1 19

2.28333 ═══ snp_p scorpion_bite [saw 6 expected 1] (coded +11+29+) INCIDENTS: 19 37 48 58 59 59

2.28333 ═══ alcoholism snp_e [saw 6 expected 0] (coded +19+23+) INCIDENTS: 1.1 2.1 3.1 4.1 5.1 16.1

2.28333 ═══ snp_b pancreatitis [saw 6 expected 1] (coded +5+13+) INCIDENTS: 8 24 25 37 48 56

FIG. 7C
TABLE 5 (cont'd): OUTPUT RANKING OF SIGNIFICANT CONJOINT EVENTS

```
2.28333====snp_b snp_e [saw 6 expected 1] (coded +5+23+) INCIDENTS: 10.1 20.1 21 22 41
50
2.28333====snp_b schizophrenia [saw 6 expected 0] (coded +5+37+) INCIDENTS: 21 22 23
50 51 53
2.28333====pancreatitis snp_q [saw 6 expected 0] (coded +13+31+) INCIDENTS: 3.1 4.1
5.1 11 58 59
2.28333====hepatic_dysfunction snp_e [saw 6 expected 1] (coded +7+23+) INCIDENTS: 1.1
2.1 3.1 4.1 5.1 6.1
2.13753====snp_c snp_b [saw 16 expected 2] (coded +3+5+) INCIDENTS: 10.1 12 17.1 20.1
21 22 23 40 41 42 51 53 55 56 60 64
2.08333====cancer snp_r [saw 5 expected 0] (coded +47+53+) INCIDENTS: 10.1 12 17.1 18
20.1
2.08333====snp_b pancreatitis scorpion_bite [saw 5 expected 0] (coded +5+13+29+)
INCIDENTS: 24 24 25 37 48
2.08333====snp_a hepatic_dysfunction snp_d [saw 5 expected 0] (coded +2+7+17+)
INCIDENTS: 1 2 5 29 30
2.08333====alcoholism snp_q [saw 5 expected 0] (coded +19+31+) INCIDENTS: 1.1 3.1 4.1
5.1 6.1
2.08333====snp_p heart_attack [saw 5 expected 0] (coded +11+43+) INCIDENTS: 36 37 39
45 46
2.08333====snp_p stress [saw 5 expected 0] (coded +11+41+) INCIDENTS: 45 46 47 48 49
2.08333====snp_b scorpion_bite [saw 5 expected 1] (coded +5+29+) INCIDENTS: 24 24 25
37 48
2.08333====snp_p alcoholism [saw 5 expected 1] (coded +11+19+) INCIDENTS: 1.1 3.1 4.1
5.1 6.1
2.08333====snp_a snp_b schizophrenia [saw 5 expected 0] (coded +2+5+37+) INCIDENTS: 21
22 23 51 53
2.08333====snp_a snp_c snp_b schizophrenia [saw 5 expected 0] (coded +2+3+5+37+)
INCIDENTS: 21 22 23 51 53
2.08333====snp_c hepatic_dysfunction alcoholism [saw 5 expected 0] (coded +3+7+19+)
INCIDENTS: 1 2 33 62 64
2.08333====snp_b cancer [saw 5 expected 0] (coded +5+47+) INCIDENTS: 10.1 1 17.1 18
20.1
```

FIG. 7D

TABLE 5 (cont'd): OUTPUT RANKING OF SIGNIFICANT CONJOINT EVENTS

2.08333===snp_c snp_r [saw 5 expected 0] (coded +3+53+) INCIDENTS: 2.1 10.1 12 17.1 20.1

2.08333===snp_b snp_r [saw 5 expected 0] (coded +5+53+) INCIDENTS: 10.1 12 17.1 18 20.1

2.08333===snp_e snp_q [saw 5 expected 0] (coded +23+31+) INCIDENTS: 1.1 3.1 4.1 5.1 6.1

2.08333===snp_c snpb snp_d [saw 5 expected 0] (coded +3+5+17+) INCIDENTS: 12 21 41 55 56

2.08333===snp_c snp_b schizophrenia [saw 5 expected 0] (coded +3+5+37+) INCIDENTS: 21 22 23 51 53

2.08333===snp_c schizophrenia [saw 5 expected 1] (coded +17+53+) INCIDENTS: 21 22 23 51 53

2.08333===snp_d snp_r [saw 5 expected 0] (coded +17+31+) INCIDENTS: 1.1 3.1 5.1 14.1 20.1

2.08333===snp_d snp_q [saw 5 expected 0] (coded +2+31+) INCIDENTS: 1.1 3.1 4.1 5.1 16.1

2.08333===snp_a snp_q [saw 5 expected 1] (coded +2+53+) INCIDENTS: 2.1 10.1 17.1 18 6.1

2.08333===snp_a snp_r [saw 5 expected 0] (coded +17+19+) INCIDENTS: 1.1 2.1 3.1 20.1

2.08333===snp_d snp_c alcoholism [saw 5 expected 0] (coded +2+3+19+) INCIDENTS: 1 2 6 61.1

2.08333===snp_a snp_c snp_e [saw 5 expected 0] (coded +2+3+23+) INCIDENTS: 6 20 21 22 62 64

2.08333===snp_a snp_c schizophrenia [saw 5 expected 0] (coded +2+3+37+) INCIDENTS: 21 22 23 51 53

-1.01    ===snp_b hepatic_dysfunction [saw 1 expected 2] (coded +5+7+) INCIDENTS: 64

FIG. 8A

TABLE 6: ALTERED RANK ORDER 14.9310===snp_a snp_c [saw 18 expected 3] (coded +2+3+) INCIDENTS: 2 5 6 10 17 20 22 23 29 30 41 51 53 60 62 63 64
13.8193===snp_c snp_b [saw 16 expected 2] (coded +3+5+) INCIDENTS: 10 12 17 20 21 22 23 40 41 42 51 53 55 56 60 64
13.7279===hepatic_dysfunction alcoholism [saw 15 expected 1] (coded +7+19+) INCIDENTS: 1 2 3 4 5 6 7 9 26 32 33 61 62 64 66
12.72   ===snp_a snp_b [saw 15 expected 2] (coded +2+5+) INCIDENTS: 8 10 17 18 20 21 22 23 24 36 41 51 53 60 64
12.5689===snp_c snp_d [saw 14 expected 1] (coded +3+17+) INCIDENTS: 1 2 5 10 12 14 16 20 21 29 30 41 55 56
11      ===pancreatitis scorpion_bite [saw 12 expected 0] (coded +13+29+) INCIDENTS: 11 19 24 24 25 37 48 52 58 59 59 61
10.6    ===snp_a snp_e [saw 12 expected 1] (coded +2+23+) INCIDENTS: 1 2 3 4 5 6 20 21 22 41 43 54
10      ===snp_p snp_q [saw 11 expected 0] (coded +11+31+) INCIDENTS: 1 3 4 5 6 14 15 16 57 58 59
10      ===snp_a snp_c snp_b [saw 11 expected 0] (coded +2+3+5+) INCIDENTS: 10 17 20 21 22 23 41 51 53 60 64
9.85344===snp_c hepatic_dysfunction [saw 12 expected 2] (coded +3+7+) INCIDENTS: 1 2 5 6 14 15 16 29 30 33 62 64
9.75    ===snp_a hepatic_dysfunction [saw 12 expected 2] (coded +2+7+) INCIDENTS: 1 2 3 4 5 6 9 29 30 62 64 66
8.6875  ===hepatic_dysfunction snp_d [saw 10 expected 1] (coded +7+17+) INCIDENTS: 1 2 3 5 14 16 27 29 30 61
8.5625  ===hepatic_dysfunction snp_p [saw 10 expected 1] (coded +7+11+) INCIDENTS: 1 3 4 5 6 14 15 16 28 29
8.52941 ===snp_a alcoholism [saw 10 expected 1] (coded +2+19+) INCIDENTS: 2 3 4 5 6 9 31 62 64 66
8.5     ===snp_a snp_d [saw 10 expected 1] (coded +2+17+)INCIDENTS: 1 2 3 5 10 18 21 29 30 41
8       ===snp_a snp_c snp_d [saw 9 expected 0] (coded +2+3+17+) INCIDENTS: 1 2 5 10 20 21 29 30 41
8       ===snp_a hepatic_dysfunction alcoholism [saw 9 expected 0] (coded [+2+7+19+) INCIDENTS: 1 2 3 4 5 6 62 64 66
7.81818 ===snp_a snp_p [saw 10 expected 2] (coded +2+11+) INCIDENTS: 1 3 4 5 6 29 36 39 46 47
7.71052 ===snp_p pancreatitis [saw 9 expected 1] (coded +11+13+) INCIDENTS: 3 4 5 19 37 45 48 58 59

FIG. 8B
TABLE 6: ALTERED RANK ORDER

```
7    ==hepatic_dysfunction snp_p snp_q [saw 8 expected 0] (coded +7+11+31+) INCIDENTS: 1 3 4
5 6 14 15 16
7    ==hepatic_dysfunction snp_q [saw 8 expected 0] (coded +7+31+) INCIDENTS: 1 3 4 5 6 14 15
16
7    ==snp_a snp_c snp_e [saw 8 expected 0] (coded +2+3+23+) INCIDENTS: 1 2 5 6 20 21 22 41
7    ==snp_a snp_d snp_e [saw 8 expected 0] (coded +2+17+23+) INCIDENTS: 1 2 2 3 5 20 21 41
7    ==snp_a snp_c hepatic_dysfunction [saw 8 expected 0] (coded +2+3+7+) INCIDENTS: 1 2 5 6
29 30 62 64
7    ==snp_d snp_e [saw 8 expected 0] (coded +17+23+) INCIDENTS: 1 2 3 5 10 20 21 41
6.68275 ==snp_c snp_e [saw 8 expected 1] (coded +3+23+) INCIDENTS: 1 2 6 10 20 21 22 41
6.66 ==snp_b snp_d [saw 8 expected 1] (coded +5+17+) INCIDENTS: 10 12 18 20 21 41 55 56
6    ==hepatic_dysfunction pancreatitis alcoholism [saw 7 expected 0] (coded +7+13+19+)
INCIDENTS: 3 4 5 7 9 26 61
6    ==snp_c snp_b snp_d [saw 7 expected 0] (coded +3+5+17+) INCIDENTS: 10 12 20 21 41 55 56
6    ==snp_c snp_d snp_e [saw 7 expected 0] (coded +3+17+23+) INCIDENTS: 1 2 5 10 20 21 41
6    ==snp_c hepatic_dysfunction snp_q [saw 7 expected 0] (coded +3+7+31+) INCIDENTS: 1 5 6
14 15 16 16
5.91950 ==pancreatitis alcoholism [saw 7 expected 1] (coded +13+19+) INCIDENTS: 3 4 5 7 9 26 61
2    ==snp_a snp_c snp_p snp_e snp_q [saw 3 expected 0] (coded +2+3+11+23+31+) INCIDENTS: 1 5
6
2    ==snp_c hepatic_dysfunction snp_e [saw 3 expected 0] (coded +3+7+11+23+) INCIDENTS:
1 5 6
2    ==snp_c snp_g snp_f [saw 3 expected 0] (coded +3+61+71+) INCIDENTS: 14 15 16
2    ==snp_c hepatic_dysfunction snp_g snp_f [saw 3 expected 0] (coded +3+7+61+71+) INCIDENTS:
14 15 16
2    ==snp_a snp_p pancreatitis alcoholism [saw 3 expected 0] (coded +2+11+13+19+) INCIDENTS:
3 4 5
1.54 ==snp_b snp_p [saw 3 expected 1] (coded +5+11+) INCIDENTS: 36 37 48
-1.01 ==snp_b hepatic_dysfunction [saw 1 expected 2] (coded +5+7+) INCIDENTS: 64
-12  ==scorpion_bite x 2 [saw 2 expected 14] (coded +29+29+) INCIDENTS: 24 59
```

FIG. 9

TABLE 7: SAMPLE INPUT FOR USE OF BIOLOGICAL SEQUENCES

```
input file=mitok5.dat
delimit record=mtDNA
delimit line=\n
delimit item=20
shift item=off
colunms=off
maximum items per record=10
maximum items per joint event=10
shift record=off
minimum frequency=off
read lines matching=[AGCT][AGCT][AGCT][AGCT]
skip lines matching=^#
lines to skip after matches=0
```

FIG. 10

TABLE 8: EXAMPLE FILE FOR INTRODUCING METADATA

```
input file=out001.csv
set Riemann zeta s=1
report scores above nats= 2
report scores below nats=0
first line metadata=on
divide all data by n=10
ignore unknown=-9
delimit record=\n
delimit line=\n
delimit item=,
shift item=off
columns=off
maximum items per record=4
maximum number of item types=100
maximum number of items per event=100
shift record=off
minimum frequency=off
skip lines matching=^#
lines to skip after matches=0
```

FIG. 11A

TABLE 9: EXAMPLE "REAL-WORLD" INPUT DATA WITH INITIAL META-RECORD (CONTAINING THE METADATA). FIRST LINES OF FILE OF 2862 RECORDS, 254 ITEMS A RECORD

```
ID, AGE_1, AGE_2, AGE_3, AGE_4, AGE_5, AGE_6, AGE_7, AGE_8, AGE_9, AGE_10, AGE_11, AGE_12, AGE_13, A
GE_14, AGE_15, AGE_16, AGE_17, AGE_18, AGE_19, AGE_20, AGE_21, CHOL_1, CHOL_2, CHOL_3, CHOL_4, CHO
L_5, CHOL_6, CHOL_7, CHOL_8, CHOL_9, CHOL_10, CHOL_11, CHOL_12, CHOL_13, CHOL_14, CHOL_15, CHOL_1
6, CHOL_17, CHOL_18, CHOL_19, CHOL_20, CHOL_21, CPD_1, CPD_2, CPD_3, CPD_4, CPD_5, CPD_6, CPD_7, CP
D_8, CPD_9, CPD_10, CPD_11, CPD_12, CPD_13, CPD_14, CPD_15, CPD_16, CPD_17, CPD_18, CPD_19, CPD_20,
CPD_21, DRINK_1, DRINK_2, DRINK_3, DRINK_4, DRINK_5, DRINK_6, DRINK_7, DRINK_8, DRINK_9, DRINK_10,
DRINK_11, DRINK_12, DRINK_13, DRINK_14, DRINK_15, DRINK_16, DRINK_17, DRINK_18, DRINK_, DR INK_20,
DRINK_21, EXAMDTH, GLUC_1, GLUC_2, GLUC_3, GLUC_4, GLUC_5, GLUC_6, GLUC_7, GLUC_8, GLUC_9,
GLUC_10, GLUC_11, GLUC_12, GLUC_13, GLUC_14, GLUC_15, GLUC_16, GLUC_17, GLUC_18, GLUC_19, GLUC_20,
GLUC_21, HBP_1, HBP_2, HBP_3, HBP_4, HBP_5, HBP_6, HBP_7, HBP_8, HBP_9, HBP_10, HBP_11, HBP_12, HBP_13,
HBP_14, HBP_15, HBP_16, HBP_17, HBP_18, HBP_19, HBP_20, HBP_21, HDL_1, HDL_2, HDL_3, HDL_4, HDL_5,
HDL_6, HDL_7, HDL_8, HDL_9, HDL_10, HDL_11, HDL_12, HDL_13, HDL_14, HDL_15, HDL_16, HDL_17, HDL_18,
HDL_19, HDL_20, HDL_21, HGT_1, HGT_2, HGT_3, HGT_4, HGT_5, HGT_6, HGT_7, HGT_8, HGT_9, HGT_10,
HGT_11, HGT_12, HGT_13, HGT_14, HGT_15, HGT_16, HGT_17, HGT_18, HGT_19, HGT_20, HGT_21, HRX_1, HRX_2,
HRX_3, HRX_4, HRX_5, HRX_6, HRX_7, HRX_8, HRX_9, HRX_10, HRX_11, HRX_12, HRX_13, HRX_14, HRX_15,
HRX_16, HRX_17, HRX_18, HRX_19, HRX_20, HRX_21, SBP_1, SBP_2, SBP_3, SBP_4, SBP_5, SBP_6, SBP_7, SBP_8,
SBP_9, SBP_10, SBP_11, SBP_12, SBP_13, SBP_14, SBP_15, SBP_16, SBP_17, SBP_18, SBP_19, SBP_20, SBP_21,
TRIG_1, TRIG_2, TRIG_3, TRIG_4, TRIG_5, TRIG_6, TRIG_7, TRIG_8, TRIG_9, TRIG_10, TRIG_11, TRIG_12, TRIG_13,
TRIG_14, TRIG_15, TRIG_16, TRIG_17, TRIG_18, TRIG_19, TRIG_20, TRIG_21, WGT_1, WGT_2, WGT_3, WGT_4,
WGT_5, WGT_6, WGT_7, WGT_8, WGT_9, WGT_10, WGT_11, WGT_12, WGT_13, WGT_14, WGT_15, WGT_16,
WGT_17, WGT_18, WGT_19, WGT_20, WGT_21
4, 29, 31, 33, 35, 37, 39, 41, 43, 45, 47, 49, 51, 53, 55, 57, -9, 61, -9, 65, -9, -9, 195, 193, 188, 188, 190, 1
81, 207, 192, 190, 195, 194, -9, 208, 213, 205, -9, -9, 20, 20, -9, 20, 20, 20, 20, -9, -9, -9, -9
20, 20, 20, 20, -9, 20, -9, -9, 102, -9, 100, 103, -9, -9, -9, -9, 0, -9, -9, -9, 0, -9, -9, 0, 0, 0, 0, 0,
-9, 0, 103, 102, 96, 102, -9, -9, -9, -9, -9, -9, 105, 97, 101, 102, -9, 103, -9, -9, -9, 98, -9, -9, 0, 0, 0, 0, -9,
0, -9, -9, -9, 0, 0, 0, 0, -9, -9, -9, 65, -9, -9, -9, -9, -9, 66, -9, -9, -9, 65, 65, -9, 65, -9, -9, 34, -9, -9, 35, -9, 0, 0,
0, 0, 0, 0, 0, 0, 0, 0, 0, -9, 0, -9, -9, -9, -9, -9, 66, -9, -9, -9, -9, 66, -9, -9, -9, 66, -9, -9, 0, 0, 0, 0,
126, 126, 131, -9, 128, -9, 132, -9, -9, -9, -9, -9, 113, 117, 115, 114, 121, 119, 119, 124, 117, 124,
-9, -9, -9, -9, 146, -9, 145, 145, 145, 140, 150, 153, 147, 152, 147, 143, 150, 145, 143, -9, 146, -9, 151, -9
,-9
11, 68, 70, 72, 74, 76, 78, 80, 82, 84, 86, -9, -9, -9, -9, -9, -9, -9, -9, -9, -9, -9, 201, 217, 228, 236, 218, -9
222, 198, 215, 224, 222, -9, -9, -9, -9, -9, -9, -9, -9, -9, -9, -9, -9, 0, -9, -9, -9, -9, -9, -9, -9, -9, -9, 11, -9
-9, -9, -9, -9, -9, -9, -9, -9, -9, -9, -9, -9, -9, -9, -9, 2, -9, -9, -9, -9, -9, -9, -9, -9, -9, -9, -9, -9, -9, -9,
92, 103, 96, 95, -9, 94, -9, 93, 98, -9, -9, -9, -9, -9, -9, -9, 0, -9, -9, -9, -9, -9, -9, -9, -9, -9, -9, 0, -9, -9,
```

FIG. 11B

TABLE 9 (cont'd): EXAMPLE INPUT DATA

TABLE 9 cont'd: EXAMPLE INPUT DATA

*FIG. 12A*

TABLE 10: EXAMPLE OUTPUT "REAL-WORLD" DATA WITH INITIAL META-RECORD (CONTAINING THE METADATA).

```
7.10151 ====hrx 15:0 hbp_15:0 [saw 682 expected 1] (coded +359+367+) INCIDENTS: 2.36
4.34 5.34 8.40 12.45 14.40 16.45 19.43 21.43 22.38 23.34 25.34 27.34 32.28 34.39 35.37 37.45
38.45 39.43 42.45 44.34 46.20 47.34 48.45 49.40 51.45 52.36 54.45 59.45 60.43 62.38 63.45
65.45 68.38 70.36 72.36 74.45 77.45 79.42 80.43 81.39 84.45 85.38 87.32 88.45 89.40 90.34
91.43 94.45 98.36 99.28 100.32 101.43 102.45 103.45 104.43 105.37 109.43 110.45 111.43
112.43 116.40 118.45 119.45 120.45 121.40 123.32 124.40 125.40 129.45 130.43 132.36 138.43
139.45 141.45 144.14 148.21 149.34 151.34 153.45 154.43 155.36 158.26 159.32 160.36 161.36
164.45 165.36 166.45 167.36 168.34 170.43 171.40 172.43 173.45 175.32 176.40 179.38 180.36
181.45 182.38 184.38 185.28 188.40 190.34 191.45 192.36 193.45 194.45 195.45 196.38 198.43
199.28 200.32 201.28 204.43 206.41 207.38 208.45 209.45 210.45 211.20 214.43 216.32 218.38
222.41 225.45 226.45 228.38 230.36 231.43 233.34 234.34 236.32 237.38 238.45 239.45 240.38
241.28 242.26 243.32 246.38 247.43 248.40 251.34 252.43 254.43 255.32 256.43 257.43 258.45
259.36 260.43 261.36 262.45 265.45 266.45 268.40 270.32 271.27 272.32 274.43 275.43 276.40
278.34 280.34 281.45 282.45 284.38 287.38 288.40 291.34 294.38 295.40 299.32 300.38 302.41
304.34 310.32 315.43 316.26 318.45 319.20 322.45 323.43 325.45 326.41 327.40 328.43 329.38
330.38 332.43 334.45 335.45 336.45 337.45 338.32 339.45 340.32 344.45 348.40 349.45 350.26
351.45 353.23 355.45 356.45 359.41 360.34 365.38 368.36 370.45 371.28 372.35 374.45 375.34
378.34 379.45 380.43 381.34 383.36 386.36 387.45 388.45 389.40 393.40 396.34 399.45 401.38
402.40 403.38 404.45 406.38 407.45 408.38 409.43 410.45 412.40 415.40 417.40 418.43 419.36
420.32 424.34 425.45 427.40 428.43 430.45 433.40 434.45 435.45 438.36 439.45 440.36 445.34
447.43 449.32 450.43 452.43 453.45 454.43 455.45 456.45 457.45 458.36 459.32 462.45 464.38
465.45 467.43 468.40 469.32 472.45 473.43 475.38 476.45 477.41 478.45 479.29 481.34 482.41
483.34 484.43 485.34 486.38 487.43 488.43 490.45 491.43 492.27 493.29 494.38 495.36 498.45
497.38 499.32 500.32 504.34 505.41 506.45 507.45 509.45 511.36 512.36 515.40 516.33 517.31
```

FIG. 12B

TABLE 10 cont'd: EXAMPLE OUTPUT DATA 519.40 522.32 523.45 524.45 525.38 526.36 528.45 529.34 530.45 536.45 540.43 541.41 542.45
544.36 546.32 547.38 548.36 550.45 551.38 552.36 555.45 559.45 563.40 569.34 571.36 574.34
575.40 576.43 577.34 579.45 583.43 584.45 585.32 588.45 590.45 591.38 592.45 593.24 594.34
595.21 596.24 597.32 600.32 602.40 604.36 606.45 607.40 608.41 609.45 610.45 611.45 612.32
617.36 618.32 619.43 621.34 622.34 628.40 630.43 631.45 632.45 633.21 635.43 636.45 637.39
638.40 643.38 647.45 650.45 653.34 654.45 655.45 656.34 657.38 659.36 662.38 664.34 665.40
667.32 668.45 671.36 673.45 675.45 676.45 677.40 679.43 681.43 682.24 684.45 685.45 686.32
687.36 688.34 689.45 690.40 691.38 693.43 694.36 697.45 698.38 699.34 701.43 702.45 703.38
705.43 706.35 707.38 708.43 709.43 710.36 713.34 714.34 715.34 716.38 721.45 722.34 723.36
724.43 725.45 727.28 728.45 729.36 733.25 735.32 736.40 737.45 738.45 739.36 740.38 741.45
742.45 744.40 745.32 747.43 750.28 752.43 759.36 762.36 764.36 766.38 767.45 768.36 773.45
775.43 777.32 778.45 779.32 780.45 781.45 783.34 785.45 788.40 789.40 792.43 793.40 796.45
797.45 798.45 800.40 801.38 805.38 806.36 807.20 808.34 809.28 811.40 812.38 814.30 815.34
816.31 817.35 818.32 819.43 820.36 821.45 822.45 827.45 828.33 829.34 832.38 833.45 835.45
839.45 842.40 843.25 844.40 847.32 849.45 850.34 853.13 855.43 856.43 858.34 859.40 861.40
862.42 863.43 867.45 868.34 875.36 876.35 878.32 879.36 883.40 888.38 889.38 897.43 899.30
900.30 904.45 905.45 906.32 910.32 911.45 912.40 913.40 916.45 918.43 919.40 920.38 923.32
926.40 928.34 929.45 930.32 931.45 933.45 934.36 935.36 940.36 949.45 952.45 953.40 955.34
957.38 962.24 964.34 965.34 969.36 970.38 972.36 973.43 974.43 976.38 978.36 980.43 981.41
982.36 983.45 986.34 989.32 990.40 992.45 993.45 994.34 996.36 999.45 1000.45 1001.45
1002.40 1005.45 1008.38 1010.39 1011.41 1013.34 1017.32 1018.45 1023.34 1024.38 1025.43
1026.36 1027.45 1028.45 1029.32 1035.38 1036.38 1037.45 1038.32 1039.43 1042.27 1045.45
1046.40 1047.38 1048.40 1051.34 1055.38 1057.34 1058.45 1060.36 1061.34 1063.34 1064.34
1068.34 1069.36 1070.36 1071.32 1073.38 1075.45 1077.45 1078.17 1080.45 1083.43 1088.40
1093.40 1096.45 1098.45 1102.34 1106.45 1107.41 1108.38 1110.34 1111.32 1112.45 1115.38
1116.32 1117.38 1118.34 1119.33 1120.45 1121.45 1122.43 1125.36 1127.40 1128.40 1129.36
1131.34 1133.45 1134.45 1135.38 1137.40 1138.43 1139.40 1140.34 1143.40 1145.34 1146.38
1149.32 1150.38 1151.45 1152.45 1156.38 1157.43 1158.43 1159.40 1167.32 1168.36 1169.32
1171.38 1172.34 1175.32 1177.45 1180.33 1182.32 1183.45 1187.34 1192.45 1195.38 1199.45
1200.36 1201.36 1204.34 1206.38 1208.36 1209.32 1210.32 1211.34 1212.43 1214.38 1215.36
1217.25 1218.32 1221.40 1222.45 1225.45 1226.43

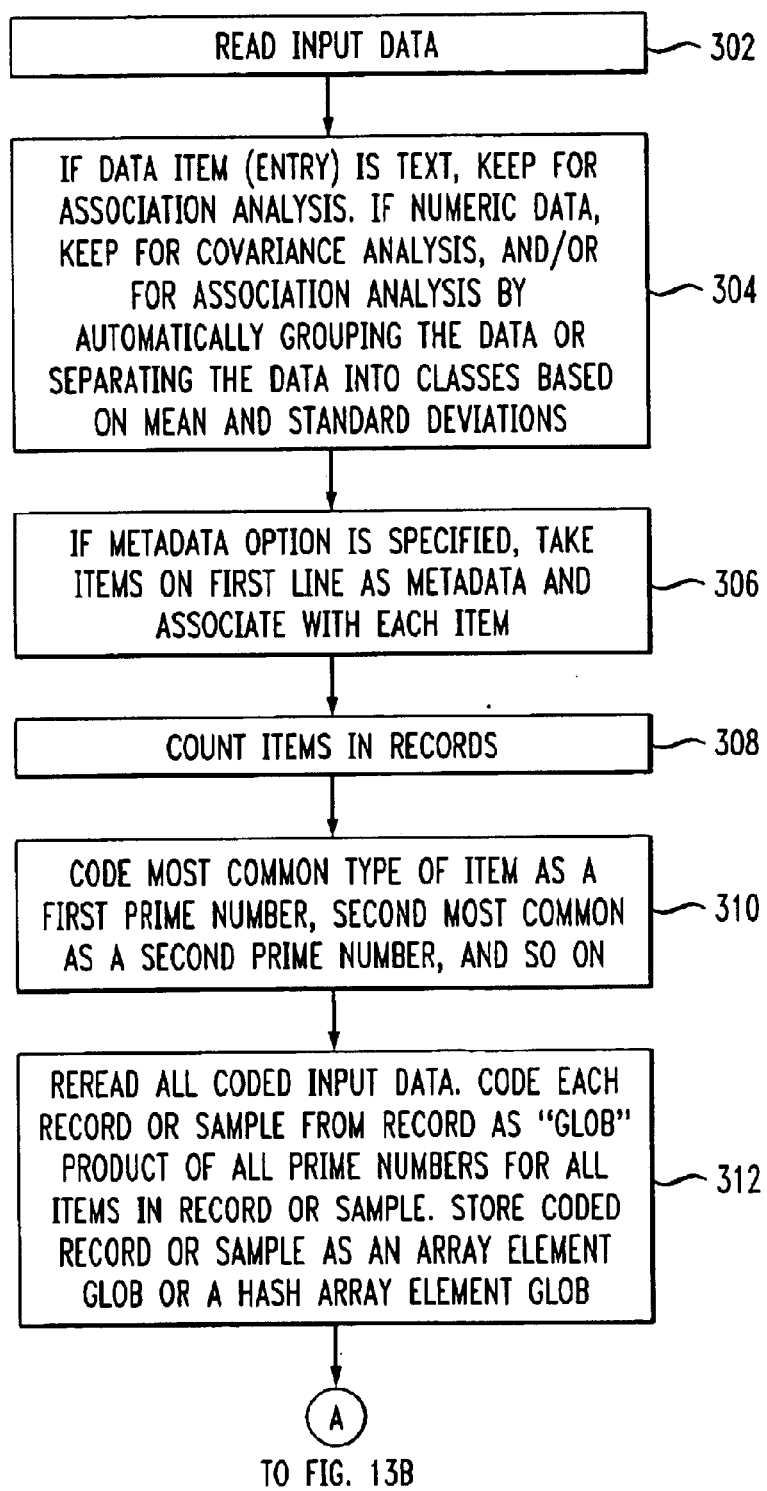

METHOD AND APPARATUS FOR DATA MINING TO DISCOVER ASSOCIATIONS AND COVARIANCES ASSOCIATED WITH DATA

FIELD OF THE INVENTION

The present invention is related to data processing techniques and, more particularly, to data processing techniques for discovering or mining information relating to a particular collection of data.

BACKGROUND OF THE INVENTION

It is known that attempting to discover or mine useful information from an amorphous collection of records, wherein each record comprises record items or entries, is quite a daunting task. Particularly, the task is made that much more difficult when: (i) data in the collection need not be rectangular (e.g., spreadsheet-like); (ii) metadata associated with the collection may be incomplete or absent; (iii) data in the collection need not always be numeric; and/or (iv) items can occur in a record more than once. The task is daunting because of the shortcomings associated with existing data mining techniques.

By way of one example, it is known that classical statistics, which are the most widely taught and used statistics, do not prepare us for the automated high throughput analysis of the vast complexity of digitized medical and pharmacogenomic data. Such data has come to the fore as a result of the human and other genome projects, and by a recent rapid increase of interest in digitizing the patient record both for healthcare and research. For example, we now know that in most cases polymophisms in not one gene but many determine a disease of primarily genetic origin. Yet, even fairly advanced textbooks usually describe methods for correlating only two sets (columns) of data at a time, whereas recent biological data contains tens, hundreds or thousands of items which come together in complex interplay. Nonetheless, most statistical textbooks have little to say about how and where to direct such analyses in practice.

Thus, a need exists for improved data mining techniques which are effective and efficient for discovering useful information from an amorphous collection or data set of records.

SUMMARY OF THE INVENTION

The present invention provides data mining techniques which are effective and efficient for discovering useful information from an amorphous collection or data set of records. For example, the present invention provides for the mining of data, e.g., of several or many records, to discover interesting associations between entries of qualitative text, and covariances between data of quantitative numerical types, in records.

Although not limited thereto, the invention has particular application and advantage when the data is of a type such as clinical, pharmacogenomic, forensic, police and financial records, which are characterized by many varied entries, since the problem is then said to be one of "high dimensionality" which has posed mathematical and technical difficulties for researchers. This is especially true when considering strong negative associations and negative covariance, i.e., between items of data which may so rarely come together that their concurrence is never seen in any record, yet the fact that this is not expected is of potential great interest.

In one illustrative aspect of the invention, an automated technique for discovering information relating to a collection of input data comprises the following steps/operations. First, the collection of input data is obtained (e.g., read). The collection of input data comprises data items. Then, information is discovered relating to the collection of input data based on a computation of a mutual information measure in accordance with at least a portion of the data items, wherein expected values of the mutual information measure are expressed as linear combinations of an incomplete Riemann zeta function. At least a portion of results associated with the computation of the mutual information measure are output, wherein at least a portion of the results represent the discovered information relating to the collection of input data.

Further, the collection of input data may comprise at least one of qualitative data and quantitative data. The information discovery step may comprise an association analysis when the collection of input data is qualitative data. Such association analysis is preferably capable of discovering negative associations. Still further, the information discovery step may comprise a covariance analysis when the collection of input data is quantitative data.

The information discovery step may also comprise encoding the data items in association with prime numbers, wherein, for example, a given prime number is assigned to a type of data item based on a frequency of occurrence of the data item type in the collection of input data. When the collection of input data comprises one or more records and each of the one or more records comprise data items, the information discovery step further comprises encoding each record as a product of the prime numbers representing the data items in the record or as a sum of the logarithms of the prime numbers representing the data items in the record. The technique may also comprise generating one or more sub-records from a record.

The invention also comprises techniques for determining similarity between two records by comparing the respective products of the two records or the respective sums of the two records.

These and other objects, features and advantages of the present invention will become apparent from the following detailed description of illustrative embodiments thereof, which is to be read in connection with the accompanying drawings.

BRIEF DESCRIPTION OF THE DRAWINGS

FIGS. 3A and 3B depict a table which represents a demonstration file of qualitative patient record extracts for use in accordance with an embodiment of the present invention;

FIG. 3C depicts a table which represents a small test file example in accordance with an embodiment of the present invention;

FIG. 3D depicts a table which represents a portion of a tabulated file of numeric data in accordance with an embodiment of the present invention;

FIG. 4 depicts a table which represents an example of a convert file in accordance with an embodiment of the present invention;

FIG. 5 depicts a table which represents an example of a control file in accordance with an embodiment of the present invention;

FIG. 6 depicts a table which represents an example of a screen output in accordance with an embodiment of the present invention;

FIGS. 7A through 7D depict a table which represents an output ranking of significant conjoint events in accordance with an embodiment of the invention;

FIGS. 8A and 8B depict a table which represents an altered rank order in accordance with an embodiment of the invention;

FIG. 9 depicts a table which represents sample input for use of biological sequences in accordance with an embodiment of the present invention;

FIG. 10 depicts a table which represents an example file for introducing metadata in accordance with an embodiment of the present invention;

Figure 11B:
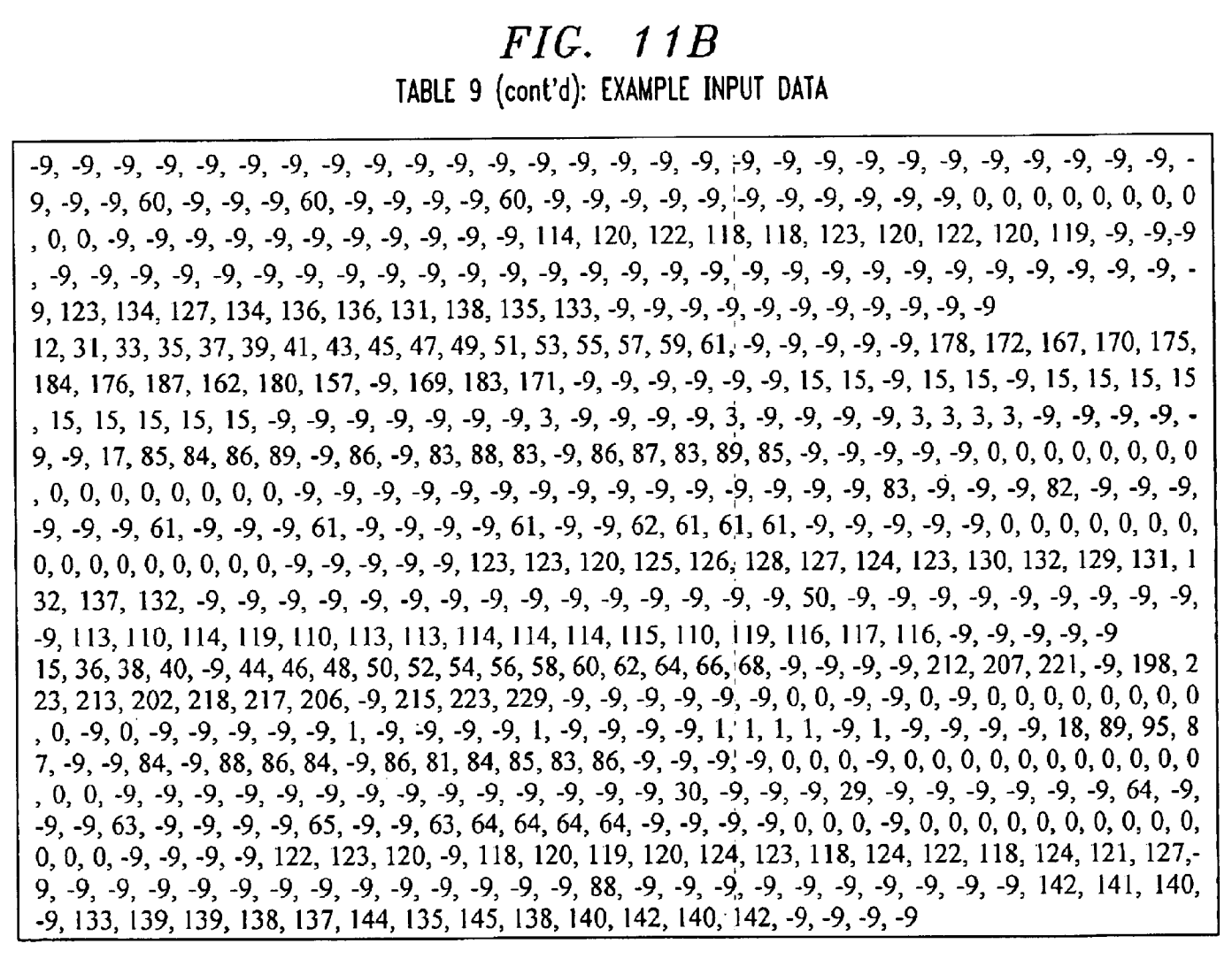
Figure 11C:
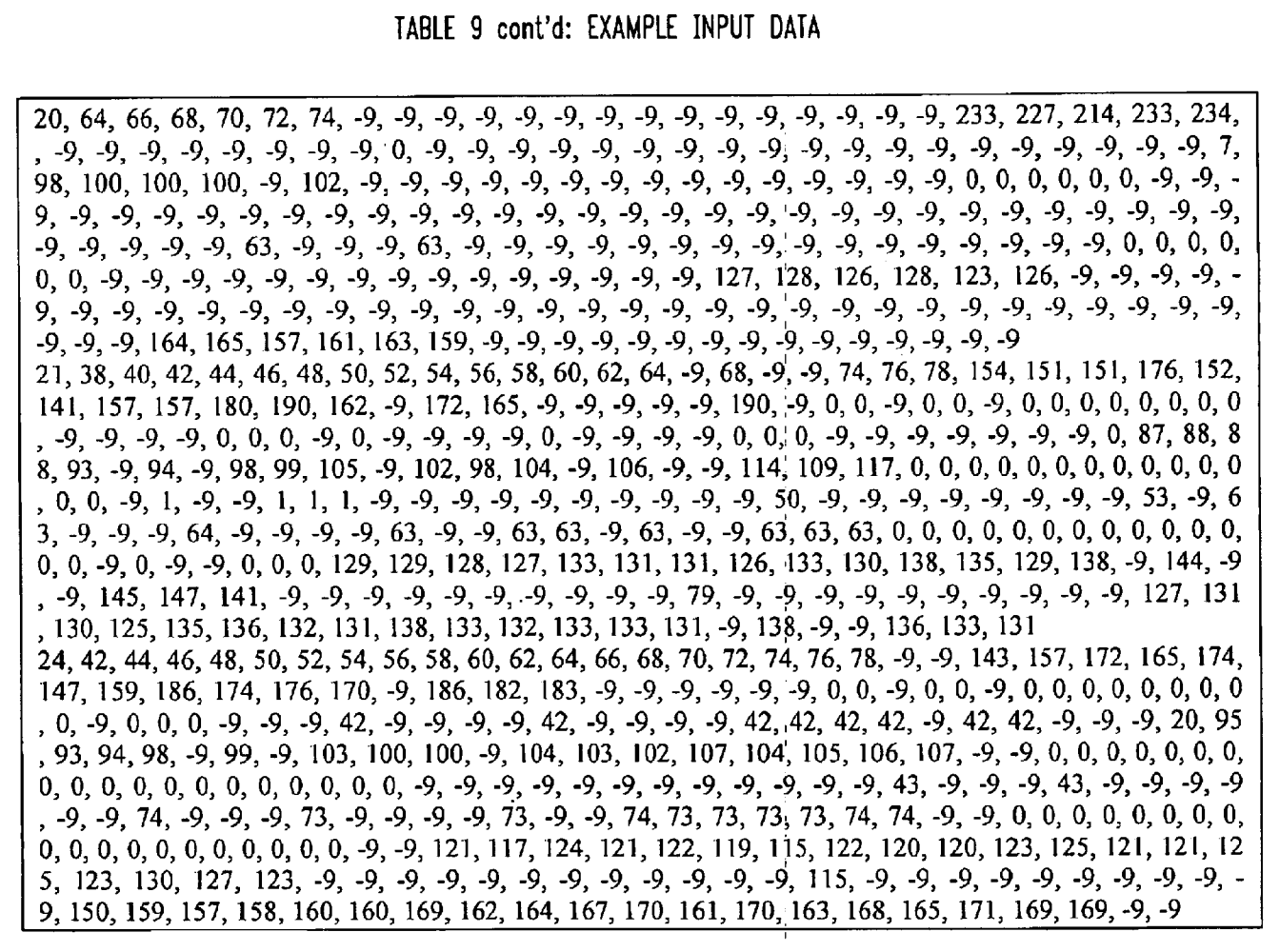

FIGS. 11A through 11C depict a table which represents real-world input data for use in accordance with an embodiment of the present invention;

FIGS. 12A and 12B depict a table which represents real-world output data in accordance with an embodiment of the present invention;

FIGS. 13A and 13B are a flow diagram illustrating a data mining methodology in accordance with an embodiment of the present invention.

DETAILED DESCRIPTION OF PREFERRED EMBODIMENTS

The following description will illustrate the invention using an exemplary data processing system architecture in the domain of medical and/or genomic data records. It should be understood, however, that the invention is not limited to use with any particular system architecture or any particular domain. The invention is instead more generally applicable to any data processing system, and with any domain, in which it is desirable to discover useful information from a collection or data set of records.

Figure 1:
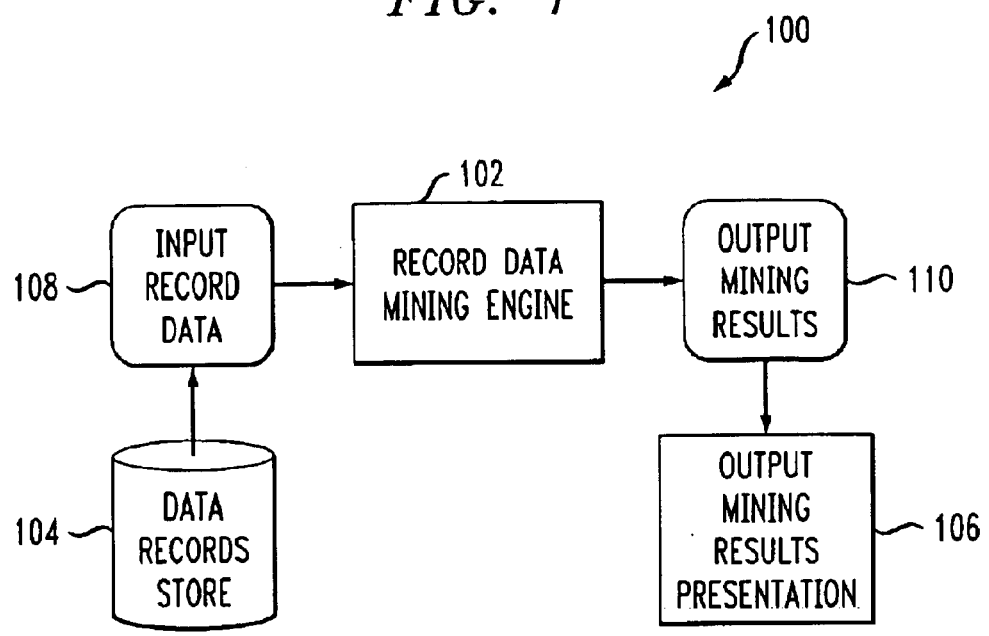
FIG. 1 is a block diagram of a data mining system according to an embodiment of the present invention.

Referring initially to FIG. 1, a block diagram of a data mining system according to an embodiment of the present invention is shown. The illustrative data mining system 100 comprises a record data mining engine 102, a data records store 104 and an output mining results presentation 106. The system 100 is responsive to input record data 108 provided by a user or read from the data records store 104. As will be explained in detail below, the record data mining engine 102 receives the input record data 108 and generates output mining results 110 based on data mining methodologies to be described in detail herein. All or a portion of the output mining results 110 are presented to a user in accordance with results presentation 106 (e.g., a display screen, printed page, audio presentation, etc.).

It is to be appreciated that the input records data 108 may, for example, be provided from a medical records database, a genomic database, or any other form of data store. The resulting output data 110 may have varied applications. For example, the output itself may contain conclusions about the information mined from the input data and/or may provide insight to a user to draw conclusions himself/herself.

Figure 2:
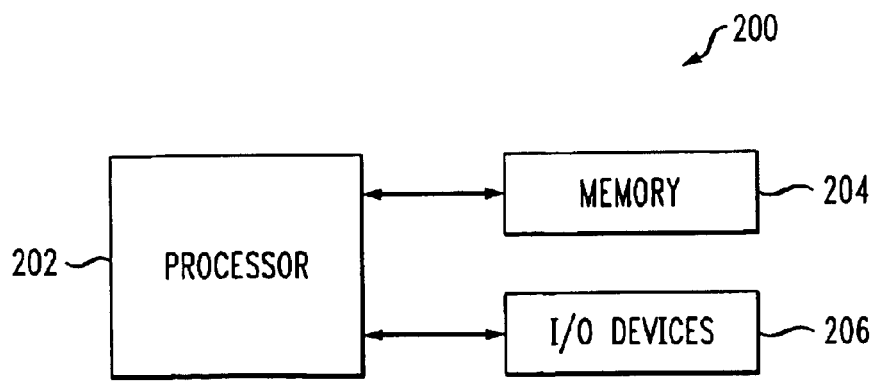
FIG. 2 is a block diagram of an exemplary hardware implementation of a data mining system according to an embodiment of the present invention.

FIG. 2 is a block diagram of an exemplary hardware implementation 200 of the data mining system 100 of FIG. 1. As shown, the system 200 may comprise a processor 202, a memory 204 and I/O devices 206. It should be understood that the term "processor" as used herein is intended to include one or more processing devices, including a central processing unit (CPU) or other processing circuitry. Also, the term "memory" as used herein is intended to include memory associated with a processor or CPU, such as RAM, ROM, a fixed, persistent memory device (e.g., hard drive), or a removable, persistent memory device (e.g., diskette or CDROM). The type of memory may be of any suitable form (e.g., magnetic, optical). In addition, the term "I/O devices" as used herein is intended to include one or more input devices (e.g., keyboard, mouse) for inputting data to the processing unit, as well as one or more output devices (e.g., CRT display, printer, audio speaker) for providing results associated with the processing unit.

Accordingly, software instructions or code for performing the methodologies of the invention, as described herein, may be stored in one or more of the associated memory devices, e.g., ROM, fixed or removable memory, and, when ready to be utilized, loaded into RAM and executed by the CPU.

It is to be appreciated that, in an alternative embodiment, the invention may be implemented in a network-based implementation. That is the user may submit input record data 108, or designate the appropriate data to be provided by the data records store 104, from a remote client computer system, while the record data mining engine 102 (and possibly the data records store 104) resides and is executed on a server computer system in communications with the client via a network such as, for example, the Internet or the World Wide Web. The network could alternatively be a private network and/or a local network.

Thus, a user operating remotely on his client computer system, e.g., a personal computer, laptop and/or some other type of personal processing device, enters a query through application software running on the computer system, e.g., web browsing software and/or a graphical user interface associated with the system. The query, containing either the input record data, itself, or identifying the input record data to be retrieved from the data records store, is passed over the network and processed by the server. The server receives the input data and executes the methodologies of the invention. The server then returns some or all of the results to the client via the network. It is to be understood that the server may include more than one computer system. That is, one or more of the elements in FIG. 1 may reside on and be executed by their own computer system, e.g., with its own processor, memory and I/O devices.

Given a general description of the elements of the data mining system of the invention and various exemplary hardware implementations, the various inventive methodologies will now be explained in detail.

For ease of reference, the remainder of detailed description will be divided into sections as follows: (1) Introduction; (2) Theory; (3) Exemplary Program and Method; (4) Output Results; and (5) Illustrative Methodologies. An illustrative computer program embodiment of the invention follows these sections in an Appendix A.

1. Introduction

In general, the present invention does not seek to replace proven classical statistics methods. Rather, it is concerned with discovering features (i.e., highlighting features of potential interest) in complex data, features to which more classical tools can subsequently be applied.

It is to be understood that, in the following discussions, the term "record" is used in a general sense to refer to arrangements of data items of any kind ("entries"), associated with an individual person (e.g., a patient), organism, thing or instance, such that at least occasionally the same type of data item can be seen to recur on different records, and in such a way that some kind of data analysis technique can be applied to deduce relationships between the data items or classes of data items. This data can be structured in a way such that the records represent lists, sets or more general data structures as described in the next paragraph.

In one embodiment, the invention leads to better ways to treat the "combinatorial explosion" problem described below via the recognition that the general record can be considered uniquely as a product of prime numbers where each prime number stands for a data item in the record. The use of prime numbers in sequence analysis is described in U.S. Pat. No. 6,434,488 issued on Aug. 13, 2002 to B. Robson, the disclosure of which is incorporated by reference herein.

In further defining the practical meaning of "record" as used in the general sense, and to help distinguish it from a simple collection of things, it would be helpful to state that it is a term which applies: (a) when there is more than one entity which can be identified as a record; and (b) when these records are at least relevant to each other in principle, such as when at least some items or values which belong to the same set (such as might for example represent patient age) recur in different records. However, that is with the caveat that the theory developed below applies even when items could never be identified as related from record to record from a data analysis perspective: a program embodying the present invention would execute on data where this was not the case and, for example, if the item at least recurred in the same record, reports by the program could be of value.

The term "record" as used here can apply for example to a tabular or spreadsheet format in which every row is analogous to a record, in which there are many columns, and every cell in the same column holds corresponding entries of data, quantitative (numbers) or qualitative (text), corresponding to what are variously called "items" or "events" by data analysts. Pharmacogenomic data as used by researchers is often in this form. Because this data is highly structured, each row represents a list in computational terms.

However, the invention also importantly covers data structures of other types more typical of real records, such as clinical or student or criminal records, which may be the precursor format to the convenient format of a spreadsheet. The characteristic of records such as clinical records, and of generally any kind of record as in a paper filing record, is that the entries (again, corresponding to what are variously called "items" or "events" by data analysts) may not be in any particular order, and may lack the metadata (columnar headings such as are at the first row of a table or spreadsheet). This data is much closer to sets, because the order is immaterial, although a tabular or ordered character of some of the data (such as association of entries with date or age) may or may not also be present.

However, the invention also importantly covers data which is not simply lists or sets, but collections of items which can occur more than once. For example, a broken leg can occur more than once in a patient's lifetime, and hence in his medical record. The latter type of general data structure is a combinatorial arrangement such as might be referred to as a "collection." Such a collection is more general than a set, and in turn a set is more general than a list. The invention covers the ability to treat the first and, since it is the most general case, the other two can be treated as well. The method, for example, of considering a collection of data as a list such as a spreadsheet is to consider the metadata headings (such as Age or a column indicator such as Column__26) as qualifiers of the data items (e.g., Age:=42 or Column__26:=smoker, respectively), which with the data make up a modified form data item (e.g., 42 becomes Age:=42).

Analysis of these data structures to discover relationships between entries is non-trivial in complex cases of practical interest. In order to consider the remarkable extent of the problem, consider a set of records of 100 items per record, corresponding to a spreadsheet in which the rows are the records and the columns are the corresponding data. As noted below, the technique of the invention also addresses the problem that not all sets of records are of these tidy, well-formed types; however, the "rectangular" situation of well ordered columns describing records of equal length, is easier to address in an initial appraisal of the scope of the problem. In data of 100 columns, there would be 100×(100−1)/2=4950 pairs to consider.

Worse still, to address discovery, we must also accept that we are not only unaware in advance which two items are in some way interrelated but also that we have no reason to believe that the number which will be correlating is two. Moreover, we cannot even assume that there will be just one group of interrelated columns: rather there could be several such groups, interrelating internally but not with each other. These assumptions are not only realistic, but typical. If there are n potential correlating columns of data drawn from N, then the number of possible combinations to analyze statistically is $N!/[(N-n)!n!]$. If we do not know n in advance, the number is $\Sigma_{n=2, \ldots N} N!/[(N-n)!n!]$.

Worse still, real records contain data items which are not confined to columns and indeed may occur more than once, a situation which creates a situation analogous to statistical sampling with replacement. An example would be "broken leg" which could occur twice in the patient's lifetime clinical record. In the limit, there would be $\Sigma_{n=2, \ldots N} n^N$. These numbers reflect the dimensionality of the problem, and one speaks of the "high dimensionality of the problem space."

Whereas the above problem is sufficiently severe, the problem becomes still worse in regard to negative associations and, when the data is numeric, covariances. By "positive association," it is meant that items occur together on records more than would be expected on a chance basis, and being able to calculate that chance basis explicitly or implicitly from the probability of the individual occurrence. Correspondingly, "negative associations" are those for items which occur together on records less than expected.

Positive associations are natural to treat as they occur, for example, as commonly associated words or phrases in text. In contrast, in regard to negative association, one can readily see that addressing associations of all possible combinations of items, to find which occurred less than expected, is a challenging and, on the face of it in most application areas, a rather pointless pursuit. There seems little value or possibility, for example, to report on all the potential combinations of words or phrases which do not actually come together often in text.

Yet, negative associations can be amongst the most important measures in certain areas such as modern medicine and pharmacogenomics. For example, a lifestyle which is pursued is negatively correlated with disease. A chemical substance, for example, which negatively associates with disease, is a potential drug. A genomic constitution which negatively correlates with certain diseases confers protection and allows a more daring or broader lifestyle in certain specific areas: a position increasingly of interest to the tobacco industry. Strong negative correlations are particularly difficult to assess because comparison must be made with the expected occurrence of a combinatorially huge number of potential events which might associate in interesting ways in theory, just to find which was less common concurrence than expected.

Most importantly, the strongest and hence most interesting negative associations concern events so rare that they are not in fact seen. They may even be impossible. Depending on the computational method, they may thus never even enter in the arrays or hash tables in order to be considered. For example, males are common features of clinical records, and so are pregnancies, but the two never occur together. This requires consideration of non-occurences of concurrent events which is particularly combinatorially explosive reflecting that the universe of potentially observable things is very large, and comparison must then be made with simpler observed events.

Indeed, such important negative associations can not only be missed but misrepresented, by other methods as positive because methods may assume positive associations of say four things at a time from the positive association of the represented events just, say, two at a time. This is quite erroneous and is sometimes called the "unicorn effect." For example, many animals are observed which can be qualified as "white," "shy," "horned" or "horses," but shy white horned horses, i.e., unicorns, have not been reproducibly observed.

Treatment of the above problem requires two aspects. The first is the means to explore such high dimensional problems, which implies methods of generating and managing all or many possible combinations of events of interest. The second is the means to treat sparse data in a way consistent with more plentiful data, since sparse data almost always arises in treatment of high dimensional problems of this type.

To understand the second aspect we note first that the association method of the present invention can deduce associations up to any number of constituent items, data and computer power permitting. A great deal of data (i.e., many hundreds of thousands records) is typically required to obtain information for associations of more than three of four types of items, and hence the more complex events will not tend to be seen in the output, information being sparse. This is a good reason for a continuum of treatment between sparse and plentiful data (see the "Theory" section below), since analyses pushed to the limit of extracting maximally complex combinations of items such as (a, b, c, f, g, j, k, l, m, n) always yields much lower frequencies of occurrence than simpler (e.g., pairwise) events such as (a, b). For example, tall blond girls who own green sports cars and houses in Peru are much rarer than tall, blond girls in general. To mine clinical and genomic data, the unexpected association or mutual avoidance of many events (i.e., the occurrence of "concurrent," "conjoint" or "complex events" with many members or qualifiers, such as "young, tall, mathematically-educated, brown-eyed, biochemists") is of interest.

Hence the associations can be in duplets, triplets, quadruplets, and so on, of events and combined and mixed in a single list because of the theoretical basis of the method. That is, a 3-plet of events can be flanked by a 2-plet or 10-plet which may or may not contain associated events. The complexity (i.e., the "N-plicity" of conjoint events) is in the most general case not bound. As discussed below, the negative case is particularly important, since by this means, the inability/ability of a drug or genetic polymorphism to not be associated with a disease, i.e., possibly to prevent a disease, is of special interest.

A comparison of the conceptual approach of the invention to other methods will now be given.

(1) Unfocused vs. Focused. This fundamental issue was also addressed above. With the exception of the need for improved methods to properly handle a mix of sparse and plentiful data, primary challenges of computation in this field of data mining are to do with the large number of possible combinations of events, not with the statistical calculation per se. The difference relates to the way in which questions are asked. Even when faced with large numbers of columns of data A,B,C,D, . . . when using classical statistical methods and data mining procedures, experimentalists have typically asked focused questions such as "what is the correlation between A, Q and Z. Such questions are relatively trivial, since it is known, or temporarily presumed, that it is A, Q, and Z which are of interest. Such directed questions will not help much when data is associated in unknown ways with large numbers of items per record, such as columns of data which might be associating/covariant, but once discovered, the data could readily be addressed with classical statistical tools.

(2) Information vs. Probability. The concept of probability is the mainstream classical one, but authors have often taken other quantities, such as expectation or information, as axiomatic and they have enjoyed huge success in areas such as communications and bioinformatics. Experimentalists trained in classical statistics usually make reference to the need to determine "probabilities" using classical tests and this needs particular care and comment. Concepts discussed here are clarified in the Theory section below. The simple answer is that a user of the invention can get the effective relevant probability ratios just by taking the "exp" function on his or her calculator. To understand this and the meaning of "effective" more deeply, however, requires deeper consideration. In one embodiment, the methods used in the invention are based on a combination of Bayesian and Information-Theory methods. Though these are typically not combined, it is however noticeable that both these approaches have one thing in common, they depart from classical statistics regarding the classical meaning of significance. Thus, this is inherited by the present invention. There are two primary difficulties in classical statistics which are tackled by newer methods:

(i) Classical statistics create the illusion of an absolute "significance" by, for example, determining the probability of reaching the 90% or 95% level by pure chance. Actually, these two numbers are not universal constants but lie on an equally valid continuum. There is in reality a sliding scale so the modem approaches admit that all things are relative, and concentrate on stating how much information is available.

(ii) Although Bayesian methods are sometimes accused of being "subjectivist," the fact is that by recognizing and, when appropriate, minimizing the inevitable "prior probability" element, they are less subjective than classical techniques which "bury" the views of their creators concerning priors. One consequence of this concerns the handling of data when it is at low data levels, and for combinatorial reasons there is always some interesting data at low levels. One consequence of this was the ongoing disagreement between Fisher, Teacher and others as to what was a reasonable amount of data in each cell of, say, the Chi-square test so that one did not have to pool data (and sacrifice resolution of states of interest).

An interesting feature of the approach is that it can handle sparse, as well as extensive data, and so bridge a gap between qualitative and quantitative research. With respect to sparse data matter in the specific field of protein sequence analysis, the techniques described in B. Robson, "Analysis of the Code Relating Sequence to Conformation in Globular Proteins: Theory and Application of Expected Information," Biochem. J. 141, 853–867, 1974, the disclosure of which is incorporated by reference herein, have been widely used, in particular, in the form of the GOR method of bioinformatics as proposed by J. Garner, D. J. Osguthorpe and B. Robson, "Analysis of the Accuracy and Implications of Simple Methods for Predicting the Secondary Structure of Globular Proteins," J. Mol. Biol. 120, 97–120, 1978, the disclosure of which is incorporated by reference herein. However, the methods were then applied to lists (specifically, only to sequences of amino acid residues) and could not be applied in that form to sets nor collections as these concepts are described above. Further, combination of this approach with matters of importance to the present invention, including encoding of records and subrecords as products of prime numbers, extension to combinatorially generating information terms contributing to the measure as opposed to predefining terms such as duplets, extension from protein sequence analysis to the data mining of records, and the broadening of the underlying information measure to the incomplete Riemann Function and hence more general modeling of counting processes as described below, are novel. The value of using the above-referenced 1974 Robson approach is that zero and single observations can be combined with larger amounts of data for related sets of events or well-founded subjective information. In fact, as noted above, this sparse data situation always arises even where data seems plentiful, because of the way in which events of increasing complexity combinatorially explode and, essentially meaning the same thing, because of the way in which many pressing problems can occur in parameter spaces of very high, and even undefined, dimensionality.

The simple counting model implies that the information available to the researcher grows in an essentially logarithmic manner with the amount of data (the use of the incomplete Riemann Zeta function also allows alternative models as discussed below). The measures returned by the invention are estimated (association or covariance) measures of the natural logarithm of the following ratio: the ratio between the probability of an event over the expected probability of that event, as expected on a random basis. That is, $I(A) = \ln [P(A)/Ep(A)]$ where A is a simple or complex event, P is a probability, and Ep is an expected probability. If $A=(a, b)$, then $I(A)=I(a;b)$, $P(A)=P(a, b)$, and $Ep(a,b)=P(a) \times P(b)$. In the case of covariance, this is particularly an empirical estimation, based on the notion of an equivalent fuzzy set analogous to the A with probability P(A) (see below).

In the instance of data which is very extensive, the above would provide sufficient theoretical description for associations. However, as noted above, in analysis of high dimensional data, some combinations of events are always sparse. A preferred embodiment measures information based on a definition of Expected Information described in the above-referenced 1974 Robson article and values are expressed in "nats" or "natural units" using logs to the base e, analogous to bits or "binary units" using logs to the base 2. Note the logarithmic scale, so that the values commonly obtained of the order of 1 or 2 or 3 nats (or less commonly of $-1$ or $-2$ or $-3$ nats) imply very "significant" ratios of $e=2.718$ and e-squared=7.389 and e-cubed=54.598 times the expected value. As with energy and entropy, it is possible to make comparisons with information, hence the ranking by the invention. $+1$ nat can be considered the information inherent in an observation when that observation confirms a hypothesis for the first time, and $-1$ nat as that information when a hypothesis is refuted for the first time.

Some appreciation of the quantitative meaning of the information, of data levels and significance as implied by information measures, can be gained by appreciating that if the information has the approximate value $1+1/2+1/3 \ldots 1/n$, then this is the same amount of information as if n observations support a hypothesis, and not refute it. The same applies to negative values except that the n observations are now those against, i.e., they refute the hypothesis. For example, $-1.888$ is equivalent to the information $1+1/2+1/3$ in favor of the complementary hypothesis. One reason for stating "approximate" is that mathematically a small constant (the Euler-Mascheroni constant) should arguably be introduced in some definitions but this cancels in practical calculations. Any information measure obtained in practice may of course be made up of data for n observations before or n' against the observation, and it is useful to note that the value obtained in the simple case is $\log(n/n')$.

In a preferred embodiment, the program first subtracts one from frequencies of observation such that no observations and one observation are not distinguished. That is, 1 nat corresponds to information content of the second observation confirming a hypothesis. In general, the information in n observations is then $1+1/2/+1/3+ \ldots +1/(n-1)$, if the Dirichlet priori density is assumed. This choice guarantees that all information measures follow a beta distribution, and then information can be added and subtracted to produce compound measures in a correct manner, without invoking a theoretical problem to do with the accumulation of marginal sums representing prior information (see Robson 1974).

(3) Trees. Nothing in appropriate classical methodology or in measure prohibits the representation in forms of trees (dendrograms). However, arguably, the inventive measure facilitates that by ranking together a list of items of varying n-plicity (pairs, triplets, etc., of items).

(4) Metadata vs. Data. The invention takes data input in such a way that it is not necessary to have complete metadata nor even to know which is metadata and which is specific values for the metadata (in which case we would set first line metadata=off). Metadata such as "Age" is like an axis on a graph, and is distinguished by the fact that a person cannot have two or more ages: the axis links values in an exclusive OR (XOR) relationship. In contrast, the description of a patient by name, age, smoking, etc., implies items in an AND relationship. In accordance with the invention, such distinctions are matters to be determined. In some cases, the former condition can be identified by a strong negative association, the latter by a positive one. Thus, the invention comprises an information-theoretic framework to help distinguish parameter dimensions (A XOR B XOR C) from other (especially A AND B AND C) data elements, mixed set and sequence characters, the combinatorial explosion of concurrent (conjoint) events, and non-sequential as well as list patterns.

(5) Collections ("globs") vs. Sets and Lists. Unlike bioinformatics methods which handle data structures which are mathematically lists, e.g., biological sequences, the invention may be applied to data structures which are more akin to mathematical sets and hence more appropriate to the content of classical file entries. Hence, the invention can treat areas to which typical bioinformatics methods cannot be applied or can be applied less naturally, and to augment them in areas where they can be applied. For example, order is not in general relevant to entries in a patient's clinical record or biological study record. Whereas, in principle, data can be rendered arbitrarily sequential by examining items examined in advance and assigning events to an extremely large spreadsheet of binary choices. The dynamically changing character of new incoming data which is required for patient decision support, the large variety of such data, the difficulty in making binary assignments, and even the difficulty in assessing in advance which are mutually exclusive entries such as patient weight, makes this impractical for real clinical data.

However, a set-based approach in contrast can embrace a list-based approach in a natural way since entries can also be qualified by date, or a spreadsheet column number, to retain temporal or position information. Hence, the invention is capable of handling data structures intermediate between list and set character, characteristic of real world records associated with typical entries in a classical file system. As stated above, the invention goes beyond the definition of a set in another important sense, that entries (e.g., "broken leg" in a medical record) can occur twice or more. A record entry of this type is sometimes referred to as an "amorph" or, colloquially, a "glob," though this term more properly relates to the use of a qualifier as described in the next paragraph.

(6) Qualification vs. Columns. Collections or globs are more general than sets or lists and that means that data which is wholly or partly associated with metadata can also be represented in the inventive approach. Instead of identifying metadata and data with a column, however, the metadata, e.g., Age, is associated with each relevant item such as 43, so producing Age:=43. Entries can be and are shuffled, losing original column "memory," to prevent bias and only the associated qualifier keeps memory of the original column structure (an exception is in the experimental multivariance component, which for speed and matrix approach, goes by column). In consequence, however, the same metadata can be applied to different columns, and properties can be chained as in Characteristic:=Age:=43 which can be used to preserve hierarchic relationships implicit in XML (Extensible Markup Language) passed at a pre-mining point of the workflow.

(7) Strong Negative Associations vs. Neglect of Negative Associations. Whereas the above are believed to be differentiators from other methods, tackling strong negative associations (and indeed negative associations of any kind) may be one of the clearest discriminators of the invention from other methods. It has been discussed extensively above.

2. Theory

The present invention provides solutions to the needs outlined above, and others, by providing improved methodologies for data mining records for associations and covariations (covariance).

2.1 Expected Information

In general, the invention provides such improved data mining methodologies by expressing expected values of mutual information measures as linear combinations of the incomplete Riemann Zeta function, as will be illustrated and explained below. The theory of mutual information is described by R. Fano in "Transmission of Information," Wiley & Sons, 1961, the disclosure of which is incorporated by reference herein. Such theory of mutual information was extended to a further generalization of the theory of expected information by B. Robson, "Analysis of the Code Relating Sequence to Conformation in Globular Proteins: Theory and Application of Expected Information," Biochem. J. 141, 853–867, 1974, the disclosure of which is incorporated by reference herein.

Thus, in accordance with the invention, expected values of mutual information measures, I[a; b; c; . . . ], are expressed as linear combinations of the incomplete Riemann Zeta Function as follows:

$$I[a; b; c] = \zeta[s=1, n(a, b, c)-1] - \zeta[s=1, \epsilon(a, b, c)-1] \quad (1)$$

I[a; b; c] is an example a triple event (a, b, c), but the measure may be computed for duplets, triplets, etc., up to M-plets, where M is the maximum record length in terms of number of items. n is the actual number of events. $\zeta$ represents the incomplete Riemann Zeta function that is well known to mathematicians. $\epsilon$ is the expected number in chi-square sense relative to isolated event a, b, etc. (non-integers are allowed in this general $\zeta$ treatment). The subtraction of one (−1) represents the Dirichlet prior density which allows for the addition/subtraction of information terms so as to be able to estimate more complex measures. That is, all other information measures can be estimated from the above measure.

The expected frequency in this case is that in the chi-square sense, $N \cdot (n(a)/N) \cdot (n(b)/N) \cdot (n(c)/N) \ldots$ which may be a real value as opposed to an integer. Note that, when the number is a non-imaginary integer, the value of the Zeta function corresponds to the limit of the summation $1 + 1/2^s + 1/3^s + 1/4^s \ldots 1/(n-1)^s$. Also note that, whereas s=1 in the usual choice, other choices have beneficial value in information-theoretic treatment of counting (see below). The appearance of the "1/(n−1)" as opposed to simply "1/n" relates to the choice of Dirchlet Prior Probability density that was mentioned in the Introduction as a preferred embodiment. It enables the quantities to be formally added and subtracted with correct treatment of implied "marginal" probabilities (e.g., see the above-referenced B. Robson article (1974)). It may be neglected (i.e., the term −1 may be omitted from equation (1)) without detriment in most instances, certainly when events and concurrence of events of interest are plentiful.

Using this measure, the various conjoint events with measures are ranked on output from positive down to negative. Filters may be applied to prune out "low" measures, i.e., measure implying information close to zero. Note that the method handles data down to zero levels and thus spans the gap between qualitative and quantitative research. The resulting measures are "nats" or "natural units" analogous to "bits" or "binary units," but the natural log is used since it arises in a natural way from the B. Robson theory (1974) and is analogous to the treatment of entropy and free energy. A value close to zero nats can arise either because there is no departure from expectation, or little or no data: it is the information available to the researcher which is implied in the theory. This approach leads to natural methods by which the search space can be pruned since sampling which would lead to close-to-zero measures can be predicted in advance.

Items on records are preferably encoded internally as distinct primes and a record is seen as a product of primes. Different simple and conjoint events such as (a), (a, b), (a, b, d), (b, d, g, p) may be generated by the method described in the above-referenced U.S. Pat. No. 6,434,488 such that any integer which can be divided into the above product without leaving a remainder generates a valid simple or conjoint event, and by repeated division all valid simple and conjoint events are generated correctly once. This is providing that the data type is of the type used in the underlying theory, i.e., a set-like collection in which however items can reappear in the same record. In practice, due to difficulty of factorizing primes, this approach is used to pre-generate code which is "hard wired" into a computer program embodying the invention, and only cases not so represented are handled numerically if justified by the data available.

The invention can estimate in advance whether evaluation of negative and positive associations are justified in view of the data levels. In practice, events such as (a,b,c, . . . ) when first seen create a hash array entry glob{(a,b,c)}. The latter is a preferred embodiment. In the present context, the benefit of a hash array is that a number like 123 is not stored in the 123rd element and the number 1234567891 is not stored in the 1234567891st element, which wastes computer memory if intervening values were never encountered, but that it is simply placed at the next available location in computer memory. In any event, methods are employed in data mining such that something which is never seen has no entry, and hence wastes no memory. Events never seen, so-called "unicorn events," are however important for detecting strong negative associations. Thus, such zero entries for pairs, triplets, quadruplets, etc., are explicitly or implicitly created up to a level allowed by machine memory. For association analysis, numeric data can be pooled by the invention into classes (e.g., dividing age by ten and taking the nearest integer so that four represents the 40–49 age group), or automatically sliced into two groups, one above and one below the mean value. The frequencies can also be "fuzzy," in this context simply meaning that covariances are calculated and used to estimated measures as if derived.

The following provides a derivation and proof of expected information. The "expected information" which is accessible to a researcher concerning the truth of a hypothesis can be evaluated in terms of the incomplete $\zeta$ (zeta) function $\zeta(s=1, D)$ or a linear combination of such terms, where D reflects the limit of summation which is a simple additive function of the number of observations. D is, in the present context, the sum f+g−1 of observed number ("frequency") f of events or observations relevant to that term plus g, a prior belief or further (e.g., subjective) evidence in the hypothesis relevant to that term and expressed as the number of relevant events or observations which would have equivalent effect. The term −1 represents the choice of the Dirichlet absolutely prior density.

The B. Robson article (1974) represented $\zeta(s=1, D)$ by the "hash" or "gate" function #[D] identified with the simple harmonic Euler series (or Euler Mascheroni series) 1+1/2+ 1/3+ . . . . The explicit retention of s and hence use of $\zeta(s=1, D)$ is preferred because of interest in extended (analytically continued) forms for s>1 and for complex s, for example, in modeling for representing uncertainty principles and sampling which perturbs complex systems, and for two-value quantitative logical systems of predicate calculus character, and the data D(x,y) about events or observations x and y. The above simple (1+1/2/+1/3+ . . . ) Euler series arose naturally in the estimation of the expected value E of information I. In the initial formulation (in B. Robson (1974)), I was the information that the observation or event y carries about the hypothesis, that the two-state observation or event x will take the value x=(1) as opposed to x=(2) (e.g., 'true' as opposed to 'false', or 'in state S' as opposed to 'in the complimentary state, not-S)'.

The need to form estimates of I by integrating I over all Bayesian degrees of belief in different values of I arises because the information I in nature cannot be estimated directly (anymore than can the probabilities P in terms of which information can also can be expressed). We can only estimate it by research. In fact, we cannot even be sure that such 'biases in nature' as 'information' or 'probability' actually exist 'behind the data', other than as convenient constructs in our minds. Fortunately, however, this does not detract from their computational value since we can chose to hold a degree of belief about the existence of such biases, and of their values as Pr[I(x=1:2;y)|D(x,y), conditional on data D(x,y) that we see. That implies a distribution of degrees of belief about the different possible values of I or P. Though the B. Robson article (1974) initially mentioned integration over all dI, that equation, though illustrative and a valid alternative model, was replaced in the actual theory and method by integration over all dP with a non-uniform probability density Pr. The estimate of the information I(x=1:2;y) 'out there' in nature, is then interpreted as the expectation of the information which is accessible to the mind of the observer as a consequence of those beliefs, and is:

$$E[I(x=1:2;y)]=\Gamma(a,b)/\Gamma(a)\Gamma(b)\int I(x=1:2;y).Pr[P(x=1:2,y)|D(x,y)].dP(x=1:2;y) \quad (2)$$

To enable a specific integration, the information function I(x=1:2y) is rendered as a linear combination of logarithmic ratios drawn from the underlying probabilities P(x=1,y), p(x=2,y), P(x=1), P(x=2), the general logarithmic term having the general form log(P/(1−P)). Then, their probability density function Pr[log P/(1−P)|D(x,y)] is recognized as a posterior probability density function to be elucidated via Bayes's theorem (posterior probability ∝ prior probability× likelihood).

The likelihood is rendered as multinomial β-distributed, i.e., of form $P(1,y)^{n(1,y)}P(2,y)^{n(2,y)}$ with parameters n which are derived from the D(x,y). The generality is noteworthy because the choice of Dirichelet absolutely prior density ("−1") guarantees that binomial, multinomial and marginal probability densities Pr all follow the β-distribution and are hence consistent. Though that choice leads to 'improper' prior densities which cannot be integrated, all material posterior estimates can be reached by integration. In practice, for most purposes, the question of whether to subtract 1 is immaterial, and it does not effect the other rules.

Though first developed for the binary X=(1) vs. X=(2) measure, the method is applicable to simpler Fano (1964) functional forms, because the contributions from the x=(1) and x=(2) states emerged as independent and additive (Robson, 1974), viz:

$$\Gamma(a,b)/\Gamma(a)\Gamma(b)\int \log(P/(1-P).P^{n(1,y)}(1-P)^{n(2,y)}.dP=\zeta(s=1, n[1,y])-\zeta(s=1, n[2,y]) \quad (3)$$

where $\zeta(s=1, n[1,y])$ can be considered as relating to the estimate of the component log(P) and $\zeta(s=1, n[2,y])$ as relating to the estimate of the component log(1−P).

One advantage of approaching the problem from the above equation is that the result demonstrates that information $\zeta(s=1, n[2,y])$ against the hypothesis is further, but negative, information in favor of the hypothesis.

2.2 Information Units

As mentioned in the Introduction section, Expected Information values measured are in 'nats' or 'natural units', and if n is sufficiently large, $\zeta(s=1, n[1,y])$ can be replaced by the natural logarithm of n plus the Euler-Mascheroni constant. The Euler Mascheroni constant is 0.5772156649 . . . . This cancels in normal applications and the above therefore simply means that $\zeta(s=1, n[1,y])-\zeta(s=1, n[2,y])$ may be evaluated as the natural logarithm of ratio $\log_e$ (n/n') when n and n' are sufficiently large:

$$Lt_{n\to\infty}, \#[n]-\#[n']\to\log_e(n/n') \quad (4)$$

In practice, when n and n' are between 10 and 20 or larger, they produce reasonable approximations of $\log_e$ (n/n').

The natural logarithm with units measured in 'nats' or 'natural units', and base 2 logarithm with units in 'binary units' or 'bits', are the two most used in information theory: the only other used significantly is the logarithm to base 10 (in which case the information units are called 'Hartleys'). The particular choice of log as $\log_e$, i.e., using natural logarithms (logarithms to base e), is persuasive because it is a scientific standard and is the basis of the units used in entropy, which is fundamentally related to information. Most importantly, the choice of the 'nat' or 'natural unit' seems a natural one because the integration gives rise to the simple Euler series.

2.3 Expected Frequencies

In the case of the treatment of joint events such as (x, y) or (x, y, z), prior information about a complex event is inherent in any prior or separate observations on the simple component events such as (x), (y), and (z) is valid prior data which cannot be ignored. Hence, all $\zeta(s=1, n)$ arguments should include a contribution from 'expected frequency' in the chi-square sense, based on those prior or separate observations.

For example, if $n=n(D)=n(x=1,y)=f(x=1, y)-1$ cannot be determined as joint frequencies of events, but the marginal-sum frequencies $f(x=1)$ and $f(y)$ are known, one may chose $n=n(D)=n(x=1, y)=e(x=1y)-1$. The typical chi-square definition of frequencies is exemplified by:

$$e(x=1;y)=f(x=1).f(y)/[f(x=1)+f(x=2)] \quad (5)$$

This is in general a real rather than integer number. The value of a decimal argument is readily obtained by linear interpolation between the results for the integral values.

Note that $[f(x=1)+f(x=2)]=\Sigma_y f(y)=f_{tot}$ is the total amount of data. An expected frequency is a kind of probability estimate which is not classically and absolutely normalized, and in fact $e(x=1;y)=p(x).p(y).f_{tot}$ for adequate data. Most cases of interest assume the $f(x=1)$ (or $f(x=2)$) come together randomly with the remaining event(s) which are treated jointly, e.g., $f(y, z)$, rather than $f(y) \cdot f(z)$. Hence, the corresponding joint frequency case is:

$$e(x=1;y,z)=f(x=1).f(y,z)/[f(x=1)+f(x=2)] \quad (6)$$

The above implies a preferred form, which measures information for joint events as compared with the independent occurrences of the constituent events, which may be expressed as:

$$I(a;b;c;\ldots)=\zeta(s=1, n[a,b,c,\ldots])-\zeta(s=1, e[a,b,c,\ldots]) \quad (7)$$

This form is usefully general because the other mutual information descriptions can be estimated from this form. For example:

$$I(a,b; c,d)=I(a;b;c;d;)-I(a;b)-I(c;d) \quad (8)$$

measures the information between complex concurrent, (conjoint) events (a,b) and (c,d).

Any expected frequency $e(x,y,z,\ldots)$ should sum over x to give $e(y,z,\ldots)$ which is independent of x, and over y to give $e(x,z,\ldots)$ which is independent of y, and so on. For example, $e(x;y,z)=f(x)f(y,z)/[f(x=1)+f(x=2)]$ so that $\Sigma_z[e(x;y,z)]=f(x).f(y)/[f(x=1)+f(x=2)]=e(x;y)$, and $e(x;y)=f(x)f(y)/[f(x=1)+f(x=2)]$ so that $\Sigma_y[e(x;y)]=e(x)=f(x)$.

Some uses may require the expected frequency conditional on another event or events, say z, in which case z appears in all frequency terms:

$$e(x=1;y/z)=f(x=1,z).f(y,z)/[f(x=1,z)+f(x=2,z)] \quad (9)$$

and conversely on y:

$$e(x=1;z/y)=f(x=1,z).f(y,z)/[f(x=1,y)+f(x=2,y)] \quad (10)$$

Note for completeness, the special cases:

$$e(x=1)=f(x=1).ftot/[f(x=1,y,z)+f(x=2,y,z)]=f(x=1) \quad (11)$$

$$e(x=1|y)=f(x=1,y).[f(x=1,y,z)+f(x=2,y,z)]/[f(x=1,y,z)+f(x=2,y,z)]=f(x=1,y) \quad (12)$$

$$e(x=1|y,z)=f(x=1,y,z).[f(x=1,y,z)+f(x=2,y,z)]/[f(x=1,y,z)+f(x=2,y,z)]=f(x=1,y,z) \quad (13)$$

2.4 Covariance Methods

Covariance also implies "correlation" in the present invention. Covariance is more powerful than association, when numeric data is available such that one can take both approaches, because we do not simply address whether values are the same or not (a binary 0/1 summary), but whether, if different, they are linked in some further way as to a common (positive or negative) trend (i.e., a real value summary). The distinction can be appreciated when, e.g., one has age data, and compares the association approach based on qualitative classification of Young:=0 Old:=1 with that based on comparison with a variety of entries Age:=n where n is a variety of numbers representing age, e.g., 10, 42, etc. The approximate idea used here is that if two or more sets of data are in some way related by a numeric trend, in the same or opposite direction, then they do not represent separate sets for which association is to be explored but some kind of "fuzzy" sets where information overlaps because of the way the sets of entries co-vary. Note that a preferred embodiment represented in a computer program is that both approaches (association and covariation) are taken for numeric data, though either can be suppressed, and that sets of data for association are divided round the mean. Splitting into other groups based on standard deviation or variance is possible, but consumes more computer memory.

As noted above, the deepest underlying computational challenge is however not the statistical techniques themselves but the treatment of the combinatorial explosion of possibilities to examine in order to discover associations and covariations of interest without prior knowledge. Both for association and covariance, the difficulty increases with the width of the data, i.e., the number of items per record, whereas in contrast the depth, i.e., the number of records, yields deeper insight at relatively little increase in computational cost. When data is numeric and mutually consistent, i.e., not simply numeric labels for qualitative items, but represents an intensity of expression of the phenomena (e.g., brightness, strength, weight, age), there is as was well noted above a further potential measure called covariance which is stronger than the measure of association in terms of the richness of the insight it reveals.

The more specific description of the relation between association and covariance is that, instead of adding in a further one for each occurrence, a sigma-normalized deviation from the mean value is added. Hence, the invention derives similar measures for the covariances, i.e., taking into account that any items which represent numerical data can show an increase or decrease from the mean value which correlates with increases or decreases from the mean value of other items, and these are contrived to be miscible with the association data in the ranking. Much data can be reinterpreted usefully as numeric. When data is two-valued such as male and female, it is meaningful to use, e.g., 1 and 2 and to speak of averages such as 1.5. Three-valued data such as 0 for no, 1 for yes, and 0 for don't know, are also meaningful when treated as numbers.

Covariance can be considered as a relationship between columns of numeric data. However, in accordance with an embodiment of the invention, it is not necessarily identified by column but is numerically qualified by the metadata (e.g., column title, such as "Age"). Covariances thus present an analogous combinatorial difficulty. But, while they are more powerful measures than association measures, for numeric data, they are not susceptible to some of the mathematical and computational devices for examining more complex events in a practical routine way. In accordance with the invention, covariances are routinely deducted for up to three correlating columns of data, and a separate technique provides a summary description of the extent to which columns of data are covariant with any and all of the other columns.

The method is primarily intended to tackle data characteristic of clinical and other records, i.e., records seen as partly disordered "packages" or "files" each containing miscellaneous, diverse entries in which new types of entries can often appear. That is, they are qualitative, non-rectangular data (records of unequal length) without necessarily having associated metadata, resembling sets rather than lists of items except that items can occur more than once per record (e.g., broken leg, flu, in a clinical record). Utilities are however available to include (wholly or partly) rectangular spreadsheet type data.

The measure of covariance is converted to effective frequency-of-occurrence terms for comparison with association and is called "fuzzy." This term loosely but not exactly relates to the widespread use of the term in "fuzzy sets" and "fuzzy logic." When data is mainly numeric and there is metadata for most of the data and a large rectangular component to the data, a specific query can be directed about a metadata feature such as age. The request is to partition the remaining space, for example, age greater or less than 50. The average value $<v>$ of every corresponding item with that metadata is calculated, conditional on being equal to or greater than, and then less than, the cut point (here 50). Effective fuzzy frequencies n' are then calculated, e.g., as:

$$n' = N'.<v>_{age>-50}/[<v>_{age>-50} + <v>_{age<50}.] \quad (14)$$

where N' is the total frequency of occurrence of items seen with that metadata. What would by comparison with association be the corresponding effective "expected" fuzzy frequencies are not really expectations, but are chosen to produce a comparable quantitative result from the method as if associations were addressed. The e' are calculated from the following:

$$e' = N' - n'. \quad (15)$$

The reason that this measure of equation (15) differs from the corresponding reference term for association is in brief as follows. Any reasonable definition of expected frequency in the covariance case (notably, Ntot×0.5 on one definition of best reference, or zero on another), when implemented within an equation analogous to that for association, leads to a bound on the information value which does not represent a reasonable comparison with similar events explored by associations. The above consideration of "expected" depend on whether the position is taken that covariance is seen as a mix of data subsets which are a mix of covariant and non-convariant data, or a mix of covariant and anti-covariant data. The closest analog in behavior of covariance with association is given by equations (14) and (15) above since it is the natural choice which gives an analogous infinite positive or negative "bound."

These estimated frequencies imply grouped sets of items and are ranked with the above measures in the output. The values returned for the associations and for the covariances are treated as comparable, and hence a covariance appears in the ranking as if it was an association, and vice versa. The theory used for the deduction of effective frequencies of occurrence form classical covariance indices was empirically discovered to provide roughly comparable measures for the same concurrence of events, in many cases, i.e., similar ranking whether viewed from the association or covariance perspective. Generally, covariances do yield more positive or more negative values than simple associations, but this is reasonable since more information, relating to a numerical trend, is being retained.

In a preferred embodiment, association or covariances are calculated separately and either can be suppressed. As for pairs of associations, pairs of covariances are also treated separately and are calculated specifically for the entire record. That is, the record is not split into more manageable parts from which pairs are sampled. To treat triplets and more complex terms, a different approach is used. In part, that is because convergence of covariance with an increase in amounts of data is different as compared with associations. A zero value does not mean that the pair does not occur but rather that its value does not depart from the mean.

Triplets in covariance are treated as follows. All items are read but a probability is set as to whether the number triplet will continue to be sampled. After any items are observed to occur ten times, triplets specified by a particular three items of metadata are discarded if the covariance is less than +0.2 and greater than −0.2. By setting to one, this means that the items are always sampled (the default). By setting to zero, all are discarded, i.e., triplets are neglected. The issue is dictated by memory. If ample memory is available, full treatment of triplets may be employed.

Covariance is combinatorially explosive as it is for association and for treatment of more than any three columns at a time, a method giving only overall summary is used. The multivariate form of covariance is as follows:

$$\Sigma(a-<a>)(b-<b>)(c-<c>) \ldots /(\sigma(a).a(b).\sigma(c). \ldots) \quad (16)$$

Where $<a>$ is the mean value of a and so on, and sigma a is the variance. The form may be resolved into separate components as:

$$S(a) = abs((a-<a/(\sigma(a.))) \quad (17)$$

and similarly for b,c . . . . From this, the function:

$$\Phi = \sum_a [(s(a)/N]^{c(a)} \quad (18)$$

is defined where N is the mean value of s(a) throughout each column (a) and ensures "normalization," and coefficient c(a) varies from −1 . . . +1. This function is minimized on the parameters c(a), . . . . A negative sign of any c(a) will indicate that the column interacts strongly with other columns: the value multiplied by −100 is taken so that 100% indicates a strong interaction and 0% indicates no interaction. Low values are thus indicative that a column of data is of little interest to the problem and can be discarded. High values may be compared with the doublets and triplets calculated as "fuzzy" frequencies. To facilitate this, pairs and triplets are used to calculated an expected corresponding coefficient for each column on the assumption that there are no more complex interactions than three at a time. The minimization method used must be of the type which can handle rough function surfaces with multiple minima. By way of example, the simplex-based method described in B. Robson and E.

Platt, "Refined models for computer calculations in protein engineering: Calculation and testing of atomic potential functions compatible with more efficient calculations," B. Mol. Biol. 188, 259–281, 1986, the disclosure of which is incorporated by reference herein, may be used.

2.5 Combinatorial Generation and Extreme Zone Sampling

Any record such as (a,b,c,d,e,f . . . . ) contains a large number of simpler conjoint (concurrent) events (a,b) (a,c,d), (c,d,e), (a,c,d,f) ("sub-records") which must be independently counted. The approach taken to generate the combinations is as follows. Recall that the data is not of the character of a list, nor exactly of a set, since entries can occur twice or more. These special data structure characteristics map to considerations in number theory. The method requires factorization of products of several small primes.

Several procedures are used to save computing time for larger problems. A method is used to generate code on a "one off" basis with the requisite combinatorial features, and the codes for records and sub-records, as well as individual items, are stored as an ordered list (e.g., [3,5,7]) or, more precisely, as concatenated strings of characters which can be probed by regular expressions. The primes need not of course be concurrent, e.g., as in [2, 7, 91]. In one embodiment, concurrent events of up to ten items of the largest valued primes encountered in each record are covered by such procedure, and the rest are generated "on the fly" by the above numerical method. Also, the above kind of list exemplified by [3,5,7] is used along with non-prime entries, e.g., [3,5,7,35], and the non-prime entries (here 35) are dissected into their components by a divisibility test when required. In addition, pre-calculation is used to establish what combinations of single events could, or could not, result in expected frequencies of less than −1 nat or greater than +1 nat. In particular, specific treatment of events which are not seen, in order to assess whether that represents a significant negative correlation, only takes place if this −1 . . . +1 filter is satisfied.

Generation of all possible conjoint events would be prohibitive in memory so there is an element of arbitrary sampling for more complex conjoint events. Simpler conjoint events which are pairs, triplets or quadruplets can be handled directly and exhaustively and are not affected by this splitting, and hence not affected by this command. The internal limit may be set to handle pairs exhaustively only, though this can be reset by "de-commenting" the triplet and quadruplet components. In a software implementation of the invention, codes are set as simple loops to make more efficient any thrashing in and out of virtual memory which might occur, though this thrashing should be avoided if possible.

A pragmatic sampling method is provided in accordance with the invention whereby associations can be established first as reliably as possible for also treating the conjoint events more complex than above, but which are still relatively simple conjoint events, say of 5–10 item members (pentuplets-decupluts and less), and in such a way that then progressively more complex conjoint can be probed while memory and precision is sacrificed in regard to simpler conjoint events. Basically, the space sampled is split into well separated "extreme" zones and the intermediate space between them is ignored.

However, pairs (or alternatively pairs, triplets and quadruplets if memory permits and the above alterations are made) are always treated exactly and exhaustively. When only pairs are treated exhaustively, sampling is incomplete and only conjoint events conditional on a space which is deemed to be "interesting": sampling is applied to all the triplets, quadruplets, pentuplets, and so on, which contain one, two, or three of the three "most interesting" items.

Apart from this conditioning, all combinations are generated up to a complexity which is governed only by record size. "Most interesting" is interpreted in two opposing senses: those items which are the most common, and those items which are the most rare. A random 50:50 decision is made as to whether the conjoint events comprising the most common component events, or the least more common component events, are taken from the record. Note that many more than one triplet, quadruplet . . . is then sampled per record, but when only pairs are treated exhaustively, conjoint events are undercounted in each and every record, irrespective of length. In other words, some are missed. Thus, from one perspective, sampling is enriched by breaking up records in to smaller records ("sub-records" or "samples"), using the command maximum number of items per record described below.

At the same time, decreasing the effective size increasingly reduces the opportunity to catch cross-terms, i.e., varieties of conjoint events which cannot be recognized because they lie in separate record sample sections. Also, the most complex events analyzed cannot be more complex than the size of the records actually used. So, while setting maximum number of items per record=5, or 6,7,8,9,10 are all generally reasonably good choices, with values set as high as memory will permit, whatever is set, say, M, then multiplets more complex than M-plets cannot be generated. When the number of records is small (e.g., Table 2 below), a choice of six is typically a good choice since the space involving the three least frequent and three most frequent items leave no intermediate events which would guaranteed to be missed from more complex conjoint events. With maximum number of items per record=3, all conjoint events are sampled exhaustively and exactly, but then a complexity of three is the greatest complexity considered, quadruplets are not generated.

3. Exemplary Program and Method

The following section describes a Perl-based computer software embodiment of the data mining concepts of the invention described above. That is, such code may be executed by the data mining engine 102 (FIG. 1) to generate output mining results 110 (FIG. 1) for presentation to a user.

3.1 Command Line Parameters

In a Perl-based embodiment, files may be determined by parameters on the command line (e.g., in UNIX or DOS), or may be partly or wholly omitted, in which case the default file names are the same as those given explicitly in the following example of command line usage. The file which can also be named in the command.dat file is the input.dat file (input file=filename) and if this is also specified on the command line outside the program, that has dominance over the specification in the command file.

The input.dat file or equivalent is the obligatory source data, typically in comma separated value (.csv) format. The absence of this file will generate an exception and warning at the screen but usually results in a usually well-formed XML output file (see below). perl5 fano103 input.dat command.dat convert.dat fano.xml The command.dat file or equivalent is optional input and if absent or empty, defaults are assumed, but it is generally needed in practice, since it is unlikely that every type of input will correspond to the defaults.

The convert.dat file or equivalent is optional input and if absent or empty, the input is read as-is (subject however to any conversions due to the commands in the command.dat file). Special variables are provided to make the content readable and easily modifiable.

The fano.xml file or equivalent is the obligatory output and contains well-formed XML with a correctly declared fano:tag name prefix. This is so even for exceptions, which are presented as <fano:possible_error type= . . . > and <fano:error type= . . . > tags. When rare but serious exceptions occur which result in the program being aborted, the screen warning shows ERROR BAD XML with some error description. The output in the fano.xml file is variously in attribute (="attribute") and content (<fano:tag>content<\fano:tag>) mode or occasionally both. It includes the contents of the commands.dat and convert.dat and the first few lines of input.dat. Importantly, it also contains between fano:ranking ranked associations up to any multiple of items per time and covariances up to three types of qualifiers (i.e., in spreadsheet terms, up to three columns) at a time. A high dimensional covariance output treated separately, in which a summary of potentially more complex covariances is described. A final summary report is printed as content between fano:report tags.

3.2 Input Data File

The data mining program of the invention attempts to do something with almost any file of characters, but it is expecting to handle records comprising a number of "items" ("entries," "events"), and care need be given to specify the delimitation of records and items (entries) in the records. The format options, primarily concerned with delimiting records and the items on them, are controlled by the contents of the command file (typically, command.dat). Typically, but not generally, the format is compatible with spreadsheet applications. Each line represents a record (patient record extract) with items delimited in comma separated variable (.csv) format. As in the typical spreadsheet application, this format also implies that commas within text in quotes are not treated as separators.

Ideally, it is considered the job of other software to process data in spreadsheet-like form, but the invention may have a variety of format handling capabilities, departing considerably from classical .csv format. Some are complex to use in accordance with the complexity of the task that they perform, and may be switched off and hidden in some installations. For example, input could resemble true text. This includes the interpretation of records as, e.g., corresponding to sentences with words separated by whitespaces and/or tabulation. Also a string of text such as deoxyribonucleic acid (DNA) or a protein sequence may be considered as, e.g., a "patient record extract" and symbols can be read in chunks of specified length (say, ten characters at a time as an item), which may also be optionally overlapping, i.e., extracting as an item characters 1 . . . 10, 2 . . . 11, 3 . . . 12, etc.

Whatever the choice of delimiter such as a comma, data may be qualitative (text), numeric, or mixed, rectangular (like a spreadsheet) or with records of unequal length, and with or without a first line as metadata. Use of metadata implies rectangularity of the data. Though, extra items may be added at the end of lines following metadata. Also, metadata may include null entries between delimiters, viz: A,B, ,D. Further, within the program, the items may be treated not as columns but as items (text or numbers) to which the metadata name is prepended as a qualifier, vz: Age:=63, where Age was the metadata and 63 was an entry under that metadata.

The data mining program attempts to see data as numeric whenever possible, and to act accordingly when metadata is specified as the first line. In that case, items which are numeric are pooled as their averages for association analysis, and as the quantities above and below the mean are distinguished for reporting covariance analysis. If this pooling of data is not required, the data should be rendered effectively non-numeric such as by converting numbers to an invalid numeric form, such as 63 to #63, or years_63, a task which may be performed by simple user-supplied code on the convert file (see below).

Note the prefixing as opposed to suffixing by non-numeric characters, 42_years, is also acceptable, but converters to other computing languages may prefer the philosophy that 43_years or 43% is read as 43. Alternatively, the facility to use the first line as metadata must be switched off and qualifiers must be added explicitly as qualifiers line by line, e.g., entering the item as Age:=23. Multiple qualifications such as in Property:=Age:=43 and Propert:=Weight:=200 is perfectly permissible and could, for example, be used to carry through from input to output the hierarchical structure of ontologies. However, in accordance with a preferred embodiment of the program, only the text following the last := is considered as the true item, and the part in front is taken as the metadata.

In the output, white space separates events, and so for readability all white space which exist within items may be converted to underscores. That is, the item high blood pressure becomes high_blood_pressure. Commas within items are converted to slashes "−" (minus sign" which is usually sensible for readability). Any quotes around items including embedded commas are retained. The character pair % has special significance and caption and is retained: (%10) means that all items with this metadata will be grouped by dividing by ten and taking the nearest integer. So, the item 42 with metadata Age(10%) becomes Age (%10):=4, indicating age group 40–49.

Some exemplary files are given to illustrate the above concepts. FIGS. 3A and 3B depict a Table 1a which represents a demonstration file of qualitative patient record extracts with one "record" per line, which is non-rectangular, and which has no metadata, for use in accordance with an embodiment of the present invention. FIG. 3C depicts a Table 1b which represents a small test file example in .csv format, with the first line comprising metadata, in accordance with an embodiment of the present invention. FIG. 3D depicts a Table 1c which represents a portion of a tabulated file of numeric data with the first line comprising metadata, in accordance with an embodiment of the present invention.

3.3 Convert File

Commands in this file are in the same source code as the main program (here Perl) but are brief and apply transformations to the items read as data, e.g., the comma-separated values. This file is open to all variables concerned with item processing and many others too, but some are of particular importance. The item is passed to this file as the variable $set, and modification of this item is the primary use.

The metadata or in terminology used herein, the qualifier, is also passed as $qualifier. $unknown contains the string which is used to indicated that experimental data is not available for an item (entry). The array $uninteresting[1] . . . which can remove a]items from associations and covariance analysis is also useful to note. The symbol # can be used to "comment out," i.e., treat as comment or effectively inactive instructions, the code on the rest of the line. FIG. 4 depicts a Table 2 which represents an example of a convert file in accordance with an embodiment of the present invention.

3.4 Control File

If the command file is empty, standard defaults are used. If present, commands can typically be set to off (i.e., by writing the word 'off' to the right of the equals sign) which is not in general the default state. Defaults are concerned with special adaptations to spreadsheet data and gene or protein sequences or text, or timesaving approximations for very large data. FIG. 5 depicts a Table 3 which represents an example of a control file in accordance with an embodiment of the present invention.

Explanation of the commands illustrated in FIG. 5 provides some useful insight into the rationale of, and challenges met by, the inventive approach, in a pragmatic setting. The default conditions are those which apply if the command is omitted. As for the convert file, commands can be "commented out" by the # symbol. Also, any line starting with the word "comment" is treated as comment.

input file=train.dat. Specifies filename for input data (the output file, in contrast, is not alterable and is fixed as rank.dat in one embodiment). Overridden by command line in DOS/Unix if specified. Use of any file named train.dat, in the same directory as that from which the program is executed, is also the default. The typical file input file is a .csv file, i.e., using comma separated values, but other formats can be selected by the commands following below. An example file content is indicated in Table 2, noting that real cases of pharmacogenomic studies may have much greater width, e.g., 100–300 items long per record, and depth consisting of perhaps 3000 records or more. As it is, because input records, such as [A,B,D,F,G . . . ] explode combinatorially into many sub-conjoint events [A,B], [A,C,F], [B,C,F] [A,C,E,G, . . . ] . . . , even analysis of a simple file content as in Table 1 is a significant computational challenge to illustrate the points. Even in this example, generating and storing all combinations of a sub-conjoint event, allowing for the possibilities that item entries per record can a priori occur more than once, while testing for negative associations (see below) for events not actually observed, would exceed the memory capacity of a typical machine.

set Riemann zeta s=1. Parameter of any value, but normally 1. Sets the incomplete zeta functions parameter s. This is concerned with intrinsic scaling and general normalization features of the measures returned. The current choice used here, s=1, is the default and is used for most purposes. As data approaches infinite levels, information values range from minus infinity to plus infinity, which is intuitive to information theorists. Other choices such as s=2 set a known finite (positive and negative) ceiling value on the amount of information that can be obtained. The choice of s=2 sets the ceiling value as $\pi^2/6$ and s=4 sets $\pi^4/90$. As data levels increase, the value of the zeta function for the observed and for the expected frequencies of events approaches these values, and the difference thus converges to zero, which is the limit also as the data becomes negligibly small.

In intermediate cases of data levels, values reflect the dispersion of the data. The choice s=0 has the effect on the incomplete zeta function of returning the value of the frequency argument, i.e., it is the same as the observed or expected number of events and this is useful for debugging and verification purposes. The limiting values of zeta are then minus infinity and plus infinity, as for s=1, but zeta for s=0 it rises linearly with data, not logarithmically.

report scores above nats=value/off. Typically two, rarely less than one. Because input records, such as [A,B,D,F,G . . . ] explode combinatorially into many sub-conjoint events [A,B], [A,C,F], [B,C,F] [A,C,E,G, . . . ] . . . , and because each of these derived from many such records could correspond to a line of output, the amount of output can be enormous. It is useful to be able to prune out those observations which contain little information (but see note on negative information for next item below). This is either because the amount of data is sparse, or because they occur about the same number of times as would be expected from the abundances of the individual events, i.e., as if the constituent events came together on a chance basis.

This pruning also speeds the program. This should be contrasted with pruning methods within the program which consider that, based on the abundances of simple events, a conjoint event comprising them could never be significant, that also speed the program. The ranked results are assigned a measure which is the number of nats, i.e., natural units based on the natural logarithm base, and analogous to binary units or bits based on the logarithm to base 2. In this case, those results in which the observed frequency of a conjoint event (e.g., a pair) occur more than $e^2$ times (i.e., 7.389) more than was expected on the basis of their original frequencies are considered, with the exception of results which are selected by the report scores below nats command described below which might be used for example to report the equally interesting case that results occur $e^2$ times less than expected. The default is +1 and if commands report scores above nats and report scores below nats are omitted, all results within one nat of zero information, including both positive and negative values, are ignored.

In some other approaches, one nat was the information inherent in a single observation confirming a hypothesis. In any event, it has some absolute theoretical significance as the largest amount of information which can be obtained from a single observation within the present approach based on the theory of expected information. In a preferred formulation, that would correspond to the information provided by a second observation which supports a hypothesis, as −1 nats would be the information contributed by the second formulation which refutes it. It may of course be argued that this default choice is arbitrary, but if that is so, no more than the arbitrary choices of confidence level such as 0.90 or 0.95 probability of obtaining an observation by chance.

report scores below nats=value. Normally zero, occasionally −1 if there are many negative associations/covariances. Partnering with the command above to define a selection window of score ranges reported, this sets the lowest value, such that all results are fully processed and reported only if they lie outside the range specified by this and the preceding command. The default is −1 reflecting the general significance of negative information discussed above, but the argument does not have to be negative.

However, some slightly different considerations apply to negative information, because of an asymmetry in the utility or worth of positive and negative information in certain application domains. This is reflected in the fact that a recommended use is to set the lower bound to zero, as in this case, indicating that all negative values are reported. Note that the argument can be any value but if it equals or exceeds the value set by the preceding command, the window is of zero height and so no output ranking is obtained.

Negative associations are of particular interest in avoiding disease. A negative correlation between administration of a chemical substance and a disease might indicate that the substances is an effective therapeutic against that disease, for example, while a negative association between a polymorphism and a disease might indicate protection by that polymorphism. Also, there may be a special worth to the user in the sense that the negative values are often harder to obtain by other techniques. As indicated above, the number of conjoint events that might exist in principle (even if not observed) is very large, yet the information that they come together must be estimated in order to demonstrate an interesting negative association. Such data is much harder to obtain and so is typically neglected in many association algorithms.

First line metadata=on/off. The invention supports a basic set of commands which allow the com.dat file to handle a variety of incoming formats. This includes handling the presence of metadata. In this case, the command requests that the program does not use the first line as metadata. Metadata is not required, and neither is rectangularity of the data. Rectangularity implies a spreadsheet-consistent form in which all records are of the same length such that complete columns of coherent types of entry, such as patient's age, can be identified. Nor is the order of items significant, so this is closer to a set than a list as noted above, except that if an item occurs twice or more, as "broken leg" might do in a clinical record, these are distinguished as further occurrences of the same item.

However, the philosophy is that metadata can appear in this approach as qualifiers which make otherwise identically named items unique (as opposed to multiple occurrences of the same item) even if the order of the items record is randomized. When the first line of the input file metadata=on, use first line as metadata and automatically add metadata item such as age to the entry, e.g., Age:54. This will generally only make sense if the input data is indeed rectangular, but if records are of different length, qualifiers are added from left to right until either the metadata record or the data record is exhausted.

divide all data by n=value/off. Data items may be numerical. In such a case the above use of metadata is important to add distinct meaning to the value, but an absence of use of metadata is valid and numbers such as 123 and 632 will merely be seen as unique items names which might be identifiers or references or pointers. Understanding the action of divide all data by n requires understanding of the three methods of assigning metadata which are: (1) use of the above metadata on command; (2) simply associating the metadata name in the data itself (by writing, e.g., Age:=42); or (3) by using XML-compatable tags and assigning the tag name to the item (see delimit item).

When numeric postscripts such as (%10) form the end of the metadata name so added, division occurs by that number and the integer part is then taken. If, however, the divide all data command specifies a number such as ten, the same action is performed on all numeric data except that which carries metadata with, e.g., (%10). In both cases, recognition of numerical data is automatic and occurs whenever the item satisfies requirements for being a number, e.g., 145, +63, −92.58, 1.4E22.

The divide all data command rescales such data when encountered as items in records, dividing the data items by the number specified and retaining the integer part of that division. This is a simple umbrella command applied to all numeric items—compare a case-by-case approach to handling values associated with command column below. Rescaling to an integer is of particular value as a quick way of pooling data: for example, by division by ten, ages 7,32, 24,56,89, become 0,3,2,5,8, signifying membership of age groups 0–9, 30–39, 50–59, 80–89.

ignore unknown=on/off. There is a difference between items which are absent because they do not occur or simply because their occurrence is unknown, or that a specific result or value has not yet been determined. Unless instructed otherwise, the program takes the view that items not present are simply unknown, and those that are present are known, and this is fundamentally reflected in the theory of expected information used. Consequently, an item zero will be interpreted as a value of zero, not the absence of a measure. This command set of "off" means "do not treat any data as unknown." In contrast, one might have for example: unknown=−9, which instructs the program to treat all items "−9" from a spread as if they were non-observations (missing information).

delimit record=character, e.g., full stop, $, \n. Usually the invisible end of line ("carriage return") character \n. Records delimited by newline character, the default. If a number was used here rather than a character, there would be that number of characters extracted from a sequence to define a record.

delimit line=character. Usually the invisible end of line ("carriage return") character \n. A record can consist of several lines, i.e., blocks of data separated by the newline character \n, or other blocks of data with other separators which can be specified.

use lines matching=regular expression. Use all lines matching the regular expression, in this case, use all lines containing at least one character, which is the default (note the regular expression "wild card" '.'). All lines which do not so match are ignored.

skip lines matching=regular expression. Skip all lines matching the regular expression, for example, if the argument is ˆ#, skip all lines starting with the symbol '#', which is the default. Typically, it is recommended that use lines matching is set for general match and thus skip lines matching may be conveniently stated as overriding use lines matching. More precisely, however, lines to be used must satisfy the matches as both commands.

lines to skip after matches=value. This is the number of lines to be skipped (ignored) after a line matched by the regular expression in the skip lines matching command. In this case, the choice has been made for none, which is the default. In a preferred embodiment, this command overrides use lines matching. The primary use is to skip blocks of comments or annotations. If skip lines matching is omitted, this command skips the specified number of lines after a line starting with character '#'.

delimit item=value/character/special string. Items in record are typically delimited by comma, the default. Other alternative uses are valuable for analyzing DNA and protein sequences, treating them as records with many items, for example. If a number was mentioned here rather than a character, there would be that number of characters extracted from each record to define each successive item. A record AGGCTGGTC would be split into three items AGG CTG GTC TCG by choosing delimit item=3. Special strings are provided for convenience as arguments, and include OR\t or \tOR, mean comma or tabulation character t, and strings such as 3wsOR\t or \tOR3ws where the number three can be any reasonable positive integer, meaning at least three white spaces or tabulation characters. These special strings actually convert the condition specified to an internal default delimiter, which is preferably the comma ','. Hence, the above commands imply, e.g., OR3wsOR, but in forms with more than two components, the comma specification is omitted for brevity.

shift item=value/off. Items could be overlapping strings, e.g., AGGCT and GGCTC are overlapping items extracted from AGGCTC. In this case, the command requests that we do not extract every overlapping run of characters in every item.

columns=on/off. The default controlling whether metadata names are built from column numbers in absence of a specific first line of metadata. When the first record specifying metadata is absent, metadata and spreadsheet characters can optionally be introduced by assigning the "column number" as the metadata. Alternative versions of the program may allow an addition of the word 'value:' that allows related values to be treated as a set qualified as high, medium or low values based on the standard deviation of the data:—
Columns=6,age value:=7, height value:=8,condition maximum items per record=value. In conjunction with minimum frequency command, this command is the preferred method of providing adequate sampling of those conjoint events without losing the ability to detect some interesting higher associations (up to pentuplets with this setting). It does not apply to pairs of associations and covariances, which use the whole original record. This command achieves the above aims by fragmenting the record: it sets the sample size, i.e., the number of items which are drawn from the record at a time for analysis for conjoint events. As discussed above, simpler conjoint events which are pairs, triplets or quadruplets can be handled directly and exhaustively, and are not affected by this splitting, and hence not affected by this command.

In one embodiment, however, the internal limit is set to handle pairs exhaustively only. The sense of the command "maximum items" is of course that the records are too long, generating huge numbers of conjoint events with a massive memory requirement. Thus, records should be split up into smaller records, six long in this case, these new smaller records being the "samples." The original record is randomized (items are shuffled) before this division and (N/M)+1 samples ("split records") are generated completely and exhaustively without overlap or duplication from a record of length M (see however the next command).

The last record handled will typically have less than M items (M-int(N/M) items). As discussed above, however, a setting of six is preferred. If less than six items are in the record or last sample from a record, then that number is used, and it may be noted that if a record or sample contains, for example, three items only, then taking the triplet conjoint event with most common or least common members is the same thing. When interest is in more complex conjoint events, settings of ten are recommended if memory permits. Up to ten, conjoint events are sampled according to "combinatorial code" in which the codes for conjoint events are preserved separately in strings. Integer division may be used to generate this code; when the number of items per sample exceeds ten, integer division is used on the excess items acting directly on the product of primes which encode the items.

Note that since the current example file has no record as long as, for example, 100 items, a setting of 100 would evaluate conjoint events with as many items as whole records, without splitting the record. Setting "off" would have the same effect in this case. With the setting of 100, the example here has only one record longer than ten and takes only about 60 seconds on a 700 MHz Personal Computer, and generates extremely similar results to the case of a limit of five or ten. However, larger problems can be extremely expensive computationally.

shift record=. In a record of N items, with M items per record, the sample frame of M items can be shifted N−M+1 times to cover a broader sampling of conjoint events. This affects the values calculated (since conjoint events are over-counted several times), and is a feature into weighting techniques. Detailed action may vary and it may also be computationally expensive. However, it may be used to avoid missing potentially interesting correlations sparsely represented in relatively small data files.

maximum items per record sample=. The maximum complexity of conjoint events such as (A,B,C) (complexity 3) and (A,B,D,F) (complexity 4). Irrespective of the above command, the internal calculations will ignore conjoint events containing more than the limiting number of items. The conjoint events are not even stored in memory, thus saving memory. However, unless set off (see below), pairs are always done.

maximum number of item types=value/off. For example, if value is 500, the 500th most frequent events, i.e., record items as opposed to conjoint events, are used, all others are deleted from consideration. This can be reset when programs become intensive of memory and cause thrashing in and out of virtual memory. The most common types of item in the database are always retained and the rest simply ignored. Setting the value to 10000 is as good as setting "off" in this case. This command is not often used, and maximum items per record and minimum frequency commands are most commonly used to manage memory requirements; those make the selection in terms of specific frequencies, rather than maximum number of item types for which the values of frequencies discarded is varied and implicit.

However, it is potentially useful and use corresponds to no worse than the classical statistical options of qualitatively deciding to ignore types of problem or parts of problems with sparse data. Indeed, it has the advantage of ordering the data items by abundance to enable a more rational selection.

minimum frequency=value/off Set/do not set frequency filter. That is, all events sampled are included independent of number of occurrences. All occurrences however infrequent will be used. In comparison, for example, minimum frequency=10 would skip all events occurring with a frequency.

maximum sparse frequency=value/off. Used in conjunction with the above command. Only frequencies of conjoint events equal to more negative than the number set here, plus results equal to or more positive than that set as above, are used.

run test=on/off. Inserts two events FANOTEST, FANOTEST, at the beginning of every read record, with metadata TEST_RECORD.

advanced mode=on/off. If there are more than ten items per complex (conjoint, concurrent) event, use this mode to generate all combinations in a number-theoretic manner.

allow duplicates=on/off. Allow/do not allow duplicate items per record in associations as in (A,A,B). Use only (A,B).

associations=on/off. For association, pairs, triplets, etc., such as (A,B), (A,B,C), etc.

fuzzy=on/off. Do covariance pairs and triplets (A,B) (A,B,C). A feature whereby, if the argument is a number 0 . . . 1, this controls the sampling density of triplets (which is otherwise 100%) to save memory.

pairs=on/off. Can be switched to off so that pairs such as (A,B) are not generated in associations.

unseen=on/off. Handles the "unicorn effect." The negative associations are calculated even for events so rare, such as pregnant males, and horses with horns, that are never seen.

read lines matching=regular expression. Explicit conditioning. Reads only lines (usually records) matching the regular expression. All associations and pairwise or triplet covariances will contain the string being matched (actually prior to combining metadata with data via :=). This can be used, for example, to select only cancer patients, or a negative regular expression to treat only non-cancer patients. This is effectively a form of conditioning the sample space. AI statistics would only apply to patients who have cancer, on the first choice. Obviously associated and covariant conjoint events drawn from this record may or may not match the explicit string mentioned, so conditioning is implicit.

uninteresting logic=string= . . . with one or more strings. Each string can be a general regular expression but is typically a simple string, e.g., uninteresting AND=ID=HRX. Explicit conditioning of the sample space on the sample selected from a record. That is, the non-occurrence of the explicit mention of the uninteresting term is guaranteed, so that this is analogous to using a negative (complement set) regular expression in the read lines matching command. Conditions the sample space on non-occurrence of certain items, i.e., so that these never appear in the relationships (A,B,C), etc. Samples drawn as specified by maximum number of items per record command are discarded if they contain these items in a logical AND or OR relationship.

interesting logic=string= . . . with one or more strings. The string can be a general regular expression but is typically a simple string, e.g., uninteresting OR=ID=HRX=TRIG=HGT. Conditions the sample space on the sample selected from a record. Unlike the read lines matching command conditioning is implicit as there will be associations and covariances drawn from the different samples from the same record which do not match the condition. This is thus useful if there is potential interest in other combinations of events, but the focus is on what is specified as interesting.

In the above example, samples drawn as specified by maximum number of items per record command are discarded if they do not contain these items in logical OR relationship. AND is also available, and the items between the equals signs can be regular expressions. Associations (A,B,C) which do not include the specified items may however appear, though the implication is that the sampling and hence the underlying probabilities are conditional on the items specified (e.g., SYSTOLIC_BLOOD_PRESSURE=>av_120, CIGARETS_PER_DAY=>av_10| HGT=>av_65).

high dimensional covariance=value % (precision)=value (iterations). For example, high dimensional covariance=0.01%=50. Derive coefficients as measures of how much items are involved in many covariances using a global minimization technique for rough surfaces with discontinuous derivatives. The first "%" parameter is the accuracy required for convergence of the mulitvariance strength on a 0 . . . 100% scale. The default is 0.0001%. This process of convergence will be repeated the number of times shown by the final parameter (here 50), the default being 100. Although a fresh random start is taken, some information is taken from the preceding passes to try and find a global solution, first assuming that the minima located may follow a trend.

result must match=off. When on, the argument is a regular expression. Ranked items (associations and covariances up to triplets) containing the regular expression in the item or its metadata are not printed to fano.xml The above command file is the example used for the run below.

4. Output Results
4.1 Example Association Output

Recall the simple input file of FIG. 3A. Each line is a patient record. Absent the invention, one would find extremely difficult an attempt by inspection to say which events or entries such as "alcoholism," "snp b," and other events occurring three, four of more items at a time, are most associated. Even more difficult would be an attempt to spot any events or entries which are strongly avoiding each other, e.g., identify a genetic polymorphism ("snp") which provides a clinically interesting protection. Note that the data is sparse. Again, medical decisions have to be in real time as best bets based on medical data, there is not time for a further statistical collection of data.

Advantageously, a data mining engine of the invention may provide a summary output (output mining results 110 in accordance with output result presentation 106 of FIG. 1) as depicted in FIG. 6 in accordance with an embodiment of the present invention. Table 4 of FIG. 6 illustrates the combinatorial explosion which occurs even in the relatively simple input data of FIG. 3A.

As is depicted, the output mining results provide the following answers. Note that INCIDENTS: points back to the record number(s) in which the combination events were found. Irrespective of the reality of the present data and the resulting analyses, the results suggest the insightful complexity that may be obtained. As shown, a scorpion bite is almost guaranteed, more than alcoholism, to cause pancreatitis. Further, it is no surprise that hepatic dysfunction does strongly correlate with alcohol, though protection is conferred by a genetic feature, snp b. There are few triplets reported as significant to more than 2 nat but they are of interest and their data remained stable in ten different repeat runs.

Snp_c seems to compound the effects of scorpion bite at the pancreas: amongst many conjectures that might be explored are that a secretin haplotype may be more similar to the venom epitope, or the receptor more accessible to antibody, or more likely the antibodies themselves correspond to a different set in the case of the b haplotype. Snps a, b and c do occur together and may so make up a feature of a hapltotype, but snp_c seems to increase chances of hepatic dysfunction, while b confers some protection. This is statistically plausible and physically possible, but it reminds that we cannot assume from the abundance of events such as (XY) and (YZ) that (XZ) are also common. There are many male patients and many pregnant patients, but pregnant male patients do not occur at all.

FIGS. 7A through 7D depict a Table 5 which represents an output ranking of significant conjoint events in accordance with an embodiment of the invention. This ranking is also presented to the user as mentioned above.

The interesting case s=0 brings the measure into alignment with a direct counting process, which is to say that the information measure is simply the difference between the actual and expected frequency. This alters the rank order since all observations are counted as having expectations independent of the fact that observations have revealed information so far, and so higher numbers of occurrences are upweighted. The altered rank order is illustrated in Table 6 of FIGS. 8A and 8B.

Complex values have significance for a model in terms of a quantitative two-valued predicate calculus with real part s and imaginary part t, as opposed to a one-valued probability or information measure. The resulting values of the zeta function are correspondingly two-valued with real part s and imaginary part t.

$$\zeta(s) = \zeta(s,n) + n^{**}(1-s) \cdot \cos(t \cdot \ln(n))$$

$$(s-1)/((s-1)^{}2 + t^{}2) -$$

$$n^{}(1-s) \cdot \sin(t \cdot \ln(n)) \cdot t/((s-1)^{}2 + t^{**}2) -$$

$$i \cdot n^{}(1-s) \cdot \sin(t \cdot \ln(n))(s-1)/((s-1)^{}2 + t^{**}2) -$$

$$i \cdot n^{}(1-s) \cdot \cos(t \cdot \ln(n)) \cdot t/((s-1)^{}2 + t^{**}2) \qquad (19)$$

This is valid for 0<s<=2, x>=|t|/pi with order s**2. The basic idea is that one can distinguish the universal "all" character of conjoint event (a,b,c) from an existential component.

4.2 Analysis of Sequences

It may be noted that, for example, a 10 unit (here character) segment of sequence, overlapping 1 with 10, 2 with 11, etc., or not overlapping, represents an item ("entry" or "event") in a record corresponding to a chromosome or DNA section. A preferred embodiment in terms of the command file is given for completeness. The method can be applied to test hypotheses regarding bioinformatics sequence data and illustrates the use of the formatting commands. In such a a case, each (mitochondrial) chromosome is treated as a "record," and in this example, every 20 (non-overlapping) letters (A,G,C,T) constitute an "item." For example, one can seek out associative patterns or avoidance of patterns in one component of the genome that are not significant to more than 1 nat of information (i.e., that there are no combinations of items which are non-random to greater than +1 nat or less than −1 nat). FIG. 9 depicts, in Table 7, sample input for use of biological sequences in accordance with one embodiment of the present invention.

4.3 Sample of Results with Quantitative Data and Metadata

FIG. 10 depicts, in Table 8, an example file for introducing metadata in accordance with one embodiment of the present invention. Further, FIGS. 1A through 11C depict, in Table 9, example "real-world" input data with initial meta-record (containing the metadata) in accordance with one embodiment of the present invention. These are the first lines of file of 2862 records, wherein there are 254 items a record. In turn, FIGS. 12A and 12B depict, in Table 10, example "real-world" output data with initial meta-record (containing the metadata) in accordance with one embodiment of the present invention. INCIDENTS: relate to which of the 2862 records the conjoint event was found. Some correlations such as between having blood pressure and receiving treatment help validate the data and give reference marks against which quantification of the degree of association, in less obvious associations, can be understood.

4.4 Conversion of Output Values to Classical Thinking: Computation of Probabilities The invention takes the notions of expectation and of information as axiomatic of all data analysis, so thinking in probability terms is not encouraged. However, a fair approximate of a probability result can be obtained readily.

The easiest approach is to note that the invention discovers and ranks relations between data, but that it reports the frequencies of occurrence when it does so. The attribute saw= gives the observed frequency, and expected= gives the expected frequency. In covariance, the latter is replaced by of=, which is, in the simple case of rectangular data with no unknown entries, the total number of rows (records).

In addition, the exponential of information (in nats) of an association in the case of adequate (say more than 20) items of data gives the ratio:

$$Ra(A;B;C; \ldots )=P(A;B;C \ldots )/P(A).P(B).P(C) \ldots \quad (20)$$

Hence:

$$P(A;B;C; \ldots )=\exp(I(A;B;C; \ldots ).Ntot/n(A).n(B).n(C). \ldots ) \quad (21)$$

Where n(A) is the observed number of event n, and Ntot is the total number of observations of A, etc.

The exponential of information (nats) of a covariation in the case of adequate data (say, 20 rows or more) is the ratio:

$$Rc(A;B;C; \ldots )=P(A;B;C; \ldots )/1-P(A;B;C; \ldots ) \quad (22)$$

if the covariances are considered as representing associations of "fuzzy" events. As noted above, the reason that this measure Rc differs from the above form for Ra is as follows.

Any reasonable definition of expected frequency in the covariance case (notably, Ntot×0.5 on one definition of best reference or zero on another), when implemented within an equation analogous to that for association, leads to a bound on the information value which does not represent a reasonable comparison with similar events explored by associations. The closest analog in behavior is in contrast given by Rc( ) above. The above consideration of "expected" depends on whether the position is taken that covariance is seen as a mix of data subsets which are a mix of covariant and non-convariant data, or a mix of covariant and anti-covariant data.

More properly, one should deduce the covariance $$Rc(A;B;C; \ldots )=Cov(A;B;C; \ldots )/(1-Cov(A;B;C; \ldots ))$$
$$Cov(A;B;C; \ldots )>0 \quad (23)$$

$$Rc(A;B;C; \ldots )=-Cov(A;B;C; \ldots )/(1+Cov(A;B;C; \ldots ))$$
$$Cov(A;B;C; \ldots )<0 \quad (24)$$

Where the Cov are the classical covariances in range −1 . . . +1. The above are estimates only.

4.5 Significance

Probability ratios from associations and covariance are classical (if in the P-ratio case lesser used) measures. So that this raises the classical issue of significance which is prominent in teaching texts. Recommendations as to significance, for example, may be: a positive covariance is sometimes significant if greater than 0.2 and a negative one is significant if less than −0.2. Most commonly, recommendation is often given according to the intervals of 1×σ (sigma), even 2×σ, etc. All such values are in some sense arbitrary because one more or one less observation out of many cannot reasonably be conceived as throwing the result from the interesting to uninteresting class, and this is underlined in the inventive approach. The invention sees the matter as simply one of how much information is available about the departure from prior expectation.

Moreover, diagnostic analysis for a physician cannot always take the option to defer treatment in an emergency case in favor of going out and collecting more data. Rather, the optimal decision must be made however weak the evidence, because, across the sample of many such decisions for main patients, the patients will then benefit.

However, for scientific purposes, it is of course valuable if any team agrees of what is or is not significant. When reporting to other groups, as in the scientific literature, one might speak of associations as being significant at a certain level (such as 0.2) which should of course be specified. Alternatively, one could simply go back to the original data and do a more classical analysis, once the association and covariance analyses have lifted at least part of the cloud of complexity from the mass of raw data.

5. Illustrative Methodologies

Given the above detailed explanations of the principles of the present invention, various illustrative methodologies will now be explained.

Figure 13B:
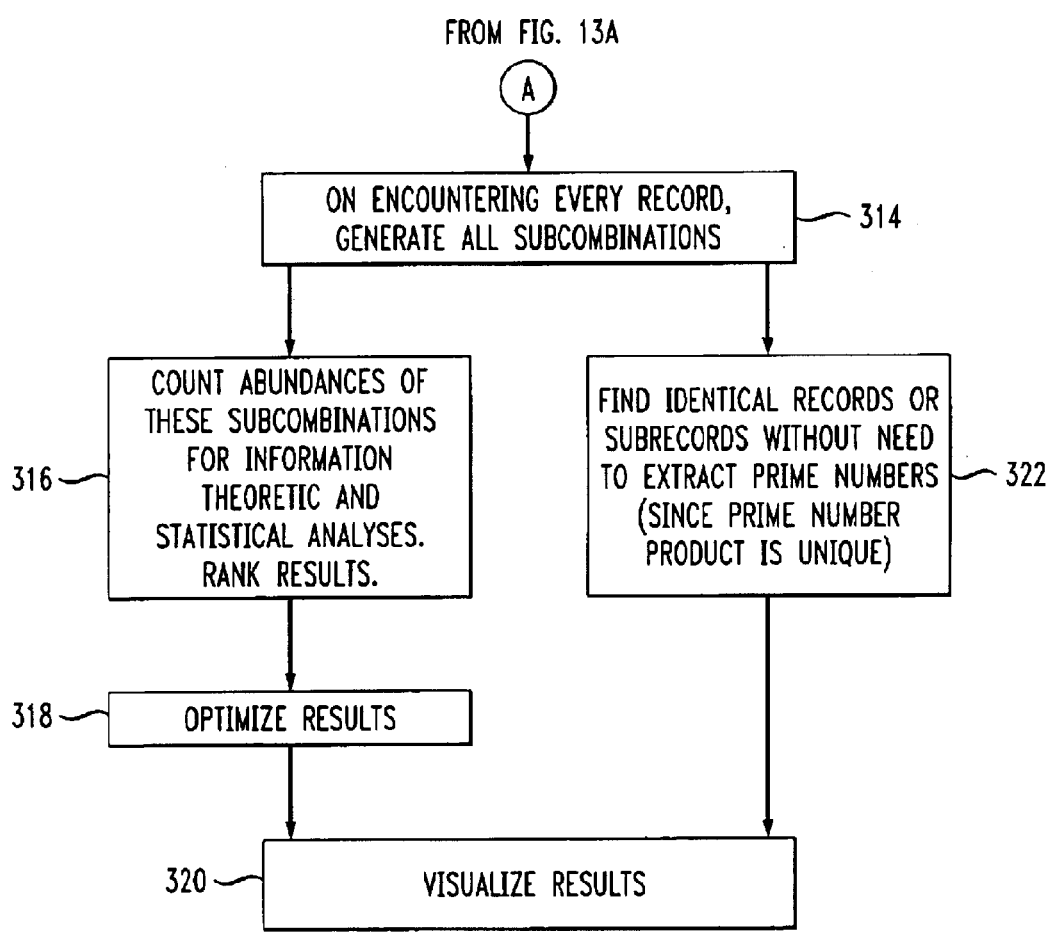

Referring to FIGS. 13A and 13B, a flow diagram generally illustrates a data mining methodology in accordance with an embodiment of the present invention. It is to be understood that the methodology 300 shown may be implemented in accordance with the data mining engine 102 of FIG. 1.

In step 302, input data is obtained. With reference again to FIG. 1, the data mining engine 102 may obtain the input data from a user or read the data from the data records store 104. As explained above, the input data comprises records where each record comprises items (also referred to herein as entries or events).

Next, in step 304, a determination is made as to whether a data item is text data or numeric data. If a data item is text, the item is kept or designated for association analysis. If numeric, the item is, kept or designated for covariance analysis. In addition or alternatively, the numeric item may also be designated for association analysis wherein the numeric data is automatically grouped (e.g., age 2 means 20–29 years old) or separated into classes based on mean and standard deviations.

In step 306, if metadata (e.g., Age) option is specified as explained above, items on the first line of a record are taken as metadata and the metadata is associated with each item, e.g., Name:=Tom_Smith, Age:=42, Smoker?:=yes.

In step 308, the items in the records are counted, e.g., "Smoker?:=yes" occurs 1042 times.

Then, in step 310, each type of item is coded. In a preferred embodiment, the most common type of item may be coded as the first prime number 2, the second most common type of item as the second prime number 3, and so on for the next most common item types (5, 7, 11, 13, . . . ). Other orders of prime numbers may be used. The use of prime numbers to code the items is one example of a coding technique that may be employed. As mentioned above, the use of prime numbers to characterize data is described in the above-referenced U.S. Pat. No. 6,434,488. However, other coding techniques may be used.

Next, in step 312, the input data as coded in step 310 is reread. Then, each record or sample from a record is coded as the "glob" (as explained above) product of all prime numbers for all items in the record or sample, e.g., 11817= 3×13×13×101. The coded record or sample may be stored, for example, as an array element glob[11817] or as a hash array element glob (11817).

In step 314, upon encountering every record, e.g., glob (11817), all subcombinations are generated such as glob{3}, glob{3×13=39} glob{13×13=139} by the various methods described herein. For example, this may be accomplished via pre-generated combinatorial code or a run-time calculation, both based on divisibility of integers without remainder, e.g., 11817/39=303 has no remainder, 39=13×13 is a subrecord (and so is 303=3×101).

In step 316, abundances of these subcombinations are counted for information theoretic and statistical analyses. The results are ranked (e.g., Table 5 of FIGS. 7A through 7D).

In step 318, the results may be optimized (e.g., Table 6 of FIGS. 8A and 8B).

In step 320, the results are visualized for the user, e.g., all or portions of the tabular results, including a summary output (Table 4 of FIG. 6), may be displayed to the user (output mining results presentation 106 of FIG. 1).

Alternatively, the subcombinations generated in step 314 can be used, in step 322, to find identical records or subrecords without need to extract prime numbers from records or subrecords. This may be accomplished since each prime number product is unique. The results of the similarity search may also be visualized and presented to the user, as mentioned above with respect to step 320.

It is to be appreciated the principles of the invention have been tested, and commands developed to facilitate, data mining of a variety of types of data (with and without metadata, and with and without rectangular spreadsheet form) which might reasonably be construed as representing "sets of records." As stated above, it is appropriate to view the definition of "record," and "items" or "entries" within it, broadly, since the only difference is in the instruction to the computer program on how the data is read. In other words, interpretation of items or entries with a record, in a particular way, is a reading-format, not mathematical, matter. A computer program embodying the inventive data mining teachings will run for all definitions of "record" providing the input format can either be defined either on the command file, or by another program preparing data for input to it. For example, the human genome represents a kind of natural biological record for the individual who carries it. A DNA example was presented above.

By way of further specific example, a study has also been performed of genetically inherited maternal diseases. Mitochondrial DNA is an extra-chromosomal DNA which is only maternally inherited. To illustrate implementation in a broader application area, full DNA sequences from human patient mitochondria were first compiled from the Internet, and correlations sought both with diseases shown by patients with mitochondrial defects reflected: (a) in simple nucleotide polymorphisms; and (b) between sections of the DNA as discussed above. The former case as obtained and compiled lacks metadata and an extract of this record is as follows:

Patient 4673D1,#967,
SNP 14364MTND6, G-A, Sporadic Parathyroid Ade., pancreatic cancer, hispanic, from USA,
Patient 4673D2, #1444
MTCO1, 6742, T-C, I-T, bone marrow, whole blood, platelets, granulocytes, acquired idiopathic
sideroblastic anemia
Patient 4673D2, #1444
SNP 14386MTND6, T-C, Sporadic Parathyroid Ade., USA, Somatic mutation, oriental, from Japan
Patient 4673D3, #?,
SNP 14470MTND6, T-C, Encephalomyopathy, Lactic Acodisis, stroke, Leber's heriditary optic
neuropathy, dystonia, Caucasian, from Spain,
Patient 4673D4, #4562,
SNP 14582MTND6, A-G, SNP G15257A, SNP G15326A, SNP 15016MTCYB.
Pancreatic cancer, PX19,
Caucasian, from Hungary An extract of output data is:
3.56002===myopathy leber_hereditary_optic_neuropathy [saw 30 expected 1] (coded+2+29+)
INCIDENTS: 29 112 207 208 211 212 213 214 215 216 217 218 219 220 225 232 235 237 238 242 244 249 249 250 251 254 255 261 264 294
3.25156===dystonia stroke-like_episodes [saw 15 expected 0] (coded +103+107+)
INCIDENTS: 206 240 243 247 248 252 256 265 274 276 278 285 287 290 296
3.25156===stroke-like_episodes ldyt_leber's_ hereditary_optic_neuropathy [saw 15 expected 0] (coded +107+113+)
INCIDENTS: 206 240 243 247 248 252 256 265 274 276 278 285 287 290 296
3.25156===lactic_acidosis encephalomyopathy ldyt_ leber's_hereditary_optic_ neuropathy [saw 15 expected 0] (coded +101+109+113+)
INCIDENTS: 206 240 243 247 248 252 252 256 265 276 278 285 287 290 296
3.25156===stroke-like_episodes encephalomyopathy ldyt_leber's_hereditary_optic_neuropathy [saw 15 expected 0]
(coded +107+109+113+) INCIDENTS: 206 240 243 247 248 252 256 265 274 276 278 285 287 290 296
2.85301===a-g mtnd4 [saw 11 expected 1] (coded +11+ 41+) INCIDENTS: 126 128 130 131 136 140 142 144 147 243 246

2.71785===myopathy mttk trna_lys [saw 9 expected 0] (coded +2+227+241+)
INCIDENTS: 328 329 330 331 333 333 334 334 334
2.71785===deafness diabetes_mellitus [saw 9 expected 0] (coded +43+223+)
INCIDENTS: 209 270 271 279 289 292 327 341 346
2.67693===myopathy trna_leu [saw 11 expected 1] (coded +2+59+) INCIDENTS: 280 283 284 286 286 288 294 295 297 345 345
1.5000===myopathy mttk trna_lys glycoside-induced_ deafness [saw 3 expected 0] (coded +2+227+241+383+) INCIDENTS: 334 334 334

1.00390===myopathy c-t [saw 5 expected 2] (coded +2+19+) INCIDENTS: 9 65 153 213 255
−1.5872===myopathy a-g [saw 1 expected 3] (coded +2+2+ 11+) INCIDENTS: 249
−1.8360===myopathy g-a [saw 1 expected 4] (coded +2+2+ 3+) INCIDENTS: 257

A segment example of output in XML format from autopsy records collected for cardiovascular diseases is given as follows:

```
<fano:covn events="TRIG:=av_120.80 SBP:=av_132.51" information="−1.51"
saw="8.67" of="46" coded="+0+1211+" incidents="all with numeric TRIG SBP" />
  −1.51=%=HDL:=av_49.93 EXAMDTH:=av_13.12
    <fano:covn events="HDL:=av_49.93 EXAMDTH:=av_13.12" information="−1.51"
saw="8.62" of="46" coded="+0+85+" incidents="all with numeric HDL EXAMDTH" />
  −1.52=%=HDL:=av_49.93 AGE:=av_49.57
    <fano:covn events="HDL:=av_49.93 AGE:=av_49.57" information="−1.52" saw="8.59"
of="46" coded="0+81+" incidents="all with numeric HDL AGE" />
  −1.53=%=TRIG:=av_120.80 AGE:=av_49.57
    <fano:covn events="TRIG:=av_120.80 AGE:=av_49.57" information="−1.53"
saw="8.47" of="46" coded="+0+121+" incidents="all with numeric TRIG AGE" />
  −1.83=%=TRIG:=av_120.80 HGT:=av_63.48
    <fano:covn events="TRIG:=av_120.80 HGT:=av_63.48" information="−1.83"
saw="6.75" of="46" coded="+0+129+" incidents="all with numeric TRIG HGT" />
  −1.96=%=HDL:=av_49.93 CHOL:=av_204.59
    <fano:covn events="HDL:=av_49.93 CHOL:=av_204.59" information="−1.96"
saw="6.03" of="46" coded="+0+82+" incidents="all with numeric HDL CHOL" />
  </fano:ranking>
- <fano:multivariance status="experimental" function_value="1470.35474615658">
    <fano:interest metastate="ID" column="0" optimized_omnivariate_value="116%"
estimated_from_fuzzy="0%" />
    <fano:interest metastate="AGE" column="1" optimized_omnivariate_value="129%"
estimated_from_fuzzy="100%" />
    <fano:interest metastate="CHOL" column="2" optimized_omnivariate_value="129%"
estimated_from_fuzzy="100%" />
    <fano:interest metastate="CPD" column="3" optimized_omnivariate_value="126%"
estimated_from_fuzzy="100%" />
    <fano:interest metastate="DRINK" column="4" optimized_omnivariate_value="82%"
estimated_from_fuzzy="0%" />
    <fano:interest metastate="EXAMDTH" column="5"
optimized_omnivariate_value="144%" estimated_from_fuzzy="100%" />
    <fano:interest metastate="GLUC" column="6" optimized_omnivariate_value="122%"
estimated_from_fuzzy="100%" />
    <fano:interest metastate="HBP" column="7" optimized_omnivariate_value="33%"
estimated_from_fuzzy="0%" />
    <fano:interest metastate="HDL" column="8" optimized_omnivariate_value="140%"
estimated_from_fuzzy="100%" />
    <fano:interest metastate="HGT" column="9" optimized_omnivariate_value="130%"
estimated_from_fuzzy="100%" />
    <fano:interest metastate="HRX" column="10" optimized_omnivariate_value="138%"
estimated_from_fuzzy="100%" />
    <fano:interest metastate="SBP" column="11" optimized_omnivariate_value="124%"
estimated_from_fuzzy="100%" />
    <fano:interest metastate="TRIG" column="12" optimized_omnivariate_value="115%"
estimated_from___fuzzy="100%" />
    <fano:interest metastate="WGT" column="13" optimized_omnivariate_value="147%"
estimated_from___fuzzy="100%" />
    <fano:interest metastate="ESTAGEDT" column="14"
optimized_omnivariate_value="119%" estimated_from_fuzzy="100%" />
  </fano:multivariance>
  <fano:report>SUMMARY: Information for conjoint vs. random events. 0 counts
distributed over 0 events, 0 results. Max record length 0. Sampling in chunks of 5.
Potential complexity of problem:- Number of potential conjoint events for maximum
0/record:- Normal combinatorics :0. IF each event can appear in a record x 2 :0. IF each
event can appear in a record x 3 :0. To examine 0 events for strong negative associations:-
Normal combinatorics :0. IF events can each appear x 2 :0. IF events can each appear x 3
:0. ASSOCIATIONS types were generated. Interesting conditioning events were none.
Unnteresting conditioning events were none. 0 types were processed. 0 record content
items were recognized. 0 recovered non-numerically. 0 recovered numerically from small
codes <1000000000000. 0 recovered numerically from big codes >10000000000000. of
these were from nonzero events > requested limit, 559 results were generated.
COVARIATIONS: 15 metadata items were generated. No pairs of 105 generated, and No
strongest triplets of 455 with density 1. 1st MOST INTERESTING CORRELATING
```

-continued

EVENT was column 13 WGT. 2nd MOST INTERESTING CORRELATING EVENT
was column 5 EXAMDTH. 3rd MOST INTERESTING CORRELATING EVENT was
column 1 AGE. 1st LEAST INTERESTING CORRELATING EVENT was column 7
HBP. 2nd LEAST INTERESTING CORRELATING EVENT was column 4 DRINK. 3rd
LEAST INTERESTING CORRELATING EVENT was column 0 ID. Start time Wed Sep
18 9:22:54 2002 Stop time Wed Sep 18 9:23:14 2002</fano:report>
   </fano:results>
  </fano:job>
 </fano:output>

The principles of the invention have also been applied to pharmacogenomic data with some 600 items per record, and in such a case runs approximately 4 hours on a 2 Gigahertz desktop computer.

Advantageously, given the framework and principles described above, many illustrative embodiments may flow.

For example, as provided herein, the invention provides techniques for encoding a record as a product of prime numbers or alternatively the sums of logarithms of prime numbers in which each item entered on the record represents one of such primes. The same unique prime number is used for the same item whenever it occurs in a database of such records and items may appear more than twice in a record in which case the same prime number will appear more than twice in such a product of sum of logarithms.

For example, if a, b and c are distinct items, the record containing items a, b, b and c might be represented uniquely by 2×3×3×5=60. In general, the prime numbers used need not be sequential nor need the set of prime numbers used be complete. Such records are, as is so often the case in the real office, not lists or spreadsheets but can be described as collections of items that are analogous to sets except that items can occur more than once. For example, as explained above, a patient's medical records may have many entries which may or may not be in a particular order and in which items entered such as "broken leg" may occur more than once in the life record. Such collections or combinations which represent records arise in classical combinatorial analysis.

Records seen in this way and also represented as products of prime numbers or alternatively sums of logarithms of prime numbers have various advantageous properties. The importance of this is that records and parts of such records (i.e., "subrecords") represent an event, say E, which should be counted in statistical and information-theoretical analyses including association analysis. Such a record so described which is a collection of specific occurrences of items which is neither list nor set is sometimes colloquially described as "glob" and in any event this term is used for variables for use by the invention which, for example, count the frequency of occurrence of an event E. For example, in one embodiment, the hash variable $glob{$E} in a program written in the Perl5 programming language is incremented by one every time specific event $E is observed, and the $E stands for the collection of items in a record as represented by a list or product of prime numbers.

An advantage of this combinatorial approach is that it is more general than a set or a list, and hence can include the case of a set or a list including data structures which are typical of real records in being mixtures of all of these types of data structures. Treating sets is a matter of simply ignoring extra occurrences of the same item in a record, while techniques for representing list or a tabular character of records or parts of records is more complex.

The invention further provides techniques for testing the similarity of any two such records by comparing the products of the prime numbers or alternatively the sums of logarithms of prime numbers.

The invention further provides techniques for assigning prime numbers to events and for discarding rare items entered on the records, such discarding typically being for the purpose of statistical and information-theoretical analysis by first counting the events and assigning the lowest prime numbers to those items with the highest frequency of occurrence. This is a preferred embodiment for efficiency and to avoid generating numbers which are too large, but the invention also covers the further technique of assigning highest prime numbers of a specified finite set of prime numbers to the items of lowest frequency of occurrence and the further technique of assigning the lowest prime numbers to the items of highest frequency of occurrence. In general, the prime numbers used need not be sequential nor need the set of prime numbers used be complete, but a preferred embodiment is that the nth lowest prime numbers 2,3,5,7, 11, . . . prime(n) are assigned to and used to encode the n items of lowest frequency of occurrence and in order such that any nth prime is the nth item most frequent item.

The invention further provides techniques for generating all the subrecords of such records (such as for example (a,c) and (b,b,c) are subrecords of the record (a,b,b,c)) for the purpose of identifying all such subrecords as events such as for the statistical or information-theoretical analysis of the database of such records. This may be done by generating the mathematical power series of the record of items by dividing the product of prime numbers by the set of natural numbers 1,2,3,4, . . . and noting those numbers which are integer results when there is no remainder. Hence, the record (a,b,b,c) represented by (2,3,3,5) contains itself (2×3×3×5)/1=90 that stands for the subrecord (a,b,b,c), (2×3×3×5)/2=45 that represents the code for the subrecord (3×3×5) which by stands for the subrecord (b,b,c), (2×3×3×5)/3=30 that is the sub-record (2×3×5) which stands for (a,b,c), (2×3×3×5)/5 that is the subrecord (2×3×3) which stands for (a,b,b), (2×3×3×5)/6 that is the sub-record (2,3) which stands for (a,b), and so on.

Note that, for example, (2×3×3×5)/4=22.5, which is not an integer, so that it cannot represent a subrecord. Methods may be employed to save time to perform such divisions, division by devisor 1 being redundant, odd products representing records not needing to be divided by even numbers, products for which the last digit is not 5 nor zero not needing to be divided by 5 or multiples thereof, and so on.

The invention may further provide for the generation of explicit computer code in advance of the calculation so that the above divisions need not be performed during the calculation, in which for example the string [2,3,3,5] explicitly represents the record coded by the integer 90.

In this invention, the generation of all possible strings in advance is done by using the above method not to generate the subrecords directly, but program code lines such as ProdABC=string A,B,C . . . where program variables A,B,C represent any prime number encoding items found by the computer program in the record being read at that time. For example, a possible portion of such code generated, here in Perl5, may be:
$p=$mf10×9×5×4;&assign;
$p=$mf10×9×5×4.'*'.$mf1;&assign;
$p=$mf10×9×5×4.'*'.$mf2;&assign;
$p=$mf10×9×5×4.'*'.$mf3;&assign;
$p=$mf10×9×5×4.'*'.$mf1.'*'.$mf2;&assign;
$p=$mf10×9×5×4.'*'.$mf1.'*'.$mf3;&assign;
$p=$mf10×9×5×4.'*'.$mf2.'*'.$mf3;&assign;
$p=$mf10×9×5×4.'*'. $mf1.'*'$mf2.'*'.$mf3;&assign;
where $p represents the string for the combination of the 10th, 9th, 5th and 4th items sampled from the record being extended to contain entries for variables representing the 1st, 2nd and 3rd items, and the symbol '*' is being used to separate the entries. In subsequent execution of this portion of the much larger code generated, strings such as '5*11*3*2' will be generated as a value of $p, where the number contents, for use of common methods of tracking, analysis and processing, specifically represent the prime numbers coding for items encountered in records.

Note that records or subrecords represented by, for example, '2*3*13' or '13*2*3' are equivalent, so that it is required to re-sort the contents of the strings into, for example, ascending order. The function assigned above performs this task and increments the hash array $glob{$p} by one, indicating that event $p has been noted a further time and the final integer value of $glob{$p} will be the frequency of occurrence of event $p, e.g., '10*9*5*4*2', in the record. Note that, though it is less intuitive to the reader of the programs and string output, the separation character '+' is preferred to the symbol '*' in certain programming languages such as Perl5 because this number arises naturally in strings such as '+37' which is standard for numbers and which are generated by procedures and variable types which are especially concerned with the handling of large numbers for programs of for example number-theoretical interest.

The invention further provides techniques for representing association of events as mutual information as a measure of degree association, as measured by the use of incomplete Riemann zeta function, $I_E=\zeta(s=1, n_E)-\zeta(s=1, e_E)$, where $I_E$, for example, I(a;b;c), is the expected mutual information for association of events or items a,b,c, where $n_E$, for example, and where $n_{E(a,b,c)}$ is the limit of the implied summation of the conjoint (also called "complex" or "concurrent") event (a,b,c) (being infinity in the complete zeta function and the complete Riemann zeta function) and is the observed frequency of an event $E such as represented by $glob{$E} in the Perl5 program.

Correspondingly, $e_E$, for example, $e_{E(a,b,c)}$ is the expected frequency of that event in the sense of classical statistics as, for example, in the chi-squared test. In a preferred embodiment, the expectation is specifically as expected on the basis that the events (say, a,b,c) making up the conjoint (or "concurrent") event E (a,b,c) come together to form E, a random basis, in which case the expected probability is P(a)×P(b)×P(c). The P's are probabilities, and the expected frequency is $n(a) \times n(b) \times n(c)/N_{tot}^2$ where n(a) is, for example, the number of occurrences observed for event or item a and $N_{tot}=n(A)+n(B)+n(c)$ is the total number of occurrences of all events or items. The limit of the summation n of the simple incomplete zeta function is in the simplest representation of the zeta function $1+1/2^s+1/3^s+ \ldots +1/n^s$.

The advantages of the Riemann extended zeta function are that the corresponding parameter n and the parameter s need not be an integer nor non-zero nor even real, and indeed this is required in that an expected frequency is not in general an integer and can be zero. A further and important advantage is that the simple form of the Riemann zeta function $1+1/2+1/3+ \ldots +1/n$ for the case s=1 relates directly to an intuitive choice of the Bayesian expected value of information measured (natural) log(n), though offset by the Euler-Mascheroni constant, such that the representative equation ($I_E=\zeta(s=1, n_E)-\zeta(s=1,e_E)$) converges to the log ratio (natural) $\log(n_E e_E)$ when the frequencies of occurrence are large, and to zero when the frequencies become progressively smaller. Because this relation with the natural logarithm to the base e arises naturally from the integration of the Bayesian expectation of information functions to generate information in terms of the incomplete Riemann zeta function, without any scaling conversion, the information is measured in units of nats or "natural units" as opposed to bits or binary units.

The above convergence to the natural logarithm of the ratio of frequencies is in accord with the above intuitive Bayesian interpretation of expectation in which the quantity measured is the quantity of information available to the observer regarding the information in the system, rather than the quantity of information per se which cannot be directly observed save by counting. In contrast to this approach, simple log ratios become erratic as the frequencies of occurrence of events ("observations") become smaller.

S is an adjustable parameter within the program in the command options file, and various settings can achieve various effects. For example, s=0 causes the function $\zeta(s=1,n)$ to take the value n, which has applications in checking the program or in regenerating the implied frequency of occurrence. Using s>1 allows modeling of processes in which observations interfere with each other, as in experiments in quantum mechanics or on complex vulnerable systems, and in applying the representative equation ($I_E=\zeta(s=1, n_E)-\zeta(s=1, e_E)$) above, they generate values which represent information about statistical uncertainty represented by the higher moments of the distribution such that the value rises when a few observations are made and then drops to zero when data is more adequate.

Finally, multivalued representations of S beyond the normal system can be used to investigate multivalued systems of logic such as the predicate calculus, when a measure of truth is not simply true or false, but relates to at least two concepts such as existential ("some x are y") and universal ("all x are y"). Note that a preferred embodiment provides for subtracting one from frequencies of occurrence (actual and expected) before applying them to the incomplete Riemann zeta function, in accord with the Dirichlet choice of prior density implied in the Bayesian approach, and so ensuring that the proper treatment is given for the implied β-distribution when many such measures are added or subtracted to obtain new measures, and for treatment of marginal sums arising from prior information.

The invention further provides techniques for generating and counting events that are never seen such that $\zeta(s=1,n_E)-\zeta(s=1,e_E)=\zeta(s=1,0)-\zeta(s=1,e_E)$ can be evaluated. This is done by calculating in advance all expected frequencies of occurrence $e_E$ for which the result of the above equation must fall outside a specified range, say plus or minus one nat, of complexity (i.e., number of events or items a,b,c, . . . ) consistent with computer memory.

The invention further provides techniques for handling complete or mixed tabular data by allowing the fist line to represent metadata and attaching the metadata name as a qualifier to each corresponding entry, e.g., Data 42 with metadata Age becomes even Age:=42, which is correspondingly encoded as a prime number. Such qualification does not require conservation of any row or column order, and indeed items in records are in a preferred embodiment shuffled and sliced for sample of more complex events, which destroys all such original column or row information save for the attachment of the qualifier.

The invention further provides techniques for taking account of the continuity in data such as age above by combining related values into sets of value range. A preferred method is that which generates the item or event Age=>35 and the complementary (remaining) state Age<35, where 35 is calculated as the average value associated with the metadata so as the combinations are into sets above and below the mean. More partitions than two and based on the standard deviation of the data may be used, but a preferred embodiment is into two sets in order to reduce the number of complex conjoint events generated.

The invention further provides techniques comprising the use of numeric data in different columns which may have the same metadata, including the case of the common baseness of metadata, such that these represent, for example, multiple measurements associated with the same record, e.g., multiple estimations of the blood glucose concentration of a patient.

The invention further provides techniques for combining concepts of association and correlation in which the multivariate covariance cov(a,b,c, . . . ) between two or more items is defined as an extension of classical two-way covariance between numeric items. This is a covariance between items with two or more different metadata and this is in turn used to generate effective so-called "fuzzy frequencies" relating to N×covariance, where N is the number of items from which, collectively, covariance can be measured (excluding, for example, cases in entries marked as "unknown" for at least one of the corresponding items with different metadata).

When the subsequent frequencies are applied to the representative equation ($I_E$=(s=1, $n_E$)-ζ(s=1, $e_E$)), the relation between multivariate covariance cov(a,b,c, . . . ) and I(a,b,c, . . . ) may be seen especially for numeric data as treated above. In addition, this includes conversion of qualitative data such as text to numbers for this purpose (e.g., male, female becomes 1, 2, and true, don't know and false becomes −1,0,+1), or by considering the covariance as based on equivalence or nonequivalence of qualitative items such as text.

The invention further provides techniques for the automatic elucidation of a complex case of covariance of high degrees of multivariance when the covariance is explicitly or implicitly treated in terms of quantities per item such as $(a-<a>)^{c(m.a)}$, where <a> is the average value of all items with the same metadata as item a and the power c(m:a) is a coefficient dependent on the metadata type of a, the set of all such coefficients over all metadata being subject to optimization in such a way that the final values of the coefficients represent the degrees of covariance between sets of items with the same metadata.

Terms such as (a−<a>) are scaled or rescaled so that a value such as the mean value is 1, in order that $(a-<a>)^{c(m.a)}$ is less than unity when values of the term such as (a−<a>) are greater than one and there is negative values of the coefficient, and also less than unity for values of the term such as (a−<a>) which are less than one and for negative values of the coefficient.

The invention further provides techniques for practical sampling of records to avoid excessive need for computer memory or to make calculations which would otherwise not be feasible because of insufficient computer memory to handle all possible combinations. Records such as (A,B,C,D,E,F,G,H) are randomized (i.e., "shuffled") using random numbers to forms such as (B,C,E,A,G,F,D,H) and are then partitioned into effective subrecords of length as specified in the command maximum items per record sample=, or such implied option. For the choice maximum items per record sample=3 (though 6 might be a more typical choice), the division into records (B,C,E),(A,G,F) and remainder or residual subrecord (D,H) is generated, and items up to multiplicity three, namely, (B,C)(C,E),(B,E) are sampled from the first record and (A,G),(G,F),(A,F) from the second record and (D,H) from the residual subrecord. Although certain interactions such as (B,A) are missed as B and A are in separate subrecords, statistical convergence can be obtained over many records and detected by statistics as convergence of measures to a stable value within a small specified error or data "noise level."

The invention further provides techniques for handling real and accidental duplicates of events. The invention keeps track of the record number (e.g., row number in the case of column or spreadsheet-like data), so that the repeated appearance of items from the same record number can be readily detected in the string of record number occurrences associated with each type of conjoint or concurrent items occurring as the key of an array or hash array element.

For example, the hash array might be glob{33} taking the value, e.g., 5, showing that such is observed 5 times in the whole database of many records, and there is created a corresponding array incidence {33} taking the string value [3,4,17,101,217] showing that these are found in records 3, 4, 17, 101 and 217. However, if the latter array contained [3,3,17,101,217], then when the 3 is added into the string, the methodology could immediately detect that the number 3, referring to record number 3, was now occurring a second time. This may or may not be real or desirable. It may arise as an accident of sampling of a record or possibly in certain types of analysis the user wishes multiple occurrences of the same item in a record to be ignored and for only one occurrence to be noted. When the command allow duplicates=on or such implied option is used, the methodology allows array elements or hash elements involving the representations of the same item (such as the prime number 7) to be created.

For example, this might be done when there is interest in events occurring twice such as when patients have brittle bone disease and the item "broken leg" occurs many times in a lifetime. However, sampling methods such as described above may lead to events being counted twice in certain circumstances when they do not occur twice in the original record, and when the command allow duplicates=off is used, the formation of the array element or hash array element is prevented.

The invention further provides techniques for treatment of metadata as qualifiers such as by which a column heading, such as "cat," is associated with data, say "female," to form a string, in this case "cat:=female," and all calculuses and methods of manipulation and management arising therefrom. Importance of this feature is, for example, in the fact that records can be advantageously randomized on entry such that items can occur in any order, both to ensure lack of bias under all circumstances of use, are to permit the sampling by the splitting of records into subrecords. Otherwise, the shuffling process implied therein would cause loss of information about which data belonged to which metadata. By way of an example of a "calculus of use," we note that any data manipulation involving notions of hierarchies and tree structure of data is enabled by this invention. Note, for example, this includes the case by which there may be first, second and third order metadata, and so on indefinitely, such as animal:=vertebrate:=mammal:=cat:=female, which retains the corresponding hierarchical XML structure <animal><verterbrate><mammal><cat>female</cat></mammal></veterbate></animal>read on input and which could be reconstituted as that XML on output.

In a preferred embodiment, only the last item here, female, is treated as data and the rest of the string, animal:=veterbrate:=mammal:=, is collectively treated as the metadata, but the original sense of the hierarchy is retained even though not manipulated. All or most tests in a preferred embodiment on metadata, at least in regard to determination of strength of associations, relate to testing on the qualifier not the specific column, say 26, from which the data item may have come. Further, by example of a "tree" structure, we extend to the concept of structures such as animal:=((vertebrate:=mammal:=(cat:=male,dog:=female), invertebrate:=worm:=male).

Figure 14:
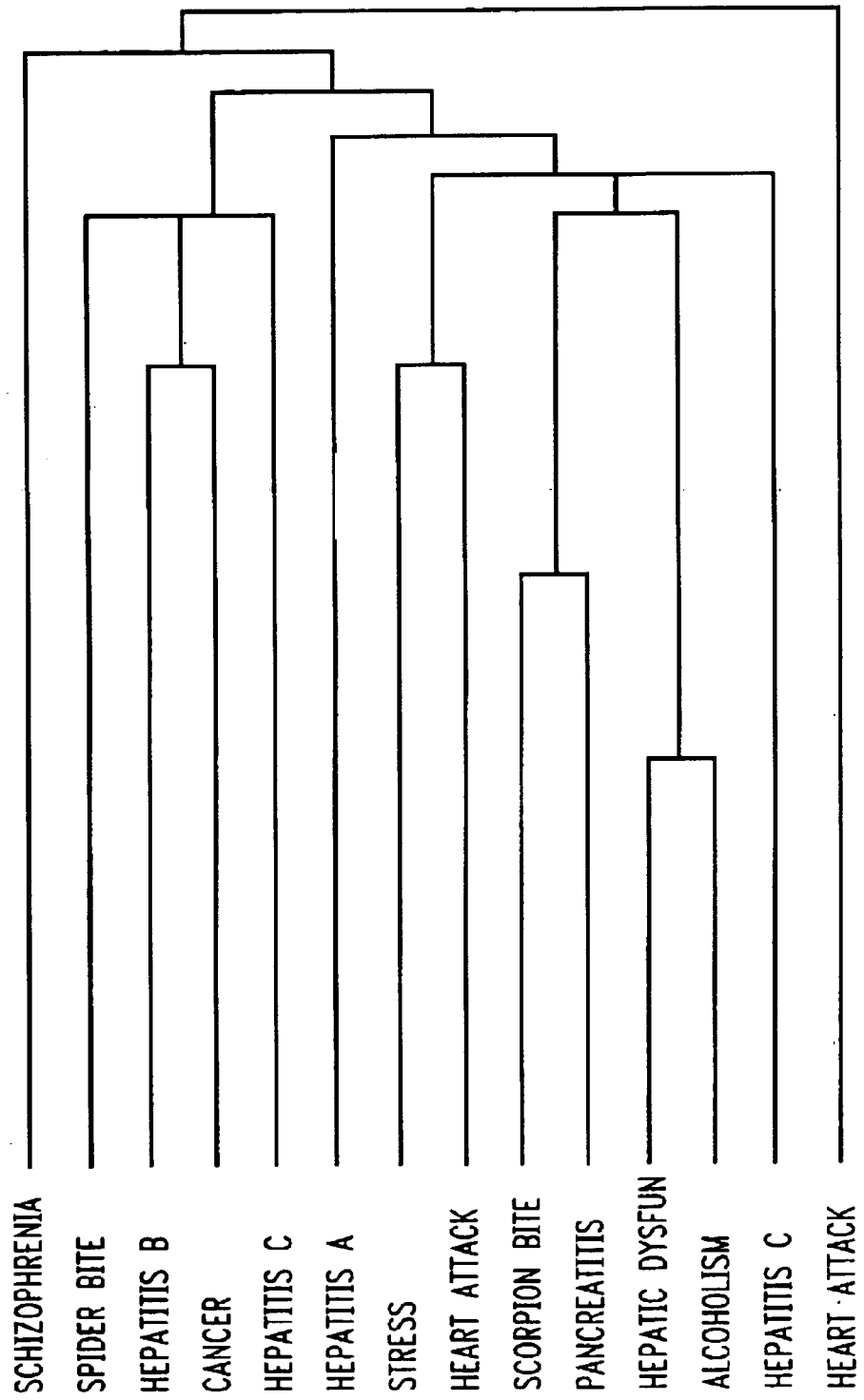
FIG. 14 illustrates a tree diagram formed in accordance with an embodiment of the present invention.

As illustrated in FIG. 14, the invention further provides techniques for generating dendrograms or tree diagrams for the ranked items in which a strong pair represents final "leaf nodes" and these in turn, for example, appear in a triplet of conjoint items which is a deeper branch. For instance, if A and B have strong associations and so do C and D, and A,B,C, D have weaker associations, then the tree forks from the (A,B,C,D) node into (A,B) and (C,D) and each of these fork in turn to the constituent members A and B, and C and D, respectively.

The invention also provides for the concept and practice of using the above to generate complex metadata forms such as animal:=vertebrate:=mamal:cat:=female which can be passed back to the program as input or to construct the corresponding XML.

The invention further provides techniques for mixing prime numbers and prime number products in a string such as the string *2*7*7*33*101* where the asterisk "*" may be replaced by any agreed symbol such as "+" in the methodology for more rapid extraction of the components without a very large number of divisions. The idea relates to the fact that the prime products such as 33 can be resolved later as primes 3 and 11, whereas 2,7,7, and 101 are already irreducibly prime numbers.

Thus, the invention provides for the mixing of primes and prime products and the testing thereof, not the simple use of a string of primes rather then their complete multiplication in order to avoid time consuming factorization. Primes and prime products need not both occur in every representation of conjoint or concurrent events which occurs in the methodology, since such mixed representation is not always needed, but more typically only when some larger numbers occur which are not resolved by earlier operations in the methodology. Such an inclusion of prime products would most typically occur when mechanisms for dealing with products of primes up to the late stage of the methodology are switched off for speed (in a preferred embodiment, by use of the command advanced mode=off), and this might typically be done when the number of types of item occurring in all the data is relatively small.

This feature may be required, for example, for robustness of the methodology such as in cases when later addition of records leads to one or more items requiring higher primes which are thus unexpectedly encountered when the above command is set. When the methodology recognizes that the component number, in this example 33, is not one in the array of prime numbers generated at the beginning of the methodology and is divisible by more that one number (which must not be zero or one) without remainder, then the divisor numbers (in this case 3×11=33) are taken.

The mixed use of primes and prime products raises a need for considerations for rapid and safe treatment in string matches. Note that the string *2*7*7*33*101 represents the concurrent or conjoint event represented by the constituent prime numbers coded by the prime numbers 2,3,7,7,11,101. Though the leading and trailing symbols such as the asterisk "*" are not essential, this is a preferred embodiment because testing for presence of, for example 3, is done by searching the string by for example "*3*". Otherwise, the test would have to be for "^3*" or "*3*" or "*3$" where symbol "A" here represents the beginning of the string and symbol "$" represents the end of the string. These are in fact the symbols actually used in computing as part of tests strings for matching in standard format and known as "regular expressions," but here represent any equivalent notion of checking at the beginning and end of the string.

Note that a simple test on "3*" is not allowable since this string would be seen in the "33*" which would incorrectly indicate the presence of a second 3 only not at the end of the process as opposed to the actual case that the number is actually 33 representing both 3 and 11.

An illustrative computer program written in the Perl programming language which implements data mining techniques of the present invention, as provided herein, is given below in Appendix A. It is to be understood that this program is an exemplary code implementation and the invention is not intended to be limited thereto, nor is the invention intended to be limited to a computer program or a computer programming language.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

APPENDIX A

```
$version = 100;
$memory = 1000000;
$precision_limit = 1E13;

$datafile = "input.dat";
$comfile = "command.dat";
$convertfile = "convert.dat";
$xmlfile = "fano.xml";

$datafile = $ARGV[0] if $ARGV[0] ne '';
$comfile = $ARGV[1] if $ARGV[1] ne '';
$convertfile = $ARGV[2] if $ARGV[2] ne '';
$xmlfile = $ARGV[3] if $ARGV[3] ne '';

$maxprime = 100000;
$maxlengthrec = 1000000;
$true = (1 == 1);
$false = !$true;

keys(%glob) = $memory;
keys(%incidents) = $memory;
use Math::BigInt;
use Math::BigFloat;
require 'ctime.pl';
$time1 = &ctime(time),"\n";
chop $time1;
srand;#initialize random number generation different each time (Perl 5)

$nkeys = 0;
$npqkeys = 0;
$npqrkeys = 0;
$generations = 0;
$mgenerations = 0;
$sgenerations = 0;
$bgenerations = 0;
$whitespaces = 0;
$condition = 'non-computable';
$igncondition = 'non-computable';
    $ov = 'none';
        $leastinteresting = 'not determined';
```

```
$leastinteresting2 = 'not determined';
$leastinteresting3 = 'not determined';
$mostinteresting = 'not determined';
$mostinteresting2 = 'not determined';
$mostinteresting3 = 'not determined';

$bigkey = Math::BigInt->new("0");
$bigi = Math::BigInt->new("0");
$bigsqrtp = Math::BigInt->new("0");
$bigdiv = Math::BigInt->new("1");
$biguse = Math::BigInt->new("1");
$bigriuse = Math::BigInt->new("1");
$bigp = Math::BigInt->new("1");
$biglimit = Math::BigInt->new("100000000000000000");
$biglimit = Math::BigInt->new("1000");

$l = 'e';

&makePrimes;

open COMFILE, "<$comfile" || die "ERROR BAD XML Cannot open command file";

while (!eof COMFILE)
    {
    $k = <COMFILE>;
    chop $k;
    $keepcom .= $k.";\n";
    } close COMFILE;

open CONVERT,"<$convertfile" || die "ERROR BAD XML Cannot open file standard.cnv";
$keepconv .= <CONVERT> while !eof CONVERT;
close CONVERT;
open CONVERT,"<$convertfile" || die "ERROR BAD XML Cannot open file standard.cnv";

open PRIMEGLOBFILE, ">$xmlfile" || die "ERROR BAD XML Cannot open out.dat file";
print PRIMEGLOBFILE <<END;
<?xml version="1.0" encoding="UTF-8"?>
<!--FANO sample output. -->
<fano:output file=\"$xmlfile\" xmlns:fano="fano_schemas"
xmlns:xsi="http://www.w3.org/2001/XMLSchema-instance">
```

```
<fano:job program=\"$0\" version=\"$version\" time=\"$time1\">
$maxlengthrec = 1000000;
<fano:settings file=\"$comfile\" maxprime=\"$maxprime\" association_memory=\"$memory\"
precision=\"$precision\" max_length_record=\"$maxlengthrec\">
$keepcom
</fano:settings>
<fano:item_conversions file=\"$convertfile\">
$keepconv
</fano:item_conversions>
<fano:results file=\"$xmlfile\">

END standardize input file on terminations of line $glob{'+1'} = '0';

&count;

&calculate_primeglob_information if $advanced eq 'on';;
&approximate_primeglob_information if $advanced eq 'off';

if ($covariance eq 'on')
    {
    &grid_initialize;
    &grid_explore;
    }

$nstate = $#statelist+1;

print "_____\n";

$maxlengthrec = $nstate if $maxlengthrec > $nstate;

$combinatorial  = &n_possible_globs($nstate,$maxlengthrec);
$combinatorialp1 = &n_possible_globs($nstate+1,$maxlengthrec);
$combinatorialp2 = &n_possible_globs($nstate+2,$maxlengthrec);
$combinatorial1 = &n_possible_globs($nstate,$nstate);
$combinatorial2 = &n_possible_globs(2*$nstate,2*$nstate);
$combinatorial3 = &n_possible_globs(3*$nstate,3*$nstate);
```

```
$poss2covs = ($#metastate+1) * $#metastate /2;
$poss3covs = ($#metastate+1) * $#metastate * ($#metastate-1) /(3 * 2);

$time2 = &ctime(time),"\n";
$condition = 'none' if $condition eq '';
$igncondition = 'none' if $igncondition eq '';
$nproc = $nkeys - $nprundedkeys;
$ms1 = $#metastate + 1;

$pqhash = 'No';
$pqrhash = 'No';
print PRIMEGLOBFILE <<END2;
```

<fano:report>
SUMMARY: Information for conjoint vs. random events.
$ntot counts distributed over $nstate events, $generations results.
Max record length $maxlengthrec. Sampling in chunks of $nrecitems.
Potential complexity of problem:-
Number of potential conjoint events for maximum $maxlengthrec/record:-
Normal combinatorics            :$combinatorial.
IF each event can appear in a record x 2 :$combinatorialp1.
IF each event can appear in a record x 3 :$combinatorialp2.
To examine $nstate events for strong negative associations:-
Normal combinatorics            :$combinatorial1.
IF events can each appear x 2      :$combinatorial2.
IF events can each appear x 3      :$combinatorial3.
ASSOCIATIONS $norigkeys types were generated.
Interesting conditioning events were $condition.
Uninteresting conditioning events were $igncondition.
$nproc types were processed.
$generations record content items were recognized.
$mgenerations recovered non-numerically.
$sgenerations recovered numerically from small codes <$precision_limit.
$bgenerations recovered numerically from big codes >$precision_limit.
$calls of these were from nonzero events > requested limit,
$#result results were generated.
COVARIATIONS: $ms1 metadata items were generated.
$pqhash pairs of $poss2covs generated, and
$pqrhash strongest triplets of $poss3covs with density $density.
1st MOST INTERESTING CORRELATING EVENT was $mostinteresting.
2nd MOST INTERESTING CORRELATING EVENT was $mostinteresting2.
3rd MOST INTERESTING CORRELATING EVENT was $mostinteresting3.
1st LEAST INTERESTING CORRELATING EVENT was $leastinteresting.
2nd LEAST INTERESTING CORRELATING EVENT was $leastinteresting2.
3rd LEAST INTERESTING CORRELATING EVENT was $leastinteresting3.

```
Start time $time1\ Stop time $time2
</fano:report>
</fano:results>
</fano:job>
</fano:output>
END2 print "Start time $time1\ Stop time $time2\n";

close CONVERT;
close PRIMEGLOBFILE;

#_____
sub count
{
&commands;

my $count=0;
my ($ii, $j, $k, $c, $item);
my %statelist;
&precount;

open DATAFILE, "<$datafile" || die "ERROR BAD XML Cannot open data file";

$readmode = 2;

$start = 0;
$record = -1;
$sample = 0;
$ntot=0;
$itemsgot = 0;
$ii = -1;
while () # read statelist as globs of events record by record
    {

$bigproduct = Math::BigInt->new("1");

$list = '';

if ($start == 0 || $ii >= $#state)
        {
```

```
last if eof DATAFILE;
$record++;
&read_state;
next if $associations ne 'on';
$sample = 0;
$itemsgot = 0;
$start = 0;
$ii = -1;

if ($simplets eq 'on')
    {
    undef @pairs;
    $ithpair = 0;
    # undef @triplets;
    # $ithtriplet = 0;
    # undef @quadruplets;
    # $ithquadruplet = 0;

#treat pairs and triplets etc exhaustively

&lowplets;
        $lowplets = 1;# flag that pairs are done;

for ($k=0;$k<=$#pairs;$k++)
            {
            $p = $pairs[$k];&assign;
            } for ($k=0;$k<=$#triplets;$k++)
        #    {
        #    $p = $triplets[$k];&assign;
        #    }
        # for ($k=0;$k<=$#quadruplets;$k++)
        #    {
        #    $p = $quadruplets[$k];&assign;
        #    }
    }
    next if $metadata >0 && $record <1;

}
else
    {
    $sample++;
```

```
if ($sampleshift >1)
    {
    $ii = $itemsgot - 1;
    }
else
    {
    $ii = $start - 1;
    }
}

################################################################
if ($#interesting > 0)
    {
$remem_itemsgot = $itemsgot;
$remem_items = $items;
$remem_start = $start;
$remem_ntot = $ntot;
$remem_ii = $ii;

$items = 0;
    $found = 0;
    for ($i=$start;$i<=$#state;$i++)
        {
        $ii++;
        $items++;

next if !(exists $statecode{$state[$ii]});

for ($jj=1;$jj<=$#interesting;$jj++)
                {
                $found++ if $state[$ii] =~ m/$interesting[$jj]/;
                } if ($items >= $nrecitems || $i >= $#state)#
            {
            if ($sampleshift>0 && $ii < $#state)
                {
                $start = $sample + 1;
                }
            else
                {
                $start = $i + 1;
                }
```

```
            $itemsgot = 0;
            $items = 0;
            last;

}
        } next if  $logicquery eq 'or' && $found == 0;
    next if  $logicquery >0 && $found != $logicquery;
    next if  $logicquery eq 'and' && $found < $#interesting;
        $itemsgot = $remem_itemsgot;
        $items = $remem_itemsgot;
        $start = $remem_start;
        $ntot = $remem_ntot;
        $ii = $remem_ii;
    }

################################################################################
   if ($#uninteresting > 0)
      {
$remem_itemsgot = $itemsgot;
$remem_items = $items;
$remem_start = $start;
$remem_ntot = $ntot;
$remem_ii = $ii;

$items = 0;
    $ignfound = 0;
    for ($i=$start;$i<=$#state;$i++)
        {
        $ii++;
        $items++;

next if !(exists $statecode{$state[$ii]});

for ($jj=1;$jj<=$#uninteresting;$jj++)
                {
                $ignfound++ if $state[$ii]
                   =~ m/$uninteresting[$jj]/;

} if ($items >= $nrecitems || $i >= $#state)#
            {
```

```
            if ($sampleshift>0 && $ii < $#state)
                {
                $start = $sample + 1;
                }
            else
                {
                $start = $i + 1;
                }
            $itemsgot = 0;
            $items = 0;
            last;

}
        } next if $ignlogicquery eq 'or' && $ignfound >= 1;
    next if $ignlogicquery >0 && $ignfound == $ignlogicquery;
    next if $ignlogicquery eq 'and' && $ignfound >= $#uninteresting;

$itemsgot = $remem_itemsgot;
        $items = $remem_itemsgot;
        $start = $remem_start;
        $ntot = $remem_ntot;
        $ii = $remem_ii;
    }

#############################################################

$remem_itemsgot = $itemsgot;
$remem_items = $items;
$remem_start = $start;
$remem_ntot = $ntot;
$remem_ii = $ii;

for ($case=1;$case<=2;$case++)
    {
    if ($case == 2)
        {
        last if $nrecitems == 10;
        $itemsgot = $remem_itemsgot;
        $items = $remem_items;
        $start = $remem_start;
        $ntot = $remem_ntot;
```

```
    $ii = $remem_ii;
    $initnmf = '10000000';
    }
  else
    {
    $initnmf = '0';
    }

$maxlengthrec = $#state if $maxlengthrec < $#state;

$nmf  = Math::BigInt->new("$initnmf");
  $nmf1 = Math::BigInt->new("$initnmf");
  $nmf2 = Math::BigInt->new("$initnmf");
  $nmf3 = Math::BigInt->new("$initnmf");
  $nmf4 = Math::BigInt->new("$initnmf");
  $nmf5 = Math::BigInt->new("$initnmf");
  $nmf6 = Math::BigInt->new("$initnmf");
  $nmf7 = Math::BigInt->new("$initnmf");
  $nmf8 = Math::BigInt->new("$initnmf");
  $nmf9 = Math::BigInt->new("$initnmf");
  $nmf10= Math::BigInt->new("$initnmf");

$mf  = '';
  $mf1 = '';
  $mf2 = '';
  $mf3 = '';
  $mf4 = '';
  $mf5 = '';
  $mf6 = '';
  $mf7 = '';
  $mf8 = '';
  $mf9 = '';
  $mf10= '';

$items = 0;

for ($i=$start;$i<=$#state;$i++)
      {
      $ii++;
      $items++;
```

```
next if !(exists $statecode{$state[$ii]});

$itemsgot++;
$ntot++;

$c = 0;
if ($case==1)
    {
    #take 10 rarest (high coded) items to form n-plets
    $c =
        $nmf1 < $statecode{$state[$ii]}
     || $nmf2 < $statecode{$state[$ii]}
     || $nmf3 < $statecode{$state[$ii]}
     || $nmf4 < $statecode{$state[$ii]}
     || $nmf5 < $statecode{$state[$ii]}
     || $nmf6 < $statecode{$state[$ii]}
     || $nmf7 < $statecode{$state[$ii]}
     || $nmf8 < $statecode{$state[$ii]}
     || $nmf9 < $statecode{$state[$ii]}
     || $nmf10< $statecode{$state[$ii]};
    }
else
    {
    #take 10 commonest (low coded) items to form n-plets
    $c =
        $nmf1 > $statecode{$state[$ii]}
     || $nmf2 > $statecode{$state[$ii]}
     || $nmf3 > $statecode{$state[$ii]}
     || $nmf4 > $statecode{$state[$ii]}
     || $nmf5 > $statecode{$state[$ii]}
     || $nmf6 > $statecode{$state[$ii]}
     || $nmf7 > $statecode{$state[$ii]}
     || $nmf8 > $statecode{$state[$ii]}
     || $nmf9 > $statecode{$state[$ii]}
     || $nmf10> $statecode{$state[$ii]};
    } if ($c)
        {
        $nmf10 = $nmf9;
        $nmf9 = $nmf8;
        $nmf8 = $nmf7;
        $nmf7 = $nmf6;
        $nmf6 = $nmf5;
        $nmf5 = $nmf4;
```

```
            $nmf4 = $nmf3;
            $nmf3 = $nmf2;
            $nmf2 = $nmf1;
            $nmf1 = $statecode{$state[$ii]};
            $nmf = $nmf1
              * $nmf2 * $nmf3
              * $nmf4 * $nmf5
              * $nmf6 * $nmf7
              * $nmf8 * $nmf9
              * $nmf10;

$mf10 = $mf9;
            $mf9 = $mf8;
            $mf8 = $mf7;
            $mf7 = $mf6;
            $mf6 = $mf5;
            $mf5 = $mf4;
            $mf4 = $mf3;
            $mf3 = $mf2;
            $mf2 = $mf1;
            $mf1 = $statecode{$state[$ii]};
            $mf = $mf1
              .$mf2 .$mf3
              .$mf4 .$mf5
              .$mf6 .$mf7
              .$mf8 .$mf9
              .$mf10.'+';

}
#determine unique product indicating glob of events
        $order[$items] = $statecode{$state[$ii]};
        $bigproduct *= $statecode{$state[$ii]};
        $list .= $statecode{$state[$ii]}.' ';
        $nkeys = keys(%glob);

print
"[$record($case).$sample.$itemsgot] $state[$ii] coded $statecode{$state[$ii]} (",
"$nkeys globs $ntot observations)\n";

if ($items >= $nrecitems || $i >= $#state)#
            { if ($mf =~ m/\+/gs)
                {
                $mf =~ s/\+\+/+/gs;
```

```perl
            &generate_vars;
            $lowplets=2;
            &mill;
            } if ($sampleshift>0 && $ii < $#state)
            {
            $start = $sample + 1;
            }
        else
            {
            $start = $i + 1;
            }
        $itemsgot = 0;
        $items = 0;
        last;

}
        }
    }

}
close DATAFILE;
}
_____
sub zeta()
{
$x = @_[0]-1;
return 0 if $x < 1;
if (!defined @zeta)
    {
    if($zetas == 1)
        {
        for ($i=1;$i<=1000;$i++)
            {
            $zeta[$i] = $zeta[$i-1] + 1/$i;
            }
        }
    else
        {
        for ($i=1;$i<=1000;$i++)
            {
            $zeta[$i] = $zeta[$i-1] + 1/($i**$zetas);
```

```perl
            }
        }
    }
if ($x <= 1000 && $zetas==1)
    {
    return $zeta[int($x)] + ($x-int($x))/($x+1);# ;
        #linear interpoln. - Euler-Mascheroni constant
    }
else
    {
    return log($x) + 0.577215665; #Euler-Mascheroni constant implied in log()
    }
}
_____
sub read_state #returns array @state and its string counterpart $event
{ my ($j,$k);
my $nbytes = 1;
my $offset = 0;
my $blanks =
'                                                                      ';

$#state = -1;
    if ($endofrecord >0)
        {
        $limit = $endofrecord;
        }
    else
        {
        $limit = 1.0E100;
        } while($#state<0 && !eof DATAFILE)
        {
        $rec = '';
        $rectest = '';
        $k = 0;

if ($endofrecord eq $endofline || $endofline eq '')
            {
            while ($k < $limit) #read chunk mode
                {
                $k++;
```

```
        read DATAFILE, $character, $nbytes, $offset;
        next if $character eq "\n"
           && $endofline <= $endofrecord
           && $endofline >0
           && $endofrecord >0;
        &delimiters_to_comma
          if $mixdelimmode eq 'on';

$rectest .= $character;
        &tags_to_comma
        if ($character eq '>' && $tagmode eq 'on');
        last if$endofrecord <=0
           && $rectest =~ m/$endofrecord/igs;

$rec = $rectest;

last if $endofline >0 && $k>= $endofline;

last if eof DATAFILE;
        }
    $_ = $rec;

next if !m/[^ ]/gs;
    next if $usewith ne '' && !($_ =~ m/$usewith/gs);
    next if m/$comment/gs && $comment ne '';
    if ($skiplines>0 && m/$comment/gs && $comment ne '')
        {
        for ($l=0;$l<=$skiplines;$l++)
            {
            <DATAFILE>;
            }
        next;
        }

}
else
    {
    $rec = '';
    while ($k < $limit)
        {

$line = '';
        $linetest = '';
        while ($k < $limit)
            {
```

```
            $k++;

read DATAFILE,
               $character, $nbytes, $offset;
            next if $character eq "\n"
               && $endofline <= $endofrecord
               && $endofline >0
               && $endofrecord >0;
            &delimiters_to_comma
               if $mixdelimmode eq 'on';

$linetest .= $character;
            if ($character eq '>' && $tagmode eq 'on')
               {

$rectest =~ s#^.*<([^> ]*)[^>]*>([^<]*)</[^>]*$#,$1:=$2,#gs;
$rectest =~ s/</</gs;
$rectest =~ s/>/>/gs;
               } last if $endofline <=0
               && $linetest =~ m/$endofline/gs;
            $line = $linetest;
            last if $k >= $limit;
            last
              if $endofline >0 && $k>= $endofline;
            last if eof DATAFILE;
            }
         $l++;
         $_ = $line;
         last if $endofline >0 && $k>= $endofline;

last if m/$endofrecord/gs;
         # next if m/$endofrecord/gs && $l<=1;
         next if !($_ =~ m/[^ ]/gs);
         next if $usewith ne '' && !($_ =~ m/$usewith/gs);
         next if m/$comment/gs && $comment ne '';
         if ($skiplines>0 && m/$comment/gs
            && $comment ne '')
               {
               for ($l=0;$l<=$skiplines;$l++)
                  {
                  <DATAFILE>;
```

```
            }
        next;
        }
    $rec .= $line;
    # print "$_ not skipped\n";

last if eof DATAFILE;
    }
} next if $rec =~ m/^ *$/;

if ($endofline >0)
        {
        $rec .= $blanks
            while length($rec) < $endofline;
        $rec = substr($rec,0,$endofline);
        }

$_ = $rec;

$_ = $rec;
$is = $endofitem;
study;
if ($is =~ m/[^0-9]/igs || $is <=0)
    {
    s/$endofrecord//gs if $endofrecord <=0;
    s/^ *//gs;
    s/ *$//gs;
    s/$is */$is/gs;
    s/ *$is/$is/gs;
    s/ / /gs while m/ /gs;

s/"([^"]*)"/<quote1>$1"/gs;

s/(<quote1>[^"$is]*)$is([^"]*")/$1 - $2/gs
    while m/(<quote1>[^"$is]*)$is([^"]*")/s;
```

```
s/(<quote1>[^$is*])$is/$1<comma>/s #take out left side comma
while m/(<quote1>[^$is*])$is/s;

s/$is([^$is]*<quote2>)/<comma>$1/s
while m/$is([^$is]*<quote2>)/s;#take out right s/<quote1>//gs;
s/<quote2>//gs;

s/"//gs;
s/<comma>/ - /gs;

s/:=/:/gs;
tr/A-Z/a-z/ if ($metadata <1 || ($metadata >0 && $record >0));

s/$is *$is/$is$unknown$is/gs while m/$is *$is/;
s/^$is *$is/$is$unknown$is/gs while m/$is *$is/;
}

$#state = -1;

if ($test eq 'on')
    {
    if ($metadata >0 && $record <1)
        {
        $_ = 'FANOTEST,FANOTEST,'.$_;
        }
    else
        {
        $_
        = 'TEST_RECORD_'.$record.','
          .'TEST_RECORD_'.$record.','.$_;
        }
    } if ($is > 0)
    {
    $r = $_.($is x ' ');
```

```perl
$m = 0;
if ($shift > 0)
    {
    for ($l=0;$l<length($_);$l++)
        {
        $state[$m] = substr($r,$l,$is);
        $m++;
        }
    }
else
    {
    for ($l=0;$l<length($_);$l+=$is)
        {
        $state[$m] = substr($r,$l,$is);
        $m++;
        }
    }
}
else
    {
    # print "_____\n";

@state = (split $is,$_);

# print @state;<STDIN>;
    # print "_____\n";

for ($j=0;$j<=$#state;$j++)
        {
        $state[$j] = $unknown
            if $state[$j] !~ m/[a-z0-9]/i;
        }
    # print @state;<STDIN>;
    # print "_____\n";
    } calculate discrimination profile
(valid if data is rectangular)

$_ = '';

if ($metadata >0 && $record >0)
    {
```

```
                    for ($j=0;$j<=$#metastate;$j++)
                        {
                        $set = $state[$j];
                        $qualifier = $metastate[$j];
                        # do standard conversions
                        do $convertfile;
                        $state[$j] = $set;
                        }

}
        if ($readmode == 1 && $metadata >0 && $record >0)
                {
                $ncols = 0;
                    for ($p=0;$p<=$#metastate;$p++)
                        {
                        #first set up standard research grid
                        #which images file structure but
                        #assumes no unknowns and is based on
                        #rows and columns, not metadata if ($covariance ne 'off')
                          {
                          if ($#interesting <1
                          && $#uninteresting <1
                          && $#uninterestingcov <1)
                           {
                           $grid[$ncols][$record]
                             = $state[$p];
                           $gridpt[$ncols] = $p;
                           $ncols++;
                           }
                          else
                           {
                           $range = $#interesting;
                           $range =$#uninteresting
                             if $range < $#uninteresting;
                           $range =$#uninterestingcov
                             if $range < $#uninterestingcov;
                           for ($jj=1;$jj<=$range;$jj++)
                            {
                            if (($#interesting>0
                            && $metastate[$p]
                            =~ m/$interesting[$jj]/)
                            || ($#uninteresting>0
                            && $metastate[$p]
```

```
                    !~ m/$uninteresting[$jj]/)
                 || ($#uninterestingcov>0
                 && $metastate[$p]
                !~ m/$uninterestingcov[$jj]/))
                    {
                       $grid[$ncols][$record]
                       = $state[$p];
                       $gridpt[$ncols] = $p;
                         $ncols++;
                         last;
                         }
                      }
                    }
                 } if ($state[$p] =~ m/[0-9]/
                 && $state[$p] !~ m/[a-df-z]/i
                 && $state[$p] ne $unknown
                 )
                   {
###################################################################
      if ($#interesting > 0)
          {
          $found = 0;
          for ($jj=1;$jj<=$#interesting;$jj++)
              {
              $found++ if $state[$p] =~ m/$interesting[$jj]/;
              }
          next if $found<1 && ($logicquery eq 'or' || $logicquery ==1);
          }
      if ($#uninteresting > 0)
          {
          $ignfound = 0;
          for ($jj=1;$jj<=$#uninteresting;$jj++)
              {
              $ignfound++ if $state[$p] =~ m/$uninteresting[$jj]/;
              }
          next if $ignfound>0 &&
             ($ignlogicquery eq 'or' || $ignlogicquery ==1);
          }
#############################################################
```

```
$profile{$metastate[$p]}
    += $state[$p];

$p2profile{$metastate[$p]}
    += $state[$p]
    * $state[$p];

$ndata{$metastate[$p]}++;

next if $fuzzy ne 'on';

for ($q=0;$q<$p;$q++)#<for self
    {
    if ($state[$q]
    =~ m/[0-9]/
    && $state[$q] !~ m/[a-df-z]/i
    && $state[$q] ne $unknown)

{
###################################################################################
    if ($#interesting > 0 && ($logicquery eq 'and'
        || $logicquery <=$#interesting))
        {
        $found2 = 0;
        for ($jj=1;$jj<=$#interesting;$jj++)
            {
            $found2++ if $state[$q] =~ m/$interesting[$jj]/;
            }
        next if !($found>0 && $found2>0);
        } if ($#uninteresting > 0 && ($ignlogicquery eq 'and'
        || $ignlogicquery <=$#interesting))

{
        $ignfound2 = 0;
        for ($jj=1;$jj<=$#uninteresting;$jj++)
            {
            $ignfound2++ if $state[$q] =~ m/$uninteresting[$jj]/;
            }
        next if ($ignfound>0 && $ignfound2>0);
        }
```

```
if ($#interesting > 0 && $logicquery eq 'or' || $logicquery ==1)
    {
    $found1 = 0;
    for ($jj=1;$jj<=$#interesting;$jj++)
        {
        $found1++ if $state[$q] =~ m/$interesting[$jj]/;
        }
    next if $found1<1;
    } if ($#uninteresting > 0 && $ignlogicquery eq 'or' || $ignlogicquery ==1)
    {
    $ignfound1 = 0;
    for ($jj=1;$jj<=$#uninteresting;$jj++)
        {
        $ignfound1++ if $state[$q] =~ m/$uninteresting[$jj]/;
        }
    next if $ignfound1>0;
    }
################################################################################
            $pqprofile{$metastate[$p]}{$metastate[$q]}
                += $state[$p]
                * $state[$q];
            $pqndata{$metastate[$p]}{$metastate[$q]}++;
            $pqhash++
            if $pqndata{$metastate[$p]}{$metastate[$q]} == 1;
            } for ($r=0;$r<$q;$r++)#<for self
            {
            if ($state[$r]
            =~ m/[0-9]/
            && $state[$r] !~ m/[a-df-z]/i
            && $state[$r] ne $unknown )
            {
################################################################################
#We only handle the OR case on queries for the 3rd correlation, for efficiency
    if ($#interesting > 0)
        {
        $found3 = 0;
        for ($jj=1;$jj<=$#interesting;$jj++)
            {
            $found3++ if $state[$r] =~ m/$interesting[$jj]/;
            }
        next if $found3<1 && ($logicquery eq 'or' || $logicquery ==1);
```

```
        }
    if ($#uninteresting > 0)
        {
        $ignfound3 = 0;
        for ($jj=1;$jj<=$#uninteresting;$jj++)
            {
            $ignfound3++ if $state[$r] =~ m/$uninteresting[$jj]/;
            }
        next if $ignfound3>0 &&
            ($ignlogicquery eq 'or' || $ignlogicquery ==1);
        }
############################################################# if ($density >= rand(1))
                {
            #create and/or update $pqrprofile{$metastate[$p]}{$metastate[$q]}{$metastate[$r]}
                    += $state[$p]
                    * $state[$q]
                    * $state[$r];
$pqrndata{$metastate[$p]}{$metastate[$q]}{$metastate[$r]}++;

$pqrhash++
if $pqrndata{$metastate[$p]}{$metastate[$q]}{$metastate[$r]} == 1;

#delete if weak
            &examtestcovariants if $density <1;
                }
            elsif (exists
$pqrndata{$metastate[$p]}{$metastate[$q]}{$metastate[$r]})
                {

$pqrprofile{$metastate[$p]}{$metastate[$q]}{$metastate[$r]}
                    += $state[$p]
                    * $state[$q]
                    * $state[$r];
$pqrndata{$metastate[$p]}{$metastate[$q]}{$metastate[$r]}++;
                }
            }
        }
    }
}
``` convert spaces to underscores within items $j=0; foreach (@state) {$state[$j++] =~ s/ /_/gs;} do not apply other modifications to metadata line we do these in readmode ==1 because they are estimated first
time round to allow asessment of number of states.

if ($metadata <1 || ($metadata >0 && $record >0))
    {
    #divide numbers to pool data
    if ($divide != 0)
        {
        for ($j=0;$j<=$#state;$j++)
            {
            $state[$j] = int($state[$j]/$divide)
                if $state[$j] != 0
                && $metatstate[$j] !~ m/\(%*\)$/s
                && ($state[$j] ne $unknown
                    ||$unknown eq 'off');
            }
        }
    if ($metadata > 0)
        {
        for ($j=0;$j<=$#metastate;$j++)
            {
            $div = $metastate[$j];
            next if $div !~ m#%(.*)\)$#;
            $div =~ s#.*\(%(.*)\)$#$1#s;

$state[$j] = int($state[$j]/$div)
                        if $div !=0;
            } if ($#colnumber > 0)
        {

```
for ($j=0;$j<=$#state;$j++)
  {
  $incol = 0;
  for ($k=1;$k<=$#colnumber;$k++)
      {
      if ($j== $colnumber[$k])
          {
          $incol = $k;
          last;
          }
      }
  $state[$j] =
   $j.':='.$state[$j]
      if $incol>0 && $colname[$incol] eq '';
  $state[$j] = $colname[$incol].
     ':='.$state[$j]
      if $incol>0 && $colname[$incol] ne '';

}
} for ($j=0;$j<=$#metastate;$j++)
  {
  next if $metastate[$j] =~ m/\(%/;
  $s = $state[$j];
  if ($s
      =~ m/[0-9]/
      && $s !~ m/[a-df-z]/i
      && $s ne $unknown)
        {
        if ($ndata{$metastate[$j]}>0)
           {
           $c = $profile{$metastate[$j]}
            /$ndata{$metastate[$j]};

if ($s>$c)
              {
              $s = '>av';
              }
           else
              {
              $s = '<av';
              }
           }
        else
```

```
                {
                $s = '>av';
                }
            $state[$j] = $s;
            }
        }
    }
} if ($metadata<1)
    {
    &shuffle;
    }
else
    {
    if ($record <1)
        {
        @metastate = @state;
        }
    else
        {
        for ($j=0;$j<=$#metastate && $j<=$#state;$j++)
            {
            $state[$j] =
               $metastate[$j].':='.$state[$j];
            }
        &shuffle;
        }
    } do not apply modifications to metadata line
if   ($metadata <1 || $record >0)
    {
    #remove unknown items
    $m = 0;
    $m1=0;
    for ($j=0;$j<=$#state;$j++)
        {
        print "$m $state[$m]";#~
        if ($state[$j] !~ m/:=\s*$/
           && $state[$j] !~ m/:=$unknown$/
           && $state[$j] !~ m/^$unknown$/
           && $state[$j] !~ m/^\s*$/)
```

```
                    {
                $state[$m++] = $state[$j]
                if ($state[$j] !~ m/:=\s*$/
                    && $state[$j] !~ m/:=$unknown$/
                    && $state[$j] !~ m/^$unknown$/
                    && $state[$j] !~ m/^\s*$/);
                $m1 = $m-1;
                $state[$m1] =~ s/^:=//gs;
                $state[$m1] =~ s/:=$//gs;
                }
            }
        $#state = $m1;
        for ($j=0;$j<=$#state;$j++)
            { die
"ERROR BAD XML Unknown='$unknown'. \n#UNKNOWN# flag survived in '$state[$m1]'
"
                if $state[$j] =~ m/#UNKNOWN#/;
            } run internal count check
            if ($fanotest eq 'on')
                {
                for ($j=0;$j<=$#state;$j++)
                    { if ($state[$j] =~ m/fanotest[0-9]/igs)
                        {
                            print
"Detected test state $state[$j] x $fanotest{$state[$j]}\n";
                            $fanotest{$state[$j]}++;
                            $_ = $state[$j];
                            s/.*fanotest(([0-9])*).*/$1/igs;
                            die
"\n\nERROR BAD XML Test check $state[$j] = $fanotest{$state[$j]} > $_ at j=$j"
                                if $fanotest{$state[$j]} > $_
                                && $sampleshift <1;
                        }
                    }
                }
                # print "$record)", $#state - $m + 1," unknowns '$unknown' removed.\n";

}
```

```perl
        $event = '';
        $j=0; foreach (@state) {$event .= $state[$j++].' ';} last if $endofline eq $endofrecord;

} chop $event;
        # print "$record)$event\n";

}
_____
sub calculate_primeglob_information
{
use Math::BigInt;
use Math::BigFloat;

print "CALCULATING THE INFORMATION FROM THE COUNTS.\n";
print "$ntot occurrences of ",$#statelist+1," events.\n";
print "Unseen UNICORN events, such as horses & horned, are scored zero\n";
print "But only events predicted as worthwhile are done.\n";
print PRIMEGLOBFILE "<fano:ranking setting=\"heavy duty\">\n";

$inter = $#interesting;
$uninter = $#uninteresting;

$inter = 'no' if $inter<1;
$uninter = 'no' if $uninter<1;

$maxlengthrec1 = $maxlengthrec + 1;
if ($associations eq 'on')
{ if ($ntot <1 && ($#interesting>0 || $#uninteresting>0))
        { print PRIMEGLOBFILE <<END3;
<fano:possible_error type="no data for association calculation">
Number of items processed for associations is zero,
Check file, file content, and delimiters in file $comfile.
```

Check processing of data by editing functions in file $convertfile.
The command file invoked $inter interesting specifications, and
$uninter uninteresting specifications.
Check the sense of such specifications in file $comfile.
Misuse of interesting/uninteresting is a common error: these are used to
condition the sample space, not prune data read from file $datafile.
They sample the events as if governed by the probability
P(items|conditions) = P(items,conditions)/P(conditions).
So note that if the user-requested sample size of $nrecitems items here is
at least the maximum record length of $maxlengthrec1, then every sample will
contain something specified uninteresting, and everything will be abandoned.
</fano:possible_error>
</fano:ranking>
</fano:results>
</fano:job>
END3
die
"Number of items zero.
See output on $xmlfile concering file checks on $comfile and $convertfile
and the comments about correct use of 'interesting'/'uninteresting'.
FANO program alert";
} if ($ntot <1)
{ print PRIMEGLOBFILE <<END4;
<fano:possible_error type="no data for association calculation">
Number of items processed for associations is zero,
Check file, file content, and delimiters in file $comfile.
Check processing of data by editing functions in file $convertfile.
You did not use interesting/uninteresting specifications, so this was
not the problem in this case.
</fano:possible_error>
</fano:ranking>
</fano:results>
</fano:job>
END4
die "Number of items zero.
See output on $xmlfile concering file checks on $comfile and $convertfile.
FANO program alert";
}

```perl
my $rntot = 1/$ntot;
$mgenerations = 0;
$sgenerations = 0;
$bgenerations = 0;
my $count = 0;
$nkeys = keys %glob;
$norigkeys = $nkeys;

&create_unseen if $unseen ne 'off';

while (($bigkey,$value) = each(%glob))
    {
        delete $glob{$bigkey};
        $nkeys--;

next if $value > $negmaximal && $value < $minimal;

$count++;
    print "Event $count left $nkeys $bigkey occurs x $value\n";

die "ERROR BAD XML CALCULATE Bad globcode $bigkey" if $bigkey =~ m/\+\+/gs;

$g = $ntot;
    $gs = '';
    $countgs = 0;
    $occurrences = 0;
    $bk = $bigkey;
    $_ = $bigkey;
    # Caution - do not use study function in order to try and save time;
    # @o = ... will choke on it.

for ($i=0;$i<=$maxstatei;$i++)
        {
        undef @o;
        @o = m/\+$prime[$i]\+/gs;

if ($#o >= 0) #if an element
            {
                $occurrences += $#o +1;
                $countgs++;
                $g *= $counts{$statelist[$i]} * $rntot;
```

```perl
            $gs .= $statelist[$i].' ';
            $mgenerations++;
            $generations++;
            # print " [($prime[$i]) $glob{$bigkey} :$countgs]";
            }
        $bigkey
          =~ s/\+$prime[$i]\+/+/gs
            while $bigkey =~ m/\+$prime[$i]\+/gs;
        } print "$countgs $occurrences $bk <$bigkey>\n";
<STDIN> if $countgs == 1;

if ($bigkey ne '+' && $bigkey !~ /\+1\+/)
#Seems at least one wasn't prime. Test by divsibility.
    {
    @s = (split '\+', $bigkey);
    while (@s)
        {
    $bigitem = shift @s;
    next if $bigitem !~ m/[0-9]/gs;
    print "Numerically processing $bigitem from $bk: found";

for ($i=0;$i<=$maxstatei;$i++)
        { if ($bigitem >= $precision_limit)
            {
            $bigp = Math::BigInt->new($prime[$i]);
            if ($bigkey == $bigp*($bigitem/$bigp)) #if a factor
                {
                $g *= $glob{$statecode{$statelist[$i]}.'+'}
                    * $mtot;
                $gs .= $statelist[$i].' ';
                $countgs++;
                $bgenerations++;
                $generations++;
                print " ",$prime[$i];
                }
            }
        else
            {
            $key = $bigitem;
```

```
            $key =~ s/\+//;
            if (0 == $key % $prime[$i])

# if ($key
          #     == $prime[$i]*int($key/$prime[$i]))
                #if a factor
                {

$g *= $glob{$statecode{$statelist[$i]}.'+'}
                  * $mtot;
                $gs .= $statelist[$i].' ';
                $countgs++;
                $sgenerations++;
                $generations++;
                print " ",$prime[$i];

}

}
      }
    print "\n";

}
  } next if $countgs<1;

goto skip; #under development to remove duplicates of metadata
  if ($metadata>0)
      {
      @meta = (split ':=', $gs);
      $dup = 0;
      for ($i1=0;$i1<=$#meta;$i1++)
          {
          $meta[$i1] =~ s/(^| )([^ ]+)$/$2/;

for ($i2=0;$i2<$i1;$i2++)
              {
              $meta[$i2] =~ s/(^| )([^ ]+)$/$2/;
              $dup = 1 if $meta[$i2] eq $meta[$i2];
              print "($meta[$i1])($meta[$i2])";<STDIN>;
              }
          }
      }
```

```
    skip:
next if $dup>0;

$zv  = &zeta($value);
$zg  = &zeta($g);
$z = $zv - $zg;
if ($z>=$zposchop || $z<=$znegchop)
        {
        $significants++;
        $info{$bigkey}=$z;
        chop $gs;

if ($gs =~ m/[_a-zA-Z0-9]/)
                {

&extract_associated_numeric_states;

$bk =~ s/\+1\+/+/;
                $_ = $bk;
                @o = m/\+/gs;
                $gs .= " x $#o " if $countgs == 1;
                $ig = $g;
                $ig =~ s/(^.*\...).*/$1/gs;

$zz = $z;
                $zz = 0 if $zz>-0.01 && $zz<0.01;
                $zz =~ s/(^[^.]*\...).*/$1/gs;
                $result[$nthresult++] =
                "$zz===$gs <fano:assn events=\"$gs\""
                ." information=\"$zz\""
                ." saw=\"$value\" expected=\"$ig\" coded=\"$bk\""
                ." incidents=\"$incidents{$bk}\"/>";

}
        #  else
        #       {
        #       $result[++nthresult] = substr($z.'       ',0,7)
        #       ."===UNCOUNTED ($gs) "
        #       ."[saw $value compared with total $ig] (coded $bk)"
        #       ."INCIDENTS: $incidents{$bk}";
        #       }
        }
    }
}
```

```perl
if ($#statelist >=0)
    {
    print "$#statelist states (including first state 0).\n";
    }
else
    {
    print "No states requested.
Associations must be switched off in the command (com) file\n";
    }

@result = sort {$b <=> $a} @result;
for ($i=0;$i<=$#result;$i++)
    {
    if ($result[$i] =~ m/\+[0-9]+\+[0-9]+\+/gs
    && $result[$i] =~ m/$query/)
        {
        $r = $result[$i];
        # $r =~ s/^[0-9\.\- ]*<\/</;
        $r =~ s/:=<\/:=</g;
        $r =~ s/:=>\/:=>/g;
        print PRIMEGLOBFILE "$r\n";
        }
    }
    $nprunedkeys = keys %glob;
print PRIMEGLOBFILE "</fano:ranking>\n";
}

_____
sub makePrimes
{
my $n = 0;
print "generating primes up to $maxprime\n";

for ($i=1;$i<=$maxprime;$i++)
    {
    $isprime[$i]=1;
    }
for ($i=2;$i<=$maxprime;$i++)
# for ($i=3;$i<=$maxprime;$i++) # if firstprime is 3;
    { if ($isprime[$i]==1)
        {
```

```perl
            $prime[$n++] = $i;
            # $prime[$n++] = $i if $i != 4; #if first prime is 3;
            for ($j=$i;$j<=$maxprime;$j+=$i)
                {
                    $isprime[$j]=0;
                }
        }

}
    # for ($i=0;$i<=$maxprime;$i++){print $prime[$i];<STDIN>};

}
_____
sub assign
{
my $i;
die "ERROR BAD XML Precision failure for \$p = $p (not an integer)" if ($p =~ m/[-.eE]/gs);

$p =~ s/^0//gs;
$p =~ s/\+0//gs;
$p =~ s/\+\+/+/gs while $p =~ m/\+\+/gs;
$p =~ s/^\+//gs;

@order = (split '\+',$p);
@order = sort {$a <=> $b} @order;

$p = '+';
    for ($i=0;$i<=$#order;$i++)
        {
            $p .= $order[$i].'+';
        }
$p =~ s/(\+)+/+/gs;

$_ = $p;

@o = m/\+/gs;
return if $#o <= $lowplets || $#o > $maxnestates;

print "$p $incidents{$p}\n";

# Since we split the space, we always look at max 3 and min 3 items and
# generate conjoints with them, double-sampling can occur.
```

```
#We will remove redundant counts.
if ($duplicates ne 'on' && $incidents{$p} =~ m/ $record( |$)/gs)
    {
print
# "Scrap duplicate $p x $glob{$p} record $record\n";
    return;
    }

$glob{$p}++;

$incs = ' '.$record;
# $incs .= '.'.$sample if $sample > 0;
$incidents{$p} .= $incs;
$calls++;
        die "ERROR BAD XML ASSIGN Processed bad globcode $p"
            if $p =~ m/\+\+/gs || $p =~ m/\+0/gs;
}
_____
sub mill
{
my ($i, $start, $step, $it);
my $count = 0;
# print "$mf entering mill with $items items\n";
$it = $items;
$it = 10 if $it > 10;
$i = "explicit $it of $items items";
set just for report to indicate explicit part of mill $biguse = $bigproduct;

$p =$mf;
return if $items <= 1;

if ($items>10) #set up parameters for integer division algorithm
    {
    print
        "Assign $items biggest event codes of $list to treat explicitly\n";

$p = $mf; &assign;

print
        "Assign list of $items minus biggest 10 primes of $list as root\n";
```

```
$nmf = 1 if $nmf<1;
$p = $biguse = $bigproduct/$nmf;

&assign;

$u = $biguse;
$u =~ s/\+//;

$bigfsqrtp = Math::BigFloat -> new($u)
    -> fsqrt(20);   #not sqrt() for big integer use $bigsqrtp = '+'.$bigfsqrtp;
$bigsqrtp =~ s/\..*//; #convert format to big integer
}

Pairs already counted in this version (done for whole record!)

$p = $mf1;&assign;
$p = $mf2;&assign;

# $p = $mf1 .'+'. $mf2;&assign;
return if $items <= 2;##########################
#_____
    ## $p = $mf3;&assign;
    # $p = $mf1 .'+'. $mf3;&assign;
    # $p = $mf2 .'+'. $mf3;&assign;
    $p = $mf1 .'+'. $mf2 .'+'. $mf3;&assign;

return if $items <= 3;##########################
#_____
    ## $p = $mf4;&assign;
    # $p = $mf4 .'+'. $mf1;&assign;
    # $p = $mf4 .'+'. $mf2;&assign;
    # $p = $mf4 .'+'. $mf3;&assign;
    $p = $mf4 .'+'. $mf1 .'+'. $mf2;&assign;
    $p = $mf4 .'+'. $mf1 .'+'. $mf3;&assign;
    $p = $mf4 .'+'. $mf2 .'+'. $mf3;&assign;
```

```
$p = $mf4 .'+'. $mf1 .'+'. $mf2 .'+'. $mf3;&assign;
``` return if $items <= 4;###############################
_____

```
$p = $mf5;&assign;
# $p = $mf5 .'+'. $mf1;&assign;
# $p = $mf5 .'+'. $mf2;&assign;
# $p = $mf5 .'+'. $mf3;&assign;
$p = $mf5 .'+'. $mf1 .'+'. $mf2;&assign;
$p = $mf5 .'+'. $mf1 .'+'. $mf3;&assign;
$p = $mf5 .'+'. $mf2 .'+'. $mf3;&assign;
$p = $mf5 .'+'. $mf1 .'+'. $mf2 .'+'. $mf3;&assign;
```

_____

```
# $p = $mf54;&assign;
$p = $mf54 .'+'. $mf1;&assign;
$p = $mf54 .'+'. $mf2;&assign;
$p = $mf54 .'+'. $mf3;&assign;
$p = $mf54 .'+'. $mf1 .'+'. $mf2;&assign;
$p = $mf54 .'+'. $mf1 .'+'. $mf3;&assign;
$p = $mf54 .'+'. $mf2 .'+'. $mf3;&assign;
$p = $mf54 .'+'. $mf1 .'+'. $mf2 .'+'. $mf3;&assign;
``` return if $items <= 5;###############################
_____

```
##$p = $mf6;&assign;
# $p = $mf6 .'+'. $mf1;&assign;
# $p = $mf6 .'+'. $mf2;&assign;
```
_____

```
# $p = $mf6 .'+'. $mf3;&assign;
$p = $mf6 .'+'. $mf1 .'+'. $mf2;&assign;
$p = $mf6 .'+'. $mf1 .'+'. $mf3;&assign;
$p = $mf6 .'+'. $mf2 .'+'. $mf3;&assign;
$p = $mf6 .'+'. $mf1 .'+'. $mf2 .'+'. $mf3;&assign;
```
_____

```
# $p = $mf64;&assign;
$p = $mf64 .'+'. $mf1;&assign;
$p = $mf64 .'+'. $mf2;&assign;
$p = $mf64 .'+'. $mf3;&assign;
$p = $mf64 .'+'. $mf1 .'+'. $mf2;&assign;
$p = $mf64 .'+'. $mf1 .'+'. $mf3;&assign;
```

```
$p = $mf64 .'+'. $mf2 .'+'. $mf3;&assign;
$p = $mf64 .'+'. $mf1 .'+'. $mf2 .'+'. $mf3;&assign;
```
_____

```
# $p = $mf65;&assign;
$p = $mf65 .'+'. $mf1;&assign;
$p = $mf65 .'+'. $mf2;&assign;
$p = $mf65 .'+'. $mf3;&assign;
$p = $mf65 .'+'. $mf1 .'+'. $mf2;&assign;
$p = $mf65 .'+'. $mf1 .'+'. $mf3;&assign;
$p = $mf65 .'+'. $mf2 .'+'. $mf3;&assign;
$p = $mf65 .'+'. $mf1 .'+'. $mf2 .'+'. $mf3;&assign;
```
_____

```
$p = $mf654;&assign;
$p = $mf654 .'+'. $mf1;&assign;
$p = $mf654 .'+'. $mf2;&assign;
$p = $mf654 .'+'. $mf3;&assign;
$p = $mf654 .'+'. $mf1 .'+'. $mf2;&assign;
$p = $mf654 .'+'. $mf1 .'+'. $mf3;&assign;
$p = $mf654 .'+'. $mf2 .'+'. $mf3;&assign;
$p = $mf654 .'+'. $mf1 .'+'. $mf2 .'+'. $mf3;&assign;
```

```
return if $items <= 6;###########################
```
_____

```
##$p = $mf7;&assign;
# $p = $mf7 .'+'. $mf1;&assign;
# $p = $mf7 .'+'. $mf2;&assign;
```
_____

```
# $p = $mf7 .'+'. $mf3;&assign;
$p = $mf7 .'+'. $mf1 .'+'. $mf2;&assign;
$p = $mf7 .'+'. $mf1 .'+'. $mf3;&assign;
$p = $mf7 .'+'. $mf2 .'+'. $mf3;&assign;
$p = $mf7 .'+'. $mf1 .'+'. $mf2 .'+'. $mf3;&assign;
```
_____

```
# $p = $mf74;&assign;
$p = $mf74 .'+'. $mf1;&assign;
$p = $mf74 .'+'. $mf2;&assign;
$p = $mf74 .'+'. $mf3;&assign;
$p = $mf74 .'+'. $mf1 .'+'. $mf2;&assign;
$p = $mf74 .'+'. $mf1 .'+'. $mf3;&assign;
$p = $mf74 .'+'. $mf2 .'+'. $mf3;&assign;
```

```
$p = $mf74 .'+'. $mf1 .'+'. $mf2 .'+'. $mf3;&assign;
```

\#

```
# $p = $mf75;&assign;
$p = $mf75 .'+'. $mf1;&assign;
$p = $mf75 .'+'. $mf2;&assign;
$p = $mf75 .'+'. $mf3;&assign;
$p = $mf75 .'+'. $mf1 .'+'. $mf2;&assign;
$p = $mf75 .'+'. $mf1 .'+'. $mf3;&assign;
$p = $mf75 .'+'. $mf2 .'+'. $mf3;&assign;
$p = $mf75 .'+'. $mf1 .'+'. $mf2 .'+'. $mf3;&assign;
```

\#

```
$p = $mf754;&assign;
$P = $mf754 .'+'. $mf1;&assign;
$p = $mf754 .'+'. $mf2;&assign;
$p = $mf754 .'+'. $mf3;&assign;
$p = $mf754 .'+'. $mf1 .'+'. $mf2;&assign;
$p = $mf754 .'+'. $mf1 .'+'. $mf3;&assign;
$p = $mf754 .'+'. $mf2 .'+'. $mf3;&assign;
$p = $mf754 .'+'. $mf1 .'+'. $mf2 .'+'. $mf3;&assign;
```

\#

```
# $p = $mf76;&assign;
$p = $mf76 .'+'. $mf1;&assign;
$p = $mf76 .'+'. $mf2;&assign;
```

\#

```
$p = $mf76 .'+'. $mf3;&assign;
$p = $mf76 .'+'. $mf1 .'+'. $mf2;&assign;
$p = $mf76 .'+'. $mf1 .'+'. $mf3;&assign;
$p = $mf76 .'+'. $mf2 .'+'. $mf3;&assign;
$p = $mf76 .'+'. $mf1 .'+'. $mf2 .'+'. $mf3;&assign;
```

\#

```
$p = $mf764;&assign;
$p = $mf764 .'+'. $mf1;&assign;
$p = $mf764 .'+'. $mf2;&assign;
$p = $mf764 .'+'. $mf3;&assign;
$p = $mf764 .'+'. $mf1 .'+'. $mf2;&assign;
$p = $mf764 .'+'. $mf1 .'+'. $mf3;&assign;
$p = $mf764 .'+'. $mf2 .'+'. $mf3;&assign;
$p = $mf764 .'+'. $mf1 .'+'. $mf2 .'+'. $mf3;&assign;
```

\#

```
$p = $mf765;&assign;
$p = $mf765 .'+'. $mf1;&assign;
$p = $mf765 .'+'. $mf2;&assign;
$p = $mf765 .'+'. $mf3;&assign;
$p = $mf765 .'+'. $mf1 .'+'. $mf2;&assign;
$p = $mf765 .'+'. $mf1 .'+'. $mf3;&assign;
$p = $mf765 .'+'. $mf2 .'+'. $mf3;&assign;
$p = $mf765 .'+'. $mf1 .'+'. $mf2 .'+'. $mf3;&assign;

#_____

$p = $mf7654;&assign;
$p = $mf7654 .'+'. $mf1;&assign;
$p = $mf7654 .'+'. $mf2;&assign;
$p = $mf7654 .'+'. $mf3;&assign;
$p = $mf7654 .'+'. $mf1 .'+'. $mf2;&assign;
$p = $mf7654 .'+'. $mf1 .'+'. $mf3;&assign;
$p = $mf7654 .'+'. $mf2 .'+'. $mf3;&assign;
$p = $mf7654 .'+'. $mf1 .'+'. $mf2 .'+'. $mf3;&assign;

return if $items <= 7;###############################
#_____

##$p = $mf8;&assign;
# $p = $mf8 .'+'. $mf1;&assign;
# $p = $mf8 .'+'. $mf2;&assign;
# $p = $mf8 .'+'. $mf3;&assign;
$p = $mf8 .'+'. $mf1 .'+'. $mf2;&assign;
$p = $mf8 .'+'. $mf1 .'+'. $mf3;&assign;
$p = $mf8 .'+'. $mf2 .'+'. $mf3;&assign;
#_____

# $p = $mf84;&assign;
$p = $mf84 .'+'. $mf1;&assign;
$p = $mf84 .'+'. $mf2;&assign;
$p = $mf84 .'+'. $mf3;&assign;
$p = $mf84 .'+'. $mf1 .'+'. $mf2;&assign;
$p = $mf84 .'+'. $mf1 .'+'. $mf3;&assign;
$p = $mf84 .'+'. $mf2 .'+'. $mf3;&assign;
$p = $mf84 .'+'. $mf1 .'+'. $mf2 .'+'. $mf3;&assign;
#_____

# $p = $mf85;&assign;
$p = $mf85 .'+'. $mf1;&assign;
$p = $mf85 .'+'. $mf2;&assign;
```

```
$p = $mf85 .'+'. $mf3;&assign;
$p = $mf85 .'+'. $mf1 .'+'. $mf2;&assign;
$p = $mf85 .'+'. $mf1 .'+'. $mf3;&assign;
$p = $mf85 .'+'. $mf2 .'+'. $mf3;&assign;
$p = $mf85 .'+'. $mf1 .'+'. $mf2 .'+'. $mf3;&assign;

$p = $mf854;&assign;
$p = $mf854 .'+'. $mf1;&assign;
$p = $mf854 .'+'. $mf2;&assign;
$p = $mf854 .'+'. $mf3;&assign;
$p = $mf854 .'+'. $mf1 .'+'. $mf2;&assign;
$p = $mf854 .'+'. $mf1 .'+'. $mf3;&assign;
$p = $mf854 .'+'. $mf2 .'+'. $mf3;&assign;
$p = $mf854 .'+'. $mf1 .'+'. $mf2 .'+'. $mf3;&assign;

# $p = $mf86;&assign;
$p = $mf86 .'+'. $mf1;&assign;
$p = $mf86 .'+'. $mf2;&assign;

$p = $mf86 .'+'. $mf3;&assign;
$p = $mf86 .'+'. $mf1 .'+'. $mf2;&assign;
$p = $mf86 .'+'. $mf1 .'+'. $mf3;&assign;
$p = $mf86 .'+'. $mf2 .'+'. $mf3;&assign;
$p = $mf86 .'+'. $mf1 .'+'. $mf2 .'+'. $mf3;&assign;

$p = $mf864;&assign;
$p = $mf864 .'+'. $mf1;&assign;
$p = $mf864 .'+'. $mf2;&assign;
$p = $mf864 .'+'. $mf3;&assign;
$p = $mf864 .'+'. $mf1 .'+'. $mf2;&assign;
$p = $mf864 .'+'. $mf1 .'+'. $mf3;&assign;
$p = $mf864 .'+'. $mf2 .'+'. $mf3;&assign;
$p = $mf864 .'+'. $mf1 .'+'. $mf2 .'+'. $mf3;&assign;

$p = $mf865;&assign;
$p = $mf865 .'+'. $mf1;&assign;
$p = $mf865 .'+'. $mf2;&assign;
$p = $mf865 .'+'. $mf3;&assign;
$p = $mf865 .'+'. $mf1 .'+'. $mf2;&assign;
$p = $mf865 .'+'. $mf1 .'+'. $mf3;&assign;
$p = $mf865 .'+'. $mf2 .'+'. $mf3;&assign;
```

```
    $p = $mf865 .'+'. $mf1 .'+'. $mf2 .'+'. $mf3;&assign;

$p = $mf8654;&assign;
    $p = $mf8654 .'+'. $mf1;&assign;
    $p = $mf8654 .'+'. $mf2;&assign;
    $p = $mf8654 .'+'. $mf3;&assign;
    $p = $mf8654 .'+'. $mf1 .'+'. $mf2;&assign;
    $p = $mf8654 .'+'. $mf1 .'+'. $mf3;&assign;
    $p = $mf8654 .'+'. $mf2 .'+'. $mf3;&assign;
    $p = $mf8654.'+'. $mf1 .'+'. $mf2 .'+'. $mf3;&assign;

# $p = $mf87;&assign;
    $p = $mf87 .'+'. $mf1;&assign;
    $p = $mf87 .'+'. $mf2;&assign;

$p = $mf87 .'+'. $mf3;&assign;
    $p = $mf87 .'+'. $mf1 .'+'. $mf2;&assign;
    $p = $mf87 .'+'. $mf1 .'+'. $mf3;&assign;
    $p = $mf87 .'+'. $mf2 .'+'. $mf3;&assign;
    $p = $mf87 .'+'. $mf1 .'+'. $mf2 .'+'. $mf3;&assign;

$p = $mf874;&assign;
    $p = $mf874 .'+'. $mf1;&assign;
    $p = $mf874 .'+'. $mf2;&assign;
    $p = $mf874 .'+'. $mf3;&assign;
    $p = $mf874 .'+'. $mf1 .'+'. $mf2;&assign;
    $p = $mf874 .'+'. $mf1 .'+'. $mf3;&assign;
    $p = $mf874 .'+'. $mf2 .'+'. $mf3;&assign;
    $p = $mf874 .'+'. $mf1 .'+'. $mf2 .'+'. $mf3;&assign;

$p = $mf875;&assign;
    $p = $mf875 .'+'. $mf1;&assign;
    $p = $mf875 .'+'. $mf2;&assign;
    $p = $mf875 .'+'. $mf3;&assign;
    $p = $mf875 .'+'. $mf1 .'+'. $mf2;&assign;
    $p = $mf875 .'+'. $mf1 .'+'. $mf3;&assign;
    $p = $mf875 .'+'. $mf2 .'+'. $mf3;&assign;
    $p = $mf875 .'+'. $mf1 .'+'. $mf2 .'+'. $mf3;&assign;

```

```
    $p = $mf8754;&assign;
    $p = $mf8754 .'+'. $mf1;&assign;
    $p = $mf8754 .'+'. $mf2;&assign;
    $p = $mf8754 .'+'. $mf3;&assign;
    $p = $mf8754 .'+'. $mf1 .'+'. $mf2;&assign;
    $p = $mf8754 .'+'. $mf1 .'+'. $mf3;&assign;
    $p = $mf8754 .'+'. $mf2 .'+'. $mf3;&assign;
#_____

$p = $mf876;&assign;
    $p = $mf876 .'+'. $mf1;&assign;
    $p = $mf876 .'+'. $mf2;&assign;
#_____

$p = $mf876 .'+'. $mf3;&assign;
    $p = $mf876 .'+'. $mf1 .'+'. $mf2;&assign;
    $p = $mf876 .'+'. $mf1 .'+'. $mf3;&assign;
    $p = $mf876 .'+'. $mf2 .'+'. $mf3;&assign;
    $p = $mf876 .'+'. $mf1 .'+'. $mf2 .'+'. $mf3;&assign;
#_____

$p = $mf8764;&assign;
    $p = $mf8764 .'+'. $mf1;&assign;
    $p = $mf8764 .'+'. $mf2;&assign;
    $p = $mf8764 .'+'. $mf3;&assign;
    $p = $mf8764 .'+'. $mf1 .'+'. $mf2;&assign;
    $p = $mf8764 .'+'. $mf1 .'+'. $mf3;&assign;
    $p = $mf8764 .'+'. $mf2 .'+'. $mf3;&assign;
    $p = $mf8764 .'+'. $mf1 .'+'. $mf2 .'+'. $mf3;&assign;
#_____

$p = $mf8765;&assign;
    $p = $mf8765 .'+'. $mf1;&assign;
    $p = $mf8765 .'+'. $mf2;&assign;
    $p = $mf8765 .'+'. $mf3;&assign;
    $p = $mf8765 .'+'. $mf1 .'+'. $mf2;&assign;
    $p = $mf8765 .'+'. $mf1 .'+'. $mf3;&assign;
    $p = $mf8765 .'+'. $mf2 .'+'. $mf3;&assign;
    $p = $mf8765 .'+'. $mf1 .'+'. $mf2 .'+'. $mf3;&assign;
#_____

$p = $mf87654;&assign;
    $p = $mf87654 .'+'. $mf1;&assign;
    $p = $mf87654 .'+'. $mf2;&assign;
    $p = $mf87654 .'+'. $mf3;&assign;
    $p = $mf87654 .'+'. $mf1 .'+'. $mf2;&assign;
```

```
    $p = $mf87654 .'+'. $mf1 .'+'. $mf3;&assign;
    $p = $mf87654 .'+'. $mf2 .'+'. $mf3;&assign;
    $p = $mf87654 .'+'. $mf1 .'+'. $mf2 .'+'. $mf3;&assign;
return if $items <= 8;###########################

    ##$p = $mf9;&assign;
    # $p = $mf9 .'+'. $mf1;&assign;
    # $p = $mf9 .'+'. $mf2;&assign;

# $p = $mf9 .'+'. $mf3;&assign;
    $p = $mf9 .'+'. $mf1 .'+'. $mf2;&assign;
    $p = $mf9 .'+'. $mf1 .'+'. $mf3;&assign;
    $p = $mf9 .'+'. $mf2 .'+'. $mf3;&assign;
    $p = $mf9 .'+'. $mf1 .'+'. $mf2 .'+'. $mf3;&assign;

# $p = $mf94;&assign;
    $p = $mf94 .'+'. $mf1;&assign;
    $p = $mf94 .'+'. $mf2;&assign;
    $p = $mf94 .'+'. $mf3;&assign;
    $p = $mf94 .'+'. $mf1 .'+'. $mf2;&assign;
    $p = $mf94 .'+'. $mf1 .'+'. $mf3;&assign;
    $p = $mf94 .'+'. $mf2 .'+'. $mf3;&assign;
    $p = $mf94 .'+'. $mf1 .'+'. $mf2 .'+'. $mf3;&assign;

# $p = $mf95;&assign;
    $p = $mf95 .'+'. $mf1;&assign;
    $p = $mf95 .'+'. $mf2;&assign;
    $p = $mf95 .'+'. $mf3;&assign;
    $p = $mf95 .'+'. $mf1 .'+'. $mf2;&assign;
    $p = $mf95 .'+'. $mf1 .'+'. $mf3;&assign;
    $p = $mf95 .'+'. $mf2 .'+'. $mf3;&assign;
    $p = $mf95 .'+'. $mf1 .'+'. $mf2 .'+'. $mf3;&assign;

$p = $mf954;&assign;
    $p = $mf954 .'+'. $mf1;&assign;
    $p = $mf954 .'+'. $mf2;&assign;
    $p = $mf954 .'+'. $mf3;&assign;
    $p = $mf954 .'+'. $mf1 .'+'. $mf2;&assign;
    $p = $mf954 .'+'. $mf1 .'+'. $mf3;&assign;
    $p = $mf954 .'+'. $mf2 .'+'. $mf3;&assign;
    $p = $mf954 .'+'. $mf1 .'+'. $mf2 .'+'. $mf3;&assign;
```

```

    # $p = $mf96;&assign;
    $p = $mf96 .'+'. $mf1;&assign;
    $p = $mf96 .'+'. $mf2;&assign;

$p = $mf96 .'+'. $mf3;&assign;
    $p = $mf96 .'+'. $mf1 .'+'. $mf2;&assign;
    $p = $mf96 .'+'. $mf1 .'+'. $mf3;&assign;
    $p = $mf96 .'+'. $mf2 .'+'. $mf3;&assign;

$p = $mf964;&assign;
    $p = $mf964 .'+'. $mf1;&assign;
    $p = $mf964 .'+'. $mf2;&assign;
    $p = $mf964 .'+'. $mf3;&assign;
    $p = $mf964 .'+'. $mf1 .'+'. $mf2;&assign;
    $p = $mf964 .'+'. $mf1 .'+'. $mf3;&assign;
    $p = $mf964 .'+'. $mf2 .'+'. $mf3;&assign;
    $p = $mf964 .'+'. $mf1 .'+'. $mf2 .'+'. $mf3;&assign;

$p = $mf965;&assign;
    $p = $mf965 .'+'. $mf1;&assign;
    $p = $mf965 .'+'. $mf2;&assign;
    $p = $mf965 .'+'. $mf3;&assign;
    $p = $mf965 .'+'. $mf1 .'+'. $mf2;&assign;
    $p = $mf965 .'+'. $mf1 .'+'. $mf3;&assign;
    $p = $mf965 .'+'. $mf2 .'+'. $mf3;&assign;
    $p = $mf965 .'+'. $mf1 .'+'. $mf2 .'+'. $mf3;&assign;

$p = $mf9654;&assign;
    $p = $mf9654 .'+'. $mf1;&assign;
    $p = $mf9654 .'+'. $mf2;&assign;
    $p = $mf9654 .'+'. $mf3;&assign;
    $p = $mf9654 .'+'. $mf1 .'+'. $mf2;&assign;
    $p = $mf9654 .'+'. $mf1 .'+'. $mf3;&assign;
    $p = $mf9654 .'+'. $mf2 .'+'. $mf3;&assign;
    $p = $mf9654 .'+'. $mf1 .'+'. $mf2 .'+'. $mf3;&assign;

# $p = $mf97;&assign;
    $p = $mf97 .'+'. $mf1;&assign;
```

```
$p = $mf97 .'+'. $mf2;&assign;
```

\#_____

```
$p = $mf97 .'+'. $mf3;&assign;
$p = $mf97 .'+'. $mf1 .'+'. $mf2;&assign;
$p = $mf97 .'+'. $mf1 .'+'. $mf3;&assign;
$p = $mf97 .'+'. $mf2 .'+'. $mf3;&assign;
$p = $mf97 .'+'. $mf1 .'+'. $mf2 .'+'. $mf3;&assign;
```

\#_____

```
$p = $mf974;&assign;
$p = $mf974 .'+'. $mf1;&assign;
$p = $mf974 .'+'. $mf2;&assign;
$p = $mf974 .'+'. $mf3;&assign;
$p = $mf974 .'+'. $mf1 .'+'. $mf2;&assign;
$p = $mf974 .'+'. $mf1 .'+'. $mf3;&assign;
$p = $mf974 .'+'. $mf2 .'+'. $mf3;&assign;
$p = $mf974 .'+'. $mf1 .'+'. $mf2 .'+'. $mf3;&assign;
```

\#_____

```
$p = $mf975;&assign;
$p = $mf975 .'+'. $mf1;&assign;
$p = $mf975 .'+'. $mf2;&assign;
$p = $mf975 .'+'. $mf3;&assign;
$p = $mf975 .'+'. $mf1 .'+'. $mf2;&assign;
$p = $mf975 .'+'. $mf1 .'+'. $mf3;&assign;
$p = $mf975 .'+'. $mf2 .'+'. $mf3;&assign;
$p = $mf975 .'+'. $mf1 .'+'. $mf2 .'+'. $mf3;&assign;
```

\#_____

```
$p = $mf9754;&assign;
$p = $mf9754 .'+'. $mf1;&assign;
$p = $mf9754 .'+'. $mf2;&assign;
$p = $mf9754 .'+'. $mf3;&assign;
$p = $mf9754 .'+'. $mf1 .'+'. $mf2;&assign;
$p = $mf9754 .'+'. $mf1 .'+'. $mf3;&assign;
$p = $mf9754 .'+'. $mf2 .'+'. $mf3;&assign;
$p = $mf9754 .'+'. $mf1 .'+'. $mf2 .'+'. $mf3;&assign;
```

\#_____

```
$p = $mf976;&assign;
$p = $mf976 .'+'. $mf1;&assign;
$p = $mf976 .'+'. $mf2;&assign;
```

\#_____

```
$p = $mf976 .'+'. $mf3;&assign;
$p = $mf976 .'+'. $mf1 .'+'. $mf2;&assign;
$p = $mf976 .'+'. $mf1 .'+'. $mf3;&assign;
$p = $mf976 .'+'. $mf2 .'+'. $mf3;&assign;
$p = $mf976 .'+'. $mf1 .'+'. $mf2 .'+'. $mf3;&assign;

$p = $mf9764;&assign;
$p = $mf9764 .'+'. $mf1;&assign;
$p = $mf9764 .'+'. $mf2;&assign;
$p = $mf9764 .'+'. $mf3;&assign;
$p = $mf9764 .'+'. $mf1 .'+'. $mf2;&assign;
$p = $mf9764 .'+'. $mf1 .'+'. $mf3;&assign;
$p = $mf9764 .'+'. $mf2 .'+'. $mf3;&assign;
$p = $mf9764 .'+'. $mf1 .'+'. $mf2 .'+'. $mf3;&assign;

$p = $mf9765;&assign;
$p = $mf9765 .'+'. $mf1;&assign;
$p = $mf9765 .'+'. $mf2;&assign;
$p = $mf9765 .'+'. $mf3;&assign;
$p = $mf9765 .'+'. $mf1 .'+'. $mf2;&assign;
$p = $mf9765 .'+'. $mf1 .'+'. $mf3;&assign;
$p = $mf9765 .'+'. $mf2 .'+'. $mf3;&assign;
$p = $mf9765 .'+'. $mf1 .'+'. $mf2 .'+'. $mf3;&assign;

$p = $mf97654;&assign;
$p = $mf97654 .'+'. $mf1;&assign;
$p = $mf97654 .'+'. $mf2;&assign;
$p = $mf97654 .'+'. $mf3;&assign;
$p = $mf97654 .'+'. $mf1 .'+'. $mf2;&assign;
$p = $mf97654 .'+'. $mf1 .'+'. $mf3;&assign;
$p = $mf97654 .'+'. $mf2 .'+'. $mf3;&assign;
$p = $mf97654 .'+'. $mf1 .'+'. $mf2 .'+'. $mf3;&assign;

# $p = $mf98;&assign;
$p = $mf98 .'+'. $mf3;&assign;
$p = $mf98 .'+'. $mf1 .'+'. $mf2;&assign;
$p = $mf98 .'+'. $mf1 .'+'. $mf3;&assign;
$p = $mf98 .'+'. $mf2 .'+'. $mf3;&assign;

$p = $mf984;&assign;
```

```
$p = $mf984 .'+'. $mf1;&assign;
$p = $mf984 .'+'. $mf2;&assign;
$p = $mf984 .'+'. $mf3;&assign;
$p = $mf984 .'+'. $mf1 .'+'. $mf2;&assign;
$p = $mf984 .'+'. $mf1 .'+'. $mf3;&assign;
$p = $mf984 .'+'. $mf2 .'+'. $mf3;&assign;
$p = $mf984 .'+'. $mf1 .'+'. $mf2 .'+'. $mf3;&assign;

$p = $mf985;&assign;
$p = $mf985 .'+'. $mf1;&assign;
$p = $mf985 .'+'. $mf2;&assign;
$p = $mf985 .'+'. $mf3;&assign;
$p = $mf985 .'+'. $mf1 .'+'. $mf2;&assign;
$p = $mf985 .'+'. $mf1 .'+'. $mf3;&assign;
$p = $mf985 .'+'. $mf2 .'+'. $mf3;&assign;
$p = $mf985 .'+'. $mf1 .'+'. $mf2 .'+'. $mf3;&assign;

$p = $mf9854;&assign;
$p = $mf9854 .'+'. $mf1;&assign;
$p = $mf9854 .'+'. $mf2;&assign;
$p = $mf9854 .'+'. $mf3;&assign;
$p = $mf9854 .'+'. $mf1 .'+'. $mf2;&assign;
$p = $mf9854 .'+'. $mf1 .'+'. $mf3;&assign;
$p = $mf9854 .'+'. $mf2 .'+'. $mf3;&assign;
$p = $mf9854 .'+'. $mf1 .'+'. $mf2 .'+'. $mf3;&assign;

$p = $mf986;&assign;
$p = $mf986 .'+'. $mf1;&assign;
$p = $mf986 .'+'. $mf2;&assign;

$p = $mf986 .'+'. $mf3;&assign;
$p = $mf986 .'+'. $mf1 .'+'. $mf2;&assign;
$p = $mf986 .'+'. $mf1 .'+'. $mf3;&assign;
$p = $mf986 .'+'. $mf2 .'+'. $mf3;&assign;
$p = $mf986 .'+'. $mf1 .'+'. $mf2 .'+'. $mf3;&assign;

$p = $mf9864;&assign;
$p = $mf9864 .'+'. $mf1;&assign;
$p = $mf9864 .'+'. $mf2;&assign;
$p = $mf9864 .'+'. $mf3;&assign;
$p = $mf9864 .'+'. $mf1 .'+'. $mf2;&assign;
```

```
$p = $mf9864 .'+'. $mf1 .'+'. $mf3;&assign;
$p = $mf9864 .'+'. $mf2 .'+'. $mf3;&assign;
$p = $mf9876 .'+'. $mf1 .'+'. $mf2 .'+'. $mf3;&assign;
```

```
$p = $mf9865;&assign;
$p = $mf9865 .'+'. $mf1;&assign;
$p = $mf9865 .'+'. $mf2;&assign;
$p = $mf9865 .'+'. $mf3;&assign;
$p = $mf9865 .'+'. $mf1 .'+'. $mf2;&assign;
$p = $mf9865 .'+'. $mf1 .'+'. $mf3;&assign;
$p = $mf9865 .'+'. $mf2 .'+'. $mf3;&assign;
$p = $mf9865 .'+'. $mf1 .'+'. $mf2 .'+'. $mf3;&assign;
```

```
$p = $mf98654;&assign;
$p = $mf98654 .'+'. $mf1;&assign;
$p = $mf98654 .'+'. $mf2;&assign;
$p = $mf98654 .'+'. $mf3;&assign;
$p = $mf98654 .'+'. $mf1 .'+'. $mf2;&assign;
$p = $mf98654 .'+'. $mf1 .'+'. $mf3;&assign;
$p = $mf98654 .'+'. $mf2 .'+'. $mf3;&assign;
$p = $mf98654 .'+'. $mf1 .'+'. $mf2 .'+'. $mf3;&assign;
```

```
$p = $mf987;&assign;
$p = $mf987 .'+'. $mf1;&assign;
$p = $mf987 .'+'. $mf2;&assign;
```

```
$p = $mf987 .'+'. $mf3;&assign;
$p = $mf987 .'+'. $mf1 .'+'. $mf2;&assign;
$p = $mf987 .'+'. $mf1 .'+'. $mf3;&assign;
$p = $mf987 .'+'. $mf2 .'+'. $mf3;&assign;
$p = $mf987 .'+'. $mf1 .'+'. $mf2 .'+'. $mf3;&assign;
```

```
$p = $mf9874;&assign;
$p = $mf9874 .'+'. $mf1;&assign;
$p = $mf9874 .'+'. $mf2;&assign;
$p = $mf9874 .'+'. $mf3;&assign;
$p = $mf9874 .'+'. $mf1 .'+'. $mf2;&assign;
$p = $mf9874 .'+'. $mf1 .'+'. $mf3;&assign;
```

```
$p = $mf9874 .'+'. $mf2 .'+'. $mf3;&assign;
$p = $mf9874 .'+'. $mf1 .'+'. $mf2 .'+'. $mf3;&assign;

```

```
$p = $mf9875;&assign;
$p = $mf9875 .'+'. $mf1;&assign;
$p = $mf9875 .'+'. $mf2;&assign;
$p = $mf9875 .'+'. $mf3;&assign;
$p = $mf9875 .'+'. $mf1 .'+'. $mf2;&assign;
$p = $mf9875 .'+'. $mf1 .'+'. $mf3;&assign;
$p = $mf9875 .'+'. $mf2 .'+'. $mf3;&assign;
$p = $mf9875 .'+'. $mf1 .'+'. $mf2 .'+'. $mf3;&assign;

```

```
$p = $mf98754;&assign;
$p = $mf98754 .'+'. $mf1;&assign;
$p = $mf98754 .'+'. $mf2;&assign;
$p = $mf98754 .'+'. $mf3;&assign;
$p = $mf98754 .'+'. $mf1 .'+'. $mf2;&assign;
$p = $mf98754 .'+'. $mf1 .'+'. $mf3;&assign;
$p = $mf98754 .'+'. $mf2 .'+'. $mf3;&assign;
$p = $mf98754 .'+'. $mf1 .'+'. $mf2 .'+'. $mf3;&assign;

```

```
$p = $mf9876;&assign;
$p = $mf9876 .'+'. $mf1;&assign;
$p = $mf9876 .'+'. $mf2;&assign;

```

```
$p = $mf9876 .'+'. $mf3;&assign;
$p = $mf9876 .'+'. $mf1 .'+'. $mf2;&assign;
$p = $mf9876 .'+'. $mf1 .'+'. $mf3;&assign;
$p = $mf9876 .'+'. $mf2 .'+'. $mf3;&assign;
$p = $mf9876 .'+'. $mf1 .'+'. $mf2 .'+'. $mf3;&assign;

```

```
$p = $mf98764;&assign;
$p = $mf98764 .'+'. $mf1;&assign;
$p = $mf98764 .'+'. $mf2;&assign;
$p = $mf98764 .'+'. $mf3;&assign;
$p = $mf98764 .'+'. $mf1 .'+'. $mf2;&assign;
$p = $mf98764 .'+'. $mf1 .'+'. $mf3;&assign;
$p = $mf98764 .'+'. $mf2 .'+'. $mf3;&assign;
$p = $mf98764 .'+'. $mf1 .'+'. $mf2 .'+'. $mf3;&assign;

```

```
    $p = $mf98765;&assign;
    $p = $mf98765 .'+'. $mf1;&assign;
    $p = $mf98765 .'+'. $mf2;&assign;
    $p = $mf98765 .'+'. $mf3;&assign;
    $p = $mf98765 .'+'. $mf1 .'+'. $mf2;&assign;
    $p = $mf98765 .'+'. $mf1 .'+'. $mf3;&assign;
    $p = $mf98765 .'+'. $mf2 .'+'. $mf3;&assign;
    $p = $mf98765 .'+'. $mf1 .'+'. $mf2 .'+'. $mf3;&assign;
#_____

$p = $mf987654;&assign;
    $p = $mf987654 .'+'. $mf1;&assign;
    $p = $mf987654 .'+'. $mf2;&assign;
    $p = $mf987654 .'+'. $mf3;&assign;
    $p = $mf987654 .'+'. $mf1 .'+'. $mf2;&assign;
    $p = $mf987654 .'+'. $mf1 .'+'. $mf3;&assign;
    $p = $mf987654 .'+'. $mf2 .'+'. $mf3;&assign;
    $p = $mf987654 .'+'. $mf1 .'+'. $mf2 .'+'. $mf3;&assign;
return if $items <= 9;#############################
#_____

##$p = $mf10;&assign;
    # $p = $mf10 .'+'. $mf1;&assign;
    # $p = $mf10 .'+'. $mf2;&assign;
#_____

# $p = $mf10 .'+'. $mf3;&assign;
    $p = $mf10 .'+'. $mf1 .'+'. $mf2;&assign;
    $p = $mf10 .'+'. $mf1 .'+'. $mf3;&assign;
    $p = $mf10 .'+'. $mf2 .'+'. $mf3;&assign;
    $p = $mf10 .'+'. $mf1 .'+'. $mf2 .'+'. $mf3;&assign;
#_____

# $p = $mf104;&assign;
    $p = $mf104 .'+'. $mf1;&assign;
    $p = $mf104 .'+'. $mf2;&assign;
    $p = $mf104 .'+'. $mf3;&assign;
    $p = $mf104 .'+'. $mf1 .'+'. $mf2;&assign;
    $p = $mf104 .'+'. $mf1 .'+'. $mf3;&assign;
    $p = $mf104 .'+'. $mf2 .'+'. $mf3;&assign;
    $p = $mf104 .'+'. $mf1 .'+'. $mf2 .'+'. $mf3;&assign;
#_____

# $p = $mf105;&assign;
    $p = $mf105 .'+'. $mf1;&assign;
    $p = $mf105 .'+'. $mf2;&assign;
```

```
    $p = $mf105 .'+'. $mf3;&assign;
    $p = $mf105 .'+'. $mf1 .'+'. $mf2;&assign;
    $p = $mf105 .'+'. $mf1 .'+'. $mf3;&assign;
    $p = $mf105 .'+'. $mf2 .'+'. $mf3;&assign;
    $p = $mf105 .'+'. $mf1 .'+'. $mf2 .'+'. $mf3;&assign;

$p = $mf1054;&assign;
    $p = $mf1054 .'+'. $mf1;&assign;
    $p = $mf1054 .'+'. $mf2;&assign;
    $p = $mf1054 .'+'. $mf3;&assign;
    $p = $mf1054 .'+'. $mf1 .'+'. $mf2;&assign;
    $p = $mf1054 .'+'. $mf1 .'+'. $mf3;&assign;
    $p = $mf1054 .'+'. $mf2 .'+'. $mf3;&assign;
    $p = $mf1054 .'+'. $mf1 .'+'. $mf2 .'+'. $mf3;&assign;

# $p = $mf106;&assign;
    $p = $mf106 .'+'. $mf1;&assign;
    $p = $mf106 .'+'. $mf2;&assign;

$p = $mf106 .'+'. $mf3;&assign;
    $p = $mf106 .'+'. $mf1 .'+'. $mf2;&assign;
    $p = $mf106 .'+'. $mf1 .'+'. $mf3;&assign;
    $p = $mf106 .'+'. $mf2 .'+'. $mf3;&assign;
    $p = $mf106 .'+'. $mf1 .'+'. $mf2 .'+'. $mf3;&assign;

$p = $mf1064;&assign;
    $p = $mf1064 .'+'. $mf1;&assign;
    $p = $mf1064 .'+'. $mf2;&assign;
    $p = $mf1064 .'+'. $mf3;&assign;
    $p = $mf1064 .'+'. $mf1 .'+'. $mf2;&assign;
    $p = $mf1064 .'+'. $mf1 .'+'. $mf3;&assign;
    $p = $mf1064 .'+'. $mf2 .'+'. $mf3;&assign;
    $p = $mf1064 .'+'. $mf1 .'+'. $mf2 .'+'. $mf3;&assign;

$p = $mf1065;&assign;
    $p = $mf1065 .'+'. $mf1;&assign;
    $p = $mf1065 .'+'. $mf2;&assign;
    $p = $mf1065 .'+'. $mf3;&assign;
    $p = $mf1065 .'+'. $mf1 .'+'. $mf2;&assign;
    $p = $mf1065 .'+'. $mf1 .'+'. $mf3;&assign;
    $p = $mf1065 .'+'. $mf2 .'+'. $mf3;&assign;
```

```
        $p = $mf1065 .'+'. $mf1 .'+'. $mf2 .'+'. $mf3;&assign;
#_____

$p = $mf10654;&assign;
        $p = $mf10654 .'+'. $mf1;&assign;
        $p = $mf10654 .'+'. $mf2;&assign;
        $p = $mf10654 .'+'. $mf3;&assign;
        $p = $mf10654 .'+'. $mf1 .'+'. $mf2;&assign;
        $p = $mf10654 .'+'. $mf1 .'+'. $mf3;&assign;
        $p = $mf10654 .'+'. $mf2 .'+'. $mf3;&assign;
        $p = $mf10654 .'+'. $mf1 .'+'. $mf2 .'+'. $mf3;&assign;
#_____

# $p = $mf107;&assign;
        $p = $mf107 .'+'. $mf1;&assign;
        $p = $mf107 .'+'. $mf2;&assign;

#_____

$p = $mf107 .'+'. $mf3;&assign;
        $p = $mf107 .'+'. $mf1 .'+'. $mf2;&assign;
        $p = $mf107 .'+'. $mf1 .'+'. $mf3;&assign;
        $p = $mf107 .'+'. $mf2 .'+'. $mf3;&assign;
        $p = $mf107 .'+'. $mf1 .'+'. $mf2 .'+'. $mf3;&assign;
        #_____

$p = $mf1074;&assign;
        $p = $mf1074 .'+'. $mf1;&assign;
        $p = $mf1074 .'+'. $mf2;&assign;
        $p = $mf1074 .'+'. $mf3;&assign;
        $p = $mf1074 .'+'. $mf1 .'+'. $mf2;&assign;
        $p = $mf1074 .'+'. $mf1 .'+'. $mf3;&assign;
        $p = $mf1074 .'+'. $mf2 .'+'. $mf3;&assign;
        $p = $mf1074 .'+'. $mf1 .'+'. $mf2 .'+'. $mf3;&assign;
#_____

$p = $mf1075;&assign;
        $p = $mf1075 .'+'. $mf1;&assign;
        $p = $mf1075 .'+'. $mf2;&assign;
        $p = $mf1075 .'+'. $mf3;&assign;
        $p = $mf1075 .'+'. $mf1 .'+'. $mf2;&assign;
        $p = $mf1075 .'+'. $mf1 .'+'. $mf3;&assign;
        $p = $mf1075 .'+'. $mf2 .'+'. $mf3;&assign;
        $p = $mf1075 .'+'. $mf1 .'+'. $mf2 .'+'. $mf3;&assign;
#_____
```

```
$p = $mf10754;&assign;
$p = $mf10754 .'+'. $mf1;&assign;
$p = $mf10754 .'+'. $mf2;&assign;
$p = $mf10754 .'+'. $mf3;&assign;
$p = $mf10754 .'+'. $mf1 .'+'. $mf2;&assign;
$p = $mf10754 .'+'. $mf1 .'+'. $mf3;&assign;
$p = $mf10754 .'+'. $mf2 .'+'. $mf3;&assign;
$p = $mf10754 .'+'. $mf1 .'+'. $mf2 .'+'. $mf3;&assign;
```

```
$p = $mf1076;&assign;
$p = $mf1076 .'+'. $mf1;&assign;
$p = $mf1076 .'+'. $mf2;&assign;
```

```
$p = $mf1076 .'+'. $mf3;&assign;
$p = $mf1076 .'+'. $mf1 .'+'. $mf2;&assign;
$p = $mf1076 .'+'. $mf1 .'+'. $mf3;&assign;
$p = $mf1076 .'+'. $mf2 .'+'. $mf3;&assign;
$p = $mf1076 .'+'. $mf1 .'+'. $mf2 .'+'. $mf3;&assign;
```

```
$p = $mf10764;&assign;
$p = $mf10764 .'+'. $mf1;&assign;
$p = $mf10764 .'+'. $mf2;&assign;
$p = $mf10764 .'+'. $mf3;&assign;
$p = $mf10764 .'+'. $mf1 .'+'. $mf2;&assign;
$p = $mf10764 .'+'. $mf1 .'+'. $mf3;&assign;
$p = $mf10764 .'+'. $mf2 .'+'. $mf3;&assign;
$p = $mf10764 .'+'. $mf1 .'+'. $mf2 .'+'. $mf3;&assign;
```

```
$p = $mf10765;&assign;
$p = $mf10765 .'+'. $mf1;&assign;
$p = $mf10765 .'+'. $mf2;&assign;
$p = $mf10765 .'+'. $mf3;&assign;
$p = $mf10765 .'+'. $mf1 .'+'. $mf2;&assign;
$p = $mf10765 .'+'. $mf1 .'+'. $mf3;&assign;
$p = $mf10765 .'+'. $mf2 .'+'. $mf3;&assign;
$p = $mf10765 .'+'. $mf1 .'+'. $mf2 .'+'. $mf3;&assign;
```

```
$p = $mf107654;&assign;
$p = $mf107654 .'+'. $mf1;&assign;
$p = $mf107654 .'+'. $mf2;&assign;
$p = $mf107654 .'+'. $mf3;&assign;
```

```
$p = $mf107654 .'+'. $mf1 .'+'. $mf2;&assign;
$p = $mf107654 .'+'. $mf1 .'+'. $mf3;&assign;
$p = $mf107654 .'+'. $mf2 .'+'. $mf3;&assign;
$p = $mf107654 .'+'. $mf1 .'+'. $mf2 .'+'. $mf3;&assign;
```
_____

```
# $p = $mf108;&assign;
$p = $mf108 .'+'. $mf3;&assign;
$p = $mf108 .'+'. $mf1 .'+'. $mf2;&assign;
$p = $mf108 .'+'. $mf1 .'+'. $mf3;&assign;
$p = $mf108 .'+'. $mf2 .'+'. $mf3;&assign;
$p = $mf108 .'+'. $mf1 .'+'. $mf2 .'+'. $mf3;&assign;
```
_____

```
$p = $mf1084;&assign;
$p = $mf1084 .'+'. $mf1;&assign;
$p = $mf1084 .'+'. $mf2;&assign;
$p = $mf1084 .'+'. $mf3;&assign;
$p = $mf1084 .'+'. $mf1 .'+'. $mf2;&assign;
$p = $mf1084 .'+'. $mf1 .'+'. $mf3;&assign;
$p = $mf1084 .'+'. $mf2 .'+'. $mf3;&assign;
$p = $mf1084 .'+'. $mf1 .'+'. $mf2 .'+'. $mf3;&assign;
```
_____

```
$p = $mf1085;&assign;
$p = $mf1085 .'+'. $mf1;&assign;
$p = $mf1085 .'+'. $mf2;&assign;
$p = $mf1085 .'+'. $mf3;&assign;
$p = $mf1085 .'+'. $mf1 .'+'. $mf2;&assign;
$p = $mf1085 .'+'. $mf1 .'+'. $mf3;&assign;
$p = $mf1085 .'+'. $mf2 .'+'. $mf3;&assign;
$p = $mf1085 .'+'. $mf1 .'+'. $mf2 .'+'. $mf3;&assign;
```
_____

```
$p = $mf10854;&assign;
$p = $mf10854 .'+'. $mf1;&assign;
$p = $mf10854 .'+'. $mf2;&assign;
$p = $mf10854 .'+'. $mf3;&assign;
$p = $mf10854 .'+'. $mf1 .'+'. $mf2;&assign;
$p = $mf10854 .'+'. $mf1 .'+'. $mf3;&assign;
$p = $mf10854 .'+'. $mf2 .'+'. $mf3;&assign;
$p = $mf10854 .'+'. $mf1 .'+'. $mf2 .'+'. $mf3;&assign;
```
_____
```
$p = $mf1086;&assign;
$p = $mf1086 .'+'. $mf1;&assign;
```

```
        $p = $mf1086 .'+'. $mf2;&assign;
#_____

$p = $mf1086 .'+'. $mf3;&assign;
        $p = $mf1086 .'+'. $mf1 .'+'. $mf2;&assign;
        $p = $mf1086 .'+'. $mf1 .'+'. $mf3;&assign;
        $p = $mf1086 .'+'. $mf2 .'+'. $mf3;&assign;
        $p = $mf1086 .'+'. $mf1 .'+'. $mf2 .'+'. $mf3;&assign;
#_____

$p = $mf10864;&assign;
        $p = $mf10864 .'+'. $mf1;&assign;
        $p = $mf10864 .'+'. $mf2;&assign;
        $p = $mf10864 .'+'. $mf3;&assign;
        $p = $mf10864 .'+'. $mf1 .'+'. $mf2;&assign;
        $p = $mf10864 .'+'. $mf1 .'+'. $mf3;&assign;
        $p = $mf10864 .'+'. $mf2 .'+'. $mf3;&assign;
        $p = $mf10864 .'+'. $mf1 .'+'. $mf2 .'+'. $mf3;&assign;
#_____

$p = $mf10865;&assign;
        $p = $mf10865 .'+'. $mf1;&assign;
        $p = $mf10865 .'+'. $mf2;&assign;
        $p = $mf10865 .'+'. $mf3;&assign;
        $p = $mf10865 .'+'. $mf1 .'+'. $mf2;&assign;
        $p = $mf10865 .'+'. $mf1 .'+'. $mf3;&assign;
        $p = $mf10865 .'+'. $mf2 .'+'. $mf3;&assign;
        $p = $mf10865 .'+'. $mf1 .'+'. $mf2 .'+'. $mf3;&assign;
#_____

$p = $mf108654;&assign;
        $p = $mf108654 .'+'. $mf1;&assign;
        $p = $mf108654 .'+'. $mf2;&assign;
        $p = $mf108654 .'+'. $mf3;&assign;
        $p = $mf108654 .'+'. $mf1 .'+'. $mf2;&assign;
        $p = $mf108654 .'+'. $mf1 .'+'. $mf3;&assign;
        $p = $mf108654 .'+'. $mf2 .'+'. $mf3;&assign;
        $p = $mf108654 .'+'. $mf1 .'+'. $mf2 .'+'. $mf3;&assign;

#_____

$p = $mf1087;&assign;
        $p = $mf1087 .'+'. $mf1;&assign;
        $p = $mf1087 .'+'. $mf2;&assign;
```

```
$p = $mf1087 .'+'. $mf3;&assign;
$p = $mf1087 .'+'. $mf1 .'+'. $mf2;&assign;
$p = $mf1087 .'+'. $mf1 .'+'. $mf3;&assign;
$p = $mf1087 .'+'. $mf2 .'+'. $mf3;&assign;
$p = $mf1087 .'+'. $mf1 .'+'. $mf2 .'+'. $mf3;&assign;
```

```
$p = $mf10874;&assign;
$p = $mf10874 .'+'. $mf1;&assign;
$p = $mf10874 .'+'. $mf2;&assign;
$p = $mf10874 .'+'. $mf3;&assign;
$p = $mf10874 .'+'. $mf1 .'+'. $mf2;&assign;
$p = $mf10874 .'+'. $mf1 .'+'. $mf3;&assign;
$p = $mf10874 .'+'. $mf2 .'+'. $mf3;&assign;
$p = $mf10874 .'+'. $mf1 .'+'. $mf2 .'+'. $mf3;&assign;
```

```
$p = $mf10875;&assign;
$p = $mf10875 .'+'. $mf1;&assign;
$p = $mf10875 .'+'. $mf2;&assign;
$p = $mf10875 .'+'. $mf3;&assign;
$p = $mf10875 .'+'. $mf1 .'+'. $mf2;&assign;
$p = $mf10875 .'+'. $mf1 .'+'. $mf3;&assign;
$p = $mf10875 .'+'. $mf2 .'+'. $mf3;&assign;
$p = $mf10875 .'+'. $mf1 .'+'. $mf2 .'+'. $mf3;&assign;
```

```
$p = $mf108754;&assign;
$p = $mf108754 .'+'. $mf1;&assign;
$p = $mf108754 .'+'. $mf2;&assign;
$p = $mf108754 .'+'. $mf3;&assign;
$p = $mf108754 .'+'. $mf1 .'+'. $mf2;&assign;
$p = $mf108754 .'+'. $mf1 .'+'. $mf3;&assign;
$p = $mf108754 .'+'. $mf2 .'+'. $mf3;&assign;
$p = $mf108754 .'+'. $mf1 .'+'. $mf2 .'+'. $mf3;&assign;
```

```
$p = $mf10876;&assign;
$p = $mf10876 .'+'. $mf1;&assign;
$p = $mf10876 .'+'. $mf2;&assign;
```

```
$p = $mf10876 .'+'. $mf3;&assign;
$p = $mf10876 .'+'. $mf1 .'+'. $mf2;&assign;
```

```
$p = $mf10876 .'+'. $mf1 .'+'. $mf3;&assign;
$p = $mf10876 .'+'. $mf2 .'+'. $mf3;&assign;
$p = $mf10876 .'+'. $mf1 .'+'. $mf2 .'+'. $mf3;&assign;
```
_____

```
$p = $mf108764;&assign;
$p = $mf108764 .'+'. $mf1;&assign;
$p = $mf108764 .'+'. $mf2;&assign;
$p = $mf108764 .'+'. $mf3;&assign;
$p = $mf108764 .'+'. $mf1 .'+'. $mf2;&assign;
$p = $mf108764 .'+'. $mf1 .'+'. $mf3;&assign;
$p = $mf108764 .'+'. $mf2 .'+'. $mf3;&assign;
$p = $mf108764 .'+'. $mf1 .'+'. $mf2 .'+'. $mf3;&assign;
```
_____

```
$p = $mf108765;&assign;
$p = $mf108765 .'+'. $mf1;&assign;
$p = $mf108765 .'+'. $mf2;&assign;
$p = $mf108765 .'+'. $mf3;&assign;
$p = $mf108765 .'+'. $mf1 .'+'. $mf2;&assign;
$p = $mf108765 .'+'. $mf1 .'+'. $mf3;&assign;
$p = $mf108765 .'+'. $mf2 .'+'. $mf3;&assign;
$p = $mf108765 .'+'. $mf1 .'+'. $mf2 .'+'. $mf3;&assign;
```
_____

```
$p = $mf1087654;&assign;
$p = $mf1087654 .'+'. $mf1;&assign;
$p = $mf1087654 .'+'. $mf2;&assign;
$p = $mf1087654 .'+'. $mf3;&assign;
$p = $mf1087654 .'+'. $mf1 .'+'. $mf2;&assign;
$p = $mf1087654 .'+'. $mf1 .'+'. $mf3;&assign;
$p = $mf1087654 .'+'. $mf2 .'+'. $mf3;&assign;
$p = $mf1087654 .'+'. $mf1 .'+'. $mf2 .'+'. $mf3;&assign;
```
_____

```
# $p = $mf109;&assign;
$p = $mf109 .'+'. $mf1;&assign;
$p = $mf109 .'+'. $mf2;&assign;
```
_____

```
$p = $mf109 .'+'. $mf3;&assign;
$p = $mf109 .'+'. $mf1 .'+'. $mf2;&assign;
$p = $mf109 .'+'. $mf1 .'+'. $mf3;&assign;
$p = $mf109 .'+'. $mf2 .'+'. $mf3;&assign;
$p = $mf109 .'+'. $mf1 .'+'. $mf2 .'+'. $mf3;&assign;
```
_____

```
$p = $mf1094;&assign;
$p = $mf1094 .'+'. $mf1;&assign;
$p = $mf1094 .'+'. $mf2;&assign;
$p = $mf1094 .'+'. $mf3;&assign;
$p = $mf1094 .'+'. $mf1 .'+'. $mf2;&assign;
$p = $mf1094 .'+'. $mf1 .'+'. $mf3;&assign;
$p = $mf1094 .'+'. $mf2 .'+'. $mf3;&assign;
$p = $mf1094 .'+'. $mf1 .'+'. $mf2 .'+'. $mf3;&assign;
#_____

$p = $mf1095;&assign;
$p = $mf1095 .'+'. $mf1;&assign;
$p = $mf1095 .'+'. $mf2;&assign;
$p = $mf1095 .'+'. $mf3;&assign;
$p = $mf1095 .'+'. $mf1 .'+'. $mf2;&assign;
$p = $mf1095 .'+'. $mf1 .'+'. $mf3;&assign;
$p = $mf1095 .'+'. $mf2 .'+'. $mf3;&assign;
$p = $mf1095 .'+'. $mf1 .'+'. $mf2 .'+'. $mf3;&assign;
#_____

$p = $mf10954;&assign;
$p = $mf10954 .'+'. $mf1;&assign;
$p = $mf10954 .'+'. $mf2;&assign;
$p = $mf10954 .'+'. $mf3;&assign;
$p = $mf10954 .'+'. $mf1 .'+'. $mf2;&assign;
$p = $mf10954 .'+'. $mf1 .'+'. $mf3;&assign;
$p = $mf10954 .'+'. $mf2 .'+'. $mf3;&assign;
$p = $mf10954 .'+'. $mf1 .'+'. $mf2 .'+'. $mf3;&assign;
#_____
$p = $mf1096;&assign;
$p = $mf1096 .'+'. $mf1;&assign;
$p = $mf1096 .'+'. $mf2;&assign;
#_____

$p = $mf1096 .'+'. $mf3;&assign;
$p = $mf1096 .'+'. $mf1 .'+'. $mf2;&assign;
$p = $mf1096 .'+'. $mf1 .'+'. $mf3;&assign;
$p = $mf1096 .'+'. $mf2 .'+'. $mf3;&assign;
$p = $mf1096 .'+'. $mf1 .'+'. $mf2 .'+'. $mf3;&assign;
#_____

$p = $mf10964;&assign;
$p = $mf10964 .'+'. $mf1;&assign;
$p = $mf10964 .'+'. $mf2;&assign;
$p = $mf10964 .'+'. $mf3;&assign;
```

```
$p = $mf10964 .'+'. $mf1 .'+'. $mf2;&assign;
$p = $mf10964 .'+'. $mf1 .'+'. $mf3;&assign;
$p = $mf10964 .'+'. $mf2 .'+'. $mf3;&assign;
$p = $mf10964 .'+'. $mf1 .'+'. $mf2 .'+'. $mf3;&assign;
```
_____

```
$p = $mf10965;&assign;
$p = $mf10965 .'+'. $mf1;&assign;
$p = $mf10965 .'+'. $mf2;&assign;
$p = $mf10965 .'+'. $mf3;&assign;
$p = $mf10965 .'+'. $mf1 .'+'. $mf2;&assign;
$p = $mf10965 .'+'. $mf1 .'+'. $mf3;&assign;
$p = $mf10965 .'+'. $mf2 .'+'. $mf3;&assign;
$p = $mf10965 .'+'. $mf1 .'+'. $mf2 .'+'. $mf3;&assign;
```
_____

```
$p = $mf109654;&assign;
$p = $mf109654 .'+'. $mf1;&assign;
$p = $mf109654 .'+'. $mf2;&assign;
$p = $mf109654 .'+'. $mf3;&assign;
$p = $mf109654 .'+'. $mf1 .'+'. $mf2;&assign;
$p = $mf109654 .'+'. $mf1 .'+'. $mf3;&assign;
$p = $mf109654 .'+'. $mf2 .'+'. $mf3;&assign;
$p = $mf109654 .'+'. $mf1 .'+'. $mf2 .'+'. $mf3;&assign;
```

_____

```
$p = $mf1097;&assign;
$p = $mf1097 .'+'. $mf1;&assign;
$p = $mf1097 .'+'. $mf2;&assign;
```

_____

```
$p = $mf1097 .'+'. $mf3;&assign;
$p = $mf1097 .'+'. $mf1 .'+'. $mf2;&assign;
$p = $mf1097 .'+'. $mf1 .'+'. $mf3;&assign;
$p = $mf1097 .'+'. $mf2 .'+'. $mf3;&assign;
$p = $mf1097 .'+'. $mf1 .'+'. $mf2 .'+'. $mf3;&assign;
```
_____

```
$p = $mf10974;&assign;
$p = $mf10974 .'+'. $mf1;&assign;
$p = $mf10974 .'+'. $mf2;&assign;
$p = $mf10974 .'+'. $mf3;&assign;
$p = $mf10974 .'+'. $mf1 .'+'. $mf2;&assign;
```

```
$p = $mf10974 .'+'. $mf1 .'+'. $mf3;&assign;
$p = $mf10974 .'+'. $mf2 .'+'. $mf3;&assign;
$p = $mf10974 .'+'. $mf1 .'+'. $mf2 .'+'. $mf3;&assign;
```

```
$p = $mf10975;&assign;
$p = $mf10975 .'+'. $mf1;&assign;
$p = $mf10975 .'+'. $mf2;&assign;
$p = $mf10975 .'+'. $mf3;&assign;
$p = $mf10975 .'+'. $mf1 .'+'. $mf2;&assign;
$p = $mf10975 .'+'. $mf1 .'+'. $mf3;&assign;
$p = $mf10975 .'+'. $mf2 .'+'. $mf3;&assign;
$p = $mf10975 .'+'. $mf1 .'+'. $mf2 .'+'. $mf3;&assign;
```

```
$p = $mf109754;&assign;
$p = $mf109754 .'+'. $mf1;&assign;
$p = $mf109754 .'+'. $mf2;&assign;
$p = $mf109754 .'+'. $mf3;&assign;
$p = $mf109754 .'+'. $mf1 .'+'. $mf2;&assign;
$p = $mf109754 .'+'. $mf1 .'+'. $mf3;&assign;
$p = $mf109754 .'+'. $mf2 .'+'. $mf3;&assign;
$p = $mf109754 .'+'. $mf1 .'+'. $mf2 .'+'. $mf3;&assign;
```

```
$p = $mf10976;&assign;
$p = $mf10976 .'+'. $mf1;&assign;
$p = $mf10976 .'+'. $mf2;&assign;
```

```
$p = $mf10976 .'+'. $mf3;&assign;
$p = $mf10976 .'+'. $mf1 .'+'. $mf2;&assign;
$p = $mf10976 .'+'. $mf1 .'+'. $mf3;&assign;
$p = $mf10976 .'+'. $mf2 .'+'. $mf3;&assign;
$p = $mf10976 .'+'. $mf1 .'+'. $mf2 .'+'. $mf3;&assign;
```

```
$p = $mf109764;&assign;
$p = $mf109764 .'+'. $mf1;&assign;
$p = $mf109764 .'+'. $mf2;&assign;
$p = $mf109764 .'+'. $mf3;&assign;
$p = $mf109764 .'+'. $mf1 .'+'. $mf2;&assign;
$p = $mf109764 .'+'. $mf1 .'+'. $mf3;&assign;
$p = $mf109764 .'+'. $mf2 .'+'. $mf3;&assign;
$p = $mf109764 .'+'. $mf1 .'+'. $mf2 .'+'. $mf3;&assign;
```

```
$p = $mf109765;&assign;
$p = $mf109765 .'+'. $mf1;&assign;
$p = $mf109765 .'+'. $mf2;&assign;
$p = $mf109765 .'+'. $mf3;&assign;
$p = $mf109765 .'+'. $mf1 .'+'. $mf2;&assign;
$p = $mf109765 .'+'. $mf1 .'+'. $mf3;&assign;
$p = $mf109765 .'+'. $mf2 .'+'. $mf3;&assign;
$p = $mf109765 .'+'. $mf1 .'+'. $mf2 .'+'. $mf3;&assign;
#_____

$p = $mf1097654;&assign;
$p = $mf1097654 .'+'. $mf1;&assign;
$p = $mf1097654 .'+'. $mf2;&assign;
$p = $mf1097654 .'+'. $mf3;&assign;
$p = $mf1097654 .'+'. $mf1 .'+'. $mf2;&assign;
$p = $mf1097654 .'+'. $mf1 .'+'. $mf3;&assign;
$p = $mf1097654 .'+'. $mf2 .'+'. $mf3;&assign;
$p = $mf1097654 .'+'. $mf1 .'+'. $mf2 .'+'. $mf3;&assign;
#_____

$p = $mf1098;&assign;
$p = $mf1098 .'+'. $mf3;&assign;
$p = $mf1098 .'+'. $mf1 .'+'. $mf2;&assign;
$p = $mf1098 .'+'. $mf1 .'+'. $mf3;&assign;
$p = $mf1098 .'+'. $mf2 .'+'. $mf3;&assign;
#_____

$p = $mf10984;&assign;
$p = $mf10984 .'+'. $mf1;&assign;
$p = $mf10984 .'+'. $mf2;&assign;
$p = $mf10984 .'+'. $mf3;&assign;
$p = $mf10984 .'+'. $mf1 .'+'. $mf2;&assign;
$p = $mf10984 .'+'. $mf1 .'+'. $mf3;&assign;
$p = $mf10984 .'+'. $mf2 .'+'. $mf3;&assign;
$p = $mf10984 .'+'. $mf1 .'+'. $mf2 .'+'. $mf3;&assign;
#_____

$p = $mf10985;&assign;
$p = $mf10985 .'+'. $mf1;&assign;
$p = $mf10985 .'+'. $mf2;&assign;
$p = $mf10985 .'+'. $mf3;&assign;
$p = $mf10985 .'+'. $mf1 .'+'. $mf2;&assign;
$p = $mf10985 .'+'. $mf1 .'+'. $mf3;&assign;
$p = $mf10985 .'+'. $mf2 .'+'. $mf3;&assign;
$p = $mf10985 .'+'. $mf1 .'+'. $mf2 .'+'. $mf3;&assign;
```

```
$p = $mf109854;&assign;
$p = $mf109854 .'+'. $mf1;&assign;
$p = $mf109854 .'+'. $mf2;&assign;
$p = $mf109854 .'+'. $mf3;&assign;
$p = $mf109854 .'+'. $mf1 .'+'. $mf2;&assign;
$p = $mf109854 .'+'. $mf1 .'+'. $mf3;&assign;
$p = $mf109854 .'+'. $mf2 .'+'. $mf3;&assign;
$p = $mf109854 .'+'. $mf1 .'+'. $mf2 .'+'. $mf3;&assign;
```

```
$p = $mf10986;&assign;
$p = $mf10986 .'+'. $mf1;&assign;
$p = $mf10986 .'+'. $mf2;&assign;
```

```
$p = $mf10986 .'+'. $mf3;&assign;
$p = $mf10986 .'+'. $mf1 .'+'. $mf2;&assign;
$p = $mf10986 .'+'. $mf1 .'+'. $mf3;&assign;
$p = $mf10986 .'+'. $mf2 .'+'. $mf3;&assign;
$p = $mf10986 .'+'. $mf1 .'+'. $mf2 .'+'. $mf3;&assign;
```

```
$p = $mf109864;&assign;
$p = $mf109864 .'+'. $mf1;&assign;
$p = $mf109864 .'+'. $mf2;&assign;
$p = $mf109864 .'+'. $mf3;&assign;
$p = $mf109864 .'+'. $mf1 .'+'. $mf2;&assign;
$p = $mf109864 .'+'. $mf1 .'+'. $mf3;&assign;
$p = $mf109864 .'+'. $mf2 .'+'. $mf3;&assign;
$p = $mf109864 .'+'. $mf1 .'+'. $mf2 .'+'. $mf3;&assign;
```

```
$p = $mf109865;&assign;
$p = $mf109865 .'+'. $mf1;&assign;
$p = $mf109865 .'+'. $mf2;&assign;
$p = $mf109865 .'+'. $mf3;&assign;
$p = $mf109865 .'+'. $mf1 .'+'. $mf2;&assign;
$p = $mf109865 .'+'. $mf1 .'+'. $mf3;&assign;
$p = $mf109865 .'+'. $mf2 .'+'. $mf3;&assign;
$p = $mf109865 .'+'. $mf1 .'+'. $mf2 .'+'. $mf3;&assign;
```

```
$p = $mf1098654;&assign;
$p = $mf1098654 .'+'. $mf1;&assign;
```

```
$p = $mf1098654 .'+'. $mf2;&assign;
$p = $mf1098654 .'+'. $mf3;&assign;
$p = $mf1098654 .'+'. $mf1 .'+'. $mf2;&assign;
$p = $mf1098654 .'+'. $mf1 .'+'. $mf3;&assign;
$p = $mf1098654 .'+'. $mf2 .'+'. $mf3;&assign;
$p = $mf1098654 .'+'. $mf1 .'+'. $mf2 .'+'. $mf3;&assign;
```

_____

```
$p = $mf10987;&assign;
$p = $mf10987 .'+'. $mf1;&assign;
$p = $mf10987 .'+'. $mf2;&assign;
```

_____

```
$p = $mf10987 .'+'. $mf3;&assign;
$p = $mf10987 .'+'. $mf1 .'+'. $mf2;&assign;
$p = $mf10987 .'+'. $mf1 .'+'. $mf3;&assign;
$p = $mf10987 .'+'. $mf2 .'+'. $mf3;&assign;
$p = $mf10987 .'+'. $mf1 .'+'. $mf2 .'+'. $mf3;&assign;
```

_____

```
$p = $mf109874;&assign;
$p = $mf109874 .'+'. $mf1;&assign;
$p = $mf109874 .'+'. $mf2;&assign;
$p = $mf109874 .'+'. $mf3;&assign;
$p = $mf109874 .'+'. $mf1 .'+'. $mf2;&assign;
$p = $mf109874 .'+'. $mf1 .'+'. $mf3;&assign;
$p = $mf109874 .'+'. $mf2 .'+'. $mf3;&assign;
$p = $mf109874 .'+'. $mf1 .'+'. $mf2 .'+'. $mf3;&assign;
```

_____

```
$p = $mf109875;&assign;
$p = $mf109875 .'+'. $mf1;&assign;
$p = $mf109875 .'+'. $mf2;&assign;
$p = $mf109875 .'+'. $mf3;&assign;
$p = $mf109875 .'+'. $mf1 .'+'. $mf2;&assign;
$p = $mf109875 .'+'. $mf1 .'+'. $mf3;&assign;
$p = $mf109875 .'+'. $mf2 .'+'. $mf3;&assign;
$p = $mf109875 .'+'. $mf1 .'+'. $mf2 .'+'. $mf3;&assign;
```

_____

```
$p = $mf1098754;&assign;
$p = $mf1098754 .'+'. $mf1;&assign;
$p = $mf1098754 .'+'. $mf2;&assign;
```

```
    $p = $mf1098754 .'+'. $mf3;&assign;
    $p = $mf1098754 .'+'. $mf1 .'+'. $mf2;&assign;
    $p = $mf1098754 .'+'. $mf1 .'+'. $mf3;&assign;
    $p = $mf1098754 .'+'. $mf2 .'+'. $mf3;&assign;
    $p = $mf1098754 .'+'. $mf1 .'+'. $mf2 .'+'. $mf3;&assign;
#_____
    $p = $mf109876;&assign;
    $p = $mf109876 .'+'. $mf1;&assign;
    $p = $mf109876 .'+'. $mf2;&assign;
#_____

$p = $mf109876 .'+'. $mf3;&assign;
    $p = $mf109876 .'+'. $mf1 .'+'. $mf2;&assign;
    $p = $mf109876 .'+'. $mf1 .'+'. $mf3;&assign;
    $p = $mf109876 .'+'. $mf2 .'+'. $mf3;&assign;
    $p = $mf109876 .'+'. $mf1 .'+'. $mf2 .'+'. $mf3;&assign;
#_____

$p = $mf1098764;&assign;
    $p = $mf1098764 .'+'. $mf1;&assign;
    $p = $mf1098764 .'+'. $mf2;&assign;
    $p = $mf1098764 .'+'. $mf3;&assign;
    $p = $mf1098764 .'+'. $mf1 .'+'. $mf2;&assign;
    $p = $mf1098764 .'+'. $mf1 .'+'. $mf3;&assign;
    $p = $mf1098764 .'+'. $mf2 .'+'. $mf3;&assign;
    $p = $mf1098764 .'+'. $mf1 .'+'. $mf2 .'+'. $mf3;&assign;
#_____

$p = $mf1098765;&assign;
    $p = $mf1098765 .'+'. $mf1;&assign;
    $p = $mf1098765 .'+'. $mf2;&assign;
    $p = $mf1098765 .'+'. $mf3;&assign;
    $p = $mf1098765 .'+'. $mf1 .'+'. $mf2;&assign;
    $p = $mf1098765 .'+'. $mf1 .'+'. $mf3;&assign;
    $p = $mf1098765 .'+'. $mf2 .'+'. $mf3;&assign;
    $p = $mf1098765 .'+'. $mf1 .'+'. $mf2 .'+'. $mf3;&assign;
#_____

$p = $mf10987654;&assign;
    $p = $mf10987654 .'+'. $mf1;&assign;
    $p = $mf10987654 .'+'. $mf2;&assign;
    $p = $mf10987654 .'+'. $mf3;&assign;
    $p = $mf10987654 .'+'. $mf1 .'+'. $mf2;&assign;
    $p = $mf10987654 .'+'. $mf1 .'+'. $mf3;&assign;
    $p = $mf10987654 .'+'. $mf2 .'+'. $mf3;&assign;
```

```
$p = $mf10987654 .'+'. $mf1 .'+'. $mf2 .'+'. $mf3;&assign;

return if $items <= 10 || $case == 2 || $nrecitems <=10 ||
$nmf<1;##############################
_____ print "Assign rest of events in $biguse = $mf9 * $list by modulus principle\n";

$ld = substr($biguse,-1,1);
if (
                    $ld eq '1'
                || $ld eq '3'
                || $ld eq '5'
                || $ld eq '7'
                || $ld eq '9'
   )
     { #odd
     $start = 1;
     $step = 2;
     }
else
     { #even
     $start = 1;
     $step = 1;
     }

$bigi = Math::BigInt->new($start);

$product = $bigproduct;

while ()
     {
     $bigi += $step;
     last if $bigi >= $bigsqrtp;
     last if $bigi >= $biglimit;

$i = $bigi;
     $i =~ s/\+//gi;  # convert $i to ordinary integer precision type
     $hit = 0;

if ($i >= $precision_limit || $i =~ m/[eE]/)
         {
         $hit = 1 if ($bigi .'+'. ($biguse/$bigi) == $biguse);
         }
```

```
else
  {

$u = $biguse;
  $u =~ s/\+//gi; # convert $u to ordinary integer precision type
  $j = $i * int($u/$i); #and so do ordinary integer division
  $hit = 1 if $j == $u;
  # print "hit=$hit with ordinary integer division $j == $u\n";
  } if ($hit == 1)
  {
  $bigriuse = $biguse/$bigi;

$p = $bigi;&assign;
  $p = $bigriuse;&assign;
  $p = $bigi .'+'. $mf;&assign;
  $p = $bigriuse .'+'. $mf;&assign;
  $p = $bigi .'+'. $mf1;&assign;
  $p = $bigriuse .'+'. $mf1;&assign;
  $p = $bigi .'+'. $mf2;&assign;
  $p = $bigriuse .'+'. $mf2;&assign;
  $p = $bigi .'+'. $mf3;&assign;
  $p = $bigriuse .'+'. $mf3;&assign;
  $p = $bigi .'+'. $mf1 .'+'. $mf2;&assign;
  $p = $bigriuse .'+'. $mf1 .'+'. $mf2;&assign;
  $p = $bigi .'+'. $mf1 .'+'. $mf3;&assign;
  $p = $bigriuse .'+'. $mf1 .'+'. $mf3;&assign;
  $p = $bigi .'+'. $mf2 .'+'. $mf3;&assign;
  $p = $bigriuse .'+'. $mf2 .'+'. $mf3;&assign;
  $p = $bigriuse .'+'. $mf1 .'+'.$mf2 .'+'. $mf3;&assign;
  #_____

# $mf4i = $mf4 * $bigi;
  # $mf4r = $mf4 * $bigriuse;

$p = $mf4 .'+'. $bigi;&assign;
  $p = $mf4 .'+'. $bigriuse;&assign;
  $p = $mf4 .'+'. $bigi .'+'. $mf;&assign;
  $p = $mf4 .'+'. $bigriuse .'+'. $mf;&assign;
  $p = $mf4 .'+'. $bigi .'+'. $mf1;&assign;
  $p = $mf4 .'+'. $bigriuse .'+'. $mf1;&assign;
  $p = $mf4 .'+'. $bigi .'+'. $mf2;&assign;
  $p = $mf4 .'+'. $bigriuse .'+'. $mf2;&assign;
```

```
$p = $mf4 .'+'. $bigi .'+'. $mf3;&assign;
$p = $mf4 .'+'. $bigriuse .'+'. $mf3;&assign;
$p = $mf4 .'+'. $bigi .'+'. $mf1 .'+'. $mf2;&assign;
$p = $mf4 .'+'. $bigriuse .'+'. $mf1 .'+'. $mf2;&assign;
$p = $mf4 .'+'. $bigi .'+'. $mf1 .'+'. $mf3;&assign;
$p = $mf4 .'+'. $bigriuse .'+'. $mf1 .'+'. $mf3;&assign;
$p = $mf4 .'+'. $bigi .'+'. $mf2 .'+'. $mf3;&assign;
$p = $mf4 .'+'. $bigriuse .'+'. $mf2 .'+'. $mf3;&assign;
$p = $mf4 .'+'. $bigriuse .'+'. $mf1 .'+'.$mf2 .'+'. $mf3;&assign;

$p = $mf5 .'+'. $bigi;&assign;
$p = $mf5 .'+'. $bigriuse;&assign;
$p = $mf5 .'+'. $bigi .'+'. $mf;&assign;
$p = $mf5 .'+'. $bigriuse .'+'. $mf;&assign;
$p = $mf5 .'+'. $bigi .'+'. $mf1;&assign;
$p = $mf5 .'+'. $bigriuse .'+'. $mf1;&assign;
$p = $mf5 .'+'. $bigi .'+'. $mf2;&assign;
$p = $mf5 .'+'. $bigriuse .'+'. $mf2;&assign;
$p = $mf5 .'+'. $bigi .'+'. $mf3;&assign;
$p = $mf5 .'+'. $bigriuse .'+'. $mf3;&assign;
$p = $mf5 .'+'. $bigi .'+'. $mf1 .'+'. $mf2;&assign;
$p = $mf5 .'+'. $bigriuse .'+'. $mf1 .'+'. $mf2;&assign;
$p = $mf5 .'+'. $bigi .'+'. $mf1 .'+'. $mf3;&assign;
$p = $mf5 .'+'. $bigriuse .'+'. $mf1 .'+'. $mf3;&assign;
$p = $mf5 .'+'. $bigi .'+'. $mf2 .'+'. $mf3;&assign;
$p = $mf5 .'+'. $bigriuse .'+'. $mf2 .'+'. $mf3;&assign;
$p = $mf5 .'+'. $bigriuse .'+'. $mf1 .'+'.$mf2 .'+'. $mf3;&assign;

$p = $mf54 .'+'. $bigi;&assign;
$p = $mf54 .'+'. $bigriuse;&assign;
$p = $mf54 .'+'. $bigi .'+'. $mf;&assign;
$p = $mf54 .'+'. $bigriuse .'+'. $mf;&assign;
$p = $mf54 .'+'. $bigi .'+'. $mf1;&assign;
$p = $mf54 .'+'. $bigriuse .'+'. $mf1;&assign;
$p = $mf54 .'+'. $bigi .'+'. $mf2;&assign;
$p = $mf54 .'+'. $bigriuse .'+'. $mf2;&assign;
$p = $mf54 .'+'. $bigi .'+'. $mf3;&assign;
$p = $mf54 .'+'. $bigriuse .'+'. $mf3;&assign;
$p = $mf54 .'+'. $bigi .'+'. $mf1 .'+'. $mf2;&assign;
$p = $mf54 .'+'. $bigriuse .'+'. $mf1 .'+'. $mf2;&assign;
$p = $mf54 .'+'. $bigi .'+'. $mf1 .'+'. $mf3;&assign;
$p = $mf54 .'+'. $bigriuse .'+'. $mf1 .'+'. $mf3;&assign;
$p = $mf54 .'+'. $bigi .'+'. $mf2 .'+'. $mf3;&assign;
$p = $mf54 .'+'. $bigriuse .'+'. $mf2 .'+'. $mf3;&assign;
$p = $mf54 .'+'. $bigriuse .'+'. $mf1 .'+'.$mf2 .'+'. $mf3;&assign;
```

```

$p = $mf6 .'+'. $bigi;&assign;
$p = $mf6 .'+'. $bigriuse;&assign;
$p = $mf6 .'+'. $bigi .'+'. $mf;&assign;
$p = $mf6 .'+'. $bigriuse .'+'. $mf;&assign;
$p = $mf6 .'+'. $bigi .'+'. $mf1;&assign;
$p = $mf6 .'+'. $bigriuse .'+'. $mf1;&assign;
$p = $mf6 .'+'. $bigi .'+'. $mf2;&assign;
$p = $mf6 .'+'. $bigriuse .'+'. $mf2;&assign;
$p = $mf6 .'+'. $bigi .'+'. $mf3;&assign;
$p = $mf6 .'+'. $bigriuse .'+'. $mf3;&assign;
$p = $mf6 .'+'. $bigi .'+'. $mf1 .'+'. $mf2;&assign;
$p = $mf6 .'+'. $bigriuse .'+'. $mf1 .'+'. $mf2;&assign;
$p = $mf6 .'+'. $bigi .'+'. $mf1 .'+'. $mf3;&assign;
$p = $mf6 .'+'. $bigriuse .'+'. $mf1 .'+'. $mf3;&assign;
$p = $mf6 .'+'. $bigi .'+'. $mf2 .'+'. $mf3;&assign;
$p = $mf6 .'+'. $bigriuse .'+'. $mf2 .'+'. $mf3;&assign;
$p = $mf6 .'+'. $bigriuse .'+'. $mf1 .'+'.$mf2 .'+'. $mf3;&assign;

$p = $mf64 .'+'. $bigi;&assign;
$p = $mf64 .'+'. $bigriuse;&assign;
$p = $mf64 .'+'. $bigi .'+'. $mf;&assign;
$p = $mf64 .'+'. $bigriuse .'+'. $mf;&assign;
$p = $mf64 .'+'. $bigi .'+'. $mf1;&assign;
$p = $mf64 .'+'. $bigriuse .'+'. $mf1;&assign;
$p = $mf64 .'+'. $bigi .'+'. $mf2;&assign;
$p = $mf64 .'+'. $bigriuse .'+'. $mf2;&assign;
$p = $mf64 .'+'. $bigi .'+'. $mf3;&assign;
$p = $mf64 .'+'. $bigriuse .'+'. $mf3;&assign;
$p = $mf64 .'+'. $bigi .'+'. $mf1 .'+'. $mf2;&assign;
$p = $mf64 .'+'. $bigriuse .'+'. $mf1 .'+'. $mf2;&assign;
$p = $mf64 .'+'. $bigi .'+'. $mf1 .'+'. $mf3;&assign;
$p = $mf64 .'+'. $bigriuse .'+'. $mf1 .'+'. $mf3;&assign;
$p = $mf64 .'+'. $bigi .'+'. $mf2 .'+'. $mf3;&assign;
$p = $mf64 .'+'. $bigriuse .'+'. $mf2 .'+'. $mf3;&assign;
$p = $mf64 .'+'. $bigriuse .'+'. $mf1 .'+'.$mf2 .'+'. $mf3;&assign;

$p = $mf65 .'+'. $bigi;&assign;
$p = $mf65 .'+'. $bigriuse;&assign;
$p = $mf65 .'+'. $bigi .'+'. $mf;&assign;
$p = $mf65 .'+'. $bigriuse .'+'. $mf;&assign;
$p = $mf65 .'+'. $bigi .'+'. $mf1;&assign;
$p = $mf65 .'+'. $bigriuse .'+'. $mf1;&assign;
```

```
$p = $mf65 .'+'. $bigi .'+'. $mf2;&assign;
$p = $mf65 .'+'. $bigriuse .'+'. $mf2;&assign;
$p = $mf65 .'+'. $bigi .'+'. $mf3;&assign;
$p = $mf65 .'+'. $bigriuse .'+'. $mf3;&assign;
$p = $mf65 .'+'. $bigi .'+'. $mf1 .'+'. $mf2;&assign;
$p = $mf65 .'+'. $bigriuse .'+'. $mf1 .'+'. $mf2;&assign;
$p = $mf65 .'+'. $bigi .'+'. $mf1 .'+'. $mf3;&assign;
$p = $mf65 .'+'. $bigriuse .'+'. $mf1 .'+'. $mf3;&assign;
$p = $mf65 .'+'. $bigi .'+'. $mf2 .'+'. $mf3;&assign;
$p = $mf65 .'+'. $bigriuse .'+'. $mf2 .'+'. $mf3;&assign;
$p = $mf65 .'+'. $bigriuse .'+'. $mf1 .'+'.$mf2 .'+'. $mf3;&assign;

$p = $mf654 .'+'. $bigi;&assign;
$p = $mf654 .'+'. $bigriuse;&assign;
$p = $mf654 .'+'. $bigi .'+'. $mf;&assign;
$p = $mf654 .'+'. $bigriuse .'+'. $mf;&assign;
$p = $mf654 .'+'. $bigi .'+'. $mf1;&assign;
$p = $mf654 .'+'. $bigriuse .'+'. $mf1;&assign;
$p = $mf654 .'+'. $bigi .'+'. $mf2;&assign;
$p = $mf654 .'+'. $bigriuse .'+'. $mf2;&assign;
$p = $mf654 .'+'. $bigi .'+'. $mf3;&assign;
$p = $mf654 .'+'. $bigriuse .'+'. $mf3;&assign;
$p = $mf654 .'+'. $bigi .'+'. $mf1 .'+'. $mf2;&assign;
$p = $mf654 .'+'. $bigriuse .'+'. $mf1 .'+'. $mf2;&assign;
$p = $mf654 .'+'. $bigi .'+'. $mf1 .'+'. $mf3;&assign;
$p = $mf654 .'+'. $bigriuse .'+'. $mf1 .'+'. $mf3;&assign;
$p = $mf654 .'+'. $bigi .'+'. $mf2 .'+'. $mf3;&assign;
$p = $mf654 .'+'. $bigriuse .'+'. $mf2 .'+'. $mf3;&assign;
$p = $mf654 .'+'. $bigriuse .'+'. $mf1 .'+'.$mf2 .'+'. $mf3;&assign;

$p = $mf7 .'+'. $bigi;&assign;
$p = $mf7 .'+'. $bigriuse;&assign;
$p = $mf7 .'+'. $bigi .'+'. $mf;&assign;
$p = $mf7 .'+'. $bigriuse .'+'. $mf;&assign;
$p = $mf7 .'+'. $bigi .'+'. $mf1;&assign;
$p = $mf7 .'+'. $bigriuse .'+'. $mf1;&assign;
$p = $mf7 .'+'. $bigi .'+'. $mf2;&assign;
$p = $mf7 .'+'. $bigriuse .'+'. $mf2;&assign;
$p = $mf7 .'+'. $bigi .'+'. $mf3;&assign;
$p = $mf7 .'+'. $bigriuse .'+'. $mf3;&assign;
$p = $mf7 .'+'. $bigi .'+'. $mf1 .'+'. $mf2;&assign;
$p = $mf7 .'+'. $bigriuse .'+'. $mf1 .'+'. $mf2;&assign;
$p = $mf7 .'+'. $bigi .'+'. $mf1 .'+'. $mf3;&assign;
$p = $mf7 .'+'. $bigriuse .'+'. $mf1 .'+'. $mf3;&assign;
$p = $mf7 .'+'. $bigi .'+'. $mf2 .'+'. $mf3;&assign;
```

```
$p = $mf7 .'+'. $bigriuse .'+'. $mf2 .'+'. $mf3;&assign;
$p = $mf7 .'+'. $bigriuse .'+'. $mf1 .'+'.$mf2 .'+'. $mf3;&assign;
#_____

$p = $mf74 .'+'. $bigi;&assign;
$p = $mf74 .'+'. $bigriuse;&assign;
$p = $mf74 .'+'. $bigi .'+'. $mf;&assign;
$p = $mf74 .'+'. $bigriuse .'+'. $mf;&assign;
$p = $mf74 .'+'. $bigi .'+'. $mf1;&assign;
$p = $mf74 .'+'. $bigriuse .'+'. $mf1;&assign;
$p = $mf74 .'+'. $bigi .'+'. $mf2;&assign;
$p = $mf74 .'+'. $bigriuse .'+'. $mf2;&assign;
$p = $mf74 .'+'. $bigi .'+'. $mf3;&assign;
$p = $mf74 .'+'. $bigriuse .'+'. $mf3;&assign;
$p = $mf74 .'+'. $bigi .'+'. $mf1 .'+'. $mf2;&assign;
$p = $mf74 .'+'. $bigriuse .'+'. $mf1 .'+'. $mf2;&assign;
$p = $mf74 .'+'. $bigi .'+'. $mf1 .'+'. $mf3;&assign;
$p = $mf74 .'+'. $bigriuse .'+'. $mf1 .'+'. $mf3;&assign;
$p = $mf74 .'+'. $bigi .'+'. $mf2 .'+'. $mf3;&assign;
$p = $mf74 .'+'. $bigriuse .'+'. $mf2 .'+'. $mf3;&assign;
$p = $mf74 .'+'. $bigriuse .'+'. $mf1 .'+'.$mf2 .'+'. $mf3;&assign;
#_____
$p = $mf75 .'+'. $bigi;&assign;
$p = $mf75 .'+'. $bigriuse;&assign;
$p = $mf75 .'+'. $bigi .'+'. $mf;&assign;
$p = $mf75 .'+'. $bigriuse .'+'. $mf;&assign;
$p = $mf75 .'+'. $bigi .'+'. $mf1;&assign;
$p = $mf75 .'+'. $bigriuse .'+'. $mf1;&assign;
$p = $mf75 .'+'. $bigi .'+'. $mf2;&assign;
$p = $mf75 .'+'. $bigriuse .'+'. $mf2;&assign;
$p = $mf75 .'+'. $bigi .'+'. $mf3;&assign;
$p = $mf75 .'+'. $bigriuse .'+'. $mf3;&assign;
$p = $mf75 .'+'. $bigi .'+'. $mf1 .'+'. $mf2;&assign;
$p = $mf75 .'+'. $bigriuse .'+'. $mf1 .'+'. $mf2;&assign;
$p = $mf75 .'+'. $bigi .'+'. $mf1 .'+'. $mf3;&assign;
$p = $mf75 .'+'. $bigriuse .'+'. $mf1 .'+'. $mf3;&assign;
$p = $mf75 .'+'. $bigi .'+'. $mf2 .'+'. $mf3;&assign;
$p = $mf75 .'+'. $bigriuse .'+'. $mf2 .'+'. $mf3;&assign;
$p = $mf75 .'+'. $bigriuse .'+'. $mf1 .'+'.$mf2 .'+'. $mf3;&assign;
#_____
$p = $mf754 .'+'. $bigi;&assign;
$p = $mf754 .'+'. $bigriuse;&assign;
$p = $mf754 .'+'. $bigi .'+'. $mf;&assign;
$p = $mf754 .'+'. $bigriuse .'+'. $mf;&assign;
$p = $mf754 .'+'. $bigi .'+'. $mf1;&assign;
```

```
$p = $mf754 .'+'. $bigriuse .'+'. $mf1;&assign;
$p = $mf754 .'+'. $bigi .'+'. $mf2;&assign;
$p = $mf754 .'+'. $bigriuse .'+'. $mf2;&assign;
$p = $mf754 .'+'. $bigi .'+'. $mf3;&assign;
$p = $mf754 .'+'. $bigriuse .'+'. $mf3;&assign;
$p = $mf754 .'+'. $bigi .'+'. $mf1 .'+'. $mf2;&assign;
$p = $mf754 .'+'. $bigriuse .'+'. $mf1 .'+'. $mf2;&assign;
$p = $mf754 .'+'. $bigi .'+'. $mf1 .'+'. $mf3;&assign;
$p = $mf754 .'+'. $bigriuse .'+'. $mf1 .'+'. $mf3;&assign;
$p = $mf754 .'+'. $bigi .'+'. $mf2 .'+'. $mf3;&assign;
$p = $mf754 .'+'. $bigriuse .'+'. $mf2 .'+'. $mf3;&assign;
$p = $mf754 .'+'. $bigriuse .'+'. $mf1 .'+'.$mf2 .'+'. $mf3;&assign;
#_____
$p = $mf76 .'+'. $bigi;&assign;
$p = $mf76 .'+'. $bigriuse;&assign;
$p = $mf76 .'+'. $bigi .'+'. $mf;&assign;
$p = $mf76 .'+'. $bigriuse .'+'. $mf;&assign;
$p = $mf76 .'+'. $bigi .'+'. $mf1;&assign;
$p = $mf76 .'+'. $bigriuse .'+'. $mf1;&assign;
$p = $mf76 .'+'. $bigi .'+'. $mf2;&assign;
$p = $mf76 .'+'. $bigriuse .'+'. $mf2;&assign;
$p = $mf76 .'+'. $bigi .'+'. $mf3;&assign;
$p = $mf76 .'+'. $bigriuse .'+'. $mf3;&assign;
$p = $mf76 .'+'. $bigi .'+'. $mf1 .'+'. $mf2;&assign;
$p = $mf76 .'+'. $bigriuse .'+'. $mf1 .'+'. $mf2;&assign;
$p = $mf76 .'+'. $bigi .'+'. $mf1 .'+'. $mf3;&assign;
$p = $mf76 .'+'. $bigriuse .'+'. $mf1 .'+'. $mf3;&assign;
$p = $mf76 .'+'. $bigi .'+'. $mf2 .'+'. $mf3;&assign;
$p = $mf76 .'+'. $bigriuse .'+'. $mf2 .'+'. $mf3;&assign;
#_____
$p = $mf76 .'+'. $bigriuse .'+'. $mf1 .'+'.$mf2 .'+'. $mf3;&assign;

$p = $mf764 .'+'. $bigi;&assign;
$p = $mf764 .'+'. $bigriuse;&assign;
$p = $mf764 .'+'. $bigi .'+'. $mf;&assign;
$p = $mf764 .'+'. $bigriuse .'+'. $mf;&assign;
$p = $mf764 .'+'. $bigi .'+'. $mf1;&assign;
$p = $mf764 .'+'. $bigriuse .'+'. $mf1;&assign;
$p = $mf764 .'+'. $bigi .'+'. $mf2;&assign;
$p = $mf764 .'+'. $bigriuse .'+'. $mf2;&assign;
$p = $mf764 .'+'. $bigi .'+'. $mf3;&assign;
$p = $mf764 .'+'. $bigriuse .'+'. $mf3;&assign;
$p = $mf764 .'+'. $bigi .'+'. $mf1 .'+'. $mf2;&assign;
$p = $mf764 .'+'. $bigriuse .'+'. $mf1 .'+'. $mf2;&assign;
```

```
$p = $mf764 .'+'. $bigi .'+'. $mf1 .'+'. $mf3;&assign;
$p = $mf764 .'+'. $bigriuse .'+'. $mf1 .'+'. $mf3;&assign;
$p = $mf764 .'+'. $bigi .'+'. $mf2 .'+'. $mf3;&assign;
$p = $mf764 .'+'. $bigriuse .'+'. $mf2 .'+'. $mf3;&assign;
$p = $mf764 .'+'. $bigriuse .'+'. $mf1 .'+'.$mf2 .'+'. $mf3;&assign;
#_____
$p = $mf765 .'+'. $bigi;&assign;
$p = $mf765 .'+'. $bigriuse;&assign;
$p = $mf765 .'+'. $bigi .'+'. $mf;&assign;
$p = $mf765 .'+'. $bigriuse .'+'. $mf;&assign;
$p = $mf765 .'+'. $bigi .'+'. $mf1;&assign;
$p = $mf765 .'+'. $bigriuse .'+'. $mf1;&assign;
$p = $mf765 .'+'. $bigi .'+'. $mf2;&assign;
$p = $mf765 .'+'. $bigriuse .'+'. $mf2;&assign;
$p = $mf765 .'+'. $bigi .'+'. $mf3;&assign;
$p = $mf765 .'+'. $bigriuse .'+'. $mf3;&assign;
$p = $mf765 .'+'. $bigi .'+'. $mf1 .'+'. $mf2;&assign;
$p = $mf765 .'+'. $bigriuse .'+'. $mf1 .'+'. $mf2;&assign;
$p = $mf765 .'+'. $bigi .'+'. $mf1 .'+'. $mf3;&assign;
$p = $mf765 .'+'. $bigriuse .'+'. $mf1 .'+'. $mf3;&assign;
$p = $mf765 .'+'. $bigi .'+'. $mf2 .'+'. $mf3;&assign;
$p = $mf765 .'+'. $bigriuse .'+'. $mf2 .'+'. $mf3;&assign;
$p = $mf765 .'+'. $bigriuse .'+'. $mf1 .'+'.$mf2 .'+'. $mf3;&assign;
#_____
$p = $mf7654 .'+'. $bigi;&assign;
$p = $mf7654 .'+'. $bigriuse;&assign;
$p = $mf7654 .'+'. $bigi .'+'. $mf;&assign;
$p = $mf7654 .'+'. $bigriuse .'+'. $mf;&assign;
$p = $mf7654 .'+'. $bigi .'+'. $mf1;&assign;
$p = $mf7654 .'+'. $bigriuse .'+'. $mf1;&assign;
$p = $mf7654 .'+'. $bigi .'+'. $mf2;&assign;
$p = $mf7654 .'+'. $bigriuse .'+'. $mf2;&assign;
$p = $mf7654 .'+'. $bigi .'+'. $mf3;&assign;
$p = $mf7654 .'+'. $bigriuse .'+'. $mf3;&assign;
$p = $mf7654 .'+'. $bigi .'+'. $mf1 .'+'. $mf2;&assign;
$p = $mf7654 .'+'. $bigriuse .'+'. $mf1 .'+'. $mf2;&assign;
$p = $mf7654 .'+'. $bigi .'+'. $mf1 .'+'. $mf3;&assign;
$p = $mf7654 .'+'. $bigriuse .'+'. $mf1 .'+'. $mf3;&assign;
$p = $mf7654 .'+'. $bigi .'+'. $mf2 .'+'. $mf3;&assign;
$p = $mf7654 .'+'. $bigriuse .'+'. $mf2 .'+'. $mf3;&assign;
$p = $mf7654 .'+'. $bigriuse .'+'. $mf1 .'+'.$mf2 .'+'. $mf3;&assign;
#_____
$p = $mf8 .'+'. $bigi;&assign;
$p = $mf8 .'+'. $bigriuse;&assign;
$p = $mf8 .'+'. $bigi .'+'. $mf;&assign;
```

```
$p = $mf8 .'+'. $bigriuse .'+'. $mf;&assign;
$p = $mf8 .'+'. $bigi .'+'. $mf1;&assign;
$p = $mf8 .'+'. $bigriuse .'+'. $mf1;&assign;
$p = $mf8 .'+'. $bigi .'+'. $mf2;&assign;
$p = $mf8 .'+'. $bigriuse .'+'. $mf2;&assign;
$p = $mf8 .'+'. $bigi .'+'. $mf3;&assign;
$p = $mf8 .'+'. $bigriuse .'+'. $mf3;&assign;
$p = $mf8 .'+'. $bigi .'+'. $mf1 .'+'. $mf2;&assign;
$p = $mf8 .'+'. $bigriuse .'+'. $mf1 .'+'. $mf2;&assign;
$p = $mf8 .'+'. $bigi .'+'. $mf1 .'+'. $mf3;&assign;
$p = $mf8 .'+'. $bigriuse .'+'. $mf1 .'+'. $mf3;&assign;
$p = $mf8 .'+'. $bigi .'+'. $mf2 .'+'. $mf3;&assign;
$p = $mf8 .'+'. $bigriuse .'+'. $mf2 .'+'. $mf3;&assign;
$p = $mf8 .'+'. $bigriuse .'+'. $mf1 .'+'.$mf2 .'+'. $mf3;&assign;

$p = $mf84 .'+'. $bigi;&assign;
$p = $mf84 .'+'. $bigriuse;&assign;
$p = $mf84 .'+'. $bigi .'+'. $mf;&assign;
$p = $mf84 .'+'. $bigriuse .'+'. $mf;&assign;
$p = $mf84 .'+'. $bigi .'+'. $mf1;&assign;
$p = $mf84 .'+'. $bigriuse .'+'. $mf1;&assign;
$p = $mf84 .'+'. $bigi .'+'. $mf2;&assign;
$p = $mf84 .'+'. $bigriuse .'+'. $mf2;&assign;
$p = $mf84 .'+'. $bigi .'+'. $mf3;&assign;
$p = $mf84 .'+'. $bigriuse .'+'. $mf3;&assign;
$p = $mf84 .'+'. $bigi .'+'. $mf1 .'+'. $mf2;&assign;
$p = $mf84 .'+'. $bigriuse .'+'. $mf1 .'+'. $mf2;&assign;
$p = $mf84 .'+'. $bigi .'+'. $mf1 .'+'. $mf3;&assign;
$p = $mf84 .'+'. $bigriuse .'+'. $mf1 .'+'. $mf3;&assign;
$p = $mf84 .'+'. $bigi .'+'. $mf2 .'+'. $mf3;&assign;
$p = $mf84 .'+'. $bigriuse .'+'. $mf2 .'+'. $mf3;&assign;
$p = $mf84 .'+'. $bigriuse .'+'. $mf1 .'+'.$mf2 .'+'. $mf3;&assign;

$p = $mf85 .'+'. $bigi;&assign;
$p = $mf85 .'+'. $bigriuse;&assign;
$p = $mf85 .'+'. $bigi .'+'. $mf;&assign;
$p = $mf85 .'+'. $bigriuse .'+'. $mf;&assign;
$p = $mf85 .'+'. $bigi .'+'. $mf1;&assign;
$p = $mf85 .'+'. $bigriuse .'+'. $mf1;&assign;
$p = $mf85 .'+'. $bigi .'+'. $mf2;&assign;
$p = $mf85 .'+'. $bigriuse .'+'. $mf2;&assign;
$p = $mf85 .'+'. $bigi .'+'. $mf3;&assign;
$p = $mf85 .'+'. $bigriuse .'+'. $mf3;&assign;
```

```
$p = $mf85 .'+'. $bigi .'+'. $mf1 .'+'. $mf2;&assign;
$p = $mf85 .'+'. $bigriuse .'+'. $mf1 .'+'. $mf2;&assign;
$p = $mf85 .'+'. $bigi .'+'. $mf1 .'+'. $mf3;&assign;
$p = $mf85 .'+'. $bigriuse .'+'. $mf1 .'+'. $mf3;&assign;
$p = $mf85 .'+'. $bigi .'+'. $mf2 .'+'. $mf3;&assign;
$p = $mf85 .'+'. $bigriuse .'+'. $mf2 .'+'. $mf3;&assign;
$p = $mf85 .'+'. $bigriuse .'+'. $mf1 .'+'.$mf2 .'+'. $mf3;&assign;

$p = $mf854 .'+'. $bigi;&assign;
$p = $mf854 .'+'. $bigriuse;&assign;
$p = $mf854 .'+'. $bigi .'+'. $mf;&assign;
$p = $mf854 .'+'. $bigriuse .'+'. $mf;&assign;
$p = $mf854 .'+'. $bigi .'+'. $mf1;&assign;
$p = $mf854 .'+'. $bigriuse .'+'. $mf1;&assign;
$p = $mf854 .'+'. $bigi .'+'. $mf2;&assign;
$p = $mf854 .'+'. $bigriuse .'+'. $mf2;&assign;
$p = $mf854 .'+'. $bigi .'+'. $mf3;&assign;
$p = $mf854 .'+'. $bigriuse .'+'. $mf3;&assign;
$p = $mf854 .'+'. $bigi .'+'. $mf1 .'+'. $mf2;&assign;
$p = $mf854 .'+'. $bigriuse .'+'. $mf1 .'+'. $mf2;&assign;
$p = $mf854 .'+'. $bigi .'+'. $mf1 .'+'. $mf3;&assign;
$p = $mf854 .'+'. $bigriuse .'+'. $mf1 .'+'. $mf3;&assign;
$p = $mf854 .'+'. $bigi .'+'. $mf2 .'+'. $mf3;&assign;
$p = $mf854 .'+'. $bigriuse .'+'. $mf2 .'+'. $mf3;&assign;
$p = $mf854 .'+'. $bigriuse .'+'. $mf1 .'+'.$mf2 .'+'. $mf3;&assign;

$p = $mf86 .'+'. $bigi;&assign;
$p = $mf86 .'+'. $bigriuse;&assign;
$p = $mf86 .'+'. $bigi .'+'. $mf;&assign;
$p = $mf86 .'+'. $bigriuse .'+'. $mf;&assign;
$p = $mf86 .'+'. $bigi .'+'. $mf1;&assign;
$p = $mf86 .'+'. $bigriuse .'+'. $mf1;&assign;
$p = $mf86 .'+'. $bigi .'+'. $mf2;&assign;
$p = $mf86 .'+'. $bigriuse .'+'. $mf2;&assign;
$p = $mf86 .'+'. $bigi .'+'. $mf3;&assign;
$p = $mf86 .'+'. $bigriuse .'+'. $mf3;&assign;
$p = $mf86 .'+'. $bigi .'+'. $mf1 .'+'. $mf2;&assign;
$p = $mf86 .'+'. $bigriuse .'+'. $mf1 .'+'. $mf2;&assign;
$p = $mf86 .'+'. $bigi .'+'. $mf1 .'+'. $mf3;&assign;
$p = $mf86 .'+'. $bigriuse .'+'. $mf1 .'+'. $mf3;&assign;
$p = $mf86 .'+'. $bigi .'+'. $mf2 .'+'. $mf3;&assign;
$p = $mf86 .'+'. $bigriuse .'+'. $mf2 .'+'. $mf3;&assign;
$p = $mf86 .'+'. $bigriuse .'+'. $mf1 .'+'.$mf2 .'+'. $mf3;&assign;

```

```
$p = $mf864 .'+'. $bigi;&assign;
$p = $mf864 .'+'. $bigriuse;&assign;
$p = $mf864 .'+'. $bigi .'+'. $mf;&assign;
$p = $mf864 .'+'. $bigriuse .'+'. $mf;&assign;
$p = $mf864 .'+'. $bigi .'+'. $mf1;&assign;
$p = $mf864 .'+'. $bigriuse .'+'. $mf1;&assign;
$p = $mf864 .'+'. $bigi .'+'. $mf2;&assign;
$p = $mf864 .'+'. $bigriuse .'+'. $mf2;&assign;
$p = $mf864 .'+'. $bigi .'+'. $mf3;&assign;
$p = $mf864 .'+'. $bigriuse .'+'. $mf3;&assign;
$p = $mf864 .'+'. $bigi .'+'. $mf1 .'+'. $mf2;&assign;
$p = $mf864 .'+'. $bigriuse .'+'. $mf1 .'+'. $mf2;&assign;
$p = $mf864 .'+'. $bigi .'+'. $mf1 .'+'. $mf3;&assign;
$p = $mf864 .'+'. $bigriuse .'+'. $mf1 .'+'. $mf3;&assign;
$p = $mf864 .'+'. $bigi .'+'. $mf2 .'+'. $mf3;&assign;
$p = $mf864 .'+'. $bigriuse .'+'. $mf2 .'+'. $mf3;&assign;
$p = $mf864 .'+'. $bigriuse .'+'. $mf1 .'+'.$mf2 .'+'. $mf3;&assign;
#_____
$p = $mf865 .'+'. $bigi;&assign;
$p = $mf865 .'+'. $bigriuse;&assign;
$p = $mf865 .'+'. $bigi .'+'. $mf;&assign;
$p = $mf865 .'+'. $bigriuse .'+'. $mf;&assign;
$p = $mf865 .'+'. $bigi .'+'. $mf1;&assign;
$p = $mf865 .'+'. $bigriuse .'+'. $mf1;&assign;
$p = $mf865 .'+'. $bigi .'+'. $mf2;&assign;
$p = $mf865 .'+'. $bigriuse .'+'. $mf2;&assign;
$p = $mf865 .'+'. $bigi .'+'. $mf3;&assign;
$p = $mf865 .'+'. $bigriuse .'+'. $mf3;&assign;
$p = $mf865 .'+'. $bigi .'+'. $mf1 .'+'. $mf2;&assign;
$p = $mf865 .'+'. $bigriuse .'+'. $mf1 .'+'. $mf2;&assign;
$p = $mf865 .'+'. $bigi .'+'. $mf1 .'+'. $mf3;&assign;
$p = $mf865 .'+'. $bigriuse .'+'. $mf1 .'+'. $mf3;&assign;
$p = $mf865 .'+'. $bigi .'+'. $mf2 .'+'. $mf3;&assign;
$p = $mf865 .'+'. $bigriuse .'+'. $mf2 .'+'. $mf3;&assign;
$p = $mf865 .'+'. $bigriuse .'+'. $mf1 .'+'.$mf2 .'+'. $mf3;&assign;
#_____
$p = $mf8654 .'+'. $bigi;&assign;
$p = $mf8654 .'+'. $bigriuse;&assign;
$p = $mf8654 .'+'. $bigi .'+'. $mf;&assign;
$p = $mf8654 .'+'. $bigriuse .'+'. $mf;&assign;
$p = $mf8654 .'+'. $bigi .'+'. $mf1;&assign;
$p = $mf8654 .'+'. $bigriuse .'+'. $mf1;&assign;
$p = $mf8654 .'+'. $bigi .'+'. $mf2;&assign;
$p = $mf8654 .'+'. $bigriuse .'+'. $mf2;&assign;
$p = $mf8654 .'+'. $bigi .'+'. $mf3;&assign;
```

```
$p = $mf8654 .'+'. $bigriuse .'+'. $mf3;&assign;
$p = $mf8654 .'+'. $bigi .'+'. $mf1 .'+'. $mf2;&assign;
$p = $mf8654 .'+'. $bigriuse .'+'. $mf1 .'+'. $mf2;&assign;
$p = $mf8654 .'+'. $bigi .'+'. $mf1 .'+'. $mf3;&assign;
$p = $mf8654 .'+'. $bigriuse .'+'. $mf1 .'+'. $mf3;&assign;
$p = $mf8654 .'+'. $bigi .'+'. $mf2 .'+'. $mf3;&assign;
$p = $mf8654 .'+'. $bigriuse .'+'. $mf2 .'+'. $mf3;&assign;
$p = $mf8654 .'+'. $bigriuse .'+'. $mf1 .'+'.$mf2 .'+'. $mf3;&assign;
#_____
$p = $mf87 .'+'. $bigi;&assign;
$p = $mf87 .'+'. $bigriuse;&assign;
$p = $mf87 .'+'. $bigi .'+'. $mf;&assign;
$p = $mf87 .'+'. $bigriuse .'+'. $mf;&assign;
$p = $mf87 .'+'. $bigi .'+'. $mf1;&assign;
$p = $mf87 .'+'. $bigriuse .'+'. $mf1;&assign;
$p = $mf87 .'+'. $bigi .'+'. $mf2;&assign;
$p = $mf87 .'+'. $bigriuse .'+'. $mf2;&assign;
$p = $mf87 .'+'. $bigi .'+'. $mf3;&assign;
$p = $mf87 .'+'. $bigriuse .'+'. $mf3;&assign;
$p = $mf87 .'+'. $bigi .'+'. $mf1 .'+'. $mf2;&assign;
$p = $mf87 .'+'. $bigriuse .'+'. $mf1 .'+'. $mf2;&assign;
$p = $mf87 .'+'. $bigi .'+'. $mf1 .'+'. $mf3;&assign;
$p = $mf87 .'+'. $bigriuse .'+'. $mf1 .'+'. $mf3;&assign;
$p = $mf87 .'+'. $bigi .'+'. $mf2 .'+'. $mf3;&assign;
$p = $mf87 .'+'. $bigriuse .'+'. $mf2 .'+'. $mf3;&assign;
$p = $mf87 .'+'. $bigriuse .'+'. $mf1 .'+'.$mf2 .'+'. $mf3;&assign;
#_____

$p = $mf874 .'+'. $bigi;&assign;
$p = $mf874 .'+'. $bigriuse;&assign;
$p = $mf874 .'+'. $bigi .'+'. $mf;&assign;
$p = $mf874 .'+'. $bigriuse .'+'. $mf;&assign;
$p = $mf874 .'+'. $bigi .'+'. $mf1;&assign;
$p = $mf874 .'+'. $bigriuse .'+'. $mf1;&assign;
$p = $mf874 .'+'. $bigi .'+'. $mf2;&assign;
$p = $mf874 .'+'. $bigriuse .'+'. $mf2;&assign;
$p = $mf874 .'+'. $bigi .'+'. $mf3;&assign;
$p = $mf874 .'+'. $bigriuse .'+'. $mf3;&assign;
$p = $mf874 .'+'. $bigi .'+'. $mf1 .'+'. $mf2;&assign;
$p = $mf874 .'+'. $bigriuse .'+'. $mf1 .'+'. $mf2;&assign;
$p = $mf874 .'+'. $bigi .'+'. $mf1 .'+'. $mf3;&assign;
$p = $mf874 .'+'. $bigriuse .'+'. $mf1 .'+'. $mf3;&assign;
$p = $mf874 .'+'. $bigi .'+'. $mf2 .'+'. $mf3;&assign;
$p = $mf874 .'+'. $bigriuse .'+'. $mf2 .'+'. $mf3;&assign;
```

```
$p = $mf874 .'+'. $bigriuse .'+'. $mf1 .'+'.$mf2 .'+'. $mf3;&assign;

$p = $mf875 .'+'. $bigi;&assign;
$p = $mf875 .'+'. $bigriuse;&assign;
$p = $mf875 .'+'. $bigi .'+'. $mf;&assign;
$p = $mf875 .'+'. $bigriuse .'+'. $mf;&assign;
$p = $mf875 .'+'. $bigi .'+'. $mf1;&assign;
$p = $mf875 .'+'. $bigriuse .'+'. $mf1;&assign;
$p = $mf875 .'+'. $bigi .'+'. $mf2;&assign;
$p = $mf875 .'+'. $bigriuse .'+'. $mf2;&assign;
$p = $mf875 .'+'. $bigi .'+'. $mf3;&assign;
$p = $mf875 .'+'. $bigriuse .'+'. $mf3;&assign;
$p = $mf875 .'+'. $bigi .'+'. $mf1 .'+'. $mf2;&assign;
$p = $mf875 .'+'. $bigriuse .'+'. $mf1 .'+'. $mf2;&assign;
$p = $mf875 .'+'. $bigi .'+'. $mf1 .'+'. $mf3;&assign;
$p = $mf875 .'+'. $bigriuse .'+'. $mf1 .'+'. $mf3;&assign;
$p = $mf875 .'+'. $bigi .'+'. $mf2 .'+'. $mf3;&assign;
$p = $mf875 .'+'. $bigriuse .'+'. $mf2 .'+'. $mf3;&assign;
$p = $mf875 .'+'. $bigriuse .'+'. $mf1 .'+'.$mf2 .'+'. $mf3;&assign;

$p = $mf8754 .'+'. $bigi;&assign;
$p = $mf8754 .'+'. $bigriuse;&assign;
$p = $mf8754 .'+'. $bigi .'+'. $mf;&assign;
$p = $mf8754 .'+'. $bigriuse .'+'. $mf;&assign;
$p = $mf8754 .'+'. $bigi .'+'. $mf1;&assign;
$p = $mf8754 .'+'. $bigriuse .'+'. $mf1;&assign;
$p = $mf8754 .'+'. $bigi .'+'. $mf2;&assign;
$p = $mf8754 .'+'. $bigriuse .'+'. $mf2;&assign;
$p = $mf8754 .'+'. $bigi .'+'. $mf3;&assign;
$p = $mf8754 .'+'. $bigriuse .'+'. $mf3;&assign;
$p = $mf8754 .'+'. $bigi .'+'. $mf1 .'+'. $mf2;&assign;
$p = $mf8754 .'+'. $bigriuse .'+'. $mf1 .'+'. $mf2;&assign;
$p = $mf8754 .'+'. $bigi .'+'. $mf1 .'+'. $mf3;&assign;
$p = $mf8754 .'+'. $bigriuse .'+'. $mf1 .'+'. $mf3;&assign;
$p = $mf8754 .'+'. $bigi .'+'. $mf2 .'+'. $mf3;&assign;
$p = $mf8754 .'+'. $bigriuse .'+'. $mf2 .'+'. $mf3;&assign;
$p = $mf8754 .'+'. $bigriuse .'+'. $mf1 .'+'.$mf2 .'+'. $mf3;&assign;

$p = $mf876 .'+'. $bigi;&assign;
$p = $mf876 .'+'. $bigriuse;&assign;
$p = $mf876 .'+'. $bigi .'+'. $mf;&assign;
$p = $mf876 .'+'. $bigriuse .'+'. $mf;&assign;
$p = $mf876 .'+'. $bigi .'+'. $mf1;&assign;
$p = $mf876 .'+'. $bigriuse .'+'. $mf1;&assign;
$p = $mf876 .'+'. $bigi .'+'. $mf2;&assign;
```

```
$p = $mf876 .'+'. $bigriuse .'+'. $mf2;&assign;
$p = $mf876 .'+'. $bigi .'+'. $mf3;&assign;
$p = $mf876 .'+'. $bigriuse .'+'. $mf3;&assign;
$p = $mf876 .'+'. $bigi .'+'. $mf1 .'+'. $mf2;&assign;
$p = $mf876 .'+'. $bigriuse .'+'. $mf1 .'+'. $mf2;&assign;
$p = $mf876 .'+'. $bigi .'+'. $mf1 .'+'. $mf3;&assign;
$p = $mf876 .'+'. $bigriuse .'+'. $mf1 .'+'. $mf3;&assign;
$p = $mf876 .'+'. $bigi .'+'. $mf2 .'+'. $mf3;&assign;
$p = $mf876 .'+'. $bigriuse .'+'. $mf2 .'+'. $mf3;&assign;
$p = $mf876 .'+'. $bigriuse .'+'. $mf1 .'+'.$mf2 .'+'. $mf3;&assign;
#_____

$p = $mf8764 .'+'. $bigi;&assign;
$p = $mf8764 .'+'. $bigriuse;&assign;
$p = $mf8764 .'+'. $bigi .'+'. $mf;&assign;
$p = $mf8764 .'+'. $bigriuse .'+'. $mf;&assign;
$p = $mf8764 .'+'. $bigi .'+'. $mf1;&assign;
$p = $mf8764 .'+'. $bigriuse .'+'. $mf1;&assign;
$p = $mf8764 .'+'. $bigi .'+'. $mf2;&assign;
$p = $mf8764 .'+'. $bigriuse .'+'. $mf2;&assign;
$p = $mf8764 .'+'. $bigi .'+'. $mf3;&assign;
$p = $mf8764 .'+'. $bigriuse .'+'. $mf3;&assign;
$p = $mf8764 .'+'. $bigi .'+'. $mf1 .'+'. $mf2;&assign;
$p = $mf8764 .'+'. $bigriuse .'+'. $mf1 .'+'. $mf2;&assign;
$p = $mf8764 .'+'. $bigi .'+'. $mf1 .'+'. $mf3;&assign;
$p = $mf8764 .'+'. $bigriuse .'+'. $mf1 .'+'. $mf3;&assign;
$p = $mf8764 .'+'. $bigi .'+'. $mf2 .'+'. $mf3;&assign;
$p = $mf8764 .'+'. $bigriuse .'+'. $mf2 .'+'. $mf3;&assign;
$p = $mf8764 .'+'. $bigriuse .'+'. $mf1 .'+'.$mf2 .'+'. $mf3;&assign;
#_____
$p = $mf8765 .'+'. $bigi;&assign;
$p = $mf8765 .'+'. $bigriuse;&assign;
$p = $mf8765 .'+'. $bigi .'+'. $mf;&assign;
$p = $mf8765 .'+'. $bigriuse .'+'. $mf;&assign;
$p = $mf8765 .'+'. $bigi .'+'. $mf1;&assign;
$p = $mf8765 .'+'. $bigriuse .'+'. $mf1;&assign;
$p = $mf8765 .'+'. $bigi .'+'. $mf2;&assign;
$p = $mf8765 .'+'. $bigriuse .'+'. $mf2;&assign;
$p = $mf8765 .'+'. $bigi .'+'. $mf3;&assign;
$p = $mf8765 .'+'. $bigriuse .'+'. $mf3;&assign;
$p = $mf8765 .'+'. $bigi .'+'. $mf1 .'+'. $mf2;&assign;
$p = $mf8765 .'+'. $bigriuse .'+'. $mf1 .'+'. $mf2;&assign;
$p = $mf8765 .'+'. $bigi .'+'. $mf1 .'+'. $mf3;&assign;
$p = $mf8765 .'+'. $bigriuse .'+'. $mf1 .'+'. $mf3;&assign;
```

```
$p = $mf8765 .'+'. $bigi .'+'. $mf2 .'+'. $mf3;&assign;
$p = $mf8765 .'+'. $bigriuse .'+'. $mf2 .'+'. $mf3;&assign;
$p = $mf8765 .'+'. $bigriuse .'+'. $mf1 .'+'. $mf2 .'+'. $mf3;&assign;
#_____
$p = $mf87654 .'+'. $bigi;&assign;
$p = $mf87654 .'+'. $bigriuse;&assign;
$p = $mf87654 .'+'. $bigi .'+'. $mf;&assign;
$p = $mf87654 .'+'. $bigriuse .'+'. $mf;&assign;
$p = $mf87654 .'+'. $bigi .'+'. $mf1;&assign;
$p = $mf87654 .'+'. $bigriuse .'+'. $mf1;&assign;
$p = $mf87654 .'+'. $bigi .'+'. $mf2;&assign;
$p = $mf87654 .'+'. $bigriuse .'+'. $mf2;&assign;
$p = $mf87654 .'+'. $bigi .'+'. $mf3;&assign;
$p = $mf87654 .'+'. $bigriuse .'+'. $mf3;&assign;
$p = $mf87654 .'+'. $bigi .'+'. $mf1 .'+'. $mf2;&assign;
$p = $mf87654 .'+'. $bigriuse .'+'. $mf1 .'+'. $mf2;&assign;
$p = $mf87654 .'+'. $bigi .'+'. $mf1 .'+'. $mf3;&assign;
$p = $mf87654 .'+'. $bigriuse .'+'. $mf1 .'+'. $mf3;&assign;
$p = $mf87654 .'+'. $bigi .'+'. $mf2 .'+'. $mf3;&assign;
$p = $mf87654 .'+'. $bigriuse .'+'. $mf2 .'+'. $mf3;&assign;
$p = $mf87654 .'+'. $bigriuse .'+'. $mf1 .'+'. $mf2 .'+'. $mf3;&assign;
#_____
$p = $mf9 .'+'. $bigi;&assign;
$p = $mf9 .'+'. $bigriuse;&assign;
$p = $mf9 .'+'. $bigi .'+'. $mf;&assign;
$p = $mf9 .'+'. $bigriuse .'+'. $mf;&assign;
$p = $mf9 .'+'. $bigi .'+'. $mf1;&assign;
$p = $mf9 .'+'. $bigriuse .'+'. $mf1;&assign;
$p = $mf9 .'+'. $bigi .'+'. $mf2;&assign;
$p = $mf9 .'+'. $bigriuse .'+'. $mf2;&assign;
$p = $mf9 .'+'. $bigi .'+'. $mf3;&assign;
$p = $mf9 .'+'. $bigriuse .'+'. $mf3;&assign;
$p = $mf9 .'+'. $bigi .'+'. $mf1 .'+'. $mf2;&assign;
$p = $mf9 .'+'. $bigriuse .'+'. $mf1 .'+'. $mf2;&assign;
$p = $mf9 .'+'. $bigi .'+'. $mf1 .'+'. $mf3;&assign;
$p = $mf9 .'+'. $bigriuse .'+'. $mf1 .'+'. $mf3;&assign;
$p = $mf9 .'+'. $bigi .'+'. $mf2 .'+'. $mf3;&assign;
$p = $mf9 .'+'. $bigriuse .'+'. $mf2 .'+'. $mf3;&assign;
$p = $mf9 .'+'. $bigriuse .'+'. $mf1 .'+'. $mf2 .'+'. $mf3;&assign;
#_____

$p = $mf94 .'+'. $bigi;&assign;
$p = $mf94 .'+'. $bigriuse;&assign;
$p = $mf94 .'+'. $bigi .'+'. $mf;&assign;
```

```
$p = $mf94 .'+'. $bigriuse .'+'. $mf;&assign;
$p = $mf94 .'+'. $bigi .'+'. $mf1;&assign;
$p = $mf94 .'+'. $bigriuse .'+'. $mf1;&assign;
$p = $mf94 .'+'. $bigi .'+'. $mf2;&assign;
$p = $mf94 .'+'. $bigriuse .'+'. $mf2;&assign;
$p = $mf94 .'+'. $bigi .'+'. $mf3;&assign;
$p = $mf94 .'+'. $bigriuse .'+'. $mf3;&assign;
$p = $mf94 .'+'. $bigi .'+'. $mf1 .'+'. $mf2;&assign;
$p = $mf94 .'+'. $bigriuse .'+'. $mf1 .'+'. $mf2;&assign;
$p = $mf94 .'+'. $bigi .'+'. $mf1 .'+'. $mf3;&assign;
$p = $mf94 .'+'. $bigriuse .'+'. $mf1 .'+'. $mf3;&assign;
$p = $mf94 .'+'. $bigi .'+'. $mf2 .'+'. $mf3;&assign;
$p = $mf94 .'+'. $bigriuse .'+'. $mf2 .'+'. $mf3;&assign;
$p = $mf94 .'+'. $bigriuse .'+'. $mf1 .'+'. $mf2 .'+'. $mf3;&assign;
#_____
$p = $mf95 .'+'. $bigi;&assign;
$p = $mf95 .'+'. $bigriuse;&assign;
$p = $mf95 .'+'. $bigi .'+'. $mf;&assign;
$p = $mf95 .'+'. $bigriuse .'+'. $mf;&assign;
$p = $mf95 .'+'. $bigi .'+'. $mf1;&assign;
$p = $mf95 .'+'. $bigriuse .'+'. $mf1;&assign;
$p = $mf95 .'+'. $bigi .'+'. $mf2;&assign;
$p = $mf95 .'+'. $bigriuse .'+'. $mf2;&assign;
$p = $mf95 .'+'. $bigi .'+'. $mf3;&assign;
$p = $mf95 .'+'. $bigriuse .'+'. $mf3;&assign;
$p = $mf95 .'+'. $bigi .'+'. $mf1 .'+'. $mf2;&assign;
$p = $mf95 .'+'. $bigriuse .'+'. $mf1 .'+'. $mf2;&assign;
$p = $mf95 .'+'. $bigi .'+'. $mf1 .'+'. $mf3;&assign;
$p = $mf95 .'+'. $bigriuse .'+'. $mf1 .'+'. $mf3;&assign;
$p = $mf95 .'+'. $bigi .'+'. $mf2 .'+'. $mf3;&assign;
$p = $mf95 .'+'. $bigriuse .'+'. $mf2 .'+'. $mf3;&assign;
$p = $mf95 .'+'. $bigriuse .'+'. $mf1 .'+'. $mf2 .'+'. $mf3;&assign;
#_____
$p = $mf954 .'+'. $bigi;&assign;
$p = $mf954 .'+'. $bigriuse;&assign;
$p = $mf954 .'+'. $bigi .'+'. $mf;&assign;
$p = $mf954 .'+'. $bigriuse .'+'. $mf;&assign;
$p = $mf954 .'+'. $bigi .'+'. $mf1;&assign;
$p = $mf954 .'+'. $bigriuse .'+'. $mf1;&assign;
$p = $mf954 .'+'. $bigi .'+'. $mf2;&assign;
$p = $mf954 .'+'. $bigriuse .'+'. $mf2;&assign;
$p = $mf954 .'+'. $bigi .'+'. $mf3;&assign;
$p = $mf954 .'+'. $bigriuse .'+'. $mf3;&assign;
$p = $mf954 .'+'. $bigi .'+'. $mf1 .'+'. $mf2;&assign;
$p = $mf954 .'+'. $bigriuse .'+'. $mf1 .'+'. $mf2;&assign;
```

```
$p = $mf954 .'+'. $bigi .'+'. $mf1 .'+'. $mf3;&assign;
$p = $mf954 .'+'. $bigriuse .'+'. $mf1 .'+'. $mf3;&assign;
$p = $mf954 .'+'. $bigi .'+'. $mf2 .'+'. $mf3;&assign;
$p = $mf954 .'+'. $bigriuse .'+'. $mf2 .'+'. $mf3;&assign;
$p = $mf954 .'+'. $bigriuse .'+'. $mf1 .'+'. $mf2 .'+'. $mf3;&assign;

$p = $mf96 .'+'. $bigi;&assign;
$p = $mf96 .'+'. $bigriuse;&assign;
$p = $mf96 .'+'. $bigi .'+'. $mf;&assign;
$p = $mf96 .'+'. $bigriuse .'+'. $mf;&assign;
$p = $mf96 .'+'. $bigi .'+'. $mf1;&assign;
$p = $mf96 .'+'. $bigriuse .'+'. $mf1;&assign;
$p = $mf96 .'+'. $bigi .'+'. $mf2;&assign;
$p = $mf96 .'+'. $bigriuse .'+'. $mf2;&assign;
$p = $mf96 .'+'. $bigi .'+'. $mf3;&assign;
$p = $mf96 .'+'. $bigriuse .'+'. $mf3;&assign;
$p = $mf96 .'+'. $bigi .'+'. $mf1 .'+'. $mf2;&assign;
$p = $mf96 .'+'. $bigriuse .'+'. $mf1 .'+'. $mf2;&assign;
$p = $mf96 .'+'. $bigi .'+'. $mf1 .'+'. $mf3;&assign;
$p = $mf96 .'+'. $bigriuse .'+'. $mf1 .'+'. $mf3;&assign;
$p = $mf96 .'+'. $bigi .'+'. $mf2 .'+'. $mf3;&assign;
$p = $mf96 .'+'. $bigriuse .'+'. $mf2 .'+'. $mf3;&assign;
$p = $mf96 .'+'. $bigriuse .'+'. $mf1 .'+'. $mf2 .'+'. $mf3;&assign;

$p = $mf964 .'+'. $bigi;&assign;
$p = $mf964 .'+'. $bigriuse;&assign;
$p = $mf964 .'+'. $bigi .'+'. $mf;&assign;
$p = $mf964 .'+'. $bigriuse .'+'. $mf;&assign;
$p = $mf964 .'+'. $bigi .'+'. $mf1;&assign;
$p = $mf964 .'+'. $bigriuse .'+'. $mf1;&assign;
$p = $mf964 .'+'. $bigi .'+'. $mf2;&assign;
$p = $mf964 .'+'. $bigriuse .'+'. $mf2;&assign;
$p = $mf964 .'+'. $bigi .'+'. $mf3;&assign;
$p = $mf964 .'+'. $bigriuse .'+'. $mf3;&assign;
$p = $mf964 .'+'. $bigi .'+'. $mf1 .'+'. $mf2;&assign;
$p = $mf964 .'+'. $bigriuse .'+'. $mf1 .'+'. $mf2;&assign;
$p = $mf964 .'+'. $bigi .'+'. $mf1 .'+'. $mf3;&assign;
$p = $mf964 .'+'. $bigriuse .'+'. $mf1 .'+'. $mf3;&assign;
$p = $mf964 .'+'. $bigi .'+'. $mf2 .'+'. $mf3;&assign;
$p = $mf964 .'+'. $bigriuse .'+'. $mf2 .'+'. $mf3;&assign;
$p = $mf965 .'+'. $bigriuse .'+'. $mf1 .'+'. $mf2 .'+'. $mf3;&assign;

$p = $mf965 .'+'. $bigi;&assign;
```

```
$p = $mf965 .'+'. $bigriuse;&assign;
$p = $mf965 .'+'. $bigi .'+'. $mf;&assign;
$p = $mf965 .'+'. $bigriuse .'+'. $mf;&assign;
$p = $mf965 .'+'. $bigi .'+'. $mf1;&assign;
$p = $mf965 .'+'. $bigriuse .'+'. $mf1;&assign;
$p = $mf965 .'+'. $bigi .'+'. $mf2;&assign;
$p = $mf965 .'+'. $bigriuse .'+'. $mf2;&assign;
$p = $mf965 .'+'. $bigi .'+'. $mf3;&assign;
$p = $mf965 .'+'. $bigriuse .'+'. $mf3;&assign;
$p = $mf965 .'+'. $bigi .'+'. $mf1 .'+'. $mf2;&assign;
$p = $mf965 .'+'. $bigriuse .'+'. $mf1 .'+'. $mf2;&assign;
$p = $mf965 .'+'. $bigi .'+'. $mf1 .'+'. $mf3;&assign;
$p = $mf965 .'+'. $bigriuse .'+'. $mf1 .'+'. $mf3;&assign;
$p = $mf965 .'+'. $bigi .'+'. $mf2 .'+'. $mf3;&assign;
$p = $mf965 .'+'. $bigriuse .'+'. $mf2 .'+'. $mf3;&assign;
$p = $mf965 .'+'. $bigriuse .'+'. $mf1 .'+'. $mf2 .'+'. $mf3;&assign;

$p = $mf9654 .'+'. $bigi;&assign;
$p = $mf9654 .'+'. $bigriuse;&assign;
$p = $mf9654 .'+'. $bigi .'+'. $mf;&assign;
$p = $mf9654 .'+'. $bigriuse .'+'. $mf;&assign;
$p = $mf9654 .'+'. $bigi .'+'. $mf1;&assign;
$p = $mf9654 .'+'. $bigriuse .'+'. $mf1;&assign;
$p = $mf9654 .'+'. $bigi .'+'. $mf2;&assign;
$p = $mf9654 .'+'. $bigriuse .'+'. $mf2;&assign;
$p = $mf9654 .'+'. $bigi .'+'. $mf3;&assign;
$p = $mf9654 .'+'. $bigriuse .'+'. $mf3;&assign;
$p = $mf9654 .'+'. $bigi .'+'. $mf1 .'+'. $mf2;&assign;
$p = $mf9654 .'+'. $bigriuse .'+'. $mf1 .'+'. $mf2;&assign;
$p = $mf9654 .'+'. $bigi .'+'. $mf1 .'+'. $mf3;&assign;
$p = $mf9654 .'+'. $bigriuse .'+'. $mf1 .'+'. $mf3;&assign;
$p = $mf9654 .'+'. $bigi .'+'. $mf2 .'+'. $mf3;&assign;
$p = $mf9654 .'+'. $bigriuse .'+'. $mf2 .'+'. $mf3;&assign;
$p = $mf9654 .'+'. $bigriuse .'+'. $mf1 .'+'. $mf2 .'+'. $mf3;&assign;

$p = $mf97 .'+'. $bigi;&assign;
$p = $mf97 .'+'. $bigriuse;&assign;
$p = $mf97 .'+'. $bigi .'+'. $mf;&assign;
$p = $mf97 .'+'. $bigriuse .'+'. $mf;&assign;
$p = $mf97 .'+'. $bigi .'+'. $mf1;&assign;
$p = $mf97 .'+'. $bigriuse .'+'. $mf1;&assign;
$p = $mf97 .'+'. $bigi .'+'. $mf2;&assign;
$p = $mf97 .'+'. $bigriuse .'+'. $mf2;&assign;
$p = $mf97 .'+'. $bigi .'+'. $mf3;&assign;
$p = $mf97 .'+'. $bigriuse .'+'. $mf3;&assign;
```

```
$p = $mf97 .'+'. $bigi .'+'. $mf1 .'+'. $mf2;&assign;
$p = $mf97 .'+'. $bigriuse .'+'. $mf1 .'+'. $mf2;&assign;
$p = $mf97 .'+'. $bigi .'+'. $mf1 .'+'. $mf3;&assign;
$p = $mf97 .'+'. $bigriuse .'+'. $mf1 .'+'. $mf3;&assign;
$p = $mf97 .'+'. $bigi .'+'. $mf2 .'+'. $mf3;&assign;
$p = $mf97 .'+'. $bigriuse .'+'. $mf2 .'+'. $mf3;&assign;
$p = $mf97 .'+'. $bigriuse .'+'. $mf1 .'+'. $mf2 .'+'. $mf3;&assign;
#_____

$p = $mf974 .'+'. $bigi;&assign;
$p = $mf974 .'+'. $bigriuse;&assign;
$p = $mf974 .'+'. $bigi .'+'. $mf;&assign;
$p = $mf974 .'+'. $bigriuse .'+'. $mf;&assign;
$p = $mf974 .'+'. $bigi .'+'. $mf1;&assign;
$p = $mf974 .'+'. $bigriuse .'+'. $mf1;&assign;
$p = $mf974 .'+'. $bigi .'+'. $mf2;&assign;
$p = $mf974 .'+'. $bigriuse .'+'. $mf2;&assign;
$p = $mf974 .'+'. $bigi .'+'. $mf3;&assign;
$p = $mf974 .'+'. $bigriuse .'+'. $mf3;&assign;
$p = $mf974 .'+'. $bigi .'+'. $mf1 .'+'. $mf2;&assign;
$p = $mf974 .'+'. $bigriuse .'+'. $mf1 .'+'. $mf2;&assign;
$p = $mf974 .'+'. $bigi .'+'. $mf1 .'+'. $mf3;&assign;
$p = $mf974 .'+'. $bigriuse .'+'. $mf1 .'+'. $mf3;&assign;
$p = $mf974 .'+'. $bigi .'+'. $mf2 .'+'. $mf3;&assign;
$p = $mf974 .'+'. $bigriuse .'+'. $mf2 .'+'. $mf3;&assign;
$p = $mf974 .'+'. $bigriuse .'+'. $mf1 .'+'. $mf2 .'+'. $mf3;&assign;
#_____
$p = $mf975 .'+'. $bigi;&assign;
$p = $mf975 .'+'. $bigriuse;&assign;
$p = $mf975 .'+'. $bigi .'+'. $mf;&assign;
$p = $mf975 .'+'. $bigriuse .'+'. $mf;&assign;
$p = $mf975 .'+'. $bigi .'+'. $mf1;&assign;
$p = $mf975 .'+'. $bigriuse .'+'. $mf1;&assign;
$p = $mf975 .'+'. $bigi .'+'. $mf2;&assign;
$p = $mf975 .'+'. $bigriuse .'+'. $mf2;&assign;
$p = $mf975 .'+'. $bigi .'+'. $mf3;&assign;
$p = $mf975 .'+'. $bigriuse .'+'. $mf3;&assign;
$p = $mf975 .'+'. $bigi .'+'. $mf1 .'+'. $mf2;&assign;
$p = $mf975 .'+'. $bigriuse .'+'. $mf1 .'+'. $mf2;&assign;
$p = $mf975 .'+'. $bigi .'+'. $mf1 .'+'. $mf3;&assign;
$p = $mf975 .'+'. $bigriuse .'+'. $mf1 .'+'. $mf3;&assign;
$p = $mf975 .'+'. $bigi .'+'. $mf2 .'+'. $mf3;&assign;
$p = $mf975 .'+'. $bigriuse .'+'. $mf2 .'+'. $mf3;&assign;
$p = $mf975 .'+'. $bigriuse .'+'. $mf1 .'+'. $mf2 .'+'. $mf3;&assign;
```

```

$p = $mf9754 .'+'. $bigi;&assign;
$p = $mf9754 .'+'. $bigriuse;&assign;
$p = $mf9754 .'+'. $bigi .'+'. $mf;&assign;
$p = $mf9754 .'+'. $bigriuse .'+'. $mf;&assign;
$p = $mf9754 .'+'. $bigi .'+'. $mf1;&assign;
$p = $mf9754 .'+'. $bigriuse .'+'. $mf1;&assign;
$p = $mf9754 .'+'. $bigi .'+'. $mf2;&assign;
$p = $mf9754 .'+'. $bigriuse .'+'. $mf2;&assign;
$p = $mf9754 .'+'. $bigi .'+'. $mf3;&assign;
$p = $mf9754 .'+'. $bigriuse .'+'. $mf3;&assign;
$p = $mf9754 .'+'. $bigi .'+'. $mf1 .'+'. $mf2;&assign;
$p = $mf9754 .'+'. $bigriuse .'+'. $mf1 .'+'. $mf2;&assign;
$p = $mf9754 .'+'. $bigi .'+'. $mf1 .'+'. $mf3;&assign;
$p = $mf9754 .'+'. $bigriuse .'+'. $mf1 .'+'. $mf3;&assign;
$p = $mf9754 .'+'. $bigi .'+'. $mf2 .'+'. $mf3;&assign;
$p = $mf9754 .'+'. $bigriuse .'+'. $mf2 .'+'. $mf3;&assign;
$p = $mf9754 .'+'. $bigriuse .'+'. $mf1 .'+'. $mf2 .'+'. $mf3;&assign;

$p = $mf976 .'+'. $bigi;&assign;
$p = $mf976 .'+'. $bigriuse;&assign;
$p = $mf976 .'+'. $bigi .'+'. $mf;&assign;
$p = $mf976 .'+'. $bigriuse .'+'. $mf;&assign;
$p = $mf976 .'+'. $bigi .'+'. $mf1;&assign;
$p = $mf976 .'+'. $bigriuse .'+'. $mf1;&assign;
$p = $mf976 .'+'. $bigi .'+'. $mf2;&assign;
$p = $mf976 .'+'. $bigriuse .'+'. $mf2;&assign;
$p = $mf976 .'+'. $bigi .'+'. $mf3;&assign;
$p = $mf976 .'+'. $bigriuse .'+'. $mf3;&assign;
$p = $mf976 .'+'. $bigi .'+'. $mf1 .'+'. $mf2;&assign;
$p = $mf976 .'+'. $bigriuse .'+'. $mf1 .'+'. $mf2;&assign;
$p = $mf976 .'+'. $bigi .'+'. $mf1 .'+'. $mf3;&assign;
$p = $mf976 .'+'. $bigriuse .'+'. $mf1 .'+'. $mf3;&assign;
$p = $mf976 .'+'. $bigi .'+'. $mf2 .'+'. $mf3;&assign;
$p = $mf976 .'+'. $bigriuse .'+'. $mf2 .'+'. $mf3;&assign;
$p = $mf976 .'+'. $bigriuse .'+'. $mf1 .'+'. $mf2 .'+'. $mf3;&assign;

$p = $mf9764 .'+'. $bigi;&assign;
$p = $mf9764 .'+'. $bigriuse;&assign;
$p = $mf9764 .'+'. $bigi .'+'. $mf;&assign;
$p = $mf9764 .'+'. $bigriuse .'+'. $mf;&assign;
$p = $mf9764 .'+'. $bigi .'+'. $mf1;&assign;
$p = $mf9764 .'+'. $bigriuse .'+'. $mf1;&assign;
```

```
$p = $mf9764 .'+'. $bigi .'+'. $mf2;&assign;
$p = $mf9764 .'+'. $bigriuse .'+'. $mf2;&assign;
$p = $mf9764 .'+'. $bigi .'+'. $mf3;&assign;
$p = $mf9764 .'+'. $bigriuse .'+'. $mf3;&assign;
$p = $mf9764 .'+'. $bigi .'+'. $mf1 .'+'. $mf2;&assign;
$p = $mf9764 .'+'. $bigriuse .'+'. $mf1 .'+'. $mf2;&assign;
$p = $mf9764 .'+'. $bigi .'+'. $mf1 .'+'. $mf3;&assign;
$p = $mf9764 .'+'. $bigriuse .'+'. $mf1 .'+'. $mf3;&assign;
$p = $mf9764 .'+'. $bigi .'+'. $mf2 .'+'. $mf3;&assign;
$p = $mf9764 .'+'. $bigriuse .'+'. $mf2 .'+'. $mf3;&assign;
$p = $mf9764 .'+'. $bigriuse .'+'. $mf1 .'+'. $mf2 .'+'. $mf3;&assign;

$p = $mf9765 .'+'. $bigi;&assign;
$p = $mf9765 .'+'. $bigriuse;&assign;
$p = $mf9765 .'+'. $bigi .'+'. $mf;&assign;
$p = $mf9765 .'+'. $bigriuse .'+'. $mf;&assign;
$p = $mf9765 .'+'. $bigi .'+'. $mf1;&assign;
$p = $mf9765 .'+'. $bigriuse .'+'. $mf1;&assign;
$p = $mf9765 .'+'. $bigi .'+'. $mf2;&assign;
$p = $mf9765 .'+'. $bigriuse .'+'. $mf2;&assign;
$p = $mf9765 .'+'. $bigi .'+'. $mf3;&assign;
$p = $mf9765 .'+'. $bigriuse .'+'. $mf3;&assign;
$p = $mf9765 .'+'. $bigi .'+'. $mf1 .'+'. $mf2;&assign;
$p = $mf9765 .'+'. $bigriuse .'+'. $mf1 .'+'. $mf2;&assign;
$p = $mf9765 .'+'. $bigi .'+'. $mf1 .'+'. $mf3;&assign;
$p = $mf9765 .'+'. $bigriuse .'+'. $mf1 .'+'. $mf3;&assign;
$p = $mf9765 .'+'. $bigi .'+'. $mf2 .'+'. $mf3;&assign;
$p = $mf9765 .'+'. $bigriuse .'+'. $mf2 .'+'. $mf3;&assign;
$p = $mf9765 .'+'. $bigriuse .'+'. $mf1 .'+'. $mf2 .'+'. $mf3;&assign;

$p = $mf97654 .'+'. $bigi;&assign;
$p = $mf97654 .'+'. $bigriuse;&assign;
$p = $mf97654 .'+'. $bigi .'+'. $mf;&assign;
$p = $mf97654 .'+'. $bigriuse .'+'. $mf;&assign;
$p = $mf97654 .'+'. $bigi .'+'. $mf1;&assign;
$p = $mf97654 .'+'. $bigriuse .'+'. $mf1;&assign;
$p = $mf97654 .'+'. $bigi .'+'. $mf2;&assign;
$p = $mf97654 .'+'. $bigriuse .'+'. $mf2;&assign;
$p = $mf97654 .'+'. $bigi .'+'. $mf3;&assign;
$p = $mf97654 .'+'. $bigriuse .'+'. $mf3;&assign;
$p = $mf97654 .'+'. $bigi .'+'. $mf1 .'+'. $mf2;&assign;
$p = $mf97654 .'+'. $bigriuse .'+'. $mf1 .'+'. $mf2;&assign;
$p = $mf97654 .'+'. $bigi .'+'. $mf1 .'+'. $mf3;&assign;
$p = $mf97654 .'+'. $bigriuse .'+'. $mf1 .'+'. $mf3;&assign;
$p = $mf97654 .'+'. $bigi .'+'. $mf2 .'+'. $mf3;&assign;
```

```
$p = $mf97654 .'+'. $bigriuse .'+'. $mf2 .'+'. $mf3;&assign;
$p = $mf97654 .'+'. $bigriuse .'+'. $mf1 .'+'. $mf2 .'+'. $mf3;&assign;
#_____
$p = $mf98 .'+'. $bigi;&assign;
$p = $mf98 .'+'. $bigriuse;&assign;
$p = $mf98 .'+'. $bigi .'+'. $mf;&assign;
$p = $mf98 .'+'. $bigriuse .'+'. $mf;&assign;
$p = $mf98 .'+'. $bigi .'+'. $mf1;&assign;
$p = $mf98 .'+'. $bigriuse .'+'. $mf1;&assign;
$p = $mf98 .'+'. $bigi .'+'. $mf2;&assign;
$p = $mf98 .'+'. $bigriuse .'+'. $mf2;&assign;
$p = $mf98 .'+'. $bigi .'+'. $mf3;&assign;
$p = $mf98 .'+'. $bigriuse .'+'. $mf3;&assign;
$p = $mf98 .'+'. $bigi .'+'. $mf1 .'+'. $mf2;&assign;
$p = $mf98 .'+'. $bigriuse .'+'. $mf1 .'+'. $mf2;&assign;
$p = $mf98 .'+'. $bigi .'+'. $mf1 .'+'. $mf3;&assign;
$p = $mf98 .'+'. $bigriuse .'+'. $mf1 .'+'. $mf3;&assign;
$p = $mf98 .'+'. $bigi .'+'. $mf2 .'+'. $mf3;&assign;
$p = $mf98 .'+'. $bigriuse .'+'. $mf2 .'+'. $mf3;&assign;
$p = $mf98 .'+'. $bigriuse .'+'. $mf1 .'+'. $mf2 .'+'. $mf3;&assign;
#_____

$p = $mf984 .'+'. $bigi;&assign;
$p = $mf984 .'+'. $bigriuse;&assign;
$p = $mf984 .'+'. $bigi .'+'. $mf;&assign;
$p = $mf984 .'+'. $bigriuse .'+'. $mf;&assign;
$p = $mf984 .'+'. $bigi .'+'. $mf1;&assign;
$p = $mf984 .'+'. $bigriuse .'+'. $mf1;&assign;
$p = $mf984 .'+'. $bigi .'+'. $mf2;&assign;
$p = $mf984 .'+'. $bigriuse .'+'. $mf2;&assign;
$p = $mf984 .'+'. $bigi .'+'. $mf3;&assign;
$p = $mf984 .'+'. $bigriuse .'+'. $mf3;&assign;
$p = $mf984 .'+'. $bigi .'+'. $mf1 .'+'. $mf2;&assign;
$p = $mf984 .'+'. $bigriuse .'+'. $mf1 .'+'. $mf2;&assign;
$p = $mf984 .'+'. $bigi .'+'. $mf1 .'+'. $mf3;&assign;
$p = $mf984 .'+'. $bigriuse .'+'. $mf1 .'+'. $mf3;&assign;
$p = $mf984 .'+'. $bigi .'+'. $mf2 .'+'. $mf3;&assign;
$p = $mf984 .'+'. $bigriuse .'+'. $mf2 .'+'. $mf3;&assign;
$p = $mf984 .'+'. $bigriuse .'+'. $mf1 .'+'. $mf2 .'+'. $mf3;&assign;
#_____
$p = $mf985 .'+'. $bigi;&assign;
$p = $mf985 .'+'. $bigriuse;&assign;
$p = $mf985 .'+'. $bigi .'+'. $mf;&assign;
$p = $mf985 .'+'. $bigriuse .'+'. $mf;&assign;
```

```
$p = $mf985 .'+'. $bigi .'+'. $mf1;&assign;
$p = $mf985 .'+'. $bigriuse .'+'. $mf1;&assign;
$p = $mf985 .'+'. $bigi .'+'. $mf2;&assign;
$p = $mf985 .'+'. $bigriuse .'+'. $mf2;&assign;
$p = $mf985 .'+'. $bigi .'+'. $mf3;&assign;
$p = $mf985 .'+'. $bigriuse .'+'. $mf3;&assign;
$p = $mf985 .'+'. $bigi .'+'. $mf1 .'+'. $mf2;&assign;
$p = $mf985 .'+'. $bigriuse .'+'. $mf1 .'+'. $mf2;&assign;
$p = $mf985 .'+'. $bigi .'+'. $mf1 .'+'. $mf3;&assign;
$p = $mf985 .'+'. $bigriuse .'+'. $mf1 .'+'. $mf3;&assign;
$p = $mf985 .'+'. $bigi .'+'. $mf2 .'+'. $mf3;&assign;
$p = $mf985 .'+'. $bigriuse .'+'. $mf2 .'+'. $mf3;&assign;
$p = $mf985 .'+'. $bigriuse .'+'. $mf1 .'+'. $mf2 .'+'. $mf3;&assign;

$p = $mf9854 .'+'. $bigi;&assign;
$p = $mf9854 .'+'. $bigriuse;&assign;
$p = $mf9854 .'+'. $bigi .'+'. $mf;&assign;
$p = $mf9854 .'+'. $bigriuse .'+'. $mf;&assign;
$p = $mf9854 .'+'. $bigi .'+'. $mf1;&assign;
$p = $mf9854 .'+'. $bigriuse .'+'. $mf1;&assign;
$p = $mf9854 .'+'. $bigi .'+'. $mf2;&assign;
$p = $mf9854 .'+'. $bigriuse .'+'. $mf2;&assign;
$p = $mf9854 .'+'. $bigi .'+'. $mf3;&assign;
$p = $mf9854 .'+'. $bigriuse .'+'. $mf3;&assign;
$p = $mf9854 .'+'. $bigi .'+'. $mf1 .'+'. $mf2;&assign;
$p = $mf9854 .'+'. $bigriuse .'+'. $mf1 .'+'. $mf2;&assign;
$p = $mf9854 .'+'. $bigi .'+'. $mf1 .'+'. $mf3;&assign;
$p = $mf9854 .'+'. $bigriuse .'+'. $mf1 .'+'. $mf3;&assign;
$p = $mf9854 .'+'. $bigi .'+'. $mf2 .'+'. $mf3;&assign;
$p = $mf9854 .'+'. $bigriuse .'+'. $mf2 .'+'. $mf3;&assign;
$p = $mf9854 .'+'. $bigriuse .'+'. $mf1 .'+'. $mf2 .'+'. $mf3;&assign;

$p = $mf986 .'+'. $bigi;&assign;
$p = $mf986 .'+'. $bigriuse;&assign;
$p = $mf986 .'+'. $bigi .'+'. $mf;&assign;
$p = $mf986 .'+'. $bigriuse .'+'. $mf;&assign;
$p = $mf986 .'+'. $bigi .'+'. $mf1;&assign;
$p = $mf986 .'+'. $bigriuse .'+'. $mf1;&assign;
$p = $mf986 .'+'. $bigi .'+'. $mf2;&assign;
$p = $mf986 .'+'. $bigriuse .'+'. $mf2;&assign;
$p = $mf986 .'+'. $bigi .'+'. $mf3;&assign;
$p = $mf986 .'+'. $bigriuse .'+'. $mf3;&assign;
$p = $mf986 .'+'. $bigi .'+'. $mf1 .'+'. $mf2;&assign;
$p = $mf986 .'+'. $bigriuse .'+'. $mf1 .'+'. $mf2;&assign;
$p = $mf986 .'+'. $bigi .'+'. $mf1 .'+'. $mf3;&assign;
```

```
$p = $mf986 .'+'. $bigriuse .'+'. $mf1 .'+'. $mf3;&assign;
$p = $mf986 .'+'. $bigi .'+'. $mf2 .'+'. $mf3;&assign;
$p = $mf986 .'+'. $bigriuse .'+'. $mf2 .'+'. $mf3;&assign;
$p = $mf986 .'+'. $bigriuse .'+'. $mf1 .'+'. $mf2 .'+'. $mf3;&assign;
#_____

$p = $mf9864 .'+'. $bigi;&assign;
$p = $mf9864 .'+'. $bigriuse;&assign;
$p = $mf9864 .'+'. $bigi .'+'. $mf;&assign;
$p = $mf9864 .'+'. $bigriuse .'+'. $mf;&assign;
$p = $mf9864 .'+'. $bigi .'+'. $mf1;&assign;
$p = $mf9864 .'+'. $bigriuse .'+'. $mf1;&assign;
$p = $mf9864 .'+'. $bigi .'+'. $mf2;&assign;
$p = $mf9864 .'+'. $bigriuse .'+'. $mf2;&assign;
$p = $mf9864 .'+'. $bigi .'+'. $mf3;&assign;
$p = $mf9864 .'+'. $bigriuse .'+'. $mf3;&assign;
$p = $mf9864 .'+'. $bigi .'+'. $mf1 .'+'. $mf2;&assign;
$p = $mf9864 .'+'. $bigriuse .'+'. $mf1 .'+'. $mf2;&assign;
$p = $mf9864 .'+'. $bigi .'+'. $mf1 .'+'. $mf3;&assign;
$p = $mf9864 .'+'. $bigriuse .'+'. $mf1 .'+'. $mf3;&assign;
$p = $mf9864 .'+'. $bigi .'+'. $mf2 .'+'. $mf3;&assign;
$p = $mf9864 .'+'. $bigriuse .'+'. $mf2 .'+'. $mf3;&assign;
$p = $mf9864 .'+'. $bigriuse .'+'. $mf1 .'+'. $mf2 .'+'. $mf3;&assign;
#_____
$p = $mf9865 .'+'. $bigi;&assign;
$p = $mf9865 .'+'. $bigriuse;&assign;
$p = $mf9865 .'+'. $bigi .'+'. $mf;&assign;
$p = $mf9865 .'+'. $bigriuse .'+'. $mf;&assign;
$p = $mf9865 .'+'. $bigi .'+'. $mf1;&assign;
$p = $mf9865 .'+'. $bigriuse .'+'. $mf1;&assign;
$p = $mf9865 .'+'. $bigi .'+'. $mf2;&assign;
$p = $mf9865 .'+'. $bigriuse .'+'. $mf2;&assign;
$p = $mf9865 .'+'. $bigi .'+'. $mf3;&assign;
$p = $mf9865 .'+'. $bigriuse .'+'. $mf3;&assign;
$p = $mf9865 .'+'. $bigi .'+'. $mf1 .'+'. $mf2;&assign;
$p = $mf9865 .'+'. $bigriuse .'+'. $mf1 .'+'. $mf2;&assign;
$p = $mf9865 .'+'. $bigi .'+'. $mf1 .'+'. $mf3;&assign;
$p = $mf9865 .'+'. $bigriuse .'+'. $mf1 .'+'. $mf3;&assign;
$p = $mf9865 .'+'. $bigi .'+'. $mf2 .'+'. $mf3;&assign;
$p = $mf9865 .'+'. $bigriuse .'+'. $mf2 .'+'. $mf3;&assign;
$p = $mf9865 .'+'. $bigriuse .'+'. $mf1 .'+'. $mf2 .'+'. $mf3;&assign;
#_____
$p = $mf98654 .'+'. $bigi;&assign;
$p = $mf98654 .'+'. $bigriuse;&assign;
```

```
$p = $mf98654 .'+'. $bigi .'+'. $mf;&assign;
$p = $mf98654 .'+'. $bigriuse .'+'. $mf;&assign;
$p = $mf98654 .'+'. $bigi .'+'. $mf1;&assign;
$p = $mf98654 .'+'. $bigriuse .'+'. $mf1;&assign;
$p = $mf98654 .'+'. $bigi .'+'. $mf2;&assign;
$p = $mf98654 .'+'. $bigriuse .'+'. $mf2;&assign;
$p = $mf98654 .'+'. $bigi .'+'. $mf3;&assign;
$p = $mf98654 .'+'. $bigriuse .'+'. $mf3;&assign;
$p = $mf98654 .'+'. $bigi .'+'. $mf1 .'+'. $mf2;&assign;
$p = $mf98654 .'+'. $bigriuse .'+'. $mf1 .'+'. $mf2;&assign;
$p = $mf98654 .'+'. $bigi .'+'. $mf1 .'+'. $mf3;&assign;
$p = $mf98654 .'+'. $bigriuse .'+'. $mf1 .'+'. $mf3;&assign;
$p = $mf98654 .'+'. $bigi .'+'. $mf2 .'+'. $mf3;&assign;
$p = $mf98654 .'+'. $bigriuse .'+'. $mf2 .'+'. $mf3;&assign;
$p = $mf98654 .'+'. $bigriuse .'+'. $mf1 .'+'. $mf2 .'+'. $mf3;&assign;
#_____
$p = $mf987 .'+'. $bigi;&assign;
$p = $mf987 .'+'. $bigriuse;&assign;
$p = $mf987 .'+'. $bigi .'+'. $mf;&assign;
$p = $mf987 .'+'. $bigriuse .'+'. $mf;&assign;
$p = $mf987 .'+'. $bigi .'+'. $mf1;&assign;
$p = $mf987 .'+'. $bigriuse .'+'. $mf1;&assign;
$p = $mf987 .'+'. $bigi .'+'. $mf2;&assign;
$p = $mf987 .'+'. $bigriuse .'+'. $mf2;&assign;
$p = $mf987 .'+'. $bigi .'+'. $mf3;&assign;
$p = $mf987 .'+'. $bigriuse .'+'. $mf3;&assign;
$p = $mf987 .'+'. $bigi .'+'. $mf1 .'+'. $mf2;&assign;
$p = $mf987 .'+'. $bigriuse .'+'. $mf1 .'+'. $mf2;&assign;
$p = $mf987 .'+'. $bigi .'+'. $mf1 .'+'. $mf3;&assign;
$p = $mf987 .'+'. $bigriuse .'+'. $mf1 .'+'. $mf3;&assign;
$p = $mf987 .'+'. $bigi .'+'. $mf2 .'+'. $mf3;&assign;
$p = $mf987 .'+'. $bigriuse .'+'. $mf2 .'+'. $mf3;&assign;
$p = $mf987 .'+'. $bigriuse .'+'. $mf1 .'+'. $mf2 .'+'. $mf3;&assign;
#_____

$p = $mf9874 .'+'. $bigi;&assign;
$p = $mf9874 .'+'. $bigriuse;&assign;
$p = $mf9874 .'+'. $bigi .'+'. $mf;&assign;
$p = $mf9874 .'+'. $bigriuse .'+'. $mf;&assign;
$p = $mf9874 .'+'. $bigi .'+'. $mf1;&assign;
$p = $mf9874 .'+'. $bigriuse .'+'. $mf1;&assign;
$p = $mf9874 .'+'. $bigi .'+'. $mf2;&assign;
$p = $mf9874 .'+'. $bigriuse .'+'. $mf2;&assign;
$p = $mf9874 .'+'. $bigi .'+'. $mf3;&assign;
```

```
$p = $mf9874 .'+'. $bigriuse .'+'. $mf3;&assign;
$p = $mf9874 .'+'. $bigi .'+'. $mf1 .'+'. $mf2;&assign;
$p = $mf9874 .'+'. $bigriuse .'+'. $mf1 .'+'. $mf2;&assign;
$p = $mf9874 .'+'. $bigi .'+'. $mf1 .'+'. $mf3;&assign;
$p = $mf9874 .'+'. $bigriuse .'+'. $mf1 .'+'. $mf3;&assign;
$p = $mf9874 .'+'. $bigi .'+'. $mf2 .'+'. $mf3;&assign;
$p = $mf9874 .'+'. $bigriuse .'+'. $mf2 .'+'. $mf3;&assign;
$p = $mf9874 .'+'. $bigriuse .'+'. $mf1 .'+'. $mf2 .'+'. $mf3;&assign;
#_____
$p = $mf9875 .'+'. $bigi;&assign;
$p = $mf9875 .'+'. $bigriuse;&assign;
$p = $mf9875 .'+'. $bigi .'+'. $mf;&assign;
$p = $mf9875 .'+'. $bigriuse .'+'. $mf;&assign;
$p = $mf9875 .'+'. $bigi .'+'. $mf1;&assign;
$p = $mf9875 .'+'. $bigriuse .'+'. $mf1;&assign;
$p = $mf9875 .'+'. $bigi .'+'. $mf2;&assign;
$p = $mf9875 .'+'. $bigriuse .'+'. $mf2;&assign;
$p = $mf9875 .'+'. $bigi .'+'. $mf3;&assign;
$p = $mf9875 .'+'. $bigriuse .'+'. $mf3;&assign;
$p = $mf9875 .'+'. $bigi .'+'. $mf1 .'+'. $mf2;&assign;
$p = $mf9875 .'+'. $bigriuse .'+'. $mf1 .'+'. $mf2;&assign;
$p = $mf9875 .'+'. $bigi .'+'. $mf1 .'+'. $mf3;&assign;
$p = $mf9875 .'+'. $bigriuse .'+'. $mf1 .'+'. $mf3;&assign;
$p = $mf9875 .'+'. $bigi .'+'. $mf2 .'+'. $mf3;&assign;
$p = $mf9875 .'+'. $bigriuse .'+'. $mf2 .'+'. $mf3;&assign;
$p = $mf9875 .'+'. $bigriuse .'+'. $mf1 .'+'. $mf2 .'+'. $mf3;&assign;
#_____
$p = $mf98754 .'+'. $bigi;&assign;
$p = $mf98754 .'+'. $bigriuse;&assign;
$p = $mf98754 .'+'. $bigi .'+'. $mf;&assign;
$p = $mf98754 .'+'. $bigriuse .'+'. $mf;&assign;
$p = $mf98754 .'+'. $bigi .'+'. $mf1;&assign;
$p = $mf98754 .'+'. $bigriuse .'+'. $mf1;&assign;
$p = $mf98754 .'+'. $bigi .'+'. $mf2;&assign;
$p = $mf98754 .'+'. $bigriuse .'+'. $mf2;&assign;
$p = $mf98754 .'+'. $bigi .'+'. $mf3;&assign;
$p = $mf98754 .'+'. $bigriuse .'+'. $mf3;&assign;
$p = $mf98754 .'+'. $bigi .'+'. $mf1 .'+'. $mf2;&assign;
$p = $mf98754 .'+'. $bigriuse .'+'. $mf1 .'+'. $mf2;&assign;
$p = $mf98754 .'+'. $bigi .'+'. $mf1 .'+'. $mf3;&assign;
$p = $mf98754 .'+'. $bigriuse .'+'. $mf1 .'+'. $mf3;&assign;
$p = $mf98754 .'+'. $bigi .'+'. $mf2 .'+'. $mf3;&assign;
$p = $mf98754 .'+'. $bigriuse .'+'. $mf2 .'+'. $mf3;&assign;
$p = $mf98754 .'+'. $bigriuse .'+'. $mf1 .'+'. $mf2 .'+'. $mf3;&assign;
#_____
```

```
$p = $mf9876 .'+'. $bigi;&assign;
$p = $mf9876 .'+'. $bigriuse;&assign;
$p = $mf9876 .'+'. $bigi .'+'. $mf;&assign;
$p = $mf9876 .'+'. $bigriuse .'+'. $mf;&assign;
$p = $mf9876 .'+'. $bigi .'+'. $mf1;&assign;
$p = $mf9876 .'+'. $bigriuse .'+'. $mf1;&assign;
$p = $mf9876 .'+'. $bigi .'+'. $mf2;&assign;
$p = $mf9876 .'+'. $bigriuse .'+'. $mf2;&assign;
$p = $mf9876 .'+'. $bigi .'+'. $mf3;&assign;
$p = $mf9876 .'+'. $bigriuse .'+'. $mf3;&assign;
$p = $mf9876 .'+'. $bigi .'+'. $mf1 .'+'. $mf2;&assign;
$p = $mf9876 .'+'. $bigriuse .'+'. $mf1 .'+'. $mf2;&assign;
$p = $mf9876 .'+'. $bigi .'+'. $mf1 .'+'. $mf3;&assign;
$p = $mf9876 .'+'. $bigriuse .'+'. $mf1 .'+'. $mf3;&assign;
$p = $mf9876 .'+'. $bigi .'+'. $mf2 .'+'. $mf3;&assign;
$p = $mf9876 .'+'. $bigriuse .'+'. $mf2 .'+'. $mf3;&assign;
$p = $mf9876 .'+'. $bigriuse .'+'. $mf1 .'+'. $mf2 .'+'. $mf3;&assign;
#_____

$p = $mf98764 .'+'. $bigi;&assign;
$p = $mf98764 .'+'. $bigriuse;&assign;
$p = $mf98764 .'+'. $bigi .'+'. $mf;&assign;
$p = $mf98764 .'+'. $bigriuse .'+'. $mf;&assign;
$p = $mf98764 .'+'. $bigi .'+'. $mf1;&assign;
$p = $mf98764 .'+'. $bigriuse .'+'. $mf1;&assign;
$p = $mf98764 .'+'. $bigi .'+'. $mf2;&assign;
$p = $mf98764 .'+'. $bigriuse .'+'. $mf2;&assign;
$p = $mf98764 .'+'. $bigi .'+'. $mf3;&assign;
$p = $mf98764 .'+'. $bigriuse .'+'. $mf3;&assign;
$p = $mf98764 .'+'. $bigi .'+'. $mf1 .'+'. $mf2;&assign;
$p = $mf98764 .'+'. $bigriuse .'+'. $mf1 .'+'. $mf2;&assign;
$p = $mf98764 .'+'. $bigi .'+'. $mf1 .'+'. $mf3;&assign;
$p = $mf98764 .'+'. $bigriuse .'+'. $mf1 .'+'. $mf3;&assign;
$p = $mf98764 .'+'. $bigi .'+'. $mf2 .'+'. $mf3;&assign;
$p = $mf98764 .'+'. $bigriuse .'+'. $mf2 .'+'. $mf3;&assign;
$p = $mf98764 .'+'. $bigriuse .'+'. $mf1 .'+'. $mf2 .'+'. $mf3;&assign;
#_____
$p = $mf98765 .'+'. $bigi;&assign;
$p = $mf98765 .'+'. $bigriuse;&assign;
$p = $mf98765 .'+'. $bigi .'+'. $mf;&assign;
$p = $mf98765 .'+'. $bigriuse .'+'. $mf;&assign;
$p = $mf98765 .'+'. $bigi .'+'. $mf1;&assign;
$p = $mf98765 .'+'. $bigriuse .'+'. $mf1;&assign;
$p = $mf98765 .'+'. $bigi .'+'. $mf2;&assign;
```

```
$p = $mf98765 .'+'. $bigriuse .'+'. $mf2;&assign;
$p = $mf98765 .'+'. $bigi .'+'. $mf3;&assign;
$p = $mf98765 .'+'. $bigriuse .'+'. $mf3;&assign;
$p = $mf98765 .'+'. $bigi .'+'. $mf1 .'+'. $mf2;&assign;
$p = $mf98765 .'+'. $bigriuse .'+'. $mf1 .'+'. $mf2;&assign;
$p = $mf98765 .'+'. $bigi .'+'. $mf1 .'+'. $mf3;&assign;
$p = $mf98765 .'+'. $bigriuse .'+'. $mf1 .'+'. $mf3;&assign;
$p = $mf98765 .'+'. $bigi .'+'. $mf2 .'+'. $mf3;&assign;
$p = $mf98765 .'+'. $bigriuse .'+'. $mf2 .'+'. $mf3;&assign;
$p = $mf98765 .'+'. $bigriuse .'+'. $mf1 .'+'. $mf2 .'+'. $mf3;&assign;

$p = $mf987654 .'+'. $bigi;&assign;
$p = $mf987654 .'+'. $bigriuse;&assign;
$p = $mf987654 .'+'. $bigi .'+'. $mf;&assign;
$p = $mf987654 .'+'. $bigriuse .'+'. $mf;&assign;
$p = $mf987654 .'+'. $bigi .'+'. $mf1;&assign;
$p = $mf987654 .'+'. $bigriuse .'+'. $mf1;&assign;
$p = $mf987654 .'+'. $bigi .'+'. $mf2;&assign;
$p = $mf987654 .'+'. $bigriuse .'+'. $mf2;&assign;
$p = $mf987654 .'+'. $bigi .'+'. $mf3;&assign;
$p = $mf987654 .'+'. $bigriuse .'+'. $mf3;&assign;
$p = $mf987654 .'+'. $bigi .'+'. $mf1 .'+'. $mf2;&assign;
$p = $mf987654 .'+'. $bigriuse .'+'. $mf1 .'+'. $mf2;&assign;
$p = $mf987654 .'+'. $bigi .'+'. $mf1 .'+'. $mf3;&assign;
$p = $mf987654 .'+'. $bigriuse .'+'. $mf1 .'+'. $mf3;&assign;
$p = $mf987654 .'+'. $bigi .'+'. $mf2 .'+'. $mf3;&assign;
$p = $mf987654 .'+'. $bigriuse .'+'. $mf2 .'+'. $mf3;&assign;
$p = $mf987654 .'+'. $bigriuse .'+'. $mf1 .'+'. $mf2 .'+'. $mf3;&assign;

$p = $mf10 .'+'. $bigi;&assign;
$p = $mf10 .'+'. $bigriuse;&assign;
$p = $mf10 .'+'. $bigi .'+'. $mf;&assign;
$p = $mf10 .'+'. $bigriuse .'+'. $mf;&assign;
$p = $mf10 .'+'. $bigi .'+'. $mf1;&assign;
$p = $mf10 .'+'. $bigriuse .'+'. $mf1;&assign;
$p = $mf10 .'+'. $bigi .'+'. $mf2;&assign;
$p = $mf10 .'+'. $bigriuse .'+'. $mf2;&assign;
$p = $mf10 .'+'. $bigi .'+'. $mf3;&assign;
$p = $mf10 .'+'. $bigriuse .'+'. $mf3;&assign;
$p = $mf10 .'+'. $bigi .'+'. $mf1 .'+'. $mf2;&assign;
$p = $mf10 .'+'. $bigriuse .'+'. $mf1 .'+'. $mf2;&assign;
$p = $mf10 .'+'. $bigi .'+'. $mf1 .'+'. $mf3;&assign;
$p = $mf10 .'+'. $bigriuse .'+'. $mf1 .'+'. $mf3;&assign;
$p = $mf10 .'+'. $bigi .'+'. $mf2 .'+'. $mf3;&assign;
```

```
$p = $mf10 .'+'. $bigriuse .'+'. $mf2 .'+'. $mf3;&assign;
$p = $mf10 .'+'. $bigriuse .'+'. $mf1 .'+'. $mf2 .'+'. $mf3;&assign;
#_____

$p = $mf104 .'+'. $bigi;&assign;
$p = $mf104 .'+'. $bigriuse;&assign;
$p = $mf104 .'+'. $bigi .'+'. $mf;&assign;
$p = $mf104 .'+'. $bigriuse .'+'. $mf;&assign;
$p = $mf104 .'+'. $bigi .'+'. $mf1;&assign;
$p = $mf104 .'+'. $bigriuse .'+'. $mf1;&assign;
$p = $mf104 .'+'. $bigi .'+'. $mf2;&assign;
$p = $mf104 .'+'. $bigriuse .'+'. $mf2;&assign;
$p = $mf104 .'+'. $bigi .'+'. $mf3;&assign;
$p = $mf104 .'+'. $bigriuse .'+'. $mf3;&assign;
$p = $mf104 .'+'. $bigi .'+'. $mf1 .'+'. $mf2;&assign;
$p = $mf104 .'+'. $bigriuse .'+'. $mf1 .'+'. $mf2;&assign;
$p = $mf104 .'+'. $bigi .'+'. $mf1 .'+'. $mf3;&assign;
$p = $mf104 .'+'. $bigriuse .'+'. $mf1 .'+'. $mf3;&assign;
$p = $mf104 .'+'. $bigi .'+'. $mf2 .'+'. $mf3;&assign;
$p = $mf104 .'+'. $bigriuse .'+'. $mf2 .'+'. $mf3;&assign;
$p = $mf104 .'+'. $bigriuse .'+'. $mf1 .'+'. $mf2 .'+'. $mf3;&assign;
#_____
$p = $mf105 .'+'. $bigi;&assign;
$p = $mf105 .'+'. $bigriuse;&assign;
$p = $mf105 .'+'. $bigi .'+'. $mf;&assign;
$p = $mf105 .'+'. $bigriuse .'+'. $mf;&assign;
$p = $mf105 .'+'. $bigi .'+'. $mf1;&assign;
$p = $mf105 .'+'. $bigriuse .'+'. $mf1;&assign;
Sp = $mf105 .'+'. $bigi .'+'. $mf2;&assign;
$p = $mf105 .'+'. $bigriuse .'+'. $mf2;&assign;
$p = $mf105 .'+'. $bigi .'+'. $mf3;&assign;
$p = $mf105 .'+'. $bigriuse .'+'. $mf3;&assign;
$p = $mf105 .'+'. $bigi .'+'. $mf1 .'+'. $mf2;&assign;
$p = $mf105 .'+'. $bigriuse .'+'. $mf1 .'+'. $mf2;&assign;
$p = $mf105 .'+'. $bigi .'+'. $mf1 .'+'. $mf3;&assign;
$p = $mf105 .'+'. $bigriuse .'+'. $mf1 .'+'. $mf3;&assign;
$p = $mf105 .'+'. $bigi .'+'. $mf2 .'+'. $mf3;&assign;
$p = $mf105 .'+'. $bigriuse .'+'. $mf2 .'+'. $mf3;&assign;
$p = $mf105 .'+'. $bigriuse .'+'. $mf1 .'+'. $mf2 .'+'. $mf3;&assign;
#_____
$p = $mf1054 .'+'. $bigi;&assign;
$p = $mf1054 .'+'. $bigriuse;&assign;
$p = $mf1054 .'+'. $bigi .'+'. $mf;&assign;
$p = $mf1054 .'+'. $bigriuse .'+'. $mf;&assign;
```

```
$p = $mf1054 .'+'. $bigi .'+'. $mf1;&assign;
$p = $mf1054 .'+'. $bigriuse .'+'. $mf1;&assign;
$p = $mf1054 .'+'. $bigi .'+'. $mf2;&assign;
$p = $mf1054 .'+'. $bigriuse .'+'. $mf2;&assign;
$p = $mf1054 .'+'. $bigi .'+'. $mf3;&assign;
$p = $mf1054 .'+'. $bigriuse .'+'. $mf3;&assign;
$p = $mf1054 .'+'. $bigi .'+'. $mf1 .'+'. $mf2;&assign;
$p = $mf1054 .'+'. $bigriuse .'+'. $mf1 .'+'. $mf2;&assign;
$p = $mf1054 .'+'. $bigi .'+'. $mf1 .'+'. $mf3;&assign;
$p = $mf1054 .'+'. $bigriuse .'+'. $mf1 .'+'. $mf3;&assign;
$p = $mf1054 .'+'. $bigi .'+'. $mf2 .'+'. $mf3;&assign;
$p = $mf1054 .'+'. $bigriuse .'+'. $mf2 .'+'. $mf3;&assign;
$p = $mf1054 .'+'. $bigriuse .'+'. $mf1 .'+'. $mf2 .'+'. $mf3;&assign;
#_____
$p = $mf106 .'+'. $bigi;&assign;
$p = $mf106 .'+'. $bigriuse;&assign;
$p = $mf106 .'+'. $bigi .'+'. $mf;&assign;
$p = $mf106 .'+'. $bigriuse .'+'. $mf;&assign;
$p = $mf106 .'+'. $bigi .'+'. $mf1;&assign;
$p = $mf106 .'+'. $bigriuse .'+'. $mf1;&assign;
$p = $mf106 .'+'. $bigi .'+'. $mf2;&assign;
$p = $mf106 .'+'. $bigriuse .'+'. $mf2;&assign;
$p = $mf106 .'+'. $bigi .'+'. $mf3;&assign;
$p = $mf106 .'+'. $bigriuse .'+'. $mf3;&assign;
$p = $mf106 .'+'. $bigi .'+'. $mf1 .'+'. $mf2;&assign;
$p = $mf106 .'+'. $bigriuse .'+'. $mf1 .'+'. $mf2;&assign;
$p = $mf106 .'+'. $bigi .'+'. $mf1 .'+'. $mf3;&assign;
$p = $mf106 .'+'. $bigriuse .'+'. $mf1 .'+'. $mf3;&assign;
$p = $mf106 .'+'. $bigi .'+'. $mf2 .'+'. $mf3;&assign;
$p = $mf106 .'+'. $bigriuse .'+'. $mf2 .'+'. $mf3;&assign;
$p = $mf106 .'+'. $bigriuse .'+'. $mf1 .'+'. $mf2 .'+'. $mf3;&assign;
#_____

$p = $mf1064 .'+'. $bigi;&assign;
$p = $mf1064 .'+'. $bigriuse;&assign;
$p = $mf1064 .'+'. $bigi .'+'. $mf;&assign;
$p = $mf1064 .'+'. $bigriuse .'+'. $mf;&assign;
$p = $mf1064 .'+'. $bigi .'+'. $mf1;&assign;
$p = $mf1064 .'+'. $bigriuse .'+'. $mf1;&assign;
$p = $mf1064 .'+'. $bigi .'+'. $mf2;&assign;
$p = $mf1064 .'+'. $bigriuse .'+'. $mf2;&assign;
$p = $mf1064 .'+'. $bigi .'+'. $mf3;&assign;
$p = $mf1064 .'+'. $bigriuse .'+'. $mf3;&assign;
$p = $mf1064 .'+'. $bigi .'+'. $mf1 .'+'. $mf2;&assign;
```

```
$p = $mf1064 .'+'. $bigriuse .'+'. $mf1 .'+'. $mf2;&assign;
$p = $mf1064 .'+'. $bigi .'+'. $mf1 .'+'. $mf3;&assign;
$p = $mf1064 .'+'. $bigriuse .'+'. $mf1 .'+'. $mf3;&assign;
$p = $mf1064 .'+'. $bigi .'+'. $mf2 .'+'. $mf3;&assign;
$p = $mf1064 .'+'. $bigriuse .'+'. $mf2 .'+'. $mf3;&assign;
$p = $mf1064 .'+'. $bigriuse .'+'. $mf1 .'+'. $mf2 .'+'. $mf3;&assign;

$p = $mf1065 .'+'. $bigi;&assign;
$p = $mf1065 .'+'. $bigriuse;&assign;
$p = $mf1065 .'+'. $bigi .'+'. $mf;&assign;
$p = $mf1065 .'+'. $bigriuse .'+'. $mf;&assign;
$p = $mf1065 .'+'. $bigi .'+'. $mf1;&assign;
$p = $mf1065 .'+'. $bigriuse .'+'. $mf1;&assign;
$p = $mf1065 .'+'. $bigi .'+'. $mf2;&assign;
$p = $mf1065 .'+'. $bigriuse .'+'. $mf2;&assign;
$p = $mf1065 .'+'. $bigi .'+'. $mf3;&assign;
$p = $mf1065 .'+'. $bigriuse .'+'. $mf3;&assign;
$p = $mf1065 .'+'. $bigi .'+'. $mf1 .'+'. $mf2;&assign;
$p = $mf1065 .'+'. $bigriuse .'+'. $mf1 .'+'. $mf2;&assign;
$p = $mf1065 .'+'. $bigi .'+'. $mf1 .'+'. $mf3;&assign;
$p = $mf1065 .'+'. $bigriuse .'+'. $mf1 .'+'. $mf3;&assign;
$p = $mf1065 .'+'. $bigi .'+'. $mf2 .'+'. $mf3;&assign;
$p = $mf1065 .'+'. $bigriuse .'+'. $mf2 .'+'. $mf3;&assign;
$p = $mf1065 .'+'. $bigriuse .'+'. $mf1 .'+'. $mf2 .'+'. $mf3;&assign;

$p = $mf10654 .'+'. $bigi;&assign;
$p = $mf10654 .'+'. $bigriuse;&assign;
$p = $mf10654 .'+'. $bigi .'+'. $mf;&assign;
$p = $mf10654 .'+'. $bigriuse .'+'. $mf;&assign;
$p = $mf10654 .'+'. $bigi .'+'. $mf1;&assign;
$p = $mf10654 .'+'. $bigriuse .'+'. $mf1;&assign;
$p = $mf10654 .'+'. $bigi .'+'. $mf2;&assign;
$p = $mf10654 .'+'. $bigriuse .'+'. $mf2;&assign;
$p = $mf10654 .'+'. $bigi .'+'. $mf3;&assign;
$p = $mf10654 .'+'. $bigriuse .'+'. $mf3;&assign;
$p = $mf10654 .'+'. $bigi .'+'. $mf1 .'+'. $mf2;&assign;
$p = $mf10654 .'+'. $bigriuse .'+'. $mf1 .'+'. $mf2;&assign;
$p = $mf10654 .'+'. $bigi .'+'. $mf1 .'+'. $mf3;&assign;
$p = $mf10654 .'+'. $bigriuse .'+'. $mf1 .'+'. $mf3;&assign;
$p = $mf10654 .'+'. $bigi .'+'. $mf2 .'+'. $mf3;&assign;
$p = $mf10654 .'+'. $bigriuse .'+'. $mf2 .'+'. $mf3;&assign;
$p = $mf10654 .'+'. $bigriuse .'+'. $mf1 .'+'. $mf2 .'+'. $mf3;&assign;

$p = $mf107 .'+'. $bigi;&assign;
$p = $mf107 .'+'. $bigriuse;&assign;
```

```
$p = $mf107 .'+'. $bigi .'+'. $mf;&assign;
$p = $mf107 .'+'. $bigriuse .'+'. $mf;&assign;
$p = $mf107 .'+'. $bigi .'+'. $mf1;&assign;
$p = $mf107 .'+'. $bigriuse .'+'. $mf1;&assign;
$p = $mf107 .'+'. $bigi .'+'. $mf2;&assign;
$p = $mf107 .'+'. $bigriuse .'+'. $mf2;&assign;
$p = $mf107 .'+'. $bigi .'+'. $mf3;&assign;
$p = $mf107 .'+'. $bigriuse .'+'. $mf3;&assign;
$p = $mf107 .'+'. $bigi .'+'. $mf1 .'+'. $mf2;&assign;
$p = $mf107 .'+'. $bigriuse .'+'. $mf1 .'+'. $mf2;&assign;
$p = $mf107 .'+'. $bigi .'+'. $mf1 .'+'. $mf3;&assign;
$p = $mf107 .'+'. $bigriuse .'+'. $mf1 .'+'. $mf3;&assign;
$p = $mf107 .'+'. $bigi .'+'. $mf2 .'+'. $mf3;&assign;
$p = $mf107 .'+'. $bigriuse .'+'. $mf2 .'+'. $mf3;&assign;
$p = $mf107 .'+'. $bigriuse .'+'. $mf1 .'+'. $mf2 .'+'. $mf3;&assign;
#_____

$p = $mf1074 .'+'. $bigi;&assign;
$p = $mf1074 .'+'. $bigriuse;&assign;
$p = $mf1074 .'+'. $bigi .'+'. $mf;&assign;
$p = $mf1074 .'+'. $bigriuse .'+'. $mf;&assign;
$p = $mf1074 .'+'. $bigi .'+'. $mf1;&assign;
$p = $mf1074 .'+'. $bigriuse .'+'. $mf1;&assign;
$p = $mf1074 .'+'. $bigi .'+'. $mf2;&assign;
$p = $mf1074 .'+'. $bigriuse .'+'. $mf2;&assign;
$p = $mf1074 .'+'. $bigi .'+'. $mf3;&assign;
$p = $mf1074 .'+'. $bigriuse .'+'. $mf3;&assign;
$p = $mf1074 .'+'. $bigi .'+'. $mf1 .'+'. $mf2;&assign;
$p = $mf1074 .'+'. $bigriuse .'+'. $mf1 .'+'. $mf2;&assign;
$p = $mf1074 .'+'. $bigi .'+'. $mf1 .'+'. $mf3;&assign;
$p = $mf1074 .'+'. $bigriuse .'+'. $mf1 .'+'. $mf3;&assign;
$p = $mf1074 .'+'. $bigi .'+'. $mf2 .'+'. $mf3;&assign;
$p = $mf1074 .'+'. $bigriuse .'+'. $mf2 .'+'. $mf3;&assign;
$p = $mf1074 .'+'. $bigriuse .'+'. $mf1 .'+'. $mf2 .'+'. $mf3;&assign;
#_____
$p = $mf1075 .'+'. $bigi;&assign;
$p = $mf1075 .'+'. $bigriuse;&assign;
$p = $mf1075 .'+'. $bigi .'+'. $mf;&assign;
$p = $mf1075 .'+'. $bigriuse .'+'. $mf;&assign;
$p = $mf1075 .'+'. $bigi .'+'. $mf1;&assign;
$p = $mf1075 .'+'. $bigriuse .'+'. $mf1;&assign;
$p = $mf1075 .'+'. $bigi .'+'. $mf2;&assign;
$p = $mf1075 .'+'. $bigriuse .'+'. $mf2;&assign;
$p = $mf1075 .'+'. $bigi .'+'. $mf3;&assign;
```

```
$p = $mf1075 .'+'. $bigriuse .'+'. $mf3;&assign;
$p = $mf1075 .'+'. $bigi .'+'. $mf1 .'+'. $mf2;&assign;
$p = $mf1075 .'+'. $bigriuse .'+'. $mf1 .'+'. $mf2;&assign;
$p = $mf1075 .'+'. $bigi .'+'. $mf1 .'+'. $mf3;&assign;
$p = $mf1075 .'+'. $bigriuse .'+'. $mf1 .'+'. $mf3;&assign;
$p = $mf1075 .'+'. $bigi .'+'. $mf2 .'+'. $mf3;&assign;
$p = $mf1075 .'+'. $bigriuse .'+'. $mf2 .'+'. $mf3;&assign;
$p = $mf1075 .'+'. $bigriuse .'+'. $mf1 .'+'. $mf2 .'+'. $mf3;&assign;
#_____
$p = $mf10754 .'+'. $bigi;&assign;
$p = $mf10754 .'+'. $bigriuse;&assign;
$p = $mf10754 .'+'. $bigi .'+'. $mf;&assign;
$p = $mf10754 .'+'. $bigriuse .'+'. $mf;&assign;
$p = $mf10754 .'+'. $bigi .'+'. $mf1;&assign;
$p = $mf10754 .'+'. $bigriuse .'+'. $mf1;&assign;
$p = $mf10754 .'+'. $bigi .'+'. $mf2;&assign;
$p = $mf10754 .'+'. $bigriuse .'+'. $mf2;&assign;
$p = $mf10754 .'+'. $bigi .'+'. $mf3;&assign;
$p = $mf10754 .'+'. $bigriuse .'+'. $mf3;&assign;
$p = $mf10754 .'+'. $bigi .'+'. $mf1 .'+'. $mf2;&assign;
$p = $mf10754 .'+'. $bigriuse .'+'. $mf1 .'+'. $mf2;&assign;
$p = $mf10754 .'+'. $bigi .'+'. $mf1 .'+'. $mf3;&assign;
$p = $mf10754 .'+'. $bigriuse .'+'. $mf1 .'+'. $mf3;&assign;
$p = $mf10754 .'+'. $bigi .'+'. $mf2 .'+'. $mf3;&assign;
$p = $mf10754 .'+'. $bigriuse .'+'. $mf2 .'+'. $mf3;&assign;
$p = $mf10754 .'+'. $bigriuse .'+'. $mf1 .'+'. $mf2 .'+'. $mf3;&assign;
#_____
$p = $mf1076 .'+'. $bigi;&assign;
$p = $mf1076 .'+'. $bigriuse;&assign;
$p = $mf1076 .'+'. $bigi .'+'. $mf;&assign;
$p = $mf1076 .'+'. $bigriuse .'+'. $mf;&assign;
$p = $mf1076 .'+'. $bigi .'+'. $mf1;&assign;
$p = $mf1076 .'+'. $bigriuse .'+'. $mf1;&assign;
$p = $mf1076 .'+'. $bigi .'+'. $mf2;&assign;
$p = $mf1076 .'+'. $bigriuse .'+'. $mf2;&assign;
$p = $mf1076 .'+'. $bigi .'+'. $mf3;&assign;
$p = $mf1076 .'+'. $bigriuse .'+'. $mf3;&assign;
$p = $mf1076 .'+'. $bigi .'+'. $mf1 .'+'. $mf2;&assign;
$p = $mf1076 .'+'. $bigriuse .'+'. $mf1 .'+'. $mf2;&assign;
$p = $mf1076 .'+'. $bigi .'+'. $mf1 .'+'. $mf3;&assign;
$p = $mf1076 .'+'. $bigriuse .'+'. $mf1 .'+'. $mf3;&assign;
$p = $mf1076 .'+'. $bigi .'+'. $mf2 .'+'. $mf3;&assign;
$p = $mf1076 .'+'. $bigriuse .'+'. $mf2 .'+'. $mf3;&assign;
$p = $mf1076 .'+'. $bigriuse .'+'. $mf1 .'+'. $mf2 .'+'. $mf3;&assign;
#_____
```

```
$p = $mf10764 .'+'. $bigi;&assign;
$p = $mf10764 .'+'. $bigriuse;&assign;
$p = $mf10764 .'+'. $bigi .'+'. $mf;&assign;
$p = $mf10764 .'+'. $bigriuse .'+'. $mf;&assign;
$p = $mf10764 .'+'. $bigi .'+'. $mf1;&assign;
$p = $mf10764 .'+'. $bigriuse .'+'. $mf1;&assign;
$p = $mf10764 .'+'. $bigi .'+'. $mf2;&assign;
$p = $mf10764 .'+'. $bigriuse .'+'. $mf2;&assign;
$p = $mf10764 .'+'. $bigi .'+'. $mf3;&assign;
$p = $mf10764 .'+'. $bigriuse .'+'. $mf3;&assign;
$p = $mf10764 .'+'. $bigi .'+'. $mf1 .'+'. $mf2;&assign;
$p = $mf10764 .'+'. $bigriuse .'+'. $mf1 .'+'. $mf2;&assign;
$p = $mf10764 .'+'. $bigi .'+'. $mf1 .'+'. $mf3;&assign;
$p = $mf10764 .'+'. $bigriuse .'+'. $mf1 .'+'. $mf3;&assign;
$p = $mf10764 .'+'. $bigi .'+'. $mf2 .'+'. $mf3;&assign;
$p = $mf10764 .'+'. $bigriuse .'+'. $mf2 .'+'. $mf3;&assign;
$p = $mf10764 .'+'. $bigriuse .'+'. $mf1 .'+'. $mf2 .'+'. $mf3;&assign;

$p = $mf10765 .'+'. $bigi;&assign;
$p = $mf10765 .'+'. $bigriuse;&assign;
$p = $mf10765 .'+'. $bigi .'+'. $mf;&assign;
$p = $mf10765 .'+'. $bigriuse .'+'. $mf;&assign;
$p = $mf10765 .'+'. $bigi .'+'. $mf1;&assign;
$p = $mf10765 .'+'. $bigriuse .'+'. $mf1;&assign;
$p = $mf10765 .'+'. $bigi .'+'. $mf2;&assign;
$p = $mf10765 .'+'. $bigriuse .'+'. $mf2;&assign;
$p = $mf10765 .'+'. $bigi .'+'. $mf3;&assign;
$p = $mf10765 .'+'. $bigriuse .'+'. $mf3;&assign;
$p = $mf10765 .'+'. $bigi .'+'. $mf1 .'+'. $mf2;&assign;
$p = $mf10765 .'+'. $bigriuse .'+'. $mf1 .'+'. $mf2;&assign;
$p = $mf10765 .'+'. $bigi .'+'. $mf1 .'+'. $mf3;&assign;
$p = $mf10765 .'+'. $bigriuse .'+'. $mf1 .'+'. $mf3;&assign;
$p = $mf10765 .'+'. $bigi .'+'. $mf2 .'+'. $mf3;&assign;
$p = $mf10765 .'+'. $bigriuse .'+'. $mf2 .'+'. $mf3;&assign;
$p = $mf10765 .'+'. $bigriuse .'+'. $mf1 .'+'. $mf2 .'+'. $mf3;&assign;

$p = $mf107654 .'+'. $bigi;&assign;
$p = $mf107654 .'+'. $bigriuse;&assign;
$p = $mf107654 .'+'. $bigi .'+'. $mf;&assign;
$p = $mf107654 .'+'. $bigriuse .'+'. $mf;&assign;
$p = $mf107654 .'+'. $bigi .'+'. $mf1;&assign;
$p = $mf107654 .'+'. $bigriuse .'+'. $mf1;&assign;
$p = $mf107654 .'+'. $bigi .'+'. $mf2;&assign;
$p = $mf107654 .'+'. $bigriuse .'+'. $mf2;&assign;
```

```
$p = $mf107654 .'+'. $bigi .'+'. $mf3;&assign;
$p = $mf107654 .'+'. $bigriuse .'+'. $mf3;&assign;
$p = $mf107654 .'+'. $bigi .'+'. $mf1 .'+'. $mf2;&assign;
$p = $mf107654 .'+'. $bigriuse .'+'. $mf1 .'+'. $mf2;&assign;
$p = $mf107654 .'+'. $bigi .'+'. $mf1 .'+'. $mf3;&assign;
$p = $mf107654 .'+'. $bigriuse .'+'. $mf1 .'+'. $mf3;&assign;
$p = $mf107654 .'+'. $bigi .'+'. $mf2 .'+'. $mf3;&assign;
$p = $mf107654 .'+'. $bigriuse .'+'. $mf2 .'+'. $mf3;&assign;
$p = $mf107654 .'+'. $bigriuse .'+'. $mf1 .'+'. $mf2 .'+'. $mf3;&assign;

#_____
$p = $mf108 .'+'. $bigi;&assign;
$p = $mf108 .'+'. $bigriuse;&assign;
$p = $mf108 .'+'. $bigi .'+'. $mf;&assign;
$p = $mf108 .'+'. $bigriuse .'+'. $mf;&assign;
$p = $mf108 .'+'. $bigi .'+'. $mf1;&assign;
$p = $mf108 .'+'. $bigriuse .'+'. $mf1;&assign;
$p = $mf108 .'+'. $bigi .'+'. $mf2;&assign;
$p = $mf108 .'+'. $bigriuse .'+'. $mf2;&assign;
$p = $mf108 .'+'. $bigi .'+'. $mf3;&assign;
$p = $mf108 .'+'. $bigriuse .'+'. $mf3;&assign;
$p = $mf108 .'+'. $bigi .'+'. $mf1 .'+'. $mf2;&assign;
$p = $mf108 .'+'. $bigriuse .'+'. $mf1 .'+'. $mf2;&assign;
$p = $mf108 .'+'. $bigi .'+'. $mf1 .'+'. $mf3;&assign;
$p = $mf108 .'+'. $bigriuse .'+'. $mf1 .'+'. $mf3;&assign;
$p = $mf108 .'+'. $bigi .'+'. $mf2 .'+'. $mf3;&assign;
$p = $mf108 .'+'. $bigriuse .'+'. $mf2 .'+'. $mf3;&assign;
$p = $mf108 .'+'. $bigriuse .'+'. $mf1 .'+'. $mf2 .'+'. $mf3;&assign;
#_____

$p = $mf1084 .'+'. $bigi;&assign;
$p = $mf1084 .'+'. $bigriuse;&assign;
$p = $mf1084 .'+'. $bigi .'+'. $mf;&assign;
$p = $mf1084 .'+'. $bigriuse .'+'. $mf;&assign;
$p = $mf1084 .'+'. $bigi .'+'. $mf1;&assign;
$p = $mf1084 .'+'. $bigriuse .'+'. $mf1;&assign;
$p = $mf1084 .'+'. $bigi .'+'. $mf2;&assign;
$p = $mf1084 .'+'. $bigriuse .'+'. $mf2;&assign;
$p = $mf1084 .'+'. $bigi .'+'. $mf3;&assign;
$p = $mf1084 .'+'. $bigriuse .'+'. $mf3;&assign;
$p = $mf1084 .'+'. $bigi .'+'. $mf1 .'+'. $mf2;&assign;
$p = $mf1084 .'+'. $bigriuse .'+'. $mf1 .'+'. $mf2;&assign;
$p = $mf1084 .'+'. $bigi .'+'. $mf1 .'+'. $mf3;&assign;
$p = $mf1084 .'+'. $bigriuse .'+'. $mf1 .'+'. $mf3;&assign;
```

```
$p = $mf1084 .'+'. $bigi .'+'. $mf2 .'+'. $mf3;&assign;
$p = $mf1084 .'+'. $bigriuse .'+'. $mf2 .'+'. $mf3;&assign;
$p = $mf1084 .'+'. $bigriuse .'+'. $mf1 .'+'. $mf2 .'+'. $mf3;&assign;

$p = $mf1085 .'+'. $bigi;&assign;
$p = $mf1085 .'+'. $bigriuse;&assign;
$p = $mf1085 .'+'. $bigi .'+'. $mf;&assign;
$p = $mf1085 .'+'. $bigriuse .'+'. $mf;&assign;
$p = $mf1085 .'+'. $bigi .'+'. $mf1;&assign;
$p = $mf1085 .'+'. $bigriuse .'+'. $mf1;&assign;
$p = $mf1085 .'+'. $bigi .'+'. $mf2;&assign;
$p = $mf1085 .'+'. $bigriuse .'+'. $mf2;&assign;
$p = $mf1085 .'+'. $bigi .'+'. $mf3;&assign;
$p = $mf1085 .'+'. $bigriuse .'+'. $mf3;&assign;
$p = $mf1085 .'+'. $bigi .'+'. $mf1 .'+'. $mf2;&assign;
$p = $mf1085 .'+'. $bigriuse .'+'. $mf1 .'+'. $mf2;&assign;
$p = $mf1085 .'+'. $bigi .'+'. $mf1 .'+'. $mf3;&assign;
$p = $mf1085 .'+'. $bigriuse .'+'. $mf1 .'+'. $mf3;&assign;
$p = $mf1085 .'+'. $bigi .'+'. $mf2 .'+'. $mf3;&assign;
$p = $mf1085 .'+'. $bigriuse .'+'. $mf2 .'+'. $mf3;&assign;
$p = $mf1085 .'+'. $bigriuse .'+'. $mf1 .'+'. $mf2 .'+'. $mf3;&assign;

$p = $mf10854 .'+'. $bigi;&assign;
$p = $mf10854 .'+'. $bigriuse;&assign;
$p = $mf10854 .'+'. $bigi .'+'. $mf;&assign;
$p = $mf10854 .'+'. $bigriuse .'+'. $mf;&assign;
$p = $mf10854 .'+'. $bigi .'+'. $mf1;&assign;
$p = $mf10854 .'+'. $bigriuse .'+'. $mf1;&assign;
$p = $mf10854 .'+'. $bigi .'+'. $mf2;&assign;
$p = $mf10854 .'+'. $bigriuse .'+'. $mf2;&assign;
$p = $mf10854 .'+'. $bigi .'+'. $mf3;&assign;
$p = $mf10854 .'+'. $bigriuse .'+'. $mf3;&assign;
$p = $mf10854 .'+'. $bigi .'+'. $mf1 .'+'. $mf2;&assign;
$p = $mf10854 .'+'. $bigriuse .'+'. $mf1 .'+'. $mf2;&assign;
$p = $mf10854 .'+'. $bigi .'+'. $mf1 .'+'. $mf3;&assign;
$p = $mf10854 .'+'. $bigriuse .'+'. $mf1 .'+'. $mf3;&assign;
$p = $mf10854 .'+'. $bigi .'+'. $mf2 .'+'. $mf3;&assign;
$p = $mf10854 .'+'. $bigriuse .'+'. $mf2 .'+'. $mf3;&assign;
$p = $mf10854 .'+'. $bigriuse .'+'. $mf1 .'+'. $mf2 .'+'. $mf3;&assign;

$p = $mf1086 .'+'. $bigi;&assign;
$p = $mf1086 .'+'. $bigriuse;&assign;
$p = $mf1086 .'+'. $bigi .'+'. $mf;&assign;
$p = $mf1086 .'+'. $bigriuse .'+'. $mf;&assign;
$p = $mf1086 .'+'. $bigi .'+'. $mf1;&assign;
```

```
$p = $mf1086 .'+'. $bigriuse .'+'. $mf1;&assign;
$p = $mf1086 .'+'. $bigi .'+'. $mf2;&assign;
$p = $mf1086 .'+'. $bigriuse .'+'. $mf2;&assign;
$p = $mf1086 .'+'. $bigi .'+'. $mf3;&assign;
$p = $mf1086 .'+'. $bigriuse .'+'. $mf3;&assign;
$p = $mf1086 .'+'. $bigi .'+'. $mf1 .'+'. $mf2;&assign;
$p = $mf1086 .'+'. $bigriuse .'+'. $mf1 .'+'. $mf2;&assign;
$p = $mf1086 .'+'. $bigi .'+'. $mf1 .'+'. $mf3;&assign;
$p = $mf1086 .'+'. $bigriuse .'+'. $mf1 .'+'. $mf3;&assign;
$p = $mf1086 .'+'. $bigi .'+'. $mf2 .'+'. $mf3;&assign;
$p = $mf1086 .'+'. $bigriuse .'+'. $mf2 .'+'. $mf3;&assign;
$p = $mf1086 .'+'. $bigriuse .'+'. $mf1 .'+'. $mf2 .'+'. $mf3;&assign;

$p = $mf10864 .'+'. $bigi;&assign;
$p = $mf10864 .'+'. $bigriuse;&assign;
$p = $mf10864 .'+'. $bigi .'+'. $mf;&assign;
$p = $mf10864 .'+'. $bigriuse .'+'. $mf;&assign;
$p = $mf10864 .'+'. $bigi .'+'. $mf1;&assign;
$p = $mf10864 .'+'. $bigriuse .'+'. $mf1;&assign;
$p = $mf10864 .'+'. $bigi .'+'. $mf2;&assign;
$p = $mf10864 .'+'. $bigriuse .'+'. $mf2;&assign;
$p = $mf10864 .'+'. $bigi .'+'. $mf3;&assign;
$p = $mf10864 .'+'. $bigriuse .'+'. $mf3;&assign;
$p = $mf10864 .'+'. $bigi .'+'. $mf1 .'+'. $mf2;&assign;
$p = $mf10864 .'+'. $bigriuse .'+'. $mf1 .'+'. $mf2;&assign;
$p = $mf10864 .'+'. $bigi .'+'. $mf1 .'+'. $mf3;&assign;
$p = $mf10864 .'+'. $bigriuse .'+'. $mf1 .'+'. $mf3;&assign;
$p = $mf10864 .'+'. $bigi .'+'. $mf2 .'+'. $mf3;&assign;
$p = $mf10864 .'+'. $bigriuse .'+'. $mf2 .'+'. $mf3;&assign;
$p = $mf10864 .'+'. $bigriuse .'+'. $mf1 .'+'. $mf2 .'+'. $mf3;&assign;

$p = $mf10865 .'+'. $bigi;&assign;
$p = $mf10865 .'+'. $bigriuse;&assign;
$p = $mf10865 .'+'. $bigi .'+'. $mf;&assign;
$p = $mf10865 .'+'. $bigriuse .'+'. $mf;&assign;
$p = $mf10865 .'+'. $bigi .'+'. $mf1;&assign;
$p = $mf10865 .'+'. $bigriuse .'+'. $mf1;&assign;
$p = $mf10865 .'+'. $bigi .'+'. $mf2;&assign;
$p = $mf10865 .'+'. $bigriuse .'+'. $mf2;&assign;
$p = $mf10865 .'+'. $bigi .'+'. $mf3;&assign;
$p = $mf10865 .'+'. $bigriuse .'+'. $mf3;&assign;
$p = $mf10865 .'+'. $bigi .'+'. $mf1 .'+'. $mf2;&assign;
$p = $mf10865 .'+'. $bigriuse .'+'. $mf1 .'+'. $mf2;&assign;
```

```
$p = $mf10865 .'+'. $bigi .'+'. $mf1 .'+'. $mf3;&assign;
$p = $mf10865 .'+'. $bigriuse .'+'. $mf1 .'+'. $mf3;&assign;
$p = $mf10865 .'+'. $bigi .'+'. $mf2 .'+'. $mf3;&assign;
$p = $mf10865 .'+'. $bigriuse .'+'. $mf2 .'+'. $mf3;&assign;
$p = $mf10865 .'+'. $bigriuse .'+'. $mf1 .'+'. $mf2 .'+'. $mf3;&assign;

$p = $mf108654 .'+'. $bigi;&assign;
$p = $mf108654 .'+'. $bigriuse;&assign;
$p = $mf108654 .'+'. $bigi .'+'. $mf;&assign;
$p = $mf108654 .'+'. $bigriuse .'+'. $mf;&assign;
$p = $mf108654 .'+'. $bigi .'+'. $mf1;&assign;
$p = $mf108654 .'+'. $bigriuse .'+'. $mf1;&assign;
$p = $mf108654 .'+'. $bigi .'+'. $mf2;&assign;
$p = $mf108654 .'+'. $bigriuse .'+'. $mf2;&assign;
$p = $mf108654 .'+'. $bigi .'+'. $mf3;&assign;
$p = $mf108654 .'+'. $bigriuse .'+'. $mf3;&assign;
$p = $mf108654 .'+'..$bigi .'+'. $mf1 .'+'. $mf2;&assign;
$p = $mf108654 .'+'. $bigriuse .'+'. $mf1 .'+'. $mf2;&assign;
$p = $mf108654 .'+'. $bigi .'+'. $mf1 .'+'. $mf3;&assign;
$p = $mf108654 .'+'. $bigriuse .'+'. $mf1 .'+'. $mf3;&assign;
$p = $mf108654 .'+'. $bigi .'+'. $mf2 .'+'. $mf3;&assign;
$p = $mf108654 .'+'. $bigriuse .'+'. $mf2 .'+'. $mf3;&assign;
$p = $mf108654 .'+'. $bigriuse .'+'. $mf1 .'+'. $mf2 .'+'. $mf3;&assign;

$p = $mf1087 .'+'. $bigi;&assign;
$p = $mf1087 .'+'. $bigriuse;&assign;
$p = $mf1087 .'+'. $bigi .'+'. $mf;&assign;
$p = $mf1087 .'+'. $bigriuse .'+'. $mf;&assign;
$p = $mf1087 .'+'. $bigi .'+'. $mf1;&assign;
$p = $mf1087 .'+'. $bigriuse .'+'. $mf1;&assign;
$p = $mf1087 .'+'. $bigi .'+'. $mf2;&assign;
$p = $mf1087 .'+'. $bigriuse .'+'. $mf2;&assign;
$p = $mf1087 .'+'. $bigi .'+'. $mf3;&assign;
$p = $mf1087 .'+'. $bigriuse .'+'. $mf3;&assign;
$p = $mf1087 .'+'. $bigi .'+'. $mf1 .'+'. $mf2;&assign;
$p = $mf1087 .'+'. $bigriuse .'+'. $mf1 .'+'. $mf2;&assign;
$p = $mf1087 .'+'. $bigi .'+'. $mf1 .'+'. $mf3;&assign;
$p = $mf1087 .'+'. $bigriuse .'+'. $mf1 .'+'. $mf3;&assign;
$p = $mf1087 .'+'. $bigi .'+'. $mf2 .'+'. $mf3;&assign;
$p = $mf1087 .'+'. $bigriuse .'+'. $mf2 .'+'. $mf3;&assign;
$p = $mf1087 .'+'. $bigriuse .'+'. $mf1 .'+'. $mf2 .'+'. $mf3;&assign;

```

```
$p = $mf10874 .'+'. $bigi;&assign;
$p = $mf10874 .'+'. $bigriuse;&assign;
$p = $mf10874 .'+'. $bigi .'+'. $mf;&assign;
$p = $mf10874 .'+'. $bigriuse .'+'. $mf;&assign;
$p = $mf10874 .'+'. $bigi .'+'. $mf1;&assign;
$p = $mf10874 .'+'. $bigriuse .'+'. $mf1;&assign;
$p = $mf10874 .'+'. $bigi .'+'. $mf2;&assign;
$p = $mf10874 .'+'. $bigriuse .'+'. $mf2;&assign;
$p = $mf10874 .'+'. $bigi .'+'. $mf3;&assign;
$p = $mf10874 .'+'. $bigriuse .'+'. $mf3;&assign;
$p = $mf10874 .'+'. $bigi .'+'. $mf1 .'+'. $mf2;&assign;
$p = $mf10874 .'+'. $bigriuse .'+'. $mf1 .'+'. $mf2;&assign;
$p = $mf10874 .'+'. $bigi .'+'. $mf1 .'+'. $mf3;&assign;
$p = $mf10874 .'+'. $bigriuse .'+'. $mf1 .'+'. $mf3;&assign;
$p = $mf10874 .'+'. $bigi .'+'. $mf2 .'+'. $mf3;&assign;
$p = $mf10874 .'+'. $bigriuse .'+'. $mf2 .'+'. $mf3;&assign;
$p = $mf10874 .'+'. $bigriuse .'+'. $mf1 .'+'. $mf2 .'+'. $mf3;&assign;
#_____
$p = $mf10875 .'+'. $bigi;&assign;
$p = $mf10875 .'+'. $bigriuse;&assign;
$p = $mf10875 .'+'. $bigi .'+'. $mf;&assign;
$p = $mf10875 .'+'. $bigriuse .'+'. $mf;&assign;
$p = $mf10875 .'+'. $bigi .'+'. $mf1;&assign;
$p = $mf10875 .'+'. $bigriuse .'+'. $mf1;&assign;
$p = $mf10875 .'+'. $bigi .'+'. $mf2;&assign;
$p = $mf10875 .'+'. $bigriuse .'+'. $mf2;&assign;
$p = $mf10875 .'+'. $bigi .'+'. $mf3;&assign;
$p = $mf10875 .'+'. $bigriuse .'+'. $mf3;&assign;
$p = $mf10875 .'+'. $bigi .'+'. $mf1 .'+'. $mf2;&assign;
$p = $mf10875 .'+'. $bigriuse .'+'. $mf1 .'+'. $mf2;&assign;
$p = $mf10875 .'+'. $bigi .'+'. $mf1 .'+'. $mf3;&assign;
$p = $mf10875 .'+'. $bigriuse .'+'. $mf1 .'+'. $mf3;&assign;
$p = $mf10875 .'+'. $bigi .'+'. $mf2 .'+'. $mf3;&assign;
$p = $mf10875 .'+'. $bigriuse .'+'. $mf2 .'+'. $mf3;&assign;
$p = $mf10875 .'+'. $bigriuse .'+'. $mf1 .'+'. $mf2 .'+'. $mf3;&assign;
#_____
$p = $mf108754 .'+'. $bigi;&assign;
$p = $mf108754 .'+'. $bigriuse;&assign;
$p = $mf108754 .'+'. $bigi .'+'. $mf;&assign;
$p = $mf108754 .'+'. $bigriuse .'+'. $mf;&assign;
$p = $mf108754 .'+'. $bigi .'+'. $mf1;&assign;
$p = $mf108754 .'+'. $bigriuse .'+'. $mf1;&assign;
$p = $mf108754 .'+'. $bigi .'+'. $mf2;&assign;
$p = $mf108754 .'+'. $bigriuse .'+'. $mf2;&assign;
$p = $mf108754 .'+'. $bigi .'+'. $mf3;&assign;
```

```
$p = $mf108754 .'+'. $bigriuse .'+'. $mf3;&assign;
$p = $mf108754 .'+'. $bigi .'+'. $mf1 .'+'. $mf2;&assign;
$p = $mf108754 .'+'. $bigriuse .'+'. $mf1 .'+'. $mf2;&assign;
$p = $mf108754 .'+'. $bigi .'+'. $mf1 .'+'. $mf3;&assign;
$p = $mf108754 .'+'. $bigriuse .'+'. $mf1 .'+'. $mf3;&assign;
$p = $mf108754 .'+'. $bigi .'+'. $mf2 .'+'. $mf3;&assign;
$p = $mf108754 .'+'. $bigriuse .'+'. $mf2 .'+'. $mf3;&assign;
$p = $mf108754 .'+'. $bigriuse .'+'. $mf1 .'+'. $mf2 .'+'. $mf3;&assign;

#_____

$p = $mf10876 .'+'. $bigi;&assign;
$p = $mf10876 .'+'. $bigriuse;&assign;
$p = $mf10876 .'+'. $bigi .'+'. $mf;&assign;
$p = $mf10876 .'+'. $bigriuse .'+'. $mf;&assign;
$p = $mf10876 .'+'. $bigi .'+'. $mf1;&assign;
$p = $mf10876 .'+'. $bigriuse .'+'. $mf1;&assign;
$p = $mf10876 .'+'. $bigi .'+'. $mf2;&assign;
$p = $mf10876 .'+'. $bigriuse .'+'. $mf2;&assign;
$p = $mf10876 .'+'. $bigi .'+'. $mf3;&assign;
$p = $mf10876 .'+'. $bigriuse .'+'. $mf3;&assign;
$p = $mf10876 .'+'. $bigi .'+'. $mf1 .'+'. $mf2;&assign;
$p = $mf10876 .'+'. $bigriuse .'+'. $mf1 .'+'. $mf2;&assign;
$p = $mf10876 .'+'. $bigi .'+'. $mf1 .'+'. $mf3;&assign;
$p = $mf10876 .'+'. $bigriuse .'+'. $mf1 .'+'. $mf3;&assign;
$p = $mf10876 .'+'. $bigi .'+'. $mf2 .'+'. $mf3;&assign;
$p = $mf10876 .'+'. $bigriuse .'+'. $mf2 .'+'. $mf3;&assign;
$p = $mf10876 .'+'. $bigriuse .'+'. $mf1 .'+'. $mf2 .'+'. $mf3;&assign;
#_____

$p = $mf108764 .'+'. $bigi;&assign;
$p = $mf108764 .'+'. $bigriuse;&assign;
$p = $mf108764 .'+'. $bigi .'+'. $mf;&assign;
$p = $mf108764 .'+'. $bigriuse .'+'. $mf;&assign;
$p = $mf108764 .'+'. $bigi .'+'. $mf1;&assign;
$p = $mf108764 .'+'. $bigriuse .'+'. $mf1;&assign;
$p = $mf108764 .'+'. $bigi .'+'. $mf2;&assign;
$p = $mf108764 .'+'. $bigriuse .'+'. $mf2;&assign;
$p = $mf108764 .'+'. $bigi .'+'. $mf3;&assign;
$p = $mf108764 .'+'. $bigriuse .'+'. $mf3;&assign;
$p = $mf108764 .'+'. $bigi .'+'. $mf1 .'+'. $mf2;&assign;
$p = $mf108764 .'+'. $bigriuse .'+'. $mf1 .'+'. $mf2;&assign;
$p = $mf108764 .'+'. $bigi .'+'. $mf1 .'+'. $mf3;&assign;
$p = $mf108764 .'+'. $bigriuse .'+'. $mf1 .'+'. $mf3;&assign;
$p = $mf108764 .'+'. $bigi .'+'. $mf2 .'+'. $mf3;&assign;
```

```
$p = $mf108764 .'+'. $bigriuse .'+'. $mf2 .'+'. $mf3;&assign;
$p = $mf108764 .'+'. $bigriuse .'+'. $mf1 .'+'. $mf2 .'+'. $mf3;&assign;

$p = $mf108765 .'+'. $bigi;&assign;
$p = $mf108765 .'+'. $bigriuse;&assign;
$p = $mf108765 .'+'. $bigi .'+'. $mf;&assign;
$p = $mf108765 .'+'. $bigriuse .'+'. $mf;&assign;
$p = $mf108765 .'+'. $bigi .'+'. $mf1;&assign;
$p = $mf108765 .'+'. $bigriuse .'+'. $mf1;&assign;
$p = $mf108765 .'+'. $bigi .'+'. $mf2;&assign;
$p = $mf108765 .'+'. $bigriuse .'+'. $mf2;&assign;
$p = $mf108765 .'+'. $bigi .'+'. $mf3;&assign;
$p = $mf108765 .'+'. $bigriuse .'+'. $mf3;&assign;
$p = $mf108765 .'+'. $bigi .'+'. $mf1 .'+'. $mf2;&assign;
$p = $mf108765 .'+'. $bigriuse .'+'. $mf1 .'+'. $mf2;&assign;
$p = $mf108765 .'+'. $bigi .'+'. $mf1 .'+'. $mf3;&assign;
$p = $mf108765 .'+'. $bigriuse .'+'. $mf1 .'+'. $mf3;&assign;
$p = $mf108765 .'+'. $bigi .'+'. $mf2 .'+'. $mf3;&assign;
$p = $mf108765 .'+'. $bigriuse .'+'. $mf2 .'+'. $mf3;&assign;
$p = $mf108765 .'+'. $bigriuse .'+'. $mf1 .'+'. $mf2 .'+'. $mf3;&assign;

$p = $mf1087654 .'+'. $bigi;&assign;
$p = $mf1087654 .'+'. $bigriuse;&assign;
$p = $mf1087654 .'+'. $bigi .'+'. $mf;&assign;
$p = $mf1087654 .'+'. $bigriuse .'+'. $mf;&assign;
$p = $mf1087654 .'+'. $bigi .'+'. $mf1;&assign;
$p = $mf1087654 .'+'. $bigriuse .'+'. $mf1;&assign;
$p = $mf1087654 .'+'. $bigi .'+'. $mf2;&assign;
$p = $mf1087654 .'+'. $bigriuse .'+'. $mf2;&assign;
$p = $mf1087654 .'+'. $bigi .'+'. $mf3;&assign;
$p = $mf1087654 .'+'. $bigriuse .'+'. $mf3;&assign;
$p = $mf1087654 .'+'. $bigi .'+'. $mf1 .'+'. $mf2;&assign;
$p = $mf1087654 .'+'. $bigriuse .'+'. $mf1 .'+'. $mf2;&assign;
$p = $mf1087654 .'+'. $bigi .'+'. $mf1 .'+'. $mf3;&assign;
$p = $mf1087654 .'+'. $bigriuse .'+'. $mf1 .'+'. $mf3;&assign;
$p = $mf1087654 .'+'. $bigi .'+'. $mf2 .'+'. $mf3;&assign;
$p = $mf1087654 .'+'. $bigriuse .'+'. $mf2 .'+'. $mf3;&assign;
$p = $mf1087654 .'+'. $bigriuse .'+'. $mf1 .'+'. $mf2 .'+'. $mf3;&assign;

$p = $mf109 .'+'. $bigi;&assign;
$p = $mf109 .'+'. $bigriuse;&assign;
$p = $mf109 .'+'. $bigi .'+'. $mf;&assign;
```

```
$p = $mf109 .'+'. $bigriuse .'+'. $mf;&assign;
$p = $mf109 .'+'. $bigi .'+'. $mf1;&assign;
$p = $mf109 .'+'. $bigriuse .'+'. $mf1;&assign;
$p = $mf109 .'+'. $bigi .'+'. $mf2;&assign;
$p = $mf109 .'+'. $bigriuse .'+'. $mf2;&assign;
$p = $mf109 .'+'. $bigi .'+'. $mf3;&assign;
$p = $mf109 .'+'. $bigriuse .'+'. $mf3;&assign;
$p = $mf109 .'+'. $bigi .'+'. $mf1 .'+'. $mf2;&assign;
$p = $mf109 .'+'. $bigriuse .'+'. $mf1 .'+'. $mf2;&assign;
$p = $mf109 .'+'. $bigi .'+'. $mf1 .'+'. $mf3;&assign;
$p = $mf109 .'+'. $bigriuse .'+'. $mf1 .'+'. $mf3;&assign;
$p = $mf109 .'+'. $bigi .'+'. $mf2 .'+'. $mf3;&assign;
$p = $mf109 .'+'. $bigriuse .'+'. $mf2 .'+'. $mf3;&assign;
$p = $mf109 .'+'. $bigriuse .'+'. $mf1 .'+'. $mf2 .'+'. $mf3;&assign;

$p = $mf1094 .'+'. $bigi;&assign;
$p = $mf1094 .'+'. $bigriuse;&assign;
$p = $mf1094 .'+'. $bigi .'+'. $mf;&assign;
$p = $mf1094 .'+'. $bigriuse .'+'. $mf;&assign;
$p = $mf1094 .'+'. $bigi .'+'. $mf1;&assign;
$p = $mf1094 .'+'. $bigriuse .'+'. $mf1;&assign;
$p = $mf1094 .'+'. $bigi .'+'. $mf2;&assign;
$p = $mf1094 .'+'. $bigriuse .'+'. $mf2;&assign;
$p = $mf1094 .'+'. $bigi .'+'. $mf3;&assign;
$p = $mf1094 .'+'. $bigriuse .'+'. $mf3;&assign;
$p = $mf1094 .'+'. $bigi .'+'. $mf1 .'+'. $mf2;&assign;
$p = $mf1094 .'+'. $bigriuse .'+'. $mf1 .'+'. $mf2;&assign;
$p = $mf1094 .'+'. $bigi .'+'. $mf1 .'+'. $mf3;&assign;
$p = $mf1094 .'+'. $bigriuse .'+'. $mf1 .'+'. $mf3;&assign;
$p = $mf1094 .'+'. $bigi .'+'. $mf2 .'+'. $mf3;&assign;
$p = $mf1094 .'+'. $bigriuse .'+'. $mf2 .'+'. $mf3;&assign;
$p = $mf1094 .'+'. $bigriuse .'+'. $mf1 .'+'. $mf2 .'+'. $mf3;&assign;

$p = $mf1095 .'+'. $bigi;&assign;
$p = $mf1095 .'+'. $bigriuse;&assign;
$p = $mf1095 .'+'. $bigi .'+'. $mf;&assign;
$p = $mf1095 .'+'. $bigriuse .'+'. $mf;&assign;
$p = $mf1095 .'+'. $bigi .'+'. $mf1;&assign;
$p = $mf1095 .'+'. $bigriuse .'+'. $mf1;&assign;
$p = $mf1095 .'+'. $bigi .'+'. $mf2;&assign;
$p = $mf1095 .'+'. $bigriuse .'+'. $mf2;&assign;
$p = $mf1095 .'+'. $bigi .'+'. $mf3;&assign;
$p = $mf1095 .'+'. $bigriuse .'+'. $mf3;&assign;
```

```
$p = $mf1095 .'+'. $bigi .'+'. $mf1 .'+'. $mf2;&assign;
$p = $mf1095 .'+'. $bigriuse .'+'. $mf1 .'+'. $mf2;&assign;
$p = $mf1095 .'+'. $bigi .'+'. $mf1 .'+'. $mf3;&assign;
$p = $mf1095 .'+'. $bigriuse .'+'. $mf1 .'+'. $mf3;&assign;
$p = $mf1095 .'+'. $bigi .'+'. $mf2 .'+'. $mf3;&assign;
$p = $mf1095 .'+'. $bigriuse .'+'. $mf2 .'+'. $mf3;&assign;
$p = $mf1095 .'+'. $bigriuse .'+'. $mf1 .'+'. $mf2 .'+'. $mf3;&assign;

$p = $mf10954 .'+'. $bigi;&assign;
$p = $mf10954 .'+'. $bigriuse;&assign;
$p = $mf10954 .'+'. $bigi .'+'. $mf;&assign;
$p = $mf10954 .'+'. $bigriuse .'+'. $mf;&assign;
$p = $mf10954 .'+'. $bigi .'+'. $mf1;&assign;
$p = $mf10954 .'+'. $bigriuse .'+'. $mf1;&assign;
$p = $mf10954 .'+'. $bigi .'+'. $mf2;&assign;
$p = $mf10954 .'+'. $bigriuse .'+'. $mf2;&assign;
$p = $mf10954 .'+'. $bigi .'+'. $mf3;&assign;
$p = $mf10954 .'+'. $bigriuse .'+'. $mf3;&assign;
$p = $mf10954 .'+'. $bigi .'+'. $mf1 .'+'. $mf2;&assign;
$p = $mf10954 .'+'. $bigriuse .'+'. $mf1 .'+'. $mf2;&assign;
$p = $mf10954 .'+'. $bigi .'+'. $mf1 .'+'. $mf3;&assign;
$p = $mf10954 .'+'. $bigriuse .'+'. $mf1 .'+'. $mf3;&assign;
$p = $mf10954 .'+'. $bigi .'+'. $mf2 .'+'. $mf3;&assign;
$p = $mf10954 .'+'. $bigriuse .'+'. $mf2 .'+'. $mf3;&assign;
$p = $mf10954 .'+'. $bigriuse .'+'. $mf1 .'+'. $mf2 .'+'. $mf3;&assign;

$p = $mf1096 .'+'. $bigi;&assign;
$p = $mf1096 .'+'. $bigriuse;&assign;
$p = $mf1096 .'+'. $bigi .'+'. $mf;&assign;
$p = $mf1096 .'+'. $bigriuse .'+'. $mf;&assign;
$p = $mf1096 .'+'. $bigi .'+'. $mf1;&assign;
$p = $mf1096 .'+'. $bigriuse .'+'. $mf1;&assign;
$p = $mf1096 .'+'. $bigi .'+'. $mf2;&assign;
$p = $mf1096 .'+'. $bigriuse .'+'. $mf2;&assign;
$p = $mf1096 .'+'. $bigi .'+'. $mf3;&assign;
$p = $mf1096 .'+'. $bigriuse .'+'. $mf3;&assign;
$p = $mf1096 .'+'. $bigi .'+'. $mf1 .'+'. $mf2;&assign;
$p = $mf1096 .'+'. $bigriuse .'+'. $mf1 .'+'. $mf2;&assign;
$p = $mf1096 .'+'. $bigi .'+'. $mf1 .'+'. $mf3;&assign;
$p = $mf1096 .'+'. $bigriuse .'+'. $mf1 .'+'. $mf3;&assign;
$p = $mf1096 .'+'. $bigi .'+'. $mf2 .'+'. $mf3;&assign;
$p = $mf1096 .'+'. $bigriuse .'+'. $mf2 .'+'. $mf3;&assign;
$p = $mf1096 .'+'. $bigriuse .'+'. $mf1 .'+'. $mf2 .'+'. $mf3;&assign;

```

```
$p = $mf10964 .'+'. $bigi;&assign;
$p = $mf10964 .'+'. $bigriuse;&assign;
$p = $mf10964 .'+'. $bigi .'+'. $mf;&assign;
$p = $mf10964 .'+'. $bigriuse .'+'. $mf;&assign;
$p = $mf10964 .'+'. $bigi .'+'. $mf1;&assign;
$p = $mf10964 .'+'. $bigriuse .'+'. $mf1;&assign;
$p = $mf10964 .'+'. $bigi .'+'. $mf2;&assign;
$p = $mf10964 .'+'. $bigriuse .'+'. $mf2;&assign;
$p = $mf10964 .'+'. $bigi .'+'. $mf3;&assign;
$p = $mf10964 .'+'. $bigriuse .'+'. $mf3;&assign;
$p = $mf10964 .'+'. $bigi .'+'. $mf1 .'+'. $mf2;&assign;
$p = $mf10964 .'+'. $bigriuse .'+'. $mf1 .'+'. $mf2;&assign;
$p = $mf10964 .'+'. $bigi .'+'. $mf1 .'+'. $mf3;&assign;
$p = $mf10964 .'+'. $bigriuse .'+'. $mf1 .'+'. $mf3;&assign;
$p = $mf10964 .'+'. $bigi .'+'. $mf2 .'+'. $mf3;&assign;
$p = $mf10964 .'+'. $bigriuse .'+'. $mf2 .'+'. $mf3;&assign;
$p = $mf10964 .'+'. $bigriuse .'+'. $mf1 .'+'. $mf2 .'+'. $mf3;&assign;

$p = $mf10965 .'+'. $bigi;&assign;
$p = $mf10965 .'+'. $bigriuse;&assign;
$p = $mf10965 .'+'. $bigi .'+'. $mf;&assign;
$p = $mf10965 .'+'. $bigriuse .'+'. $mf;&assign;
$p = $mf10965 .'+'. $bigi .'+'. $mf1;&assign;
$p = $mf10965 .'+'. $bigriuse .'+'. $mf1;&assign;
$p = $mf10965 .'+'. $bigi .'+'. $mf2;&assign;
$p = $mf10965 .'+'. $bigriuse .'+'. $mf2;&assign;
$p = $mf10965 .'+'. $bigi .'+'. $mf3;&assign;
$p = $mf10965 .'+'. $bigriuse .'+'. $mf3;&assign;
$p = $mf10965 .'+'. $bigi .'+'. $mf1 .'+'. $mf2;&assign;
$p = $mf10965 .'+'. $bigriuse .'+'. $mf1 .'+'. $mf2;&assign;
$p = $mf10965 .'+'. $bigi .'+'. $mf1 .'+'. $mf3;&assign;
$p = $mf10965 .'+'. $bigriuse .'+'. $mf1 .'+'. $mf3;&assign;
$p = $mf10965 .'+'. $bigi .'+'. $mf2 .'+'. $mf3;&assign;
$p = $mf10965 .'+'. $bigriuse .'+'. $mf2 .'+'. $mf3;&assign;
$p = $mf10965 .'+'. $bigriuse .'+'. $mf1 .'+'. $mf2 .'+'. $mf3;&assign;

$p = $mf109654 .'+'. $bigi;&assign;
$p = $mf109654 .'+'. $bigriuse;&assign;
$p = $mf109654 .'+'. $bigi .'+'. $mf;&assign;
$p = $mf109654 .'+'. $bigriuse .'+'. $mf;&assign;
$p = $mf109654 .'+'. $bigi .'+'. $mf1;&assign;
$p = $mf109654 .'+'. $bigriuse .'+'. $mf1;&assign;
$p = $mf109654 .'+'. $bigi .'+'. $mf2;&assign;
$p = $mf109654 .'+'. $bigriuse .'+'. $mf2;&assign;
$p = $mf109654 .'+'. $bigi .'+'. $mf3;&assign;
```

```
$p = $mf109654 .'+'. $bigriuse .'+'. $mf3;&assign;
$p = $mf109654 .'+'. $bigi .'+'. $mf1 .'+'. $mf2;&assign;
$p = $mf109654 .'+'. $bigriuse .'+'. $mf1 .'+'. $mf2;&assign;
$p = $mf109654 .'+'. $bigi .'+'. $mf1 .'+'. $mf3;&assign;
$p = $mf109654 .'+'. $bigriuse .'+'. $mf1 .'+'. $mf3;&assign;
$p = $mf109654 .'+'. $bigi .'+'. $mf2 .'+'. $mf3;&assign;
$p = $mf109654 .'+'. $bigriuse .'+'. $mf2 .'+'. $mf3;&assign;
$p = $mf109654 .'+'. $bigriuse .'+'. $mf1 .'+'. $mf2 .'+'. $mf3;&assign;

$p = $mf1097 .'+'. $bigi;&assign;
$p = $mf1097 .'+'. $bigriuse;&assign;
$p = $mf1097 .'+'. $bigi .'+'. $mf;&assign;
$p = $mf1097 .'+'. $bigriuse .'+'. $mf;&assign;
$p = $mf1097 .'+'. $bigi .'+'. $mf1;&assign;
$p = $mf1097 .'+'. $bigriuse .'+'. $mf1;&assign;
$p = $mf1097 .'+'. $bigi .'+'. $mf2;&assign;
$p = $mf1097 .'+'. $bigriuse .'+'. $mf2;&assign;
$p = $mf1097 .'+'. $bigi .'+'. $mf3;&assign;
$p = $mf1097 .'+'. $bigriuse .'+'. $mf3;&assign;
$p = $mf1097 .'+'. $bigi .'+'. $mf1 .'+'. $mf2;&assign;
$p = $mf1097 .'+'. $bigriuse .'+'. $mf1 .'+'. $mf2;&assign;
$p = $mf1097 .'+'. $bigi .'+'. $mf1 .'+'. $mf3;&assign;
$p = $mf1097 .'+'. $bigriuse .'+'. $mf1 .'+'. $mf3;&assign;
$p = $mf1097 .'+'. $bigi .'+'. $mf2 .'+'. $mf3;&assign;
$p = $mf1097 .'+'. $bigriuse .'+'. $mf2 .'+'. $mf3;&assign;
$p = $mf1097 .'+'. $bigriuse .'+'. $mf1 .'+'. $mf2 .'+'. $mf3;&assign;

$p = $mf10974 .'+'. $bigi;&assign;
$p = $mf10974 .'+'. $bigriuse;&assign;
$p = $mf10974 .'+'. $bigi .'+'. $mf;&assign;
$p = $mf10974 .'+'. $bigriuse .'+'. $mf;&assign;
$p = $mf10974 .'+'. $bigi .'+'. $mf1;&assign;
$p = $mf10974 .'+'. $bigriuse .'+'. $mf1;&assign;
$p = $mf10974 .'+'. $bigi .'+'. $mf2;&assign;
$p = $mf10974 .'+'. $bigriuse .'+'. $mf2;&assign;
$p = $mf10974 .'+'. $bigi .'+'. $mf3;&assign;
$p = $mf10974 .'+'. $bigriuse .'+'. $mf3;&assign;
$p = $mf10974 .'+'. $bigi .'+'. $mf1 .'+'. $mf2;&assign;
$p = $mf10974 .'+'. $bigriuse .'+'. $mf1 .'+'. $mf2;&assign;
$p = $mf10974 .'+'. $bigi .'+'. $mf1 .'+'. $mf3;&assign;
$p = $mf10974 .'+'. $bigriuse .'+'. $mf1 .'+'. $mf3;&assign;
$p = $mf10974 .'+'. $bigi .'+'. $mf2 .'+'. $mf3;&assign;
```

```
$p = $mf10974 .'+'. $bigriuse .'+'. $mf2 .'+'. $mf3;&assign;
$p = $mf10974 .'+'. $bigriuse .'+'. $mf1 .'+'. $mf2 .'+'. $mf3;&assign;

$p = $mf10975 .'+'. $bigi;&assign;
$p = $mf10975 .'+'. $bigriuse;&assign;
$p = $mf10975 .'+'. $bigi .'+'. $mf;&assign;
$p = $mf10975 .'+'. $bigriuse .'+'. $mf;&assign;
$p = $mf10975 .'+'. $bigi .'+'. $mf1;&assign;
$p = $mf10975 .'+'. $bigriuse .'+'. $mf1;&assign;
$p = $mf10975 .'+'. $bigi .'+'. $mf2;&assign;
$p = $mf10975 .'+'. $bigriuse .'+'. $mf2;&assign;
$p = $mf10975 .'+'. $bigi .'+'. $mf3;&assign;
$p = $mf10975 .'+'. $bigriuse .'+'. $mf3;&assign;
$p = $mf10975 .'+'. $bigi .'+'. $mf1 .'+'. $mf2;&assign;
$p = $mf10975 .'+'. $bigriuse .'+'. $mf1 .'+'. $mf2;&assign;
$p = $mf10975 .'+'. $bigi .'+'. $mf1 .'+'. $mf3;&assign;
$p = $mf10975 .'+'. $bigriuse .'+'. $mf1 .'+'. $mf3;&assign;
$p = $mf10975 .'+'. $bigi .'+'. $mf2 .'+'. $mf3;&assign;
$p = $mf10975 .'+'. $bigriuse .'+'. $mf2 .'+'. $mf3;&assign;
$p = $mf10975 .'+'. $bigriuse .'+'. $mf1 .'+'. $mf2 .'+'. $mf3;&assign;

$p = $mf109754 .'+'. $bigi;&assign;
$p = $mf109754 .'+'. $bigriuse;&assign;
$p = $mf109754 .'+'. $bigi .'+'. $mf;&assign;
$p = $mf109754 .'+'. $bigriuse .'+'. $mf;&assign;
$p = $mf109754 .'+'. $bigi .'+'. $mf1;&assign;
$p = $mf109754 .'+'. $bigriuse .'+'. $mf1;&assign;
$p = $mf109754 .'+'. $bigi .'+'. $mf2;&assign;
$p = $mf109754 .'+'. $bigriuse .'+'. $mf2;&assign;
$p = $mf109754 .'+'. $bigi .'+'. $mf3;&assign;
$p = $mf109754 .'+'. $bigriuse .'+'. $mf3;&assign;
$p = $mf109754 .'+'. $bigi .'+'. $mf1 .'+'. $mf2;&assign;
$p = $mf109754 .'+'. $bigriuse .'+'. $mf1 .'+'. $mf2;&assign;
$p = $mf109754 .'+'. $bigi .'+'. $mf1 .'+'. $mf3;&assign;
$p = $mf109754 .'+'. $bigriuse .'+'. $mf1 .'+'. $mf3;&assign;
$p = $mf109754 .'+'. $bigi .'+'. $mf2 .'+'. $mf3;&assign;
$p = $mf109754 .'+'. $bigriuse .'+'. $mf2 .'+'. $mf3;&assign;
$p = $mf109754 .'+'. $bigriuse .'+'. $mf1 .'+'. $mf2 .'+'. $mf3;&assign;

$p = $mf10976 .'+'. $bigi;&assign;
$p = $mf10976 .'+'. $bigriuse;&assign;
$p = $mf10976 .'+'. $bigi .'+'. $mf;&assign;
$p = $mf10976 .'+'. $bigriuse .'+'. $mf;&assign;
$p = $mf10976 .'+'. $bigi .'+'. $mf1;&assign;
```

```
$p = $mf10976 .'+'. $bigriuse .'+'. $mf1;&assign;
$p = $mf10976 .'+'. $bigi .'+'. $mf2;&assign;
$p = $mf10976 .'+'. $bigriuse .'+'. $mf2;&assign;
$p = $mf10976 .'+'. $bigi .'+'. $mf3;&assign;
$p = $mf10976 .'+'. $bigriuse .'+'. $mf3;&assign;
$p = $mf10976 .'+'. $bigi .'+'. $mf1 .'+'. $mf2;&assign;
$p = $mf10976 .'+'. $bigriuse .'+'. $mf1 .'+'. $mf2;&assign;
$p = $mf10976 .'+'. $bigi .'+'. $mf1 .'+'. $mf3;&assign;
$p = $mf10976 .'+'. $bigriuse .'+'. $mf1 .'+'. $mf3;&assign;
$p = $mf10976 .'+'. $bigi .'+'. $mf2 .'+'. $mf3;&assign;
$p = $mf10976 .'+'. $bigriuse .'+'. $mf2 .'+'. $mf3;&assign;
$p = $mf10976 .'+'. $bigriuse .'+'. $mf1 .'+'. $mf2 .'+'. $mf3;&assign;
#_____

$p = $mf109764 .'+'. $bigi;&assign;
$p = $mf109764 .'+'. $bigriuse;&assign;
$p = $mf109764 .'+'. $bigi .'+'. $mf;&assign;
$p = $mf109764 .'+'. $bigriuse .'+'. $mf;&assign;
$p = $mf109764 .'+'. $bigi .'+'. $mf1;&assign;
$p = $mf109764 .'+'. $bigriuse .'+'. $mf1;&assign;
$p = $mf109764 .'+'. $bigi .'+'. $mf2;&assign;
$p = $mf109764 .'+'. $bigriuse .'+'. $mf2;&assign;
$p = $mf109764 .'+'. $bigi .'+'. $mf3;&assign;
$p = $mf109764 .'+'. $bigriuse .'+'. $mf3;&assign;
$p = $mf109764 .'+'. $bigi .'+'. $mf1 .'+'. $mf2;&assign;
$p = $mf109764 .'+'. $bigriuse .'+'. $mf1 .'+'. $mf2;&assign;
$p = $mf109764 .'+'. $bigi .'+'. $mf1 .'+'. $mf3;&assign;
$p = $mf109764 .'+'. $bigriuse .'+'. $mf1 .'+'. $mf3;&assign;
$p = $mf109764 .'+'. $bigi .'+'. $mf2 .'+'. $mf3;&assign;
$p = $mf109764 .'+'. $bigriuse .'+'. $mf2 .'+'. $mf3;&assign;
$p = $mf109764 .'+'. $bigriuse .'+'. $mf1 .'+'. $mf2 .'+'. $mf3;&assign;

#_____
$p = $mf109765 .'+'. $bigi;&assign;
$p = $mf109765 .'+'. $bigriuse;&assign;
$p = $mf109765 .'+'. $bigi .'+'. $mf;&assign;
$p = $mf109765 .'+'. $bigriuse .'+'. $mf;&assign;
$p = $mf109765 .'+'. $bigi .'+'. $mf1;&assign;
$p = $mf109765 .'+'. $bigriuse .'+'. $mf1;&assign;
$p = $mf109765 .'+'. $bigi .'+'. $mf2;&assign;
$p = $mf109765 .'+'. $bigriuse .'+'. $mf2;&assign;
$p = $mf109765 .'+'. $bigi .'+'. $mf3;&assign;
$p = $mf109765 .'+'. $bigriuse .'+'. $mf3;&assign;
$p = $mf109765 .'+'. $bigi .'+'. $mf1 .'+'. $mf2;&assign;
```

```
$p = $mf109765 .'+'. $bigriuse .'+'. $mf1 .'+'. $mf2;&assign;
$p = $mf109765 .'+'. $bigi .'+'. $mf1 .'+'. $mf3;&assign;
$p = $mf109765 .'+'. $bigriuse .'+'. $mf1 .'+'. $mf3;&assign;
$p = $mf109765 .'+'. $bigi .'+'. $mf2 .'+'. $mf3;&assign;
$p = $mf109765 .'+'. $bigriuse .'+'. $mf2 .'+'. $mf3;&assign;
$p = $mf109765 .'+'. $bigriuse .'+'. $mf1 .'+'. $mf2 .'+'. $mf3;&assign;

$p = $mf1097654 .'+'. $bigi;&assign;
$p = $mf1097654 .'+'. $bigriuse;&assign;
$p = $mf1097654 .'+'. $bigi .'+'. $mf;&assign;
$p = $mf1097654 .'+'. $bigriuse .'+'. $mf;&assign;
$p = $mf1097654 .'+'. $bigi .'+'. $mf1;&assign;
$p = $mf1097654 .'+'. $bigriuse .'+'. $mf1;&assign;
$p = $mf1097654 .'+'. $bigi .'+'. $mf2;&assign;
$p = $mf1097654 .'+'. $bigriuse .'+'. $mf2;&assign;
$p = $mf1097654 .'+'. $bigi .'+'. $mf3;&assign;
$p = $mf1097654 .'+'. $bigriuse .'+'. $mf3;&assign;
$p = $mf1097654 .'+'. $bigi .'+'. $mf1 .'+'. $mf2;&assign;
$p = $mf1097654 .'+'. $bigriuse .'+'. $mf1 .'+'. $mf2;&assign;
$p = $mf1097654 .'+'. $bigi .'+'. $mf1 .'+'. $mf3;&assign;
$p = $mf1097654 .'+'. $bigriuse .'+'. $mf1 .'+'. $mf3;&assign;
$p = $mf1097654 .'+'. $bigi .'+'. $mf2 .'+'. $mf3;&assign;
$p = $mf1097654 .'+'. $bigriuse .'+'. $mf2 .'+'. $mf3;&assign;
$p = $mf1097654 .'+'. $bigriuse .'+'. $mf1 .'+'. $mf2 .'+'. $mf3;&assign;

$p = $mf1098 .'+'. $bigi;&assign;
$p = $mf1098 .'+'. $bigriuse;&assign;
$p = $mf1098 .'+'. $bigi .'+'. $mf;&assign;
$p = $mf1098 .'+'. $bigriuse .'+'. $mf;&assign;
$p = $mf1098 .'+'. $bigi .'+'. $mf1;&assign;
$p = $mf1098 .'+'. $bigriuse .'+'. $mf1;&assign;
$p = $mf1098 .'+'. $bigi .'+'. $mf2;&assign;
$p = $mf1098 .'+'. $bigriuse .'+'. $mf2;&assign;
$p = $mf1098 .'+'. $bigi .'+'. $mf3;&assign;
$p = $mf1098 .'+'. $bigriuse .'+'. $mf3;&assign;
$p = $mf1098 .'+'. $bigi .'+'. $mf1 .'+'. $mf2;&assign;
$p = $mf1098 .'+'. $bigriuse .'+'. $mf1 .'+'. $mf2;&assign;
$p = $mf1098 .'+'. $bigi .'+'. $mf1 .'+'. $mf3;&assign;
$p = $mf1098 .'+'. $bigriuse .'+'. $mf1 .'+'. $mf3;&assign;
$p = $mf1098 .'+'. $bigi .'+'. $mf2 .'+'. $mf3;&assign;
$p = $mf1098 .'+'. $bigriuse .'+'. $mf2 .'+'. $mf3;&assign;
$p = $mf1098 .'+'. $bigriuse .'+'. $mf1 .'+'. $mf2 .'+'. $mf3;&assign;

```

```
$p = $mf10984 .'+'. $bigi;&assign;
$p = $mf10984 .'+'. $bigriuse;&assign;
$p = $mf10984 .'+'. $bigi .'+'. $mf;&assign;
$p = $mf10984 .'+'. $bigriuse .'+'. $mf;&assign;
$p = $mf10984 .'+'. $bigi .'+'. $mf1;&assign;
$p = $mf10984 .'+'. $bigriuse .'+'. $mf1;&assign;
$p = $mf10984 .'+'. $bigi .'+'. $mf2;&assign;
$p = $mf10984 .'+'. $bigriuse .'+'. $mf2;&assign;
$p = $mf10984 .'+'. $bigi .'+'. $mf3;&assign;
$p = $mf10984 .'+'. $bigriuse .'+'. $mf3;&assign;
$p = $mf10984 .'+'. $bigi .'+'. $mf1 .'+'. $mf2;&assign;
$p = $mf10984 .'+'. $bigriuse .'+'. $mf1 .'+'. $mf2;&assign;
$p = $mf10984 .'+'. $bigi .'+'. $mf1 .'+'. $mf3;&assign;
$p = $mf10984 .'+'. $bigriuse .'+'. $mf1 .'+'. $mf3;&assign;
$p = $mf10984 .'+'. $bigi .'+'. $mf2 .'+'. $mf3;&assign;
$p = $mf10984 .'+'. $bigriuse .'+'. $mf2 .'+'. $mf3;&assign;
$p = $mf10984 .'+'. $bigriuse .'+'. $mf1 .'+'. $mf2 .'+'. $mf3;&assign;

$p = $mf10985 .'+'. $bigi;&assign;
$p = $mf10985 .'+'. $bigriuse;&assign;
$p = $mf10985 .'+'. $bigi .'+'. $mf;&assign;
$p = $mf10985 .'+'. $bigriuse .'+'. $mf;&assign;
$p = $mf10985 .'+'. $bigi .'+'. $mf1;&assign;
$p = $mf10985 .'+'. $bigriuse .'+'. $mf1;&assign;
$p = $mf10985 .'+'. $bigi .'+'. $mf2;&assign;
$p = $mf10985 .'+'. $bigriuse .'+'. $mf2;&assign;
$p = $mf10985 .'+'. $bigi .'+'. $mf3;&assign;
$p = $mf10985 .'+'. $bigriuse .'+'. $mf3;&assign;
$p = $mf10985 .'+'. $bigi .'+'. $mf1 .'+'. $mf2;&assign;
$p = $mf10985 .'+'. $bigriuse .'+'. $mf1 .'+'. $mf2;&assign;
$p = $mf10985 .'+'. $bigi .'+'. $mf1 .'+'. $mf3;&assign;
$p = $mf10985 .'+'. $bigriuse .'+'. $mf1 .'+'. $mf3;&assign;
$p = $mf10985 .'+'. $bigi .'+'. $mf2 .'+'. $mf3;&assign;
$p = $mf10985 .'+'. $bigriuse .'+'. $mf2 .'+'. $mf3;&assign;
$p = $mf10985 .'+'. $bigriuse .'+'. $mf1 .'+'. $mf2 .'+'. $mf3;&assign;

$p = $mf109854 .'+'. $bigi;&assign;
$p = $mf109854 .'+'. $bigriuse;&assign;
$p = $mf109854 .'+'. $bigi .'+'. $mf;&assign;
$p = $mf109854 .'+'. $bigriuse .'+'. $mf;&assign;
$p = $mf109854 .'+'. $bigi .'+'. $mf1;&assign;
$p = $mf109854 .'+'. $bigriuse .'+'. $mf1;&assign;
$p = $mf109854 .'+'. $bigi .'+'. $mf2;&assign;
$p = $mf109854 .'+'. $bigriuse .'+'. $mf2;&assign;
```

```
$p = $mf109854 .'+'. $bigi;&assign;
$p = $mf109854 .'+'. $bigriuse .'+'. $mf3;&assign;
$p = $mf109854 .'+'. $bigi .'+'. $mf1 .'+'. $mf2;&assign;
$p = $mf109854 .'+'. $bigriuse .'+'. $mf1 .'+'. $mf2;&assign;
$p = $mf109854 .'+'. $bigi .'+'. $mf1 .'+'. $mf3;&assign;
$p = $mf109854 .'+'. $bigriuse .'+'. $mf1 .'+'. $mf3;&assign;
$p = $mf109854 .'+'. $bigi .'+'. $mf2 .'+'. $mf3;&assign;
$p = $mf109854 .'+'. $bigriuse .'+'. $mf2 .'+'. $mf3;&assign;
$p = $mf109854 .'+'. $bigriuse .'+'. $mf1 .'+'. $mf2 .'+'. $mf3;&assign;

#_____
$p = $mf10986 .'+'. $bigi;&assign;
$p = $mf10986 .'+'. $bigriuse;&assign;
$p = $mf10986 .'+'. $bigi .'+'. $mf;&assign;
$p = $mf10986 .'+'. $bigriuse .'+'. $mf;&assign;
$p = $mf10986 .'+'. $bigi .'+'. $mf1;&assign;
$p = $mf10986 .'+'. $bigriuse .'+'. $mf1;&assign;
$p = $mf10986 .'+'. $bigi .'+'. $mf2;&assign;
$p = $mf10986 .'+'. $bigriuse .'+'. $mf2;&assign;
$p = $mf10986 .'+'. $bigi .'+'. $mf3;&assign;
$p = $mf10986 .'+'. $bigriuse .'+'. $mf3;&assign;
$p = $mf10986 .'+'. $bigi .'+'. $mf1 .'+'. $mf2;&assign;
$p = $mf10986 .'+'. $bigriuse .'+'. $mf1 .'+'. $mf2;&assign;
$p = $mf10986 .'+'. $bigi .'+'. $mf1 .'+'. $mf3;&assign;
$p = $mf10986 .'+'. $bigriuse .'+'. $mf1 .'+'. $mf3;&assign;
$p = $mf10986 .'+'. $bigi .'+'. $mf2 .'+'. $mf3;&assign;
$p = $mf10986 .'+'. $bigriuse .'+'. $mf2 .'+'. $mf3;&assign;
$p = $mf10986 .'+'. $bigriuse .'+'. $mf1 .'+'. $mf2 .'+'. $mf3;&assign;
#_____

$p = $mf109864 .'+'. $bigi;&assign;
$p = $mf109864 .'+'. $bigriuse;&assign;
$p = $mf109864 .'+'. $bigi .'+'. $mf;&assign;
$p = $mf109864 .'+'. $bigriuse .'+'. $mf;&assign;
$p = $mf109864 .'+'. $bigi .'+'. $mf1;&assign;
$p = $mf109864 .'+'. $bigriuse .'+'. $mf1;&assign;
$p = $mf109864 .'+'. $bigi .'+'. $mf2;&assign;
$p = $mf109864 .'+'. $bigriuse .'+'. $mf2;&assign;
$p = $mf109864 .'+'. $bigi .'+'. $mf3;&assign;
$p = $mf109864 .'+'. $bigriuse .'+'. $mf3;&assign;
$p = $mf109864 .'+'. $bigi .'+'. $mf1 .'+'. $mf2;&assign;
$p = $mf109864 .'+'. $bigriuse .'+'. $mf1 .'+'. $mf2;&assign;
$p = $mf109864 .'+'. $bigi .'+'. $mf1 .'+'. $mf3;&assign;
$p = $mf109864 .'+'. $bigriuse .'+'. $mf1 .'+'. $mf3;&assign;
```

```
$p = $mf109864 .'+'. $bigi .'+'. $mf2 .'+'. $mf3;&assign;
$p = $mf109864 .'+'. $bigriuse .'+'. $mf2 .'+'. $mf3;&assign;
$p = $mf109864 .'+'. $bigriuse .'+'. $mf1 .'+'. $mf2 .'+'. $mf3;&assign;

$p = $mf109865 .'+'. $bigi;&assign;
$p = $mf109865 .'+'. $bigriuse;&assign;
$p = $mf109865 .'+'. $bigi .'+'. $mf;&assign;
$p = $mf109865 .'+'. $bigriuse .'+'. $mf;&assign;
$p = $mf109865 .'+'. $bigi .'+'. $mf1;&assign;
$p = $mf109865 .'+'. $bigriuse .'+'. $mf1;&assign;
$p = $mf109865 .'+'. $bigi .'+'. $mf2;&assign;
$p = $mf109865 .'+'. $bigriuse .'+'. $mf2;&assign;
$p = $mf109865 .'+'. $bigi .'+'. $mf3;&assign;
$p = $mf109865 .'+'. $bigriuse .'+'. $mf3;&assign;
$p = $mf109865 .'+'. $bigi .'+'. $mf1 .'+'. $mf2;&assign;
$p = $mf109865 .'+'. $bigriuse .'+'. $mf1 .'+'. $mf2;&assign;
$p = $mf109865 .'+'. $bigi .'+'. $mf1 .'+'. $mf3;&assign;
$p = $mf109865 .'+'. $bigriuse .'+'. $mf1 .'+'. $mf3;&assign;
$p = $mf109865 .'+'. $bigi .'+'. $mf2 .'+'. $mf3;&assign;
$p = $mf109865 .'+'. $bigriuse .'+'. $mf2 .'+'. $mf3;&assign;
$p = $mf109865 .'+'. $bigriuse .'+'. $mf1 .'+'. $mf2 .'+'. $mf3;&assign;

$p = $mf1098654 .'+'. $bigi;&assign;
$p = $mf1098654 .'+'. $bigriuse;&assign;
$p = $mf1098654 .'+'. $bigi .'+'. $mf;&assign;
$p = $mf1098654 .'+'. $bigriuse .'+'. $mf;&assign;
$p = $mf1098654 .'+'. $bigi .'+'. $mf1;&assign;
$p = $mf1098654 .'+'. $bigriuse .'+'. $mf1;&assign;
$p = $mf1098654 .'+'. $bigi .'+'. $mf2;&assign;
$p = $mf1098654 .'+'. $bigriuse .'+'. $mf2;&assign;
$p = $mf1098654 .'+'. $bigi .'+'. $mf3;&assign;
$p = $mf1098654 .'+'. $bigriuse .'+'. $mf3;&assign;
$p = $mf1098654 .'+'. $bigi .'+'. $mf1 .'+'. $mf2;&assign;
$p = $mf1098654 .'+'. $bigriuse .'+'. $mf1 .'+'. $mf2;&assign;
$p = $mf1098654 .'+'. $bigi .'+'. $mf1 .'+'. $mf3;&assign;
$p = $mf1098654 .'+'. $bigriuse .'+'. $mf1 .'+'. $mf3;&assign;
$p = $mf1098654 .'+'. $bigi .'+'. $mf2 .'+'. $mf3;&assign;
$p = $mf1098654 .'+'. $bigriuse .'+'. $mf2 .'+'. $mf3;&assign;
$p = $mf1098654 .'+'. $bigriuse .'+'. $mf1 .'+'. $mf2 .'+'. $mf3;&assign;

$p = $mf10987 .'+'. $bigi;&assign;
$p = $mf10987 .'+'. $bigriuse;&assign;
```

```
$p = $mf10987 .'+'. $bigi .'+'. $mf;&assign;
$p = $mf10987 .'+'. $bigriuse .'+'. $mf;&assign;
$p = $mf10987 .'+'. $bigi .'+'. $mf1;&assign;
$p = $mf10987 .'+'. $bigriuse .'+'. $mf1;&assign;
$p = $mf10987 .'+'. $bigi .'+'. $mf2;&assign;
$p = $mf10987 .'+'. $bigriuse .'+'. $mf2;&assign;
$p = $mf10987 .'+'. $bigi .'+'. $mf3;&assign;
$p = $mf10987 .'+'. $bigriuse .'+'. $mf3;&assign;
$p = $mf10987 .'+'. $bigi .'+'. $mf1 .'+'. $mf2;&assign;
$p = $mf10987 .'+'. $bigriuse .'+'. $mf1 .'+'. $mf2;&assign;
$p = $mf10987 .'+'. $bigi .'+'. $mf1 .'+'. $mf3;&assign;
$p = $mf10987 .'+'. $bigriuse .'+'. $mf1 .'+'. $mf3;&assign;
$p = $mf10987 .'+'. $bigi .'+'. $mf2 .'+'. $mf3;&assign;
$p = $mf10987 .'+'. $bigriuse .'+'. $mf2 .'+'. $mf3;&assign;
$p = $mf10987 .'+'. $bigriuse .'+'. $mf1 .'+'. $mf2 .'+'. $mf3;&assign;
#_____

$p = $mf109874 .'+'. $bigi;&assign;
$p = $mf109874 .'+'. $bigriuse;&assign;
$p = $mf109874 .'+'. $bigi .'+'. $mf;&assign;
$p = $mf109874 .'+'. $bigriuse .'+'. $mf;&assign;
$p = $mf109874 .'+'. $bigi .'+'. $mf1;&assign;
$p = $mf109874 .'+'. $bigriuse .'+'. $mf1;&assign;
$p = $mf109874 .'+'. $bigi .'+'. $mf2;&assign;
$p = $mf109874 .'+'. $bigriuse .'+'. $mf2;&assign;
$p = $mf109874 .'+'. $bigi .'+'. $mf3;&assign;
$p = $mf109874 .'+'. $bigriuse .'+'. $mf3;&assign;
$p = $mf109874 .'+'. $bigi .'+'. $mf1 .'+'. $mf2;&assign;
$p = $mf109874 .'+'. $bigriuse .'+'. $mf1 .'+'. $mf2;&assign;
$p = $mf109874 .'+'. $bigi .'+'. $mf1 .'+'. $mf3;&assign;
$p = $mf109874 .'+'. $bigriuse .'+'. $mf1 .'+'. $mf3;&assign;
$p = $mf109874 .'+'. $bigi .'+'. $mf2 .'+'. $mf3;&assign;
$p = $mf109874 .'+'. $bigriuse .'+'. $mf2 .'+'. $mf3;&assign;
$p = $mf109874 .'+'. $bigriuse .'+'. $mf1 .'+'. $mf2 .'+'. $mf3;&assign;

#_____
$p = $mf109875 .'+'. $bigi;&assign;
$p = $mf109875 .'+'. $bigriuse;&assign;
$p = $mf109875 .'+'. $bigi .'+'. $mf;&assign;
$p = $mf109875 .'+'. $bigriuse .'+'. $mf;&assign;
$p = $mf109875 .'+'. $bigi .'+'. $mf1;&assign;
$p = $mf109875 .'+'. $bigriuse .'+'. $mf1;&assign;
$p = $mf109875 .'+'. $bigi .'+'. $mf2;&assign;
$p = $mf109875 .'+'. $bigriuse .'+'. $mf2;&assign;
```

```
$p = $mf109875 .'+'. $bigi .'+'. $mf3;&assign;
$p = $mf109875 .'+'. $bigriuse .'+'. $mf3;&assign;
$p = $mf109875 .'+'. $bigi .'+'. $mf1 .'+'. $mf2;&assign;
$p = $mf109875 .'+'. $bigriuse .'+'. $mf1 .'+'. $mf2;&assign;
$p = $mf109875 .'+'. $bigi .'+'. $mf1 .'+'. $mf3;&assign;
$p = $mf109875 .'+'. $bigriuse .'+'. $mf1 .'+'. $mf3;&assign;
$p = $mf109875 .'+'. $bigi .'+'. $mf2 .'+'. $mf3;&assign;
$p = $mf109875 .'+'. $bigriuse .'+'. $mf2 .'+'. $mf3;&assign;
$p = $mf109875 .'+'. $bigriuse .'+'. $mf1 .'+'. $mf2 .'+'. $mf3;&assign;

$p = $mf1098754 .'+'. $bigi;&assign;
$p = $mf1098754 .'+'. $bigriuse;&assign;
$p = $mf1098754 .'+'. $bigi .'+'. $mf;&assign;
$p = $mf1098754 .'+'. $bigriuse .'+'. $mf;&assign;
$p = $mf1098754 .'+'. $bigi .'+'. $mf1;&assign;
$p = $mf1098754 .'+'. $bigriuse .'+'. $mf1;&assign;
$p = $mf1098754 .'+'. $bigi .'+'. $mf2;&assign;
$p = $mf1098754 .'+'. $bigriuse .'+'. $mf2;&assign;
$p = $mf1098754 .'+'. $bigi .'+'. $mf3;&assign;
$p = $mf1098754 .'+'. $bigriuse .'+'. $mf3;&assign;
$p = $mf1098754 .'+'. $bigi .'+'. $mf1 .'+'. $mf2;&assign;
$p = $mf1098754 .'+'. $bigriuse .'+'. $mf1 .'+'. $mf2;&assign;
$p = $mf1098754 .'+'. $bigi .'+'. $mf1 .'+'. $mf3;&assign;
$p = $mf1098754 .'+'. $bigriuse .'+'. $mf1 .'+'. $mf3;&assign;
$p = $mf1098754 .'+'. $bigi .'+'. $mf2 .'+'. $mf3;&assign;
$p = $mf1098754 .'+'. $bigriuse .'+'. $mf2 .'+'. $mf3;&assign;
$p = $mf1098754 .'+'. $bigriuse .'+'. $mf1 .'+'. $mf2 .'+'. $mf3;&assign;

$p = $mf109876 .'+'. $bigi;&assign;
$p = $mf109876 .'+'. $bigriuse;&assign;
$p = $mf109876 .'+'. $bigi .'+'. $mf;&assign;
$p = $mf109876 .'+'. $bigriuse .'+'. $mf;&assign;
$p = $mf109876 .'+'. $bigi .'+'. $mf1;&assign;
$p = $mf109876 .'+'. $bigriuse .'+'. $mf1;&assign;
$p = $mf109876 .'+'. $bigi .'+'. $mf2;&assign;
$p = $mf109876 .'+'. $bigriuse .'+'. $mf2;&assign;
$p = $mf109876 .'+'. $bigi .'+'. $mf3;&assign;
$p = $mf109876 .'+'. $bigriuse .'+'. $mf3;&assign;
$p = $mf109876 .'+'. $bigi .'+'. $mf1 .'+'. $mf2;&assign;
$p = $mf109876 .'+'. $bigriuse .'+'. $mf1 .'+'. $mf2;&assign;
$p = $mf109876 .'+'. $bigi .'+'. $mf1 .'+'. $mf3;&assign;
$p = $mf109876 .'+'. $bigriuse .'+'. $mf1 .'+'. $mf3;&assign;
$p = $mf109876 .'+'. $bigi .'+'. $mf2 .'+'. $mf3;&assign;
```

```
$p = $mf109876 .'+'. $bigriuse .'+'. $mf2 .'+'. $mf3;&assign;
$p = $mf109876 .'+'. $bigriuse .'+'. $mf1 .'+'. $mf2 .'+'. $mf3;&assign;

#_____

$p = $mf1098764 .'+'. $bigi;&assign;
$p = $mf1098764 .'+'. $bigriuse;&assign;
$p = $mf1098764 .'+'. $bigi .'+'. $mf;&assign;
$p = $mf1098764 .'+'. $bigriuse .'+'. $mf;&assign;
$p = $mf1098764 .'+'. $bigi .'+'. $mf1;&assign;
$p = $mf1098764 .'+'. $bigriuse .'+'. $mf1;&assign;
$p = $mf1098764 .'+'. $bigi .'+'. $mf2;&assign;
$p = $mf1098764 .'+'. $bigriuse .'+'. $mf2;&assign;
$p = $mf1098764 .'+'. $bigi .'+'. $mf3;&assign;
$p = $mf1098764 .'+'. $bigriuse .'+'. $mf3;&assign;
$p = $mf1098764 .'+'. $bigi .'+'. $mf1 .'+'. $mf2;&assign;
$p = $mf1098764 .'+'. $bigriuse .'+'. $mf1 .'+'. $mf2;&assign;
$p = $mf1098764 .'+'. $bigi .'+'. $mf1 .'+'. $mf3;&assign;
$p = $mf1098764 .'+'. $bigriuse .'+'. $mf1 .'+'. $mf3;&assign;
$p = $mf1098764 .'+'. $bigi .'+'. $mf2 .'+'. $mf3;&assign;
$p = $mf1098764 .'+'. $bigriuse .'+'. $mf2 .'+'. $mf3;&assign;
$p = $mf1098764 .'+'. $bigriuse .'+'. $mf1 .'+'. $mf2 .'+'. $mf3;&assign;

#_____
$p = $mf1098765 .'+'. $bigi;&assign;
$p = $mf1098765 .'+'. $bigriuse;&assign;
$p = $mf1098765 .'+'. $bigi .'+'. $mf;&assign;
$p = $mf1098765 .'+'. $bigriuse .'+'. $mf;&assign;
$p = $mf1098765 .'+'. $bigi .'+'. $mf1;&assign;
$p = $mf1098765 .'+'. $bigriuse .'+'. $mf1;&assign;
$p = $mf1098765 .'+'. $bigi .'+'. $mf2;&assign;
$p = $mf1098765 .'+'. $bigriuse .'+'. $mf2;&assign;
$p = $mf1098765 .'+'. $bigi .'+'. $mf3;&assign;
$p = $mf1098765 .'+'. $bigriuse .'+'. $mf3;&assign;
$p = $mf1098765 .'+'. $bigi .'+'. $mf1 .'+'. $mf2;&assign;
$p = $mf1098765 .'+'. $bigriuse .'+'. $mf1 .'+'. $mf2;&assign;
$p = $mf1098765 .'+'. $bigi .'+'. $mf1 .'+'. $mf3;&assign;
$p = $mf1098765 .'+'. $bigriuse .'+'. $mf1 .'+'. $mf3;&assign;
$p = $mf1098765 .'+'. $bigi .'+'. $mf2 .'+'. $mf3;&assign;
$p = $mf1098765 .'+'. $bigriuse .'+'. $mf2 .'+'. $mf3;&assign;
$p = $mf1098765 .'+'. $bigriuse .'+'. $mf1 .'+'. $mf2 .'+'. $mf3;&assign;

#_____
$p = $mf10987654 .'+'. $bigi;&assign;
```

```
        $p = $mf10987654 .'+'. $bigriuse;&assign;
        $p = $mf10987654 .'+'. $bigi .'+'. $mf;&assign;
        $p = $mf10987654 .'+'. $bigriuse .'+'. $mf;&assign;
        $p = $mf10987654 .'+'. $bigi .'+'. $mf1;&assign;
        $p = $mf10987654 .'+'. $bigriuse .'+'. $mf1;&assign;
        $p = $mf10987654 .'+'. $bigi .'+'. $mf2;&assign;
        $p = $mf10987654 .'+'. $bigriuse .'+'. $mf2;&assign;
        $p = $mf10987654 .'+'. $bigi .'+'. $mf3;&assign;
        $p = $mf10987654 .'+'. $bigriuse .'+'. $mf3;&assign;
        $p = $mf10987654 .'+'. $bigi .'+'. $mf1 .'+'. $mf2;&assign;
        $p = $mf10987654 .'+'. $bigriuse .'+'. $mf1 .'+'. $mf2;&assign;
        $p = $mf10987654 .'+'. $bigi .'+'. $mf1 .'+'. $mf3;&assign;
        $p = $mf10987654 .'+'. $bigriuse .'+'. $mf1 .'+'. $mf3;&assign;
        $p = $mf10987654 .'+'. $bigi .'+'. $mf2 .'+'. $mf3;&assign;
        $p = $mf10987654 .'+'. $bigriuse .'+'. $mf2 .'+'. $mf3;&assign;
        $p = $mf10987654 .'+'. $bigriuse .'+'. $mf1 .'+'. $mf2 .'+'. $mf3;&assign;

#_____
       }
      }
     }
    }
    #_____ sub generate_vars
{

$mf10987654 = $mf10.'+'.$mf9.'+'.$mf8.'+'.$mf7.'+'.$mf6.'+'.$mf5.'+'.$mf4;
$mf1098765 = $mf10.'+'.$mf9.'+'.$mf8.'+'.$mf7.'+'.$mf6.'+'.$mf5;
$mf1098764 = $mf10.'+'.$mf9.'+'.$mf8.'+'.$mf7.'+'.$mf6.'+'.$mf4;
$mf109876 = $mf10.'+'.$mf9.'+'.$mf8.'+'.$mf7.'+'.$mf6;
$mf1098754 = $mf10.'+'.$mf9.'+'.$mf8.'+'.$mf7.'+'.$mf5.'+'.$mf4;
$mf109875 = $mf10.'+'.$mf9.'+'.$mf8.'+'.$mf7.'+'.$mf5;
$mf109874 = $mf10.'+'.$mf9.'+'.$mf8.'+'.$mf7.'+'.$mf4;
$mf10987 = $mf10.'+'.$mf9.'+'.$mf8.'+'.$mf7;

$mf1098654 = $mf10.'+'.$mf9.'+'.$mf8.'+'.$mf6.'+'.$mf5.'+'.$mf4;
$mf109865 = $mf10.'+'.$mf9.'+'.$mf8.'+'.$mf6.'+'.$mf5;
$mf109864 = $mf10.'+'.$mf9.'+'.$mf8.'+'.$mf6.'+'.$mf4;
$mf10986 = $mf10.'+'.$mf9.'+'.$mf8.'+'.$mf6;
$mf109854 = $mf10.'+'.$mf9.'+'.$mf8.'+'.$mf5.'+'.$mf4;
$mf10985 = $mf10.'+'.$mf9.'+'.$mf8.'+'.$mf5;
$mf10984 = $mf10.'+'.$mf9.'+'.$mf8.'+'.$mf4;
$mf1098 = $mf10.'+'.$mf9.'+'.$mf8;
```

```
$mf1097654 = $mf10.'+'.$mf9.'+'.$mf7.'+'.$mf6.'+'.$mf5.'+'.$mf4;
$mf109765 = $mf10.'+'.$mf9.'+'.$mf7.'+'.$mf6.'+'.$mf5;
$mf109764 = $mf10.'+'.$mf9.'+'.$mf7.'+'.$mf6.'+'.$mf4;
$mf10976 = $mf10.'+'.$mf9.'+'.$mf7.'+'.$mf6;
$mf109754 = $mf10.'+'.$mf9.'+'.$mf7.'+'.$mf5.'+'.$mf4;
$mf10975 = $mf10.'+'.$mf9.'+'.$mf7.'+'.$mf5;
$mf10974 = $mf10.'+'.$mf9.'+'.$mf7.'+'.$mf4;
$mf1097 = $mf10.'+'.$mf9.'+'.$mf7;

$mf109654 = $mf10.'+'.$mf9.'+'.$mf6.'+'.$mf5.'+'.$mf4;
$mf10965 = $mf10.'+'.$mf9.'+'.$mf6.'+'.$mf5;
$mf10964 = $mf10.'+'.$mf9.'+'.$mf6.'+'.$mf4;
$mf1096 = $mf10.'+'.$mf9.'+'.$mf6;
$mf10954 = $mf10.'+'.$mf9.'+'.$mf5.'+'.$mf4;
$mf1095 = $mf10.'+'.$mf9.'+'.$mf5;
$mf1094 = $mf10.'+'.$mf9.'+'.$mf4;
$mf109 = $mf10.'+'.$mf9;

$mf1087654 = $mf10.'+'.$mf8.'+'.$mf7.'+'.$mf6.'+'.$mf5.'+'.$mf4;
$mf108765 = $mf10.'+'.$mf8.'+'.$mf7.'+'.$mf6.'+'.$mf5;
$mf108764 = $mf10.'+'.$mf8.'+'.$mf7.'+'.$mf6.'+'.$mf4;
$mf10876 = $mf10.'+'.$mf8.'+'.$mf7.'+'.$mf6;
$mf108754 = $mf10.'+'.$mf8.'+'.$mf7.'+'.$mf5.'+'.$mf4;
$mf10875 = $mf10.'+'.$mf8.'+'.$mf7.'+'.$mf5;
$mf10874 = $mf10.'+'.$mf8.'+'.$mf7.'+'.$mf4;
$mf1087 = $mf10.'+'.$mf8.'+'.$mf7;

$mf108654 = $mf10.'+'.$mf8.'+'.$mf6.'+'.$mf5.'+'.$mf4;
$mf10865 = $mf10.'+'.$mf8.'+'.$mf6.'+'.$mf5;
$mf10864 = $mf10.'+'.$mf8.'+'.$mf6.'+'.$mf4;
$mf1086 = $mf10.'+'.$mf8.'+'.$mf6;
$mf10854 = $mf10.'+'.$mf8.'+'.$mf5.'+'.$mf4;
$mf1085 = $mf10.'+'.$mf8.'+'.$mf5;
$mf1084 = $mf10.'+'.$mf8.'+'.$mf4;
$mf108 = $mf10.'+'.$mf8;

$mf107654 = $mf10.'+'.$mf7.'+'.$mf6.'+'.$mf5.'+'.$mf4;
$mf10765 = $mf10.'+'.$mf7.'+'.$mf6.'+'.$mf5;
$mf10764 = $mf10.'+'.$mf7.'+'.$mf6.'+'.$mf4;
$mf1076 = $mf10.'+'.$mf7.'+'.$mf6;
$mf10754 = $mf10.'+'.$mf7.'+'.$mf5.'+'.$mf4;
$mf1075 = $mf10.'+'.$mf7.'+'.$mf5;
$mf1074 = $mf10.'+'.$mf7.'+'.$mf4;
$mf107 = $mf10.'+'.$mf7;
```

```
$mf10654 = $mf10.'+'.$mf6.'+'.$mf5.'+'.$mf4;
$mf1065 = $mf10.'+'.$mf6.'+'.$mf5;
$mf1064 = $mf10.'+'.$mf6.'+'.$mf4;
$mf106 = $mf10.'+'.$mf6;
$mf1054 = $mf10.'+'.$mf5.'+'.$mf4;
$mf105 = $mf10.'+'.$mf5;
$mf104 = $mf10.'+'.$mf4;

$mf987654 = $mf9.'+'.$mf8.'+'.$mf7.'+'.$mf6.'+'.$mf5.'+'.$mf4;
$mf98765 = $mf9.'+'.$mf8.'+'.$mf7.'+'.$mf6.'+'.$mf5;
$mf98764 = $mf9.'+'.$mf8.'+'.$mf7.'+'.$mf6.'+'.$mf4;
$mf9876 = $mf9.'+'.$mf8.'+'.$mf7.'+'.$mf6;
$mf98754 = $mf9.'+'.$mf8.'+'.$mf7.'+'.$mf5.'+'.$mf4;
$mf9875 = $mf9.'+'.$mf8.'+'.$mf7.'+'.$mf5;
$mf9874 = $mf9.'+'.$mf8.'+'.$mf7.'+'.$mf4;
$mf987 = $mf9.'+'.$mf8.'+'.$mf7;

$mf98654 = $mf9.'+'.$mf8.'+'.$mf6.'+'.$mf5.'+'.$mf4;
$mf9865 = $mf9.'+'.$mf8.'+'.$mf6.'+'.$mf5;
$mf9864 = $mf9.'+'.$mf8.'+'.$mf6.'+'.$mf4;
$mf986 = $mf9.'+'.$mf8.'+'.$mf6;
$mf9854 = $mf9.'+'.$mf8.'+'.$mf5.'+'.$mf4;
$mf985 = $mf9.'+'.$mf8.'+'.$mf5;
$mf984 = $mf9.'+'.$mf8.'+'.$mf4;
$mf98 = $mf9.'+'.$mf8;

$mf97654 = $mf9.'+'.$mf7.'+'.$mf6.'+'.$mf5.'+'.$mf4;
$mf9765 = $mf9.'+'.$mf7.'+'.$mf6.'+'.$mf5;
$mf9764 = $mf9.'+'.$mf7.'+'.$mf6.'+'.$mf4;
$mf976 = $mf9.'+'.$mf7.'+'.$mf6;
$mf9754 = $mf9.'+'.$mf7.'+'.$mf5.'+'.$mf4;
$mf975 = $mf9.'+'.$mf7.'+'.$mf5;
$mf974 = $mf9.'+'.$mf7.'+'.$mf4;
$mf97 = $mf9.'+'.$mf7;

$mf9654 = $mf9.'+'.$mf6.'+'.$mf5.'+'.$mf4;
$mf965 = $mf9.'+'.$mf6.'+'.$mf5;
$mf964 = $mf9.'+'.$mf6.'+'.$mf4;
$mf96 = $mf9.'+'.$mf6;
$mf954 = $mf9.'+'.$mf5.'+'.$mf4;
$mf95 = $mf9.'+'.$mf5;
$mf94 = $mf9.'+'.$mf4;

$mf87654 = $mf8.'+'.$mf7.'+'.$mf6.'+'.$mf5.'+'.$mf4;
$mf8765 = $mf8.'+'.$mf7.'+'.$mf6.'+'.$mf5;
```

```
$mf8764 = $mf8.'+'.$mf7.'+'.$mf6.'+'.$mf4;
$mf876 = $mf8.'+'.$mf7.'+'.$mf6;
$mf8754 = $mf8.'+'.$mf7.'+'.$mf5.'+'.$mf4;
$mf875 = $mf8.'+'.$mf7.'+'.$mf5;
$mf874 = $mf8.'+'.$mf7.'+'.$mf4;
$mf87 = $mf8.'+'.$mf7;

$mf8654 = $mf8.'+'.$mf6.'+'.$mf5.'+'.$mf4;
$mf865 = $mf8.'+'.$mf6.'+'.$mf5;
$mf864 = $mf8.'+'.$mf6.'+'.$mf4;
$mf86 = $mf8.'+'.$mf6;
$mf854 = $mf8.'+'.$mf5.'+'.$mf4;
$mf85 = $mf8.'+'.$mf5;
$mf84 = $mf8.'+'.$mf4;

$mf7654 = $mf7.'+'.$mf6.'+'.$mf5.'+'.$mf4;
$mf765 = $mf7.'+'.$mf6.'+'.$mf5;
$mf764 = $mf7.'+'.$mf6.'+'.$mf4;
$mf76 = $mf7.'+'.$mf6;
$mf754 = $mf7.'+'.$mf5.'+'.$mf4;
$mf75 = $mf7.'+'.$mf5;
$mf74 = $mf7.'+'.$mf4;

$mf654 = $mf6.'+'.$mf5.'+'.$mf4;
$mf65 = $mf6.'+'.$mf5;
$mf64 = $mf6.'+'.$mf4;

$mf54 = $mf5.'+'.$mf4;

}
_____
sub n_possible_globs
{
my ($n,$r) = @_;
my $m = 0;
my $k;

for ($k=1;$k<=$r;$k++)
    {
    $m += &combinatorial_choose($n,$k);
    }
return $m;
}
_____
```

```perl
sub combinatorial_choose
{
my ($n,$k) = @_;
my ($result,$j) = (1, 1);
return 0 if $k > $n || $k<0;
$k = ($n-$k) if ($n-$k) < $k;

while ($j <= $k)
    {
    $result *= $n--;
    $result /= $j++;
    }
return $result;
}
_____
sub shuffle
{
my ($i,$j,$k);
for ($i=0;$i<=$#state;$i++)
    {
    $randvalue = int rand ($i+1);
    $randsum += $randvalue;
    $j = $randvalue;
    $randgenerations++;
    next if $i == $j;
    $k = $state[$i];
    $state[$i] = $state[$j];
    $state[$j] = $k;
    }
}
_____
sub commands
{
my ($i,$j);
&defaults;
$keepcom = '';

open COMFILE, "<$comfile" || die "ERROR BAD XML Cannot open command file";

while (!eof COMFILE)
    {
    $com = '';
    $com = <COMFILE> while $com !~ m/[A-Za-z]/ && !eof COMFILE;
```

```
            print
"_____\n";

print "$com";
        chop $com;

next if $com eq '' || $com =~ m/^ *#/ || $com =~ m/^ *comment/;

#special "interest command" format
    $com =~ s/interesting +OR/interesting=OR/gs;
    $com =~ s/interesting +AND/interesting=AND/gs;
    $com =~ s/interesting +([0-9]*)/interesting=$1/gs;
    $com =~ s/uninteresting +OR/uninteresting=OR/gs;
    $com =~ s/uninteresting +AND/uninteresting=AND/gs;
    $com =~ s/uninteresting +([0-9]*)/uninteresting=$1/gs;

@compart = split '=',$com;

$compart[1] =~ s/^ *//gs;
    $compart[1] =~ s/ *$//gs;
    if ($compart[0] =~ m/delimit record/igs)
            {
    print "Define what constitutes a record.\n";
    print "Entering a number e.g 10 means take 10 characters as a record\n";
    print
    "unless you enter more for items, whence it is the number of items.\n";
    print "Entering separator between records. Default is 'newline'.\n";

$endofrecord = $compart[1];
            $endofrecord = "\n"
                if $endofrecord eq '\n' || $endofrecord eq '';

$endofrecord *= $is
                if $endofrecord>0 && $endofrecord < 2*$is;
            print "Record delimeter is set as $compart[1]\n";
            } elsif ($compart[0] =~ m/delimit line/igs)
            {
    print "Define a line is a multi-line record.\n";
    print "Entering a regular expression.\n";
            $endofline = $compart[1];
            $endofline = "\n"
                if $endofline eq '\n' || $endofline eq '';
            print
```

```perl
            "Lines on multiline records are separated by $compart[1]\n";
        } elsif ($compart[0] =~ m/delimit item/igs)
        { print "Define what constitutes an item in a record.\n";
print "Entering a number e.g 2 means take 2 characters as an item.\n";
print
"Entering separator between items per record. Default is comma ','.\n";
print
"Delimit item=,OR\\t or \\tOR, means use commas OR tabulations.\n";
print
"Delimit item=3wsOR\\t or \\tOR3s means use 3 white spaces OR tabulations,\n";
print
"any number may be used. Runs of spaces of at least this, become delimter.\n";
print
"delimit item=<tag>item</tag> extracts item as 'tag:=item'.\n";
print
"Tags can have full xml form. It is the tag name that becomes metadata.\n";
        $endofitem = $compart[1];
        $tagmode = 'on' if $endofitem eq '<tag>item</tag>';
        $endofitem = "," if $endofitem eq '<tag>item</tag>';
        $endofitem = "\t" if $endofitem eq '\t';
        $endofitem = "\n" if $endofitem eq '\n';
        $endofitem = ',' if $endofitem eq '';
        $endofitem = '1' if $endofitem eq '' && $endofline > 0;
        if ($endofitem eq ',OR\t' || $endofitem eq '\tOR,'
        || $endofitem =~ m/wsOR\\t/ || $endofitem =~ m/\tORws/)

{
                $mixdelimmode='on';
                $wsmode = $endofitem;
                $wsmode =~ tr/0-9//cd;
                $wsmode = 0 if $wsmode <= 0;
                $endofitem = ',';
                }
        $endofline *= $endofitem if $endofline>0 && $endofline < 2*$endofitem;
        print "Mixed delimiter mode is $mixdelimmode\n";
        if ($wsmode >0)
                {
                print
            "At least $wsmode whites spaces are used as delimiter.\n"
                }
            else
```

```
            {
            print "Whitespace delimiter is switched off.\n";
            }
     } elsif ($compart[0] =~ m/shift item/igs)
            {
print
"If items are defined by N characters,frameshift to get all N combinations.\n";

$shift = 1 if $compart[1] =~ m/on/;
            print "Item frameshift is set as $shift (1 = on)\n";
            } elsif ($compart[0] =~ m/first line metadata/igs)
            {
print
"Read first line as metadata and apply to all data.\n";
print
"The data should be rectangular (all lines equal content and  length)\n";

$metadata = 1 if $compart[1] =~ m/on/;
            print "Metadata is set as $metadata (1 = on)\n";
            } elsif ($compart[0] =~ m/divide all data by n/igs)
            {
print
"Divide numbers by value and keep integer part\n";

$divide = $compart[1] if $compart[1] !~ m/off/;
            print "Numbers to be reduced by $divide\n";
            } elsif ($compart[0] =~ m/ignore unknown/igs)
            {
            print "Ignore unknown entries.\n";
            print "If ignore unknown is not set to 'off'",
              "#UNKNOWN# is assummed to mean an unknown.\n";
            $unknown = '#UNKNOWN#' if $unknown eq "off" || $unknown eq ";
            $unknown = $compart[1] if $compart[1] !~ m/off/;
            print "Unknown entries are indicated by '$unknown'\n";
```

```
        } elsif ($compart[0] =~ m/columns/igs)
        {
print
"Entering column numbers & qualifiers for columns to be treated as ",
"spreadsheet.\nSeparate number and qualifier (title of column) by ':'.\n",
"For example, columns=6:age=7:weight =8:blood presure \n",
"If the name part is ommitted, only the item number is used.\n";
        if (!($compart[1] =~ m/off/))
            {
            $metadata =1;
            for ($j=1;$j<=$#compart;$j++)
                {
                print "Entering column number $j, column name";

$_ = $compart[$j];
                last if !($_ =~ m/[0-9]/);
                @ranges = (split ':',$_);
                $colnumber[$j] = $ranges[0];
                $colname[$j] = $ranges[1];
                print "Accepted range $colnumber[$j], $colname[$j]\n";
                }
            }
        } elsif ($compart[0] =~ m/^interesting/igs)
        {
print
"Entering items which must occur in pairs or triplets etc to be examined.\n";
print "Only the OR case is available for fuzzy triplets (for efficiency)\n";
print "interesting=OR=.. means just one item must occur .\n";
print "interesting=3=.. means exactly 3 items must occur .\n";
print "interesting=AND=.. means all items must occur .\n";
print "Focussing on ";
        $condition = '';
        if (!($compart[1] =~ m/off/))
            {
            $logicquery = 'or';
            $logicquery = 'and' if $compart[1] =~ m/^AND$/;
            $logicquery = $compart[1] if $compart[1] >0;
```

```perl
            for ($j=2;$j<=$#compart;$j++)
                {
                $interesting[$j-1] = $compart[$j];
                print $j-1,":'$interesting[$j-1]' ";
                $condition .= "$logicquery $interesting[$j] ";
                } print " with $logicquery logic\n";
            $condition =~ s/^(and|or)/CONDITIONAL ON/;
            }

} elsif ($compart[0] =~ m/^uninteresting/igs)
            {
print
"Ignore items occurring in pairs, triplets etc.\n";
print "Only the OR case is available for fuzzy triplets (for efficiency)\n";
print "ignore=OR=.. means just one item must occur .\n";
print "ignore=3=.. means exactly 3 items must occur .\n";
print "ignore=AND=.. means all items must occur .\n";
print "Ignoring on ";
            $igncondition = '';
            if (!($compart[1] =~ m/off/))
                {
                $ignlogicquery = 'or';
                $ignlogicquery = 'and' if $compart[1] =~ m/^AND$/;
                $ignlogicquery = $compart[1] if $compart[1] >0;

for ($j=2;$j<=$#compart;$j++)
                    {
                    $uninteresting[$j-1] = $compart[$j];
                    print $j-1,":'$uninteresting[$j-1]' ";
                    $igncondition .= "$ignlogicquery $uninteresting[$j] ";
                    } print " with $ignlogicquery logic\n";
                $igncondition =~ s/^(and|or)/CONDITIONAL ON/;
                }
            }
    elsif ($compart[0] =~ m/^noncovariant/igs)
            {
print
"Ignore items matching expression, in covariance study only.\n";
            if (!($compart[1] =~ m/off/))
```

```
            {
            for ($j=1;$j<=$#compart;$j++)
                {
                $uninterestingcov[$j] = $compart[$j];
                print $j,":'$uninterestingcov[$j]' ";
                }
            print " neglected in multivariance study.\n";
            }
        } elsif ($compart[0] =~ m/maximum number of item types/igs)
        { print "Largest number (of most frequent states) of interest.\n";
print "Entering number (10 or more) of top states to use (default 10000).\n";
        if (!($compart[1] =~ m/off/))
            {
            $maxnstates=$compart[1];
            $maxnstates = 10 if $maxnstates < 10;
            }
            print "Set for $maxnstates states\n";

} elsif ($compart[0] =~ m/maximum number of items per event/igs)
        { print "Largest number of states per event.\n";
print "Entering maximum number states per record (default 10).\n";
        if (!($compart[1] =~ m/off/))
            {
            $maxnestates=$compart[1];
            $maxnestates = 2 if $maxnestates < 2;
            }
            print "Set for $maxnestates states\n";
        } elsif ($compart[0] =~ m/maximum items per record sample/igs)
        { print "Largest number of states per record (before splitting).\n";
print "If records are short and number of records small, enter e.g. 10\n";
print "so that records <=10 items in length_are not cut.\n";
print "A value of 6 is recommended for good sampling for typical problems.\n";
print "Values above 10 require considerable memory and computation time.\n";
```

```perl
print "Cutting without lots of data generates false high negatives.\n";
print "Entering cut size of record (default 6)\n";
        if (!($compart[1] =~ m/off/))
            {
            $nrecitems=$compart[1];
            $nrecitems = 2 if $nrecitems<2;
            }
            print "Record length is set for $nrecitems items\n";
        } elsif ($compart[0] =~ m/shift record/igs)
        {
        $sampleshift = 1 if $compart[1] =~ m/on/;
print "If record is split, generate every frameshifted set of items.\n";
print "All combinations are represented, but overcounted.\n";
        print "Record frameshift is set as $sampleshift (1 = on)\n";

} elsif ($compart[0] =~ m/minimum frequency/igs)
        { print "Smallest number-of-occurrences to consider for any event.\n";
print
"If this is > 1, some rare but interesting conjoint events are not counted\n";
print "and negative associations are quanititively overestimated.\n";
print "Entering minimum number of observations per item (default 1).\n";
        if (!($compart[1] =~ m/off/))
            {
            $minimal=$compart[1];
            $minimal = 1 if $minimal <1;
            }
            print "Minimal frequency of events set as $minimal\n";

} elsif ($compart[0] =~ m/maximum sparse frequency/igs)
        { print "Largest number-of-occurrences to consider for negative correlations.\n";
print "Entering minimum number of observations per item (default 1).\n";
```

```perl
        if (!($compart[1] =~ m/off/))
            {
            $negmaximal = $compart[1];
            $negmaximal = 0 if $negmaximal =~ 'off';
            }
        print
        "Maximal low frequency of sparse events set as $negmaximal\n";

} elsif ($compart[0] =~ m/report scores above nats/igs)
        { print "Report information values (scores) above a specified upper threshold.\n";
        if (!($compart[1] =~ m/off/))
            {
            $zposchop=$compart[1];
            }
        print "Upper threshold value is set as $zposchop\n";

} elsif ($compart[0] =~ m/report scores below nats/igs)
        { print "Report information values (scores) below a specified lower threshold.\n";
        if (!($compart[1] =~ m/off/))
            {
            $znegchop=$compart[1];
            }
        print "Lower threshold value is set as $znegchop\n";

} elsif ($compart[0] =~ m/set Riemann zeta s/igs)
        { print
"set the Riemann zeta function s parameter to a real number (default s=1).\n";
        if (!($compart[1] =~ m/off/))
            {
            $zetas=$compart[1];
            if (!($compart[1] =~ m/off/))
                {
```

```
            $zetas=$compart[1];
            }

}
    print "The parameter value is set as $zetas\n";

} elsif ($compart[0] =~ m/skip lines matching/igs)
        {
        $comment = $compart[1];
        print "Records to skip match Regular Expression $comment\n";
        } elsif ($compart[0] =~ m/lines to skip after matches/igs)
        {
        $skiplines = $compart[1];
        print
"$skiplines lines are skipped after record matching $comment\n";
        } elsif ($compart[0] =~ m/read lines matching/igs)
        {
        $usewith = $compart[1];
        print "Lines to use match Regular Expression $usewith\n";
        } elsif ($compart[0] =~ m/input file/igs)
        {
        $datafile = $compart[1];
        $datafile = $ARGV[0] if $ARGV[0] ne ";
        print
"Input file is $datafile\n";
        } elsif ($compart[0] =~ m/run test/igs)
        {
        $test = $compart[1];
        $test = "on" if !($test =~ m/off/igs);
        print
"Test is $test\n";
        } elsif ($compart[0] =~ m/advanced mode/igs)
```

```
{
$advanced = $compart[1];
$advanced = "on" if !($advanced =~ m/off/igs);
print
"Advanced mode is $advanced\n";
} elsif ($compart[0] =~ m/associations/igs)
    {
    $associations = $compart[1];
    $associations = "on" if !($associations =~ m/off/igs);
    print
    "Associations are $associations\n";
    } elsif ($compart[0] =~ m/fuzzy/igs)
    {
    $fuzzy = $compart[1];
    $density = $fuzzy if $fuzzy >0;
    $density = 1 if $density >=1 || $fuzzy eq 'on';
    $fuzzy = "on" if !($fuzzy =~ m/off/igs);
    print
    "Fuzzy correlation-based counting is $fuzzy\n";
    } elsif ($compart[0] =~ m/unseen/igs)
    {
    $unseen = $compart[1];
    $unseen = "on" if !($unseen =~ m/off/igs);
    print
    "Treating unseen events is $unseen\n";
    } elsif ($compart[0] =~ m/simplets/igs || $compart[0] =~ m/pairs/igs)
    {
    $simplets = $compart[1];
    $simplets = "on" if !($simplets =~ m/off/igs);
    print
    "Simplets (pairs only in 2002 Version) counting is $simplets\n";
    } elsif ($compart[0] =~ m/high dimensional covariance/igs || $compart[0] =~ m/pairs/igs)
    {
    $convergence = 0;
```

```
        $covariance = $compart[1];
        $covariance =~ s/%//gs;
        $convergence = $covariance/100 if $covariance>0;
        $covariance = "on" if !($covariance =~ m/off/igs);
        $iterations = $compart[2];
        $iterations = 100 if $iterations <1;
        print
        "High dimensional covariance testing is $covariance\n";
        print
        " with convergence = $convergence iterations=$iterations\n"
         if $covariance eq 'on';
        } elsif ($com =~ m/result must match/igs)
        {
        $query = $com;
        $query =~ s/^[^=]*=(.*)$/$1/;
        $query = '.' if $query =~ m/^off/igs;
        print
        "Results reported must match \'$query\'\n";
        } elsif ($compart[0] =~ m/screen check/igs)
        {
        $screencheck = $compart[1];
        $screencheck = "on" if !($screencheck =~ m/off/igs);
        print
        "Screen check is $screencheck\n";
        } elsif ($compart[0] =~ m/allow duplicates/igs)
        {
        $duplicates = $compart[1];
        $duplicates = "off" if !($duplicates =~ m/on/igs);
        print
        "Permission for duplicates is switched $duplicates\n";
        } elsif ($compart[0] =~ m/pause/igs)
        {
        print "OK?";
        $a = <STDIN>;
        exit if substr($a,0,1) eq 'n';
        }
    else
```

```
        {
            die "ERROR BAD XML Command \'$com\' not recognized";
        }

<STDIN> if $screencheck eq "on";
    } if ($nrecitems > 3 and $duplicates eq 'on')
    {
print PRIMEGLOBFILE
"
<fano:error type=\"command\">
Duplicates mode=$duplicates not allowed when items per record.
 Sample $nrecitems > 3. 3 is the preferred record sample for this mode.
Terminated
</fano:error>
</fano:results>
</fano:job>
</fano:output>
";
die
"Duplicates mode=$duplicates not allowed when items per record
 Sample $nrecitems > 3. 3 is the preferred record sample for this mode.
Terminated";
    } if ($maxnestates > $nrecitems)
    {
print PRIMEGLOBFILE
"
<fano:error type=\"command\">
Assigned number of items per event $maxnestates exceeds number of items
per record sample $nrecitems. This does not make much sense. Terminated
</fano:error>
</fano:results>
</fano:job>
</fano:output>
";
die
"Assigned number of items per event $maxnestates exceeds number of items
per record sample $nrecitems. This does not make much sense. Terminated"
    } if ($advanced eq 'off' && $maxnestates > 10)
    {
```

```
print PRIMEGLOBFILE
"
<fano:error type=\"command\">
Advanced mode should be on if items per event exceeds 10. Terminated.
</fano:error>
</fano:results>
</fano:job>
</fano:output>
";
die
"Advanced mode should be on if items per event exceeds 10. Terminated."
    }
close COMFILE;
}
_____
sub defaults
{

$datafile = "input.dat";
$datafile = $ARGV[0] if $ARGV[0] ne '';
$endofline = '';
$endofrecord = "\n";
$endofitem = ",";

$maxnstates = 10000;
$maxnestates = 10;

$nrecitems = 10;

undef @ranges;

$shift = 0;

$zetas = 1;

$sampleshift = 0;

$minimal = 1;
$negmaximal = 0;

$comment = '^#';

$usewith = '.';

$skiplines = 0;
```

```
$screencheck = "off";

$metadata = 0;

$unknown = "#UNKNOWN#";

$query = '.';
$condition = '';
$igcondition = '';

$zposchop = 1;
$znegchop = -1;
$test = 'off';
$associations = 'on';
$fuzzy = 'on';
$density = 1;
$simplets = 'on';
$advanced = 'off';
$duplicates = 'off';
$mixdelimmode='off';
$wsmode = 0;
$tagmode = 'off';
$convergence = 0.00001;# not entered as a % (100 tikmes this) in command fi
$iterations = 100;
$covariance = 'off';
}
_____
sub create_unseen
{
my @order;
for ($i=0;$i<=$hotstates;$i++) #extract working statecodes
    {
    $_ = $statecode{$statelist[$i]};
    s/\+//gs;
    $order[$i] = $_;
    }
@order = sort {$b <=> $a} @order;

$a=0;$b=0;$c=0;$d=0;$e=0;$f=0;$g=0;$h=0;$i=0;$j=0;$k=0;$l=0;$m=0;
$n=0;$o=0;$p=0;$q=0;$r=0;$s=0;$t=0;$u=0;$v=0;$w=0;$x=0;$y=0,$z=0;

for ($i=0;$i<=$hotstates;$i++) #extract working statecodes
    {
    $order[$i] = $order[$i].'+';
```

} print "Testing zero incidences for events containing ",@order,"\n";
order reduced list to satisfy $max = $hotstates;
$max = $maxlengthrec if $max > $maxlengthrec;
$max = $maxnestates if $max > $maxnestates ;

print "The maximum ideally for ",$reducedstatelist+1,
" states (for max record length $maxlengthrec) is $max-plets\n";

Explicitly assign zeros
for ($a=0;$a<=$hotstates;$a++) #do all pairs to get negatives
{

$pa = '+'.$order[$a];

for ($b=0;$b<$a;$b++)
{

$pb = $pa . $order[$b];
$_ = $pb; &unseen_case;
next if $max <=2;

for ($c=0;$c<$b;$c++)
{
$pc = $pb . $order[$c];
$_ = $pc; &unseen_case;
next if $max <=3;

for ($d=0;$d<$c;$d++)
{
$pd = $pc . $order[$d];
$_ = $pd; &unseen_case;
next if $max <=4;

for ($e=0;$e<$d;$e++)
{
$pe = $pd . $order[$e];

```
$_ = $pe; &unseen_case;
#print
#"Zeroing $a $b $c $d $e...of $max. ",
#"$statelist[$a] $statelist[$b] $statelist[$c]...\n";

next if $max <=5;

for ($f=0;$f<$e;$f++)
{
$pf = $pe . $order[$f];
$_ = $pf; &unseen_case;
next if $max <=6;

for ($g=0;$g<$f;$g++)
{
$pg = $pf . $order[$g];
$_ = $pg; &unseen_case;
next if $max <=7;

for ($h=0;$h<$g;$h++)
{
$ph = $pg . $order[$h];
$_ = $ph; &unseen_case;

next if $max <=8;

for ($i=0;$i<$h;$i++)
{
$pi = $ph . $order[$i];
$_ = $pi; &unseen_case;

next if $max <=9;

for ($j=0;$j<$i;$j++)
{
$pj = $pi . $order[$j];
$_ = $pj; &unseen_case;
next if $max <=10;

for ($k=0;$k<$j;$k++)
{
$pk = $pj . $order[$k];
$_ = $pk; &unseen_case;
next if $max <=11;
```

```
for ($l=0;$l<$k;$l++)
{
$pl = $pk . $order[$l];
$_ = $pl; &unseen_case;
next if $max <=12;

for ($m=0;$m<$l;$m++)
{
$pm = $pl . $order[$m];
$_ = $pm; &unseen_case;
next if $max <=13;

for ($n=0;$n<$m;$n++)
{
$pn = $pm . $order[$n];
$_ = $pn; &unseen_case;
next if $max <=14;

for ($o=0;$o<$n;$o++)
{
$po = $pn . $order[$o];
$_ = $po; &unseen_case;
next if $max <=15;

for ($p=0;$p<$o;$p++)
{
$pp = $po . $order[$p];
$_ = $pp; &unseen_case;
next if $max <=16;

for ($q=0;$q<$p;$q++)
{
$pq = $pp . $order[$q];
$_ = $pq; &unseen_case;
next if $max <=17;

for ($r=0;$r<$q;$r++)
{
$pr = $pq . $order[$r];
$_ = $pr; &unseen_case;
next if $max <=18;

for ($s=0;$s<$r;$s++)
{
$ps = $pr . $order[$s];
```

```
$_ = $ps; &unseen_case;
next if $max <=19;

for ($t=0;$t<$s;$t++)
{
$pt = $ps . $order[$t];
$_ = $pt; &unseen_case;
next if $max <=20;

for ($u=0;$u<$t;$u++)
{
$pu = $pt . $order[$u];
$_ = $pu; &unseen_case;
next if $max <=21;

for ($v=0;$v<$u;$v++)
{
$pv = $pu . $order[$v];
$_ = $pv; &unseen_case;
next if $max <=22;

for ($w=0;$w<$v;$w++)
{
$pw = $pv . $order[$w];
$_ = $pw; &unseen_case;
next if $max <=23;

for ($x=0;$x<$q;$x++)
{
$px = $pw . $order[$x];
$_ = $px; &unseen_case;
next if $max <=24;

for ($y=0;$y<$x;$y++)
{
$py = $px . $order[$y];
$_ = $py; &unseen_case;
next if $max <=25;

for ($z=0;$z<$y;$z++)
{
$pz = $py . $order[$z];
$_ = $pz; &unseen_case;
```

```perl
}}}}}}}}}}}}}}}}}}}}}}}}
#this line can be used with a goto loop exit to reduce time.
sadly_no_supercomputer:
}}}

}
_____
sub precount
{
$logof2 = log(2);
open DATAFILE, "<$datafile" || die "ERROR BAD XML Cannot open file $datafile";

$readmode = 1;

# undef (@n, @sumv, @sumv2);# some Perl compilers don't like this as list
undef @n;
undef @sumv;
undef @sumv2;

my $start = 0;
$ntot=0;
$start = 0;
$record = -1;
$sample = 0;
$itemsgot = 0;

print "\nPrecounting content of records:\n";
print PRIMEGLOBFILE
    "<fano:processing file=\"$datafile\" type =\"record\" extract=\"first 4 records\">\n";

$maxlengthrec = 0;
$ii = -1;
$maxstatei = -1;
while () # read statelist as globs of events line by line
    # First read establishes codes for items. It is done same way as
    # main read operation so that count of single events correspnds
    # to that for concurrent (conjoint) events.

{

$list = '';
```

```
if ($start == 0 || $ii >= $#state)
    {
    if (eof DATAFILE)
        {
        print
"End of file called '$datafile' on record number $record.\n";
print "Requested file name error.\n" if $filedata eq '';
        if ($record <0)
            {
            print
        "WARNING: File called \"$filedata\" is empty.\n";
            print
    "Check command in format 'file name=FILENAME' exists\n";
            }
        last;
        }
    $record++;
    &read_state;
    $maxlengthrec = $#state if $maxlengthrec < $#state;

if ($record<4)
        {
        print PRIMEGLOBFILE
"<fano:record number=\"$record\">$rec</fano:record>\n";
        } next if $associations ne 'on';
    $sample = 0;
    $itemsgot = 0;
    $start = 0;
    $ii = -1;

next if $metadata >0 && $record <1;

}
else
    {
    $sample++;
    if ($sampleshift >1)
        {
        $ii = $itemsgot - 1;
        }
    else
        {
        $ii = $start - 1;
```

```
                }
            }

$items = 0;
        for ($i=$start;$i<=$#state;$i++)
            {
            $ii++;
            $items++;
            $ntot++;

#build list 'statelist' of statelist seen
            if (!(exists $statecode{$state[$ii]}))
                        #Doesn't exist? Create it
                {
                $statelist[$count]=$state[$ii] ;
                $statecode{$state[$ii]} = Math::BigInt
                    ->new($prime[$count]);
                $count++;
                $maxstatei = $count
                    if $maxstatei < $prime[$count];
                }
            $counts{$state[$ii]}++;

if ($items >= $nrecitems)
                {
                $items=0;
                if ($sampleshift>0 && $ii < $#state)
                    {
                    $start = $sample + 1;
                    last;
                    }
                else
                    {
                    $start = $i + 1;
                    last;
                    }

}
            }

}
    $original_statelist = $#statelist;
```

```
print "Abundances and state assignments:\n";

for ($i=0;$i<=$#statelist;$i++)
    {
    $statelist[$i] = $counts{$statelist[$i]}.' x '.$statelist[$i];
    } undef %counts;

@statelist = sort {$b <=> $a} @statelist;

for ($i=0;$i<=$#statelist;$i++)
    {
    $statelist[$i] =~ s/\n//;
    print $statelist[$i];
    $s = $statelist[$i];
    $s =~ s/ x .*//gs;
    $statelist[$i] =~ s/^.* x //;
    $counts{$statelist[$i]} = $s;
    delete $statecode{$statelist[$i]};
    $statecode{$statelist[$i]} = Math::BigInt
            ->new($prime[$i]);
    print " $statecode{$statelist[$i]}\n";
    } if ($associations eq 'on')
{
    if ($ntot <1)
        { print PRIMEGLOBFILE <<END5;
<fano:ranking setting="heavy duty">
<fano:possible_error type="input processing in precount">
Number of items processed for associations is zero,
 Check file, file content, and delimiters in file $comfile.
 Check processing of data by editing functions in file $convertfile.
 You did not use interesting/uninteresting specifications, so this was
 not the problem in this case.
</fano:possible_error>
</fano:ranking>
```

```
</fano:processing>
</fano:results>
</fano:job>
</fano:output>
END5
die "Number of items zero.
See output on $xmlfile concering file checks on $comfile and $convertfile.
FANO program alert";
        }

$rntot = 1/$ntot;
$x = $counts{$statelist[0]} * $ntot * $ntot; #prune states not likely to
# give significant expected frequency
for ($i=1;$i<=$#statelist;$i++)
    {
    $x *= $counts{$statelist[$i]} * $rntot;
    print
"$i \'$statelist[$i]\' x $counts{$statelist[$i]} scores ",substr($x,0,4);
    $hotstates = $i;
    last if $x < $minimal;
    print " excede minimal expected frequency of $minimal.\n";
    }
$hotstates++;
print " less than minimal expected frequency.\n";

print "Of ",$#statelist+1," original states ";

$reducedstatelist = $#statelist;
#Throw away events occurring < $minimal.
for ($i=0;$i<=$#statelist;$i++)
    {
    $reducedstatelist = $i if $counts{$statelist[$i]} >= $minimal;
    }
$reducedstatelist++;
print $reducedstatelist,
    " states occur $minimal times or more. Rest discarded.\n";

$reducedstatelist = $maxnstates-1 if $reducedstatelist > $maxnstates-1;

$hotstates = $reducedstatelist if $reducedstatelist < $hotstates
        || !defined $hotstates;
```

```
for ($i=0;$i<=$original_statelist;$i++)
    {
    delete $statecode{$statelist[$i]}
      if $i > $reducedstatelist;
    }

}
print "Processing gathered input:\n";

if ($fuzzy eq 'on')
{
undef @var;
for ($p=0;$p<=$#metastate;$p++)
{
next if ($ndata{$metastate[$p]}<1);

$np = $ndata{$metastate[$p]};
        $pexpectav = $profile{$metastate[$p]} /$np;

$pex = $pexpectav;
        $pex = 0 if $pexpectav>-0.01 && $pexpectav<0.01;
        $pex =~ s/(^[^.]*\...).*/$1/gs;

$psigma = $p2profile{$metastate[$p]}
              + $pexpectav * $pexpectav * $np
              - 2 * $pexpectav * $profile{$metastate[$p]};

die
"ERROR BAD XML psigma=$psigma less than zero  at [$p]" if $psigma<0;

$mp = $metastate[$p];
        $mp =~ s/(^([^(]+)\(%([0-9])*\)/$1/gs;

for ($q=0;$q<$p;$q++)
{
next if ($ndata{$metastate[$q]}<1);

next if $ndata{$metastate[$q]} < 1
        || $metastate[$p] eq $metastate[$q]
```

```
        || !exists $pqprofile{$metastate[$p]}{$metastate[$q]}
        || $pqndata{$metastate[$p]}{$metastate[$q]}<1;

$mq = $metastate[$q];
    $mq =~ s/(^([^(]+)\(%([0-9])*\)/$1/gs;
if ($mq ne " && $profile{$metastate[$q]} =~ m/^([+-])?[0-9]+/)
    {

$nq = $ndata{$metastate[$q]};
    $qexpectav = $profile{$metastate[$q]}/$nq;

$qex = $qexpectav;
    $qex = 0 if $qex>-0.01 && $qex<0.01;
    $qex =~ s/(^[^.]*\...).*/$1/gs;

$qsigma = $p2profile{$metastate[$q]}
            + $qexpectav * $qexpectav * $nq
            - 2 * $qexpectav * $profile{$metastate[$q]};
    die
"ERROR BAD XML qsigma=$qsigma less than zero at [$q]" if $qsigma<0;

$pqn = $pqndata{$metastate[$p]}{$metastate[$q]};

$cov = $pqprofile{$metastate[$p]}{$metastate[$q]}
        - $pexpectav * $profile{$metastate[$q]};
        - $qexpectav * $profile{$metastate[$p]};
        + $pexpectav * $qexpectav * $pqndata;

delete $pqprofile{$metastate[$p]}{$metastate[$q]};
    delete $pqndata{$metastate[$p]}{$metastate[$q]};

adjust \observed average to minimum at zero & make symmetric $div = sqrt($psigma * $qsigma);
    $rdiv = $div>0? 1/$div :0;

#scale covariance to -1...+1
    $rho = $cov * $rdiv;
    if ($rho>1)
        {
```

```
        $rho = $rho/($rho+1);
        }
if ($rho<-1)
        {
        $rho = -$rho/($rho-1);
        }
$rho = ($rho+1)*0.5;

$pfuzzy = $pqn * $rho;
$qfuzzy = $pqn - $pfuzzy;

$z = &zeta($pfuzzy)-&zeta($qfuzzy);
next if !($z>=$zposchop || $z<=$znegchop);

$z = 0 if $z>-0.01 && $z<0.01;

$qex = $qexpectav;
$qex = 0 if $qex>-0.01 && $qex<0.01;
$qex =~ s/(^[^.]*\...).*/$1/gs;

$pfuzzy = 0 if $pfuzzy>-0.01 && $pfuzzy<0.01;
$qfuzzy = 0 if $qfuzzy>-0.01 && $qfuzzy<0.01;
$pfuzzy =~ s/(^.*\...).*/$1/gs;
$qfuzzy =~ s/(^.*\...).*/$1/gs;
$pqn =~ s/(^.*\...).*/$1/gs;

$zz = $z;
        $zz = 0 if $zz>-0.01 && $zz<0.01;
        $zz =~ s/(^[^.]*\...).*/$1/gs;
        $gs = "$mp:=av_$pex $mq:=av_$qex";
        $result[$nthresult++] =
        "$zz=%=$gs <fano:covn events=\"$gs\""
        ." information=\"$zz\""
        ." saw=\"$pfuzzy\" of=\"$pqn\" coded=\"+0+$p$q+\""
        ." incidents=\"all with numeric $mp $mq\"/>";

$truevar[$p] += abs($z);
        $truevar[$q] += abs($z);

for ($r=0;$r<$q;$r++ )#< to include self use =<
    { next if $ndata{$metastate[$r]} < 1
        || $metastate[$p] eq $metastate[$q]
        || $metastate[$q] eq $metastate[$r]
```

```
|| $metastate[$p] eq $metastate[$r]
|| !exists
  $pqrprofile{$metastate[$p]}{$metastate[$q]}{$metastate[$r]}
|| $pqrndata{$metastate[$p]}{$metastate[$q]}{$metastate[$r]}<1;

$mr = $metastate[$r];
  $mr =~ s/(^([^(]+)\(%([0-9])*\)/$1/gs;
if($mr ne " && $profile{$metastate[$r]} =~ m/^([+-])?[0-9]+/)
  {

$nr = $ndata{$metastate[$r]};
  $rexpectav = $profile{$metastate[$r]}/$nr;
  $rex = $rexpectav;
  $rex = 0 if $rexpectav>-0.01 && $rexpectav<0.01;
  $rex =~ s/(^[^.]*\...).*/$1/gs;

$rsigma = $p2profile{$metastate[$r]}
         + $rexpectav * $rexpectav * $nr
         - 2 * $rexpectav * $profile{$metastate[$r]};
  die
"ERROR BAD XML rsigma=$rsigma less than zero at [$r]" if $rsigma<0;

$pqrn =
  $pqrndata{$metastate[$p]}{$metastate[$q]}{$metastate[$r]};

$cov =
  $pqrprofile{$metastate[$p]}{$metastate[$q]}{$metastate[$r]}
    - $pexpectav
      * $pqprofile{$metastate[$q]}{$metastate[$r]}
    - $qexpectav
      * $pqprofile{$metastate[$p]}{$metastate[$r]}
    + $qexpectav * $pexpectav
         * $profile{$metastate[$r]}

- $pqprofile{$metastate[$p]}{$metastate[$q]}
         * $rexpectav

+ $pexpectav * $profile{$metastate[$q]}
         * $rexpectav
    + $qexpectav * $profile{$metastate[$p]}
```

```
            * $rexpectav
        - $qexpectav * $pexpectav
            * $rexpectav * $pqrn;
delete
$pqrprofile{$metastate[$p]}{$metastate[$q]}{$metastate[$r]};
delete
$pqrndata{$metastate[$p]}{$metastate[$q]}{$metastate[$r]};

adjust \observed average to minimum at zero & make symmetric $div = sqrt($psigma * $qsigma * $rsigma);
$rdiv = $div>0? 1/$div :0;

#scale covariance to -1...+1
$rho = $cov * $rdiv;
if ($rho>1)
    {
    $rho = $rho/($rho+1);
    }
if ($rho<-1)
    {
    $rho = -$rho/($rho-1);
    }
$rho = ($rho+1)*0.5;

$pfuzzy = $pqrn * $rho;
$qfuzzy = $pqrn - $pfuzzy;

$z = &zeta($pfuzzy)-&zeta($qfuzzy);
next if !($z>=$zposchop || $z<=$znegchop);

$z = 0 if $z>-0.01 && $z<0.01;

$pfuzzy = 0 if $pfuzzy>-0.01 && $pfuzzy<0.01;
$qfuzzy = 0 if $qfuzzy>-0.01 && $qfuzzy<0.01;
$pfuzzy =~ s/(^.*\...).*/$1/gs;
$qfuzzy =~ s/(^.*\...).*/$1/gs;

$pqrn =~ s/(^.*\...).*/$1/gs;
```

```perl
            $zz = Sz;
            $zz = 0 if $zz>-0.01 && $zz<0.01;
            $zz =~ s/(^[^.]*\...).*/$1/gs;
            $gs =
             "$mp:=av_$pex $mq:=av_$qex $mr:=av_$rex";
            $result[$nthresult++] =
            "$zz=%=$gs <fano:covn".
            " events=\"$gs\" information=\"$zz\""
            ." saw=\"$pfuzzy\" of=\"$pqrn\" coded=\"+0+$p$q$r+\""
            ." incidents=\"all with numeric $mp $mq $mr\"/>";

$truevar[$p] += abs($z);
          $truevar[$q] += abs($z);
          $truevar[$r] += abs($z);
          }

}
    }
   }
  }
 }
print PRIMEGLOBFILE "</fano:processing>\n";

undef @profile;
undef @p2profile;
undef @pqprofile;
undef @ndata;
undef @pqndata;
undef %fanotest;
close DATAFILE;
}
_____
sub lowplets
{ my ($i,$k);
my ($k,$kk,$kkk);

for ($i=0;$i<=$#state;$i++)
   {
   if (exists $statecode{$state[$i]})
      {
      if ($#interesting > 0)
         {
         $found = 0;
```

```perl
        for ($jj=1;$jj<=$#interesting;$jj++)
            {
            $found++ if $state[$i] =~ m/$interesting[$jj]/;
            }
        next if $found<1 && ($logicquery eq 'or' || $logicquery ==1);
        }
    if ($#uninteresting > 0)
        {
        $ignfound = 0;
        for ($jj=1;$jj<=$#uninteresting;$jj++)
            {
            $ignfound++ if $state[$i] =~ m/$uninteresting[$jj]/;
            }
        next if $ignfound>0 &&
           ($ignlogicquery eq 'or' || $ignlogicquery ==1);
        } for ($k=0;$k<$i;$k++)
        {
        next if !exists $statecode{$state[$k]};

if ($#interesting > 0 && ($logicquery eq 'and'
         || $logicquery <=$#interesting))
        {
        $found2 = 0;
        for ($jj=1;$jj<=$#interesting;$jj++)
            {
            $found2++ if $state[$k] =~ m/$interesting[$jj]/;
            }
        next if !($found>0 && $found2>0);
        }
    if ($#uninteresting > 0 && ($ignlogicquery eq 'and'
         || $ignlogicquery <=$#interesting))

{
        $ignfound2 = 0;
        for ($jj=1;$jj<=$#uninteresting;$jj++)
            {
            $ignfound2++ if $state[$k] =~ m/$uninteresting[$jj]/;
            }
        next if ($ignfound>0 && $ignfound2>0);
```

```
        } if ($#interesting > 0 && $logicquery eq 'or' || $logicquery ==1)
        {
        $found1 = 0;
        for ($jj=1;$jj<=$#interesting;$jj++)
            {
            $found1++ if $state[$k] =~ m/$interesting[$jj]/;
            }
        next if $found1<1;
        } if ($#uninteresting > 0 && $ignlogicquery eq 'or' || $ignlogicquery ==1)
        {
        $ignfound1 = 0;
        for ($jj=1;$jj<=$#uninteresting;$jj++)
            {
            $ignfound1++ if $state[$k] =~ m/$uninteresting[$jj]/;
            }
        next if $ignfound1>0;
        }

$pairs [$ithpair++] = $statecode{$state[$k]}.
                $statecode{$state[$i]};

#   for ($kk=0;$kk<$k;$kk++)
#       {
#       next if !exists $statecode{$state[$kk]};

#       $triplets[$ithtriplet++]
#           = $statecode{$state[$kk]}.
#             $statecode{$state[$k]}.
$statecode{$state[$i]}.'+';

#       for ($kkk=0;$kkk<$kk;$kkk++)
#           {
#           next if !exists $statecode{$state[$kkk]};

#           $quadruplets[$ithquadruplet++]
#               = $statecode{$state[$kkk]}.
#                 $statecode{$state[$kk]}.
```

```
#       $statecode{$state[$k]}.
$statecode{$state[$i]}.'+';
#       }

}

}
        }
    }
}

_____
sub approximate_primeglob_information
{ if ($associations eq 'on')
{
die "ERROR BAD XML Number of items zero. Failed to find anything interesting?" if $ntot <1;
my $rntot = 1/$ntot;
my $count=0;

print "APPROXIMATING THE INFORMATION FROM THE COUNTS.\n";
print PRIMEGLOBFILE "<fano:ranking setting=\"light duty\">\n";

$nkeys = keys %glob;
$norigkeys = $nkeys;

&create_unseen;

while (($bigkey,$value) = each(%glob))
    {
        delete $glob{$bigkey};
        $nkeys--;

next if ($value > $negmaximal && $value < $minimal);
    $count++;
    print "Event $count left $nkeys $bigkey occurs x $value\n"
       if $count =~ m/000$/;
    $_ = $bigkey;

$gs = '';
    $g = $ntot;
    for ($i=0;$i<=$maxstatei;$i++)
```

```
        {
        undef @o;
        @o = m/\+$prime[$i]\+/gs;

if ($#o >= 0) #if an element
                {
                $g *= $counts{$statelist[$i]} * $rntot;

$gs .= $statelist[$i].' ';
                $generations++;

}
        }

$ig = $g;
$ig =~ s/(^.*\...).*/$1/gs;

$z = &zeta($value) - &zeta($g);

next if !($z>=$zposchop || $z<=$znegchop);

&extract_associated_numeric_states;

$zz = $z;
        $zz = 0 if $zz>-0.01 && $zz<0.01;
        $zz =~ s/(^[^.]*\...).*/$1/gs;

$result[$nthresult++] =
        "$zz=~=$gs <fano:assn events=\"$gs\""
        ." information=\"$zz\""
        ." saw=\"$value\" expected=\"$ig\" coded=\"$_\""
        ." incidents=\"$incidents{$_}\"/>";

}
} if ($#statelist >=0)
        {
        print "$#statelist states (including first state 0).\n";
        }
else
        {
        print "No states requested.
Associations must be switched off in the command (com) file\n";
        }
```

```perl
@result = sort {$b <=> $a} @result;
for ($i=0;$i<=$#result;$i++)
    {
    if ($result[$i] =~ m/\+[0-9]+\+[0-9]+\+/gs
    && $result[$i] =~ m/$query/)
        {
        $r = $result[$i];
        # $r =~ s/^[0-9\.\- ]*</</;
        $r =~ s/:=</:=</g;
        $r =~ s/:=>/:=>/g;
        print PRIMEGLOBFILE "$r\n";
        }
    }
    $nprunedkeys = keys %glob;

print PRIMEGLOBFILE "</fano:ranking>\n";

}
_____,_____ sub unseen_case
{
my $mtot = 1/$ntot;

return if exists $glob{$_};

$gs = '';
    $g0 = $ntot;
    for ($i=0;$i<=$maxstatei;$i++)
        {
        undef @o;
        @o = m/\+$prime[$i]\+/gs;

if ($#o >= 0) #if an element
            {
            $g0 *= $counts{$statelist[$i]} * $mtot;

$gs .= $statelist[$i].' ';
            $generations++;

}
        }

$ig = $g0;
```

```perl
$ig =~ s/(^.*\...).*/$1/gs;

$z0 = -&zeta($g0);
return if $z0>$znegchop;

s/\+1\+/+/;
        $zz = $z0;

$zz = 0 if $zz>-0.01 && $zz<0.01;
        return if $zz == 0;
        $zz =~ s/(^[^.]*\...).*/$1/gs;
        $result[$nthresult++] =
        "$zz=Z=$gs <fano:assn events=\"$gs\""
        ." information=\"$zz\""
        ." saw=\"0\" expected=\"$ig\" coded=\"$_\""
        ." incidents=\"$incidents{$_}\"/>";

}

sub examtestcovariants
{

$pqrn =
        $pqrndata{$metastate[$p]}{$metastate[$q]}{$metastate[$r]};

return if $pqrn <= 10;#give 10 chances to shape up
        $np = $ndata{$metastate[$p]};
        $nq = $ndata{$metastate[$q]};
        $nr = $ndata{$metastate[$r]};
        $pexpectav = $np>0? $profile{$metastate[$p]} /$np : 0;
        $qexpectav = $nq>0? $profile{$metastate[$q]} /$nq : 0;
        $rexpectav = $nr>0? $profile{$metastate[$r]} /$nr : 0;
        $rex = $rexpectav * $nr;
        $rex = 0 if $rexpectav>-0.01 && $rexpectav<0.01;
        $rex =~ s/(^.*\...).*/$1/gs;

$psigma = $p2profile{$metastate[$p]}
                + $pexpectav * $pexpectav * $np
                - 2 * $pexpectav * $profile{$metastate[$p]};
        die
"ERROR BAD XML psigma=$psigma less than zero at [$p]" if $psigma<0;

$qsigma = $p2profile{$metastate[$q]}
                + $qexpectav * $qexpectav * $nq
```

```
            - 2 * $qexpectav * $profile{$metastate[$q]};
die
"ERROR BAD XML qsigma=$qsigma less than zero at [$q]" if $qsigma<0;

$rsigma = $p2profile{$metastate[$r]}
        + $rexpectav * $rexpectav * $nr
        - 2 * $rexpectav * $profile{$metastate[$r]};
die
"ERROR BAD XML rsigma=$rsigma less than zero at [$r]" if $rsigma<0;

$cov =
$pqrprofile{$metastate[$p]}{$metastate[$q]}{$metastate[$r]}
    - $pexpectav
        * $pqprofile{$metastate[$q]}{$metastate[$r]}
    - $qexpectav
        * $pqprofile{$metastate[$p]}{$metastate[$r]}
    + $qexpectav * $pexpectav
            * $profile{$metastate[$r]}

- $pqprofile{$metastate[$p]}{$metastate[$q]}
            * $rexpectav

+ $pexpectav * $profile{$metastate[$q]}
            * $rexpectav
    + $qexpectav * $profile{$metastate[$p]}
            * $rexpectav
    - $qexpectav * $pexpectav
            * $rexpectav * $pqrn;

$div = sqrt($psigma * $qsigma * $rsigma);
$rdiv = $div>0? 1/$div :0;
$cov *= $rdiv;
if ($cov*$cov < 0.04)
    {
    $pqrhash--;
    delete
$pqrprofile{$metastate[$p]}{$metastate[$q]}{$metastate[$r]};
    delete
$pqrndata{$metastate[$p]}{$metastate[$q]}{$metastate[$r]};
```

```
                }
        }
_____
sub extract_associated_numeric_states
{
                $gs = ' '.$gs;
                while ($gs =~ m/:=(<|>)av/)
                    {
                    #extract metadata
                    # print "1 $gs\n";
                    $sta = $gs;
                    $sta =~ s/^.* ([^ ]+):=(<|>)av.*$/$1/;
                    $sta =~ s/^ //gs;
                    # print "$sta\n";
                    if (exists $ndata{$sta})
                        {
                        $av = $profile{$sta}/$ndata{$sta};
                        $av =~ s/(^.*\...).*/$1/;
                        $av =~ s/ //g;
                        }
                    else
                        {
                        $av = 'no_data';
                        }
                    $gs =~ s/(^.* ([^ ]+):=(<|>))av(.*$)/$1$av$4/;
                    # print "2 $gs  $profile{$sta}/$ndata{$sta}";<STDIN>;
                    }
                $gs =~ s/^ //gs;

$gs =~ s/:=av/:=no_data/gs;

}
_____
sub delimiters_to_comma
{

$character = ',' if $character eq "\t";

return if $wsmode <=0;

if ($character eq " ")
        {
```

```
        $whitespaces++;
        }
else
        {
        $character = ','.$character if $whitespaces >= $wsmode;
        $whitespaces = 0;
        }
}
_____
sub tags_to_comma
{
        $rectest =~ s#^(.*)<([^> ]*)[^>]*>([^<]*)(</[^>]*>)$#$1$2:==$3#gs;
}
_____
sub grid_initialize
{
$ncols--;
if ($ncols<1)
        {
        print "No grid matrix generated.\n";
        return;
        }
$big = 1.0E200;
$minenergy = $big;
$conv = 1;
$rconv = 1/$conv;
die "ERROR BAD XML Check input file= and delimit commands. No data detected"
  if $maxlengthrec <1;

#go column by column
for ($i=0;$i<=$ncols;$i++)
        { get average of each column
        $av = 0;
        for ($j=1;$j<=$record;$j++) # g = (x-<x>)...
                {
                $av += $grid[$i][$j];
                # print "$grid[$i][$j] ($i,$j)";<STDIN>;#check values
                }
        $av/= $record;
```

```
#convert to deltas e.g. (x-<x>)/<x>
    for ($j=1;$j<=$record;$j++) # g = (x-<x>)...
        {
        $grid[$i][$j] -= $av;
        # print "$grid[$i][$j] ($i,$j)";<STDIN>;#check values
        } get sum of squared values in each column
    $sum2[$i] = 0;
    for ($j=1;$j<=$record;$j++)
        {
        $sum2[$i] += $grid[$i][$j]*$grid[$i][$j];
        } normalize grid elements by sigma
    if ($sum2[$i]>0)
        {
        $rsum2 = 1 / sqrt($sum2[$i]);
        for ($j=1;$j<=$record;$j++)
            {
            $grid[$i][$j] *= $rsum2;
            }
        }
    else
        { for ($j=1;$j<=$record;$j++)
            {
            $grid[$i][$j] = 1;#1 is neutral value in log-product
            }
        }

#Take absolute values and determine avergage absolute value
    $avabs = 0;
    for ($j=1;$j<=$record;$j++)
        {
        $grid[$i][$j] = abs($grid[$i][$j]);
        $avabs += $grid[$i][$j];
        }
    $avabs /= $record;
```

```perl
rescale relative to absolute value and take log $avabs = log($avabs);
        for ($j=1;$j<=$record;$j++)
            {
                $grid[$i][$j] = log($grid[$i][$j]) - $avabs;
            # print "$i $j $grid[$i][$j]";<STDIN>;#check values
            }

}# end of column by column loop initialize variable coefficients $numberofconfs = $ncols + 2;

for ($i=0;$i<=$ncols;$i++)
            {
            $origvar[$i] = $truevar[$gridpt[$i]];
                if ($sum2[$i] >0)
                    {
                    $origvar[$i] /= ($origvar[$i] + 1);
                        #above, we convert to zero to 1 scale.
                    $origvar[$i] = -$origvar[$i];
                    } else
                {
                $origvar[$i] = 1;
                }

}

}
##################################################################
sub grid_explore
{ print PRIMEGLOBFILE "<fano:multivariance status=\"experimental\">\n";
if ($numberofconfs<1)
    {
```

```
        print PRIMEGLOBFILE <<END8;
<fano:possible_error type="no data for multivariance optimization">
Analysis is discontinued.
Check file, file content, and delimiters in file $comfile.
Check processing of data by editing functions in file $convertfile.
</fano:possible_error>
</fano:multivariance>
</fano:results>
</fano:job>
</fano:output>
END8
die
"Number of conformations zero but high dimensional covariance requested\n";

} for ($nthtry=0;$nthtry<=$iterations;$nthtry++)
    {
    print "FANO MULTIVARIANCE: Iteration $nthtry of $iterations ";
    $nth = 0;
    for ($konf=1;$konf<=$numberofconfs;$konf++)
        {
        if ($konf>$#estack)
            {
            for ($i=0;$i<=$ncols;$i++)
                {
                $var[$i] = (2 * $origvar[$i] -1) * rand(1);
                $conformation[$konf][$i] = $var[$i];
                }
            $energy[$konf] = &grid_energy(@var);
            }
        else
            {
            for ($i=0;$i<=$ncols;$i++)
                {
                $conformation[$konf][$i]
                     = $stack[$nth][$i];
                }
            $energy[$konf] = $estack[$nth];
            $nth++;
            }
        }
    $converged = $false;
    $nconfsdone = 0;
    undef @meanvar;
```

```perl
undef @oldmeanvar;
&kreep while !$converged;

if ($minenergy >= $centroidE)
    {
    $minenergy = $centroidE; #improvement!
    }
else
    {
    print "\n";
    next;
    } for ($i=0;$i<=$#var;$i++)
    {
    $stack[$nthentry][$i] = $centroid[$i];
    $bestmeanvar[$i] = $meanvar[$i] * $rnconfsdone;
    }

$nthentry++;

$estack[$nthentry] = $centroidE;
$bestenergy = $centroidE;
$bestnthtry = $nthtry;
print "new function value=$bestenergy\n";
} print
"Coefficient-optimization pass=$bestnthtry function value=$bestenergy\n";

print PRIMEGLOBFILE
"<fano:covariance_Coefficient_optimization pass=\"$bestnthtry\"",
" function_value=\"$bestenergy\">\n";

$least = 1.0E200;
$least2 = 1.0E200;
$most = -1.0E200;
$most2 = -1.0E200;

$rnconfsdone = 1/$nconfsdone;
```

```
for ($ithvar=0;$ithvar<=$ncols;$ithvar++)
    {
    $mv = 1 - $bestmeanvar[$ithvar];
    if ($mv>0)
        {
        $mv = 25 + 150 * $mv/($mv + 1)
        }
    else
        {
        $mv = 25 - 25 * $mv/($mv - 1);
        }

$mv = 100 if $mv >100;
    $mv = 0 if $mv < 0;
    $mv = int(0.5 + $mv);

$ov = 'none';
    $ov = 1 - $origvar[$ithvar];
    $ov = 150 * $ov/($ov + 1);
    $ov = int(0.5 + $ov);

print PRIMEGLOBFILE
  "<fano:interest metatstate=\"$metastate[$gridpt[$ithvar]]\" ",
    "column=\"$ithvar\" optimized_omnivariate_value=\"$mv%\"",
    " estimated_from_fuzzy=\"$ov%\"",
    ,"/>\n";
    if ($least>$mv)
        {
        $least3 = $least2;
        $least2 = $least;
        $leastinteresting3 = $leastinteresting2;
        $leastinteresting2 = $leastinteresting;
        $least = $mv;
        $leastinteresting
          = "column $ithvar $metastate[$ithvar]";
        }
    if ($most<$mv)
        {
        $most3 = $most2;
        $most2 = $most;
        $mostinteresting3 = $mostinteresting2;
        $mostinteresting2 = $mostinteresting;
        $most = $mv;
```

```
            $mostinteresting
              = "column $ithvar $metastate[$ithvar]";
            }
        } print PRIMEGLOBFILE
    "</fano:covariance_Coefficient_optimization>\n";

print PRIMEGLOBFILE "</fano:multivariance>\n";

}
_____ sub grid_energy
{
@var = @_;

#set energy wall outside 0...1 range, plus torsin penalty
    $torsion = 0;
    for ($i=0;$i<=$ncols;$i++)
        {
        $v = 0;
        $v = $var[$i]+0.99 if $v >= 0.99;
        $v = $var[$i]-0.99 if $v <= 0.99;
        $torsion += 100*$v*$v;
        }

$sum = 0;

for ($j=1;$j<=$record;$j++)
        {
        $prod = 0;
        for ($i=0;$i<=$ncols;$i++)
            {
            # print "rec=$j grid = $grid[$i][$j] var=$var[$i] \n";#~
            $prod += $grid[$i][$j]*$var[$i];
            }
        $sum += exp($prod);
        #~ print "sum[$j] = $sum";<STDIN>;
        } return $sum + $torsion;
```

```
}
_____
#############################KREEP################################### sub kreep
{ if ($numberofconfs<1)
    {
    print PRIMEGLOBFILE <<END6;
<fano:possible_error type="no data for multivariance optimization">
Analysis is discontinued.
Check file, file content, and delimiters in file $comfile.
Check processing of data by editing functions in file $convertfile.
</fano:possible_error>
</fano:variance>
</fano:results>
</fano:job>
</fano:output>
END6
die
"Number of conformations zero but high dimensional covariance requested\n";
    }

$convergence = 0.0000001 if $convergence < 0.0000001;

#Find high & low point
$highEnergy = -$big;
$lowEnergy = $big;
for ($konf=1;$konf<=$numberofconfs;$konf++)
    {
    if ($energy[$konf]>$highEnergy)
        {
        $highEnergy = $energy[$konf];
        $highEconf = $konf;
        }
    if ($energy[$konf]<$lowEnergy)
        {
        $lowEnergy = $energy[$konf];
        $lowEconf = $konf;
        }
    }
```

```
if ($numberofconfs<1)
    {
    print PRIMEGLOBFILE <<END7;
<fano:possible_error type="no data for multivariance optimization">
Analysis is discontinued.
Check file, file content, and delimiters in file $comfile.
Check processing of data by editing functions in file $convertfile.
You probably ran metadata=off but used the high dimensional covariance
command which thus had no extracted numeric data on which to act.
</fano:possible_error>
</fano:variance>
</fano:results>
</fano:job>
</fano:output>
END7
die
"Number of conformations zero but high dimensional covariance requested\n";
    }

#Find centroid
$rpointsm1 =1/($numberofconfs-1);
$rpoints = 1/$numberofconfs;
for ($ithvar=0;$ithvar<=$ncols;$ithvar++)
    {
    $centroid[$ithvar] = 0;
    } for ($konf=1;$konf<=$numberofconfs;$konf++)
    {
    for ($ithvar=0;$ithvar<=$ncols;$ithvar++)
        {
        $centroid[$ithvar] += $conformation[$konf][$ithvar];
        }
    }
for ($ithvar=0;$ithvar<=$ncols;$ithvar++)
    {
    $centroid[$ithvar] *= $rpoints;
    }

#Calculate meanvar
for ($konf=1;$konf<=$numberofconfs;$konf++)
    {
    $nconfsdone++;
```

```
for ($ithvar=0;$ithvar<=$ncols;$ithvar++)
    {
    $oldmeanvar[$ithvar] = $meanvar[$ithvar];
    $meanvar[$ithvar] += $conformation[$konf][$ithvar];
    }
}

$rnconfsdone = 1/$nconfsdone;

$converged = $true;
for ($ithvar=0;$ithvar<=$ncols;$ithvar++)
    {
    $mv = $rnconfsdone * abs($meanvar[$ithvar]-$oldmeanvar[$ithvar]);

$converged = !$true if $mv > $convergence;
    } correct centroid to be of all points except highest for ($ithvar=0;$ithvar<=$ncols;$ithvar++)
    {
    $centroid[$ithvar] = $centroid[$ithvar]*$numberofconfs
       + $conformation[$highEconf][$ithvar];
    $centroid[$ithvar] *= $rpointsm1;
    }
$centroidE = &grid_energy(@centroid);

return if $converged;

# Reflect High Point
$oldTryE = $big;
$tryE = $big * 0.1;

$step = 0;
do   {
    $step++;
    @sparevar = @var;

for ($ithvar=0;$ithvar<=$ncols;$ithvar++)
```

```perl
        {
        if ($step<=1)
            {
            $var[$ithvar] = $centroid[$ithvar]
              + $centroid[$ithvar]
               - $conformation[$highEconf][$ithvar];

}
        }

$oldTryE = $tryE;
    $tryE = &grid_energy(@var);
    # print "kreep9100 REITERATED QUADRATIC x $step";

# printf (" E[%i]=%g\n",$highEconf,$tryE);
    }
    while ($oldTryE > $tryE);

@var = @sparevar;
    $tryE = $oldTryE;

if ($tryE <= $energy[$lowEconf])
    {
    # print "kreep9100 LOW POINT IMPROVED (because $tryE =< low energy)\n";

for ($ithvar=0;$ithvar<=$ncols;$ithvar++)
        {
        $conformation[$highEconf][$ithvar]
          = $var[$ithvar];
        }
    $energy[$highEconf] = $tryE;
    }
elsif ($tryE < $energy[$secondHighEconf])
    {
    # print "kreep9100 HIGH POINT MUCH IMPROVED(because $tryE < 2nd high E )\n";

for ($ithvar=0;$ithvar<=$ncols;$ithvar++)
        {
        $conformation[$highEconf][$ithvar]
          = $var[$ithvar];
        }
    $energy[$highEconf] = $tryE;
```

```
        }
else
    {
    $xa = $conformation[$highEconf][$ithvar];
    $xb = $centroid[$ithvar];
    $xc = $var[$ithvar];

if (abs($xc-$xb)>abs($xb-$xa))
    #Last interpolation probably hit high energy to right of centroid
        {
        # print "kreep9100 INTERPOLATION LEFT OF CENTROID ";
        for ($ithvar=0;$ithvar<=$ncols;$ithvar++)
            {
            $var[$ithvar]
              = $centroid[$ithvar]
                + rand(1) * ($conformation[$highEconf][$ithvar]
                  - $centroid[$ithvar]);
            }

}
    else
        {
        # print "kreep9100 INTERPOLATION RIGHT OF CENTROID ";
    #Interpolatation probably hit high energy left of centroid for ($ithvar=0;$ithvar<=$ncols;$ithvar++)
            {
            $var[$ithvar]
              = $centroid[$ithvar] + rand(1) * ($var[$ithvar]
                - $centroid[$ithvar]);
            }
        }

$tryE = &grid_energy(@var);

if ($tryE < $energy[$highEconf])
        {
        # printf ("TRY $nthtry SUCEEDED (E=%g). KEEP IT.\n",$tryE);
        for ($ithvar=0;$ithvar<=$ncols;$ithvar++)
            {
            $conformation[$highEconf][$ithvar]
              = $var[$ithvar];
            }
        $energy[$highEconf] = $tryE;
```

```
            }
    else
        {
        # printf ("FAILED (E=%g). CONTRACT.\n",$tryE);

for ($konf=1;$konf<=$numberofconfs;$konf++)
            {
            if ($konf != $lowEconf)
                {
                for ($ithvar=0;$ithvar<=$ncols; $ithvar++)
                    {
                    $var[$ithvar] =
                # 0.5 * ($conformation[$konf][$ithvar]
                    rand(0.9) * ($conformation[$konf][$ithvar]
                        + $conformation[$lowEconf][$ithvar]);
                        $conformation[$konf][$ithvar]
                            = $var[$ithvar];
                    }
                $energy[$konf] = &grid_energy(@var);

}
            }
        }

}
}
####################################################################################
```

What is claimed is:

1. An automated method of discovering information relating to a collection of input data, the method comprising the steps of:
   obtaining the collection of input data, wherein the collection of input data comprises data items;
   discovering information relating to the collection of input data based on a computation of a mutual information measure in accordance with at least a portion of the data items, wherein expected values of the mutual information measure are expressed as linear combinations of an incomplete Riemann zeta function; and
   outputting at least a portion of results associated with the computation of the mutual information measure, wherein at least a portion of the results represent the discovered infonnation relating to the collection of input data.

2. The method of claim 1, wherein the mutual information measure is represented as $I=\zeta-\zeta$, wherein I represents the measure computed with respect to M items, n represents the actual number of items, $\zeta$ represents the incomplete Riemann zeta function, $\epsilon$ represents an expected frequency, the subtraction of one represents a Dirichlet prior density, and s represents an adjustable parameter.

3. The method of claim 1, wherein the collection of input data comprises at least one of qualitative data and quantitative data.

4. The method of claim 1, wherein the information discovery step comprises an association analysis when the collection of input data is qualitative data.

5. The method of claim 4, wherein the association analysis is capable of discovering negative associations.

6. The method of claim 1, wherein the information discovery step comprises a covariance analysis when the collection of input data is quantitative data.

7. The method of claim 1, wherein the information discovery step comprises encoding the data items in association with prime numbers.

8. The method of claim 7, wherein a given prime number is assigned to a type of data item based on a frequency of occurrence of the data item type in the collection of input data.

9. The method of claim 7, wherein, when the collection of input data comprises one or more records and each of the one or more records comprise data items, the information discovery step further comprises encoding each record as a product of the prime numbers representing the data items in the record or as a sum of the logarithms of the prime numbers representing the data items in the record.

10. The method of claim 9, further comprising the step of generating one or more subrecords from a record.

11. The method of claim 9, further comprising the step of determining similarity between two records by comparing the respective products of the two records or the respective sums of the two records.

12. Apparatus for discovering information relating to a collection of input data, the apparatus comprising:
   at least one processor operative to: (i) obtain the collection of input data, wherein the collection of input data comprises data items; (ii) discover information relating to the collection of input data based on a computation of a mutual information measure in accordance with at least a portion of the data items, wherein expected values of the mutual information measure are expressed as linear combinations of an incomplete Riemann zeta function; and (iii) output at least a portion of results associated with the computation of the mutual information measure, wherein at least a portion of the results represent the discovered information relating to the collection of input data; and
   memory, coupled to the at least one processor, for storing at least a portion of results associated with one or more of the obtaining, discovering and outputting operations.

13. The apparatus of claim 12, wherein the mutual information measure is represented as $I=\zeta-\zeta$, wherein I represents the measure computed with respect to M items, n represents the actual number of items, $\zeta$ represents the incomplete Riemann zeta function, $\epsilon$ represents an expected frequency, the subtraction of one represents a Dirichlet prior density, and s represents an adjustable parameter.

14. The apparatus of claim 12, wherein the collection of input data comprises at least one of qualitative data and quantitative data.

15. The apparatus of claim 12, wherein the information discovery operation comprises an association analysis when the collection of input data is qualitative data.

16. The apparatus of claim 15, wherein the association analysis is capable of discovering negative associations.

17. The apparatus of claim 12, wherein the information discovery operation comprises a covariance analysis when the collection of input data is quantitative data.

18. The apparatus of claim 12, wherein the information discovery operation comprises encoding the data items in association with prime numbers.

19. The apparatus of claim 18, wherein a given prime number is assigned to a type of data item based on a frequency of occurrence of the data item type in the collection of input data.

20. The apparatus of claim 18, wherein, when the collection of input data comprises one or more records and each of the one or more records comprise data items, the information discovery operation further comprises encoding each record as a product of the prime numbers representing the data items in the record or as a sum of the logarithms of the prime numbers representing the data items in the record.

21. The apparatus of claim 20, wherein the at least one processor is further operative to generate one or more subrecords from a record.

22. The apparatus of claim 20, wherein the at least one processor is further operative to determine similarity between two records by comparing the respective products of the two records or the respective sums of the two records.

23. An article of manufacture for discovering information relating to a collection of input data, comprising a machine readable medium containing one or more programs which when executed implement the steps of:
   obtaining the collection of input data, wherein the collection of input data comprises data items;
   discovering information relating to the collection of input data based on a computation of a mutual information measure in accordance with at least a portion of the data items, wherein expected values of the mutual information measure are expressed as linear combinations of an incomplete Riemann zeta function; and
   outputting at least a portion of results associated with the computation of the mutual information measure, wherein at least a portion of the results represent the discovered information relating to the collection of input data.

24. The method of claim 1, wherein the linear combinations of the incomplete Riemann zeta function are defined so as to allow positive and negative values for the expected values of the mutual information measure.

25. The method of claim 2, wherein the adjustable parameter comprises a value of one.

26. An automated method of discovering information relating to a collection of input data, the method comprising the steps of:

associating unique prime numbers with each of a plurality of data items from the collection of input data, the collection of input data also comprising a plurality of records, each record corresponding to a set of the data items;

associating a value to each record, a given value corresponding to prime numbers associated with the set of the data items from a given record;

discovering information relating to the collection of input data based on a computation of a mutual information measure in accordance with at least a portion of the data items, wherein the values and the prime numbers are utilized during the discovery step; and outputting at least a portion of results associated with the computation of the mutual information measure, wherein at least a portion of the results represent the discovered information relating to the collection of input data.

27. The method of claim 26, wherein expected values of the mutual information measure are expressed as linear combinations of an incomplete Riemaim zeta function.

28. The method of claim 26, wherein a given prime number is assigned to a given data item based on a frequency of occurrence of a type of the data item in the collection of input data.

29. The method of claim 26, wherein the step of associating a value to each record further comprises the step of associating a value for a given record equivalent to a product of the prime numbers representing the data items in the given record or to a sum of the logarithms of the prime numbers representing the data items in the given record.

30. The method of claim 26, wherein the step of discovering information further comprises the step of comparing values corresponding to two or more given records to determine similarity between the two or more given records.

31. The method of claim 26, wherein a given set of data items for a given record comprises a plurality of data items, wherein the step of discovering further comprises the step of generating every subrecord for the given record, each subrecord corresponding to one or more of the data items in the given set, the step of generating utilizing prime numbers associated with the data items in the given set.

32. The method of claim 31, wherein the value for the given record is equivalent to a product of the prime numbers representing the data items in the given record, wherein the step of generating every subrecord for the given record further comprises the steps of dividing the product by a set of natural numbers and determining which of the divisions result in integer results with no remainder, each division corresponding to a given one of the set of natural numbers, wherein each of the given natural numbers corresponds to one or more given data items from the given set and to a corresponding subrecord.

33. An apparatus for discovering information relating to a collection of input data, the apparatus comprising:

at least one processor operative to:

associate unique prime numbers with each of a plurality of data items from the collection of input data, the collection of input data also comprising a plurality of records, each record corresponding to a set of the data items;

associate a value to each record, a given value corresponding to prime numbers associated with the set of the data items from a given record;

discover information relating to the collection of input data based on a computation of a mutual information measure in accordance with at least a portion of the data items, wherein the values and the prime numbers are utilized during the discovery step; and output at least a portion of results associated with the computation of the mutual information measure, wherein at least a portion of the results represent the discovered information relating to the collection of input data.

34. An article of manufacture for discovering information relating to a collection of input data, comprising a machine readable medium containing one or more programs which when executed implement the steps of:

associating unique prime numbers with each of a plurality of data items from the collection of input data, the collection of input data also comprising a plurality of records, each record corresponding to a set of the data items;

associating a value to each record, a given value corresponding to prime numbers associated with the set of the data items from a given record;

discovering information relating to the collection of input data based on a computation of a mutual information measure in accordance with at least a portion of the data items, wherein the values and the prime numbers are utilized during the discovery step; and outputting at least a portion of results associated with the computation of the mutual information measure, wherein at least a portion of the results represent the discovered information relating to the collection of input data.

* * * * *

UNITED STATES PATENT AND TRADEMARK OFFICE
CERTIFICATE OF CORRECTION

PATENT NO. : 7,043,476 B2
APPLICATION NO. : 10/269375
DATED : May 9, 2006
INVENTOR(S) : Robson It is certified that error appears in the above-identified patent and that said Letters Patent is hereby corrected as shown below:

Column 15, line 67, replace "e(x =1;y/z)" with -- e(x =1; y | z) --.

Column 16, line 3, replace "e(x =1;y/z)" with -- e(x =1; y | z) --.

Column 31, line 23, before "through 11C" and after "Further," replace "FIGS. 1A" with -- FIGS. 11A --.

Column 44, line 38, after "where symbol" replace "A" with -- "^" --.

Column 397, line 19, before "wherein I" and after "represented as" replace "$I = \xi - \xi$" with -- $I[a; b; c; ...; M] = \zeta [s = 1, n(a, b, c, ..., M) - 1] - \zeta [s = 1, \varepsilon (a, b, c, ..., M) - 1]$ --.

Column 398, line 8, before "wherein I" and after "represented as" replace "$I = \xi - \xi$" with -- $I[a; b; c; ...; M] = \zeta [s = 1, n(a, b, c, ..., M) - 1] - \zeta [s = 1, \varepsilon (a, b, c, ..., M) - 1]$ --.

Signed and Sealed this

Tenth Day of October, 2006

JON W. DUDAS
*Director of the United States Patent and Trademark Office*